United States Patent
Ingham et al.

(10) Patent No.: US 6,630,148 B1
(45) Date of Patent: *Oct. 7, 2003

(54) COMPOSITIONS COMPRISING HEDGEHOG PROTEINS

(75) Inventors: Philip W. Ingham, Summertown (GB); Andrew P. McMahon, Lexington, MA (US); Clifford J. Tabin, Cambridge, MA (US)

(73) Assignees: Imperial Cancer Research Technology Ltd., London (GB); President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/954,740

(22) Filed: Oct. 20, 1997

Related U.S. Application Data

(63) Continuation of application No. 08/462,386, filed on Jun. 5, 1995, which is a continuation-in-part of application No. 08/435,093, filed on May 4, 1995, now abandoned, which is a continuation-in-part of application No. 08/356,060, filed on Dec. 14, 1994, now Pat. No. 5,844,079, which is a continuation-in-part of application No. 08/176,427, filed on Dec. 30, 1993, now Pat. No. 5,789,543.

(51) Int. Cl.$^7$ ............................................... A61K 39/00
(52) U.S. Cl. ..................... 424/185.1; 424/422; 530/350; 530/402; 536/23.5; 514/12; 514/7; 514/8; 435/69.1
(58) Field of Search .................. 530/350; 536/23.5; 435/6

(56) References Cited

U.S. PATENT DOCUMENTS

| | | | | |
|---|---|---|---|---|
| 5,223,408 A | 6/1993 | Goeddel et al. | ............ | 435/69.3 |
| 5,585,087 A | 12/1996 | Lustig et al. | ................ | 424/9.2 |

FOREIGN PATENT DOCUMENTS

| | | |
|---|---|---|
| WO | WO 90/02809 | 3/1990 |
| WO | WO 92/15679 | 9/1992 |

OTHER PUBLICATIONS

Chang et al., "Products genetic linkage, and limb patterning activity of a murine hedgehog gene", Development 120:3339–3353 (1994).
Anderson, R. et al., "Maintenance of ZPA signaling in cultured mouse limb bud cells", Devel. 117:142–1433 (1993).
Angier, N. "Biologists find key genes that shape patterning of embryos", New York Times, Jan. 11, 1994, C–1.
Basler, K. and G. Struhl, "Compartment boundaries and the control of Drosophila limb pattern by hedgehog protein", Nature 368: 208–214 (1994).
Basler, K. et al., "Control of cell pattern in the neural Tube: Regulation of cell differentiation by dorsalin–1, a novel TGFβ family member", Cell 73:687–702 (1993).

Bass, S. et al., "Hormone phage: An Enrichment Method for Variant Proteins with Altered Binding Properties", Proteins: Structure, Function, and Genetics 8:309–314 (1990).
Bejsovec, A. and E. Wieschaus, "Segment polarity gene interactions modulate epidermal patterning in Drosophila embryos", Devel. 119:501–517 (1993).
Bienz, M., "Homeotic genes and positional signalling in the Drosophila viscera", TIG 10:22–26 (Jan. 1994).
Bitgood, M. and McMahon, A., "Hedgehog and Bmp Genes are Coexpressed at Many Diverse Sites of Cell–Cell Interaction in the Mouse Embryo", Dev. Biol. 172 (1):126–138 (1995).
Blair, S.S., "Hedgehog digs up an old friend", Nature 373:656–657 (Feb. 23, 1995).
Bone et al., Endo. Meta. 2:160–184 (1995).
Brand–Saberi, B. et al., "The ventralizing effect of the notochord on somite differentiation in chick embryos", Anat. Embryol. 188: 239–245 (1993).
Brockes, J., "We may not have a morphogen", Nature 350:15 (1991).
Bumcrot, D.A. and McMahon A. "Sonic Hedgehog: Making the gradient", Chem. Biol. 3 (1):13–16 (Jan. 1996).
Bumcrot, D.A. and McMahon, A., "Somite differentiation. Sonic signals somites", Curr. Biol. 5 (6):612–614 (Jun. 1995).
Bumcrot, D.A. et al., "Proteolytic processing yields two secreted forms of sonic hedgehog", Mol. Cell. Biol. 15 (4):2294–2303 (4/95).
Charité, J. et al., "Ectopic Expression of Hoxb–8 Causes Duplication of the ZPA in the Forelimb and Homeotic Transformation of Axial Structures", Cell 78:589–601 (1994).
Coffman et al., "Xotch, the Xenopus homolog of Drosophila notch", Science 249:1438–1441 (1990).
Concordet, J. and Ingham, P., "Developmental biology. Patterning goes sonic", Nature 375 (6529):279–280 (May 1995).
Currie et al., "Induction of a specific muscle cell type by a hedgehog–like protein in zebrafish", Nature 383:452–455 (1996).
Curry et al., "Sequence analysis reveals homology between two proteins of the flagellar radial spoke", Mol. Cell. Biol. 12:3967–3977 (1992).

(List continued on next page.)

Primary Examiner—Lorraine Spector
Assistant Examiner—Eileen B. O'Hara
(74) Attorney, Agent, or Firm—Ropes & Gray LLP

(57) ABSTRACT

The present invention concerns the discovery that proteins encoded by a family of vertebrate genes, termed here hedgehog-related genes, comprise morphogenic signals produced by embryonic patterning centers, and are involved in the formation of ordered spatial arrangements of differentiated tissues in vertebrates. The present invention makes available compositions and methods that can be utilized, for example to generate and/or maintain an array of different vertebrate tissue both in vitro and in vivo.

52 Claims, 19 Drawing Sheets

OTHER PUBLICATIONS

Davidson, E.H., "How embryos work: a comparative view of diverse modes of cell fate specification", *Devel. 108*:365–389 (1990).

Davis, A.P. and M.R. Capecchi, "Axial homeosis and appendicular skeleton defects in mice with a targeted disruption of hoxd–1", *Devel. 120*:2187–2198 (1994).

Dickinson W., "Molecules and morphology: Where's the homology", *TIG 11*, (4):119–120 (1995).

Dingemanse, M.A. et al., "The expression of liver–specific genes within rat embryonic hepatocytes is a discontinuous process", *Differentiation 56*:153–162 (1994).

DolléP. et al., "Coordinate expression of the murine Hox–5 complex homoeobox–containing genes during limb pattern formation", *Nature 342*:767–772 (1989).

Dollé, P. et al., "Disruption of the Hoxd–13 gene induces localized heterochrony leading to mice with neotenic limbs", *Cell 75*:431–441 (1993).

Echelard, Y. et al., "Sonic hedgehog, a member of a family of putative signaling molecules, is implicated in the regulation of CNS polarity", *Cell 75*:1417–1430 (1993).

Ekker, S. et al., "Distinct expression and shared activities of members of the hedgehog gene family of xenopus laevis", *Devel. 121* (8):2337–2347 (Aug. 1995).

Ericson, J. et al., "Sonic hedgehog induces the differentiation of ventral forebrain neurons: a common signal for ventral patterning within the neural tube", *Cell 81* (5):747–756 (Jun. 1995).

Ettelaie, C. et al. "The effect of lipid peroxidation and lipolysis on the ability of lipoproteins to influence thromboplastin activity", *Biochem. Biophys. Acta. 1257* (1):25–30 (Jun. 1995).

Fahrner, K. et al., "Transcription of H–2 and Qa genes in embryonic and adult mice", *EMBO J. 6*:1265–1271 (1987).

Fallon, J.F. et al., "FGF–2: Apical ectodermal ridge growth signal for chick limb development", *Science 264*:104–107 (1994).

Fan, C. et al., "Long–range sclerotome induction by sonic hedgehog: Direct role of the amino–terminal cleavage product and modulation by the cyclic AMP signaling pathway", *Cell 81*:457–465 (May 5, 1995).

Fietz, M. et al., "The hedgehog gene family in Drosophila and vertebrate development", *Devel. Supp*: 43–51 (1994).

Forbes, A.J. et al., "Genetic analysis of hedgehog signalling in the Drosophila embryo", *Devel. 119* (Supp.):115–124 (1993).

Francis, P.H. et al., "Bone morphogenetic proteins and a signalling pathway that controls patterning in the developing chick limb", *Devel. 120*:209–218 (1994).

Gallop, M. et al., "Applications of combinatorial technologies to drug discovery. 1. Background and peptide combinatorial libraries", *J. of Med. Chem. 37* (9):1233–1251 (1994).

Gérard, M. et al., "Structure and activity of regulatory elements involved in the activation the the Hoxd–11 gene during late gastrulation", *EMBO J. 12*:3539–3550 (1993).

Gurdon, J.B., "The Generation of diversity and pattern in animal development", *Cell 68*:185–199 (1992).

Gustin, K. et al., "Characterization of the role of individual protein binding motifs within the hepatitis B virus enhancer 1 on X promoter activity using linker scanning mutageneis", *Virology 193*:653–660 (1993).

Hall, T., et al., "A potential catalytic site revealed by the 1.7–A crystal structure of the amino–terminal signalling domain of Sonic hedgehog", *Nature 378* (6553):212–216 (Nov. 1995).

Halpern, M.E., et al., "Induction of muscle pioneers and floor plate is distinguished by the zebrafish no tail mutation", *Cell 75*:99–111 (1993).

Hamburger, V. and H.L. Hamilton, "A series of normal stages in the development of the chick embryo", *J. Morph. 88*:49–92 (1951).

Hammerschmidt, M. et al., "The world according to hedgehog", *TIG 13*(1):14–21 (1997).

Haramis, A. et al., "The limb deformity mutation disrupts the SHH/FGF–4 feedback loop and regulation of 5–HoxD genes during limb pattern formation", *Devel. 121* (12):4161–4170 (Dec. 1995).

Hardy, A., et al., "Gene expression, polarising activity and skeletal patterning in reaggregated hind limb mesenchyme", *Devel. 121* (12):4329–4337 (Dec. 1995).

Hatta, K. et al., "The cyclops mutation blocks specification of the floor plate of the zebrafish central nervous system", *Nature 350*: 339–341 (1991).

Heberlein, U. et al., "The TGBβ homolog dpp and the segment polarity gene hedgehog are required for propagation of a morpho–genetic wave in the Drosophila retina", *Cell 75*:913–926 (1993).

Heemskerk, J. and S. DiNardo, "Drosophila hedgehog acts as a morphogen in cellular patterning", *Cell 76*:449–460 (1994).

Hidalgo, A. and P. Ingham, "Cell patterning in Drosophila segment: spatial regulation of the segment polarity gene patched", *Devel. 110*:291–301 (1990).

Hooper, J. and Scott, M., "The Drosophila patched gene encodes a putative membrane protein required for segmental patterning", *Cell 59*:751–765 (1989).

Hynes, R.O., "Integrins: A family of Cell Surface Receptors", *Cell 48*:549–554 (1987).

Hynes, M., et al., "Induction of midbrain dopaminergic neurons by Sonic hedgehog", *Neuron 15*(1):35–44 (Jul. 1995).

Ingham, P.W., "Signalling by hedgehog family proteins in Drosophila and vertebrate development", *Curr. Opin. Genet. Dev. 5* (4): 478–484 (Aug. 1995).

Ingham, P.W., "Hedgehog points the way", *Current Biology 4* (4):347–350 (1994).

Ingham, P.W., "Localized hedgehog activity controls spatial limits of wingless transcription in the Drosophila embryo", *Nature 366*:560–562 (1993).

Ingham, P.W. and A. Hidalgo, "Regulation of wingless transcription in the Drosophila embryo", *Devel. 117*:283–291 (1993).

Ingham, P.W. et al., "Role of the *Drosophila patched* gene in positional signalling", *Nature 353*:184–187 (1991).

Izpisúa–Belmonte, J.–C. et al., "Expression of the homeobox Hox–4 genes and the specification of position in chick wing development", *Nature 350*:585–589 (1991).

Izpisúa–Belmonte, J.–C. et al., "Expression of Hox–4 genes in the chick wings links pattern formation to the epithelial–mesenchymal interactions and mediate growth",*EMBO J. 11*:1451–1457 (1992).

Jiang, J. and Struhl, G., "Protein kinase A in hedgehog singalling in Drosophila limb development", *Cell 80* (4):563–572 (Feb. 1995).

Jessel, T.M. and D.A. Melton, "Diffusible factors in vertebrate embryonic induction", *Cell* 68:257–270 (1992).

Johnson, R.L. and C. Tabin, "The long and short of hedgehog signaling", *Cell* 81:313–315 (May 5, 1995).

Johnson, R.L. et al., "Patched overexpression alters wing disc size and pattern: transcriptional and post–transcriptional effects on hedgehog targets", *Devel.* 121 (12):4237–4245 (Dec. 1995).

Johnson, R.L., et al., "Ectopic expression of Sonic hedgehog alters dorsal–ventral patterning of somosites", *Cell* 79 (7):1165–1173 (Dec. 1994).

Johnson, R.L. et al., "Mechanism of limb patterning", *Curr. Opin. Genet. Dev.* 4 (4):535–542 (Aug. 1994).

Johnson, R.L. et al., "Sonic hedgehog: a key mediator of anterior–posterior patterning of the limb and dorso–ventral patterning of axial embryonic structures", *Biochem. Soc. Trans.* 22 (3):569–574 (Aug. 1994).

Jones, M. et al., "Involvement of bone morphogenetic protein–4 (BMP–4) and Vgr–L in morphogenesis and neurogenesis in the mouse", *Devel.* 111:531–542 (1991).

Kalderon, D., "Morphogenetic signaling. Responses to hedgehog" *Curr. Biol.* 5 (6):580–582 (Jun. 1995).

Koonin, E., "A protein splice–junction motif in hedgehog family proteins", *Trends in Biochem. Sci.* 20 (4):141–142 (Apr. 1995).

Kornblihtt, A.R. et al., "Primary structure of human fibronectin: differential splicing may generate at least 10 polypeptides from a single gene", *EMBO J.* 4:1755–1759 (1985).

Kornfeld, R. and S. Kornfeld, "Assembly of asparagine–Linked oligosaccharides", *Ann. Rev. Biochem.* 54:631–664 (1985).

Krauss, S. et al., "Expression of the zebrafish paired box gene pax[zf–b] during early neurogenesis", *Devel.* 113:1193–1206 (1991).

Krauss, S. et al., "A functionally conserved homolog of the Drosophila segment polarity gene hh Is expressed in tissues with polarizing activity in zebrafish embryos", *Cell* 75:1431–1444 (1993).

Lai, C. et al., "Patterning of the neural ectoderm of *Xenopus laevis* by the amino–terminal product of hedgehog autoprolytic cleavage", *Devel.* 121 (8):2349–2360 (Aug. 1995).

Laufer, E. et al., "*Sonic hedgehog* and Fgf–4 acb through a signaling cascade and feedback loop to integrate growth and patterning of the developing limb Bud", *Cell* 79:993–1003 (Dec. 16, 1994).

Lee, J.J. et al., "Secretion and localized transcription suggest a role in positional signaling for products of the segmentation gene hedgehog", *Cell* 71:33–50 (1992).

Lee, J, et al., "Autoproteolysis in hedgehog protein biogenesis", *Science* 266 (5190):1528–1537 (Dec. 1994).

Levin, M. et al., "A molecular pathway determining left–right asymmetry in chick embryogenesis", *Cell* 82 (5):803–814 (Sep. 1995).

Li, W. et al., "Function of protein kinase A in hedgehog signal transduction and Drosophila imaginal disc development", *Cell* 80 (4):553–562 (Feb. 1995).

Lopez–Martinez, A. et al., "Limb–patterning activity and restricted posterior localization of the amino–terminal product of Sonic hedgehog cleavage", *Curr. Biol.* 5 (7):791–796 (Jul. 1995).

Lumsden, A. and Graham, A., "Neural patterning: A forward role for hedgehog", *Curr. Biol.* 5 (12):1347–1350 (Dec. 1995).

Ma, C. et al., "The segment polarity gene hedgehog is required for progression of the morphogenetic furrow in the developing Drosophila eye", *Cell* 75:927–938 (1993).

Ma, C. and Moses, K., "Wingless and patched are negative regulators of the morphogenetic furrow and can affect tissue polarity in the developing Drosophila compound eye", *Devel.* 121 (8) 2279–2289 (Aug. 1995).

Marigo, V. et al., "Biochemical evidence that patched is the hedgehog receptor", *Nature* 384: 176–179 (1996).

Maccabe, J.A. and B.W. Parker, "The target tissue of limb–bud polarizing activity in the induction of supernumerary structures", *J. Embryol. Exp. Morph.* 53:67–73 (1979).

Marti, E. et al., "Distribution of Sonic hedgehog peptides in the developing chick and mouse embryo", *Devel.* 121 (8):2537–2547 (Aug. 1995).

Marti, E. et al., "Requirement of 19K form of Sonic hedgehog for induction of distinct ventral cell types in CNS explants" *Nature* 375 (6529):322–325 (May 1995).

Mavillo, F. et al., "Activation of four homeobox gene clusters in human embryonal carcinoma cells induced to differentiate by retinoic acid", *Differentiation* 37:73–79 (1988).

McGinnis, W. and R. Krumlauf, "Homeobox genes and axial patterning", *Cell* 68:283–302 (1992).

Mohler, J., "Requirements for hedgehog, a segmental polarity gene, in patterning larval and adult cuticle of Drosophila", *Genetics* 120:1061–1072 (1988).

Mohler, J. and K. Vani, "Molecular organization and embryonic expression of the hedgehog gene involved in cell–cell communication in segmental patterning of Drosophila", *Devel.* 115:957–971 (1992).

Morgan, B.A. et al., "Targeted misexpression of Hox–4.6 in the avian limb bud causes apparent homeotic transformations", *Nature* 358:236–239 (1992).

Munsterberg A. et al., "Combinatorial signaling by Sonic hedgehog and Wnt family members induces myogenic bH1H gene expression in the somite", *Genes Dev.* 9 (23):2911–2922 (Dec. 1995).

Nakano, Y. et al., "A protein with several possible membrane–spanning domains encoded by the Drosophila segment polarity gene patched", *Nature* 341:508–513 (1989).

Ngo, J. et al., "The protein folding problem and tertiary structure prediction", Merz and LeGrand, ed. Birkhauser, Boston (1994).

Niswander, L. and G.R. Martin, "FGF–4 and BMP–2 have opposite effects on limb growth", *Nature* 361:68–71 (1993).

Niswander, L. et al., "A positive feedback loop coordinates growth and patterning in the vertebrate limb", *Nature* 371 (6498): 609–612 (Oct. 1994).

Nohno, T. et al., "Involvement of the Chox–4 chicken homeobox genes in determination of anteroposterior axial polarity during limb development", *Cell* 64:1197–1205 (1991).

Nohno, T. et al., "Involvement of the Sonic hedgehog gene in chick feather formation", *Biochem. Biophys. Res. Comm.* 206(1): 33–39 (Jan. 1995).

O'Farrell, P.H., "Unanimity waits in the wings", *Nature* 368:188–189 (1994).

Parr, B.A. et al., "Mouse Wnt genes exhibit discrete domains of expression in the early embryonic CNS and limb buds", *Devel.* 119:247–261 (1993).

Patel, N.H. et al., "The role of segment polarity genes during Drosophila neurogenesis", *Genes Devel.* 3:890–904 (1989).

Peifer, M., "The two faces of hedgehog", *Science* 266 (5190):1492–1493 (Dec. 1994).

Perrimon, N., "Hedgehog and beyond", *Cell* 80:517–520 (Feb. 24, 1995).

Pham, A. et al., "The suppressor of fused gene encodes a novel PEST protein involved in Drosophila segment polarity establishment", *Genetics* 140 (2):587–598 (Jun. 1995).

Placzek, M. et al., "Induction of floor plate differentiation by contact–dependent, homeogenetic signals", *Devel.* 117:205–218 (1993).

Placzek, M. et al., "Orientation of commissural axons in vitro in response to a floor plate–derived chemoattractant", *Devel.* 110:19–30 (1990).

Pollack, R.A. et al., "Altering the boundaries of Hox3.1 expression: Evidence for antipodal gene regulation", *Cell* 71:911–923 (1992).

Porter, J, et al., "The product of hedgehog autoproteolytic cleavage active in local and long–range signalling", *Nature* 374 (6520): 363–366 (Mar. 1995).

Reeck et al., "Homology in proteins and nucleic acids: A terminology muddle and a way out of it", *Cell* 50:667 (1987).

Rennie, J., "Super Sonic", *Scientific American* :20 (Apr. 1994).

Riddle, R.D. et al., "*Sonic hedgehog* Mediates the Polarizing Activity of the ZPA", *Cell* 75:1401–1416 (1993).

Riddle, R.D. et al., "Induction of the LIM homeobox gene Lmx1 by WNT7 a established dorsovenral pattern in the vertebrate limb", *Cell* 83 (6553):212–216 (Nov. 1995).

Riley, B.B. et al., "Retroviral expression of FGF–2 (bFGF) affects patterning in chick limb bud", *Devel.* 118:95–104 (1993).

Roberts, D. et al., "Sonic hedgehog is an endothermal signal inducing Bmp–4 and Hox genes during induction and regionalization of the chick hindgut", *Devel.* 121 (10): 3163–74 (Oct. 1995).

Roelink, H. et al., "Floor plate and motor neuron Induction by different concentrations of the amino–terminal cleavage product of sonic hedgehog autoproteolysis", *Cell* 81:445–455 (May 5, 1995).

Roelink, H. et al., Floor plate and motor neuron induction by vhh–1, a Vertebrate Homolog of hedgehog expressed by the notochord, *Cell* 76:761–775 (1994).

Sambrook et al., *Molecular Cloning CSH*:11.47 (1989).

Sasaki, H. and B.L.M. Hogan, "Differential expression of multiple fork head related genes during gastrulation and axial pattern formation in the mouse embryo", *Devel.* 118:47–59 (1993).

Savage, M. et al., "Distribution of FGH–2 suggests is has a role in chick limb bud growth", *Devel. Dynamics* 198:159–170 (1993).

Schuske, K. et al., "Patched overexpression causes loss of wingless expression in drosophila embryos", *Devel. Biol.* 164:300–311 (1994).

Smith, J.C., "Hedgehog, the floor plate, and the zone of polarizing activity", *Cell* 76:193–196 (1994).

Stachel, S.E. et al., "Lithium perturbation and goosecoid expression identify a dorsal specification pathway in the pregastrula zebrafish", *Devel.* 117:1261–1274 (1993).

Stolow, M. and Shi, Y., Xenopus sonic hedgehog as a potential morphogen during embryogenesis and thyroid hormone–dependent metamorphosis, *Nucleic Acids Res.* 23 (13):2555–1562 (Jul. 1995).

Tabata, T. and T.B. Kornberg, "Hedgehog Is a signaling protein with a key Role in patterning Drosophila imaginal discs", *Cell* 76:89–102 (1994).

Tabata, T. et al., "The *Drosophila hedgehog* gene is expressed specifically in posterior compartment cells and is a target of engrailed regulation", *Genes Devel.* 6:2635–2645 (1992).

Tabin, C.J., "Retinoids, homeoboxes, and growth factors: Toward molecular models for limb development", *Cell* 66:199–217 (1991).

Tanebe, Y. et al., "Induction of motor neurons by *Sonic hedgehog* is independent of floor plate differentiation", *Curr. Biol.* 5 (6): 651–658 (Jun. 1995).

Tanaka, E. and Gann, A., "Limb development", *Curr. Biol.* 5(6):594–597 (Jun. 1995).

Tashiro, S. et al., "Structure and expression of hedgehog, a Drosophila segment–polarity gene required for cell–cell communication", *Gene* 124:183–189 (1993).

Taylor, A.M. et al., "Contrasting distributions of patched and hedgehog proteins in the Drosophila embryo", *Mech. Dev.* 42:89–96 (1993).

Thaller, C. and G. Eichele, "Identification and spatial distribution of retinoids in the developing chick limb bud", *Nature* 327:625–628 (1987).

Tickle, C. et al., "A Quantitative Analysis of the Effect of all–trans–Retinoic Acid on the Pattern of Chick Wing Development", *Devel. Biol.* 109:82–95 (1985).

Tickle, C., "Vertebrate limb development", *Curr. Opin. Genet. Dev.* 5(4):478–484 (Aug. 1995).

Tickle, C. and Eichele, G., "Vertebrate limb development", *Ann. Rev. Cell Biol.* 10:121–152 (1994).

van Straaten, H.W.M. et al., "Effect of the notochord on the differentiation of a floor plate area in the neural tube of the chick embryo," *Anat. Embryol.* 177:317–324 (1988).

Vogel, A. and C. Tickle, "FGF–4 maintains polarizing activity of posterior limb bud cells in vivo and in vitro", *Devel.* 119:199–206 (1993).

Wallace et al., "Oligonucleotide probes for the screening of recombinant DNA libraries", *Methods in Enzymology* 152:432 (1987).

Wanek, N. et al., "Conversion by retinoic acid of anterior cells into ZPA cells in the chick wing bud", *Nature* 350:81–83 (1991).

Wang, M. et al., "Induction of dopaminergic neuron phenotype in the midbrain by *Sonic hedgehog* protein", *Nat. Med.* 1 (11):1184–1188 (Nov. 1995).

Yamada, T. et al., "Control of cell pattern in the developing nervous system: Polarizing activity of the floor plate and notochord", *Cell* 64:635–647 (1991).

Yang, Y. and L. Niswander, "Interaction between the signalling molecules WNT7a and SHH during vertebrate limb development: Dorsal signals regulate anteroposterior patterning" *Cell* 80:939–947 (Mar. 1995).

Zappavigna et al., "Hox4 genes encode transcription factors with potential auto– and cross–regulatory capacities", *EMBO* 10:4177–4187 (1991).

Zardoya et al., "Evolution and orthology of hedgehog genes", TIG 12 (12):496–467 (1996).

Zecca, M. et al., "Sequential organizing activities of engrailed, hedgehog and decapentaplegic in the Drosophlia wing", *Devel.* 121 (8):2265–2278 (Aug. 1995).

| | | | | | | | | | | | | | | | | | |
|---|---|---|---|---|---|---|---|---|---|---|---|---|---|---|---|---|---|
| DROSOPHILA HEDGEHOG | R | C | K | E | K | L | N | V | L | A | Y | S | V | M | N | E | W | P | G | I | R | L | L | V | T |
| CHICKEN HEDGEHOG-A | R | C | K | E | R | V | N | S | L | A | I | A | V | M | H | M | W | P | G | V | R | L | R | V | T |
| CHICKEN HEDGEHOG-B | R | C | K | D | K | L | N | A | L | A | I | S | V | M | N | Q | W | P | G | V | K | L | R | V | T |

| | | | | | | | | | | | | | | | | | |
|---|---|---|---|---|---|---|---|---|---|---|---|---|---|---|---|---|---|
| DROSOPHILA HEDGEHOG | E | S | W | D | E | D | Y | H | H | G | Q | E | S | L | H | Y | E | G | R | A | V | T | I | A | T |
| CHICKEN HEDGEHOG-A | E | G | W | D | E | D | G | H | H | L | P | D | S | L | H | Y | E | G | R | A | L | D | I | H | T |
| CHICKEN HEDGEHOG-B | E | G | W | D | E | D | G | H | H | S | E | E | S | L | H | Y | E | G | R | A | V | D | I | T | T |

| | | | | | | | | | | | | | | | | | |
|---|---|---|---|---|---|---|---|---|---|---|---|---|---|---|---|---|---|
| DROSOPHILA HEDGEHOG | S | D | R | D | Q | S | K | Y | G | M | L | A | R | L | A | V | E | A | G | F | D | W | V |
| CHICKEN HEDGEHOG-A | S | D | R | D | R | H | K | Y | G | M | L | A | R | L | A | V | E | A | G | F | D | W | V |
| CHICKEN HEDGEHOG-B | S | D | R | D | R | S | K | Y | G | M | L | A | R | L | A | V | E | A | G | F | D | W | V |

```
       1
D-hh   MDNHSSVPWA  SAASVTCLSL  DAKCHSSSSS  SSSKSAASSI  SAIPQEETQT
M-Dhh  ..........  ..........  ..........  ..........  ..........
M-Ihh  ..........  ..........  ..........  ..........  ..........
M-Shh  ..........  ..........  ..........  ..........  ..........
C-Shh  ..........  ..........  ..........  ..........  ..........
Z-Shh  ..........  ..........  ..........  ..........  ..........

51                                  ▼
D-hh   MRHIAHTQRC  LSRLTSLVAL  LLIVLPMVFS  PAHSCGPGRG  LGRHR...AR
M-Dhh  ..........  ..MALPASLL  PLCCLALLAL  SAQSCGPGRG  PVGRRRYVRK
M-Ihh  ..........  ..........  ..........  ..........  ..........
M-Shh  ..........  MLLLLARCFL  VILASSLLVC  PGLACGPGRG  FGKRRH..PK
C-Shh  ........MV  EMLLLTRILL  VGFICALLVS  SGLTCGPGRG  IGKRRH..PK
Z-Shh  ..........  .MRLLTRVLL  VSLLTLSLVV  SGLACGPGRG  YGRRRH..PK

101
D-hh   NLYPLVLKQT  IPNLSEYTNS  ASGPLEGVIR  RDSPKFKDLV  PNYNRDILFR
M-Dhh  QLVPLLYKQF  VPSMPERTLG  ASGPAEGRVT  RGSERFRDLV  PNYNPDIIFK
M-Ihh  ..........  ..........  ..........  ...ERFKELT  PNYNPDIIFK
M-Shh  KLTPLAYKQF  IPNVAEKTLG  ASGRYEGKIT  RNSERFKELT  PNYNPDIIFK
C-Shh  KLTPLAYKQF  IPNVAEKTLG  ASGRYEGKIT  RNSERFKELT  PNYNPDIIFK
Z-Shh  KLTPLAYKQF  IPNVAEKTLG  ASGRYEGKIT  RNSERFKELT  PNYNPDIIFK

151         ▼
D-hh   DEEGTGADRL  MSKRCKEKLN  VLAYSVMNEW  PGIRLLVTES  WDEDYHHGQE
M-Dhh  DEENSGADRL  MTERCKERVN  ALAIAVMNMW  PGVRLRVTEG  WDEDGHHAQD
M-Ihh  DEENTGADRL  MTQRCKDRLN  SLAISVMNQW  PGVKLRVTEG  RDEDGHHSEE
M-Shh  DEENTGADRL  MTQRCKDKLN  ALAISVMNQW  PGVRLRVTEG  WDEDGHHSEE
C-Shh  DEENTGADRL  MTQRCKDKLN  ALAISVMNQW  PGVKLRVTEG  WDEDGHHSEE
Z-Shh  DEENTGADRL  MTQRCKDKLN  SLAISVMNHW  PGVKLRVTEG  WDEDGHHFEE

201
D-hh   SLHYEGRAVT  IATSDRDQSK  YGMLARLAVE  AGFDWVSYVS  RRHIYCSVKS
M-Dhh  SLHYEGRALD  ITTSDRDRNK  YGLLARLAVE  AGFDWVYYES  RNHIHVSVKA
M-Ihh  SLHYEGRAVD  ITTSDRDRNK  YGLLARLAVE  AGFDWVYYES  KAHVHCSVKS
M-Shh  SLHYEGRAVD  ITTSDRDRSK  YGMLARLAVE  AGFDWVYYES  KAHIHCSVKA
C-Shh  SLHYEGRAVD  ITTSDRDRSK  YGMLARLAVE  AGFDWVYYES  KAHIHCSVKA
Z-Shh  SLHYEGRAVD  ITTSDRDKSK  YGTLSRLAVE  AGFDWVYYES  KAHIHCSVKA
       ▼
       251
D-hh   DSSISSHVHG  CFTPESTALL  ESGVRKPLGE  LSIGDRVLSM  TANGQAVYSE
M-Dhh  DNSLAVRAGG  CFPGNATVRL  RSGERKGLRE  LHRGDWVLAA  DAAGRVVPTP
M-Ihh  EHSAAAKTGG  CFPAGAQVRL  ENGERVALSA  VKPGDRVLAM  GEDGTPTFSD
M-Shh  ENSVAAKSGG  CFPGSATVHL  EQGGTKLVKD  LRPGDRVLAA  DDQGRLLYSD
C-Shh  ENSVAAKSGG  CFPGSATVHL  EHGGTKLVKD  LSPGDRVLAA  DADGRLLYSD
Z-Shh  ENSVAAKSGG  CFPGSALVSL  QDGGQKAVKD  LNPGDKVLAA  DSAGNLVFSD

301
D-hh   VILFMDRNLE  QMQNFVQLHT  .DGGAVLTVT  PAHLVSVWQ.  ......PESQ
M-Dhh  VLLFLDRDLQ  RRASFVAVET  ERPPRKLLLT  PWHLVPAAR.  ...GPAPAPG
M-Ihh  VLIFLDREPN  RLRAFQVIET  QDPPRRLALT  PAHLLFIADN  HTE....PAA
M-Shh  FLTFLDRDEG  AKKVFYVIET  LEPRERLLLT  AAHLLFVAP.  HNDSGPTPGP
C-Shh  FLTFLDRMDS  SRKLFYVIET  RQPRARLLLT  AAHLLFVAPQ  HNQSEATGST
Z-Shh  FIMFTDRDST  TRRVFYVIET  QEPVEKITLT  AAHLLFVLDN  STEDLHTMT.
```

Fig. 5A-1

```
        351
D-hh    KLTFVFADRI  EEKNQVLV..  RDVETGELRP  QRVVKVG.SV  RSKGVVAPLT
M-Dhh   DFAPVFARRL  RAGDSVLA..  ..PGGDALQP  ARVARVA.RE  EAVGVFAPLT
M-Ihh   HFRATFASHV  QPGQYVLV..  ..SGVPGLQP  ARVAAVS.TH  VALGSYAPLT
M-Shh   S..ALFASRV  RPGQRVYVVA  ERGGDRRLLP  AAVHSVTLRE  EEAGAYAPLT
C-Shh   SGQALFASNV  KPGQRVYVLG  E..GGQQLLP  ASVHSVSLRE  EASGAYAPLT
Z-Shh   ...AAYASSV  RAGQKVMVVD  DSGQLKSVIV  QRIYT....E  EQRGSFAPVT

401
D-hh    REGTIVVNSV  AASCYAVINS  QSLAHWGLAP  MRLLSTLEAW  LPAKEQLHSS
M-Dhh   AHGTLLVNDV  LASCYAVLES  HQWAHRAFAP  LRLLHALGAL  LP........
M-Ihh   RHGTLVVEDV  VASCFAAVAD  HHLAQLAFWP  LRLFPSL...  ..........
M-Shh   AHGTILINRV  LASCYAVIEE  HSWAHRAFAP  FRLAHALLAA  LAPARTDGGG
C-Shh   AQGTILINRV  LASCYAVIEE  HSWAHWAFAP  FRLAQGLLAA  LCP.......
Z-Shh   AHGTIVVDRI  LASCYAVIED  QGLAHLAFAP  ARLYYYVSSF  LSP.......

451
D-hh    PKVV......  ...SSAQQQN  GIHWYANALY  KVKDYVLPQS  WRHD*
M-Dhh   ..........  ...GGAVQPT  GMHWYSRLLY  RLAEELMG*
M-Ihh   ..........  .AWGSWTPSE  GVHSYPQMLY  RLGRLLLEES  TFHPLGMSGA
M-Shh   GGSIPAAQSA  TEARGAEPTA  GIHWYSQLLY  HIGTWLLDSE  RMHPLGMAVK
C-Shh   DGAIPTA...  .....ATTTT  GIHWYSRLLY  RIGSWVLDGD  ALHPLGMVAP
Z-Shh   KTPAVGPMRL  YNRRGSTGTP  GSC......H  QMGTWLLDSN  MLHPLGMSVN

501
M-Ihh   GS*
M-Shh   SS*
C-Shh   AS*
Z-Shh   SS*
```

Fig. 5A-2

```
M-Dhh:  CGPGRGPVGRRRYVRKQLVPLLYKQFVPSMPERTLGASGPAEGRVTRGSERFRDLV
M-Ihh:  * * * * * * * * * * * * * * * * * * * * * * * * * * * * * * * ERFKELT
H-Ihh:  * * * * * * * * * * * * * * * * * * * * * * * * * * * * * * * * * * * *
H-Shh:  CGPGRGPGKRRH * * PKKLTPLAYKQFIPNVAEKTLGASGRYEGKISRNSERFKELT
C-Shh:  * * * * * * * * * * * * * * * * * * * * * * * * * * * * * * * * * * * *
M-Shh:  CGPGRGFGKRRH * * PKKLTPLAYKQFIPNVAEKTLGASGRYEGKITRNSERFKELT
Z-Shh:  CGPGRGYGRRRH * * PKKLTPLAYKQFIPNVAEKTLGASGRYEGKITRNSERFKELT
CON:    CGPGRGXXXRRXXXPKKLXPLXYKQFXPXXXEXTLGASGXXEGXXXRXSERFXXLT

M-Dhh:  PNYNPDIIFKDEENSGADRLMTERCKERVNALAIAVMNMWPGVRLRVTEGWDEDGH
M-Ihh:  PNYNPDIIFKDEENTGADRLMTQRCKDRLNSLAISVMNQWPGVKLRVTEGRDEDGH
H-Ihh:  * * * * * * * * * * * * * * * * * * * * * * * * * * * * * * * * * * * *
H-Shh:  PNYNPDIIFKDEENTGADRLMTQRCKDRLNSLAISVMNQWPGVKLRVTEGWDEDGH
C-Shh:  PNYNPDIIFKDEENTGADRLMTQRCKDKLNALAISVMNQWPGVKLRVTEGWDEDGH
M-Shh:  PNYNPDIIFKDEENTGADRLMTQRCKDKLNALAISVMNQWPGVRLRVTEGWDEDGH
Z-Shh:  PNYNPDIIFKDEENXGADRLMTXRCKXXXNXLAISVMNXWPGVXLRVTEGXDEDGH
CON:    PNYNPDIIFKDEENXGADRLMTXRCKXXXNXLAISVMNXWPGVXLRVTEGXDEDGH

M-Dhh:  HAQDSLHYEGRALDITTSDRDRNKYGLLARLAVEAGFDWVYYESRNHIHVSVKAD
M-Ihh:  HSEESLHYEGRAVDITTSDRDRNKYGLLARLAVEAGFDWVYYESKAHVHCSVKSE
H-Ihh:  HSEESLHYEGRAVDITTSDRDRNKYGLLARLAVEAGFDWVYYESKAHVHCSVKSE
H-Shh:  HSEESLHYEGRAVDITTSDRDSKYGMLARLAVEAGFDWVYYESKAHIHCSVKAE
C-Shh:  HSEESLHYEGRAVDITTSDRDSKYGMLARLAVEAGFDWVYYESKAHIHCSVKAE
M-Shh:  HSEESLHYEGRAVDITTSDRDSKYGMLARLAVEAGFDWVYYESKAHIHCSVKAE
Z-Shh:  HFEESLHYEGRAVDITTSDRDKSKYGTLSRLAVEAGFDWVYYESKAHIHCSVKAE
CON:    HXXXSLHYEGRAXDITTSDRDXXKYGXLXRLAVEAGFDWVYYESXHXHXSVKXX
```

Fig. 5B

|  | M-Dhh | M-Ihh | C-Shh | Zf-Shh | D-hh |
|---|---|---|---|---|---|
| M-Shh | 61 (77) | 63 (78) | 84 (92) | 68 (80) | 48 (64) |
| M-Dhh |  | 58 (75) | 61 (77) | 54 (71) | 51 (68) |
| M-Ihh |  |  | 64 (78) | 61 (75) | 48 (68) |
| C-Shh |  |  |  | 68 (80) | 49 (64) |
| Zf-Shh |  |  |  |  | 47 (64) |

Fig. 6

```
hh    1     MDNHSSVPWASAASVTCLSLDAKCHSSSSSSSSKSAASSISAIPQEETQT shh         ..................................................

hh    51    MRHIAHTQRCLSRLTSLVALLLIVLPMVFSPAHSCGPGRGLGRHR.ARNL
                        | |    | | |   | |||||| || |        |
shh   1     ..........MRLLTRVLLVSLLTLSLVVS.GLACGPGRGYGRRRHPKKL hh    100   YPLVLKQTIPNLSEYTNSASGPLEGVIRRDSPKFKDLVPNYNRDILFRDE
             ||  || |||  | |   |||   ||  | |   ||  ||||  || | ||
shh   40    TPLAYKQFIPNVAEKTLGASGRYEGKITRNSERFKELTPNYNPDIIFKDE hh    150   EGTGADRLMSKRCKEKLNVLAYSVMNEWPGIRLVVTESWDEDYHHGQESL
            |  ||||||||  |||  ||| || |||| ||  | | |||| ||    |||
shh   90    ENTGADRLMTQRCKDKLNSLAISVMNHWPGVKLRVTEGWDEDGHHFEESL hh    200   HYEGRAVTIATSDRDQSKYGMLARLAVEAGFDWVSYVSRRHIYCSVKSDS
            |||||||  |  |||||| ||||    |||||||||||||| | |  ||  ||||
shh   140   HYEGRAVDITTSDRDKSKYGTLSRLAVEAGFDWVYYESKAHIHCSVKAEN hh    250   SISSHVHGCFTPESTALLESGVRKPLGELSIGDRVLSMTANGQAVYSEVI
              |        |||          |    |     |   ||  ||      |  |  |
shh   190   SVAAKSGGCFPGSALVSLQDGGQKAVKDLNPGDKVLAADSAGNLVFSDFI hh    300   LFMDRNLEQMQNFVQLHT.DGGAVLTVPAHLVSVWQPESQKL...TFVF
             | ||      |     |        | |||    |                |    |
shh   240   MFTDRDSTTRRVFYVIETQEPVEKITLTAAHLLFVLDNSTEDLHTMTAAY hh    347   ADRIEEKNQVLVRDVETGELRPQRVVKVGSVRSKGVVAPLTREGTIVVNS
            |         | | |          | |              || |    |||||
shh   290   ASSVRAGQKVMVVD.DSGQLKSVIVQRIYTEEQRGSFAPVTAHGTIVVDR hh    397   VAASCYAVINSQSLAHWGLAPMRLLSTLEAWLPAKEQL.........HSS
             ||||||| |  |||    || ||        | |                      |
shh   339   ILASCYAVIEDQGLAHLAFAPARLYYYVSSFLSPKTPAVGPMRLYNRRGS hh    438   PKVVSSAQQQNGIHWYANALYKVKDYVLPQSWRHD 471
             | |         | |     | |
shh   389   TGTPGSCHQMGTWLLDSNMLHPLGMSV........ 415
```

Fig. 9A

```
            61              250        383 413    471
hh  [        ░░              |          |   |      ]
       1           190           326    356  415
shh [  ░░ 75  |        49     | 83 | 45 ]
```

Fig. 9B

| | |
|---|---|
| hh | KRCKEKLNVLAYSVMNEWPGIRLVVTESWDEDYHHGQESLHYEGRAVTIATSDRDQSKYGMLAR |
| shh | QRCKDKLNSLAISVMNHWPGVKLRVTEGWDEDGNHFEESLHYEGRAVDITTSDRDKSKYGTLSR |
| hh[a] | QRCKEKLNSLAISVMNMWPGVKLRVTEGWDEDGNHFEDSLHYEGRAVDITTSDRDRNKYGMFAR |
| hh[b] | QRCKDKLNSLAISVMNLWPGVKLRVTEGWDEDGLHSEESLHYEGRAVDITTSDRDRNKYRMLAR |

Fig. 10

SEQUENCE LISTING (1) GENERAL INFORMATION:

(iii) NUMBER OF SEQUENCES: 48

(2) INFORMATION FOR SEQ ID NO:1:

(i) SEQUENCE CHARACTERISTICS:
      (A) LENGTH: 1277 base pairs
      (B) TYPE: nucleic acid
      (C) STRANDEDNESS: both
      (D) TOPOLOGY: linear (ii) MOLECULE TYPE: cDNA (ix) FEATURE:
      (A) NAME/KEY: CDS
      (B) LOCATION: 1..1275

(xi) SEQUENCE DESCRIPTION: SEQ ID NO:1:

```
ATG GTC GAA ATG CTG CTG TTG ACA AGA ATT CTC TTG GTG GGC TTC ATC        48
Met Val Glu Met Leu Leu Leu Thr Arg Ile Leu Leu Val Gly Phe Ile
 1               5                  10                  15

TGC GCT CTT TTA GTC TCC TCT GGG CTG ACT TGT GGA CCA GGC AGG GGC        96
Cys Ala Leu Leu Val Ser Ser Gly Leu Thr Cys Gly Pro Gly Arg Gly
                20                  25                  30

ATT GGA AAA AGG AGG CAC CCC AAA AAG CTG ACC CCG TTA GCC TAT AAG       144
Ile Gly Lys Arg Arg His Pro Lys Lys Leu Thr Pro Leu Ala Tyr Lys
            35                  40                  45

CAG TTT ATT CCC AAT GTG GCA GAG AAG ACC CTA GGG GCC AGT GGA AGA       192
Gln Phe Ile Pro Asn Val Ala Glu Lys Thr Leu Gly Ala Ser Gly Arg
        50                  55                  60

TAT GAA GGG AAG ATC ACA AGA AAC TCC GAG AGA TTT AAA GAA CTA ACC       240
Tyr Glu Gly Lys Ile Thr Arg Asn Ser Glu Arg Phe Lys Glu Leu Thr
 65                  70                  75                  80

CCA AAT TAC AAC CCT GAC ATT ATT TTT AAG GAT GAA GAG AAC ACG GGA       288
Pro Asn Tyr Asn Pro Asp Ile Ile Phe Lys Asp Glu Glu Asn Thr Gly
                85                  90                  95

GCT GAC AGA CTG ATG ACT CAG CGC TGC AAG GAC AAG CTG AAT GCC CTG       336
Ala Asp Arg Leu Met Thr Gln Arg Cys Lys Asp Lys Leu Asn Ala Leu
            100                 105                 110

GCG ATC TCG GTG ATG AAC CAG TGG CCC GGG GTG AAG CTG CGG GTG ACC       384
Ala Ile Ser Val Met Asn Gln Trp Pro Gly Val Lys Leu Arg Val Thr
        115                 120                 125

GAG GGC TGG GAC GAG GAT GGC CAT CAC TCC GAG GAA TCG CTG CAC TAC       432
Glu Gly Trp Asp Glu Asp Gly His His Ser Glu Glu Ser Leu His Tyr
    130                 135                 140

GAG GGT CGC GCC GTG GAC ATC ACC ACG TCG GAT CGG GAC CGC AGC AAG       480
Glu Gly Arg Ala Val Asp Ile Thr Thr Ser Asp Arg Asp Arg Ser Lys
145                 150                 155                 160

TAC GGA ATG CTG GCC CGC CTC GCC GTC GAG GCC GGC TTC GAC TGG GTC       528
Tyr Gly Met Leu Ala Arg Leu Ala Val Glu Ala Gly Phe Asp Trp Val
                165                 170                 175
```

```
TAC TAC GAG TCC AAG GCG CAC ATC CAC TGC TCC GTC AAA GCA GAA AAC        576
Tyr Tyr Glu Ser Lys Ala His Ile His Cys Ser Val Lys Ala Glu Asn
            180                 185                 190

TCA GTG GCA GCG AAA TCA GGA GGC TGC TTC CCT GGC TCA GCC ACA GTG        624
Ser Val Ala Ala Lys Ser Gly Gly Cys Phe Pro Gly Ser Ala Thr Val
        195                 200                 205

CAC CTG GAG CAT GGA GGC ACC AAG CTG GTG AAG GAC CTG AGC CCT GGG        672
His Leu Glu His Gly Gly Thr Lys Leu Val Lys Asp Leu Ser Pro Gly
    210                 215                 220

GAC CGC GTG CTG GCT GCT GAC GCG GAC GGC CGG CTG CTC TAC AGT GAC        720
Asp Arg Val Leu Ala Ala Asp Ala Asp Gly Arg Leu Leu Tyr Ser Asp
225                 230                 235                 240

TTC CTC ACC TTC CTC GAC CGG ATG GAC AGC TCC CGA AAG CTC TTC TAC        768
Phe Leu Thr Phe Leu Asp Arg Met Asp Ser Ser Arg Lys Leu Phe Tyr
                245                 250                 255

GTC ATC GAG ACG CGG CAG CCC CGG GCC CGG CTA CTG ACG GCG GCC            816
Val Ile Glu Thr Arg Gln Pro Arg Ala Arg Leu Leu Leu Thr Ala Ala
            260                 265                 270

CAC CTG CTC TTT GTG GCC CCC CAG CAC AAC CAG TCG GAG GCC ACA GGG        864
His Leu Leu Phe Val Ala Pro Gln His Asn Gln Ser Glu Ala Thr Gly
        275                 280                 285

TCC ACC AGT GGC CAG GCG CTC TTC GCC AGC AAC GTG AAG CCT GGC CAA        912
Ser Thr Ser Gly Gln Ala Leu Phe Ala Ser Asn Val Lys Pro Gly Gln
    290                 295                 300

CGT GTC TAT GTG CTG GGC GAG GGC GGG CAG CAG CTG CTG CCG GCG TCT        960
Arg Val Tyr Val Leu Gly Glu Gly Gly Gln Gln Leu Leu Pro Ala Ser
305                 310                 315                 320

GTC CAC AGC GTC TCA TTG CGG GAG GAG GCG TCC GGA GCC TAC GCC CCA       1008
Val His Ser Val Ser Leu Arg Glu Glu Ala Ser Gly Ala Tyr Ala Pro
                325                 330                 335

CTC ACC GCC CAG GGC ACC ATC CTC ATC AAC CGG GTG TTG GCC TCC TGC       1056
Leu Thr Ala Gln Gly Thr Ile Leu Ile Asn Arg Val Leu Ala Ser Cys
            340                 345                 350

TAC GCC GTC ATC GAG GAG CAC AGT TGG GCC CAT TGG GCC TTC GCA CCA       1104
Tyr Ala Val Ile Glu Glu His Ser Trp Ala His Trp Ala Phe Ala Pro
        355                 360                 365

TTC CGC TTG GCT CAG GGG CTG CTG GCC GCC CTC TGC CCA GAT GGG GCC       1152
Phe Arg Leu Ala Gln Gly Leu Leu Ala Ala Leu Cys Pro Asp Gly Ala
    370                 375                 380

ATC CCT ACT GCC GCC ACC ACC ACC ACT GGC ATC CAT TGG TAC TCA CGG       1200
Ile Pro Thr Ala Ala Thr Thr Thr Thr Gly Ile His Trp Tyr Ser Arg
385                 390                 395                 400

CTC CTC TAC CGC ATC GGC AGC TGG GTG CTG GAT GGT GAC GCG CTG CAT       1248
Leu Leu Tyr Arg Ile Gly Ser Trp Val Leu Asp Gly Asp Ala Leu His
                405                 410                 415

CCG CTG GGC ATG GTG GCA CCG GCC AGC TG                                1277
Pro Leu Gly Met Val Ala Pro Ala Ser
            420                 425

(2) INFORMATION FOR SEQ ID NO:2:

(i) SEQUENCE CHARACTERISTICS:
        (A) LENGTH: 1190 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..1188
```

(xi) SEQUENCE DESCRIPTION: SEQ ID NO:2:

| | | | | | | | | | | | | | | | | |
|---|---|---|---|---|---|---|---|---|---|---|---|---|---|---|---|---|
| ATG | GCT | CTG | CCG | GCC | AGT | CTG | TTG | CCC | CTG | TGC | TGC | TTG | GCA | CTC | TTG | 48 |
| Met | Ala | Leu | Pro | Ala | Ser | Leu | Leu | Pro | Leu | Cys | Cys | Leu | Ala | Leu | Leu | |
| 1 | | | | 5 | | | | | 10 | | | | | 15 | | |
| GCA | CTA | TCT | GCC | CAG | AGC | TGC | GGG | CCG | GGC | CGA | GGA | CCG | GTT | GGC | CGG | 96 |
| Ala | Leu | Ser | Ala | Gln | Ser | Cys | Gly | Pro | Gly | Arg | Gly | Pro | Val | Gly | Arg | |
| | | | | 20 | | | | 25 | | | | | 30 | | | |
| CGG | CGT | TAT | GTG | CGC | AAG | CAA | CTT | GTG | CCT | CTG | CTA | TAC | AAG | CAG | TTT | 144 |
| Arg | Arg | Tyr | Val | Arg | Lys | Gln | Leu | Val | Pro | Leu | Leu | Tyr | Lys | Gln | Phe | |
| | | 35 | | | | | 40 | | | | | 45 | | | | |
| GTG | CCC | AGT | ATG | CCC | GAG | CGG | ACC | CTG | GGC | GCG | AGT | GGG | CCA | GCG | GAG | 192 |
| Val | Pro | Ser | Met | Pro | Glu | Arg | Thr | Leu | Gly | Ala | Ser | Gly | Pro | Ala | Glu | |
| | 50 | | | | | 55 | | | | | 60 | | | | | |
| GGG | AGG | GTA | ACA | AGG | GGG | TCG | GAG | CGC | TTC | CGG | GAC | CTC | GTA | CCC | AAC | 240 |
| Gly | Arg | Val | Thr | Arg | Gly | Ser | Glu | Arg | Phe | Arg | Asp | Leu | Val | Pro | Asn | |
| 65 | | | | | 70 | | | | | 75 | | | | | 80 | |
| TAC | AAC | CCC | GAC | ATA | ATC | TTC | AAG | GAT | GAG | GAG | AAC | AGC | GGC | GCA | GAC | 288 |
| Tyr | Asn | Pro | Asp | Ile | Ile | Phe | Lys | Asp | Glu | Glu | Asn | Ser | Gly | Ala | Asp | |
| | | | | 85 | | | | | 90 | | | | | 95 | | |
| CGC | CTG | ATG | ACA | GAG | CGT | TGC | AAA | GAG | CGG | GTG | AAC | GCT | CTA | GCC | ATC | 336 |
| Arg | Leu | Met | Thr | Glu | Arg | Cys | Lys | Glu | Arg | Val | Asn | Ala | Leu | Ala | Ile | |
| | | | 100 | | | | | 105 | | | | | 110 | | | |
| GCG | GTG | ATG | AAC | ATG | TGG | CCC | GGA | GTA | CGC | CTA | CGT | GTG | ACT | GAA | GGC | 384 |
| Ala | Val | Met | Asn | Met | Trp | Pro | Gly | Val | Arg | Leu | Arg | Val | Thr | Glu | Gly | |
| | | 115 | | | | | 120 | | | | | 125 | | | | |
| TGG | GAC | GAG | GAC | GGC | CAC | CAC | GCA | CAG | GAT | TCA | CTC | CAC | TAC | GAA | GGC | 432 |
| Trp | Asp | Glu | Asp | Gly | His | His | Ala | Gln | Asp | Ser | Leu | His | Tyr | Glu | Gly | |
| | 130 | | | | | 135 | | | | | 140 | | | | | |
| CGT | GCC | TTG | GAC | ATC | ACC | ACG | TCT | GAC | CGT | GAC | CGT | AAT | AAG | TAT | GGT | 480 |
| Arg | Ala | Leu | Asp | Ile | Thr | Thr | Ser | Asp | Arg | Asp | Arg | Asn | Lys | Tyr | Gly | |
| 145 | | | | | 150 | | | | | 155 | | | | | 160 | |
| TTG | TTG | GCG | CGC | CTA | GCT | GTG | GAA | GCC | GGA | TTC | GAC | TGG | GTC | TAC | TAC | 528 |
| Leu | Leu | Ala | Arg | Leu | Ala | Val | Glu | Ala | Gly | Phe | Asp | Trp | Val | Tyr | Tyr | |
| | | | | 165 | | | | | 170 | | | | | 175 | | |
| GAG | TCC | CGC | AAC | CAC | ATC | CAC | GTA | TCG | GTC | AAA | GCT | GAT | AAC | TCA | CTG | 576 |
| Glu | Ser | Arg | Asn | His | Ile | His | Val | Ser | Val | Lys | Ala | Asp | Asn | Ser | Leu | |
| | | | 180 | | | | | 185 | | | | | 190 | | | |
| GCG | GTC | CGA | GCC | GGA | GGC | TGC | TTT | CCG | GGA | AAT | GCC | ACG | GTG | CGC | TTG | 624 |
| Ala | Val | Arg | Ala | Gly | Gly | Cys | Phe | Pro | Gly | Asn | Ala | Thr | Val | Arg | Leu | |
| | | 195 | | | | | 200 | | | | | 205 | | | | |
| CGG | AGC | GGC | GAA | CGG | AAG | GGG | CTG | AGG | GAA | CTA | CAT | CGT | GGT | GAC | TGG | 672 |
| Arg | Ser | Gly | Glu | Arg | Lys | Gly | Leu | Arg | Glu | Leu | His | Arg | Gly | Asp | Trp | |
| | 210 | | | | | 215 | | | | | 220 | | | | | |
| GTA | CTG | GCC | GCT | GAT | GCA | GCG | GGC | CGA | GTG | GTA | CCC | ACG | CCA | GTG | CTG | 720 |
| Val | Leu | Ala | Ala | Asp | Ala | Ala | Gly | Arg | Val | Val | Pro | Thr | Pro | Val | Leu | |
| 225 | | | | | 230 | | | | | 235 | | | | | 240 | |
| CTC | TTC | CTG | GAC | CGG | GAT | CTG | CAG | CGC | CGC | GCC | TCG | TTC | GTG | GCT | GTG | 768 |
| Leu | Phe | Leu | Asp | Arg | Asp | Leu | Gln | Arg | Arg | Ala | Ser | Phe | Val | Ala | Val | |
| | | | | 245 | | | | | 250 | | | | | 255 | | |
| GAG | ACC | GAG | CGG | CCT | CCG | CGC | AAA | CTG | TTG | CTC | ACA | CCC | TGG | CAT | CTG | 816 |
| Glu | Thr | Glu | Arg | Pro | Pro | Arg | Lys | Leu | Leu | Leu | Thr | Pro | Trp | His | Leu | |
| | | | 260 | | | | | 265 | | | | | 270 | | | |
| GTG | TTC | GCT | GCT | CGC | GGG | CCA | GCG | CCT | GCT | CCA | GGT | GAC | TTT | GCA | CCG | 864 |
| Val | Phe | Ala | Ala | Arg | Gly | Pro | Ala | Pro | Ala | Pro | Gly | Asp | Phe | Ala | Pro | |
| | | 275 | | | | | 280 | | | | | 285 | | | | |
| GTG | TTC | GCG | CGC | CGC | TTA | CGT | GCT | GGC | GAC | TCG | GTG | CTG | GCT | CCC | GGC | 912 |
| Val | Phe | Ala | Arg | Arg | Leu | Arg | Ala | Gly | Asp | Ser | Val | Leu | Ala | Pro | Gly | |
| | 290 | | | | | 295 | | | | | 300 | | | | | |
| GGG | GAC | GCG | CTC | CAG | CCG | GCG | CGC | GTA | GCC | CGC | GTG | GCG | CGC | GAG | GAA | 960 |

```
Gly Asp Ala Leu Gln Pro Ala Arg Val Ala Arg Val Ala Arg Glu Glu
305                 310                 315                 320

GCC GTG GGC GTG TTC GCA CCG CTC ACT GCG CAC GGG ACG CTG CTG GTC      1008
Ala Val Gly Val Phe Ala Pro Leu Thr Ala His Gly Thr Leu Leu Val
                325                 330                 335

AAC GAC GTC CTC GCC TCC TGC TAC GCG GTT CTA GAG AGT CAC CAG TGG      1056
Asn Asp Val Leu Ala Ser Cys Tyr Ala Val Leu Glu Ser His Gln Trp
            340                 345                 350

GCC CAC CGC GCC TTC GCC CCT TTG CGG CTG CTG CAC GCG CTC GGG GCT      1104
Ala His Arg Ala Phe Ala Pro Leu Arg Leu Leu His Ala Leu Gly Ala
        355                 360                 365

CTG CTC CCT GGG GGT GCA GTC CAG CCG ACT GGC ATG CAT TGG TAC TCT      1152
Leu Leu Pro Gly Gly Ala Val Gln Pro Thr Gly Met His Trp Tyr Ser
370                 375                 380

CGC CTC CTT TAC CGC TTG GCC GAG GAG TTA ATG GGC TG                    1190
Arg Leu Leu Tyr Arg Leu Ala Glu Glu Leu Met Gly
385                 390                 395

(2) INFORMATION FOR SEQ ID NO:3:

(i) SEQUENCE CHARACTERISTICS:
        (A) LENGTH: 1281 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..1233

(xi) SEQUENCE DESCRIPTION: SEQ ID NO:3:

ATG TCT CCC GCC TGG CTC CGG CCC CGA CTG CGG TTC TGT CTG TTC CTG       48
Met Ser Pro Ala Trp Leu Arg Pro Arg Leu Arg Phe Cys Leu Phe Leu
1                 5                   10                  15

CTG CTG CTG CTT CTG GTG CCG GCG GCG CGG GGC TGC GGG CCG GGC CGG       96
Leu Leu Leu Leu Leu Val Pro Ala Ala Arg Gly Cys Gly Pro Gly Arg
                20                  25                  30

GTG GTG GGC AGC CGC CGG AGG CCG CCT CGC AAG CTC GTG CCT CTT GCC      144
Val Val Gly Ser Arg Arg Arg Pro Pro Arg Lys Leu Val Pro Leu Ala
            35                  40                  45

TAC AAG CAG TTC AGC CCC AAC GTG CCG GAG AAG ACC CTG GGC GCC AGC      192
Tyr Lys Gln Phe Ser Pro Asn Val Pro Glu Lys Thr Leu Gly Ala Ser
        50                  55                  60

GGG CGC TAC GAA GGC AAG ATC GCG CGC AGC TCT GAG CGC TTC AAA GAG      240
Gly Arg Tyr Glu Gly Lys Ile Ala Arg Ser Ser Glu Arg Phe Lys Glu
65                  70                  75                  80

CTC ACC CCC AAC TAC AAT CCC GAC ATC ATC TTC AAG GAC GAG GAG AAC      288
Leu Thr Pro Asn Tyr Asn Pro Asp Ile Ile Phe Lys Asp Glu Glu Asn
                85                  90                  95

ACG GGT GCC GAC CGC CTC ATG ACC CAG CGC TGC AAG GAC CGT CTG AAC      336
Thr Gly Ala Asp Arg Leu Met Thr Gln Arg Cys Lys Asp Arg Leu Asn
            100                 105                 110

TCA CTG GCC ATC TCT GTC ATG AAC CAG TGG CCT GGT GTG AAA CTG CGG      384
Ser Leu Ala Ile Ser Val Met Asn Gln Trp Pro Gly Val Lys Leu Arg
        115                 120                 125

GTG ACC GAA GGC TGG GAT GAA GAT GGC CAT CAC TCA GAG GAG TCT TTA      432
Val Thr Glu Gly Trp Asp Glu Asp Gly His His Ser Glu Glu Ser Leu
130                 135                 140

CAC TAT GAG GGC CGC GCG GTG GAT ATC ACC ACC TCA GAC CGT GAC CGA      480
His Tyr Glu Gly Arg Ala Val Asp Ile Thr Thr Ser Asp Arg Asp Arg
                150                 155                 160
```

```
AAT AAG TAT GGA CTG CTG GCG CGC TTA GCA GTG GAG GCC GGC TTC GAC         528
Asn Lys Tyr Gly Leu Leu Ala Arg Leu Ala Val Glu Ala Gly Phe Asp
            165                 170                 175

TGG GTG TAT TAC GAG TCC AAG GCC CAC GTG CAT TGC TCT GTC AAG TCT         576
Trp Val Tyr Tyr Glu Ser Lys Ala His Val His Cys Ser Val Lys Ser
            180                 185                 190

GAG CAT TCG GCC GCT GCC AAG ACA GGT GGC TGC TTT CCT GCC GGA GCC         624
Glu His Ser Ala Ala Ala Lys Thr Gly Gly Cys Phe Pro Ala Gly Ala
            195                 200                 205

CAG GTG CGC CTA GAG AAC GGG GAG CGT GTG GCC CTG TCA GCT GTA AAG         672
Gln Val Arg Leu Glu Asn Gly Glu Arg Val Ala Leu Ser Ala Val Lys
            210                 215                 220

CCA GGA GAC CGG GTG CTG GCC ATG GGG GAG GAT GGG ACC CCC ACC TTC         720
Pro Gly Asp Arg Val Leu Ala Met Gly Glu Asp Gly Thr Pro Thr Phe
225                 230                 235                 240

AGT GAT GTG CTT ATT TTC CTG GAC CGC GAG CCA AAC CGG CTG AGA GCT         768
Ser Asp Val Leu Ile Phe Leu Asp Arg Glu Pro Asn Arg Leu Arg Ala
            245                 250                 255

TTC CAG GTC ATC GAG ACT CAG GAT CCT CCG CGT CGG CTG GCG CTC ACG         816
Phe Gln Val Ile Glu Thr Gln Asp Pro Pro Arg Arg Leu Ala Leu Thr
            260                 265                 270

CCT GCC CAC CTG CTC TTC ATT GCG GAC AAT CAT ACA GAA CCA GCA GCC         864
Pro Ala His Leu Leu Phe Ile Ala Asp Asn His Thr Glu Pro Ala Ala
            275                 280                 285

CAC TTC CGG GCC ACA TTT GCC AGC CAT GTG CAA CCA GGC CAA TAT GTG         912
His Phe Arg Ala Thr Phe Ala Ser His Val Gln Pro Gly Gln Tyr Val
            290                 295                 300

CTG GTA TCA GGG GTA CCA GGC CTC CAG CCT GCT CGG GTG GCA GCT GTC         960
Leu Val Ser Gly Val Pro Gly Leu Gln Pro Ala Arg Val Ala Ala Val
305                 310                 315                 320

TCC ACC CAC GTG GCC CTT GGG TCC TAT GCT CCT CTC ACA AGG CAT GGG        1008
Ser Thr His Val Ala Leu Gly Ser Tyr Ala Pro Leu Thr Arg His Gly
            325                 330                 335

ACA CTT GTG GTG GAG GAT GTG GTG GCC TCC TGC TTT GCA GCT GTG GCT        1056
Thr Leu Val Val Glu Asp Val Val Ala Ser Cys Phe Ala Ala Val Ala
            340                 345                 350

GAC CAC CAT CTG GCT CAG TTG GCC TTC TGG CCC CTG CGA CTG TTT CCC        1104
Asp His His Leu Ala Gln Leu Ala Phe Trp Pro Leu Arg Leu Phe Pro
            355                 360                 365

AGT TTG GCA TGG GGC AGC TGG ACC CCA AGT GAG GGT GTT CAC TCC TAC        1152
Ser Leu Ala Trp Gly Ser Trp Thr Pro Ser Glu Gly Val His Ser Tyr
370                 375                 380

CCT CAG ATG CTC TAC CGC CTG GGG CGT CTC TTG CTA GAA GAG AGC ACC        1200
Pro Gln Met Leu Tyr Arg Leu Gly Arg Leu Leu Leu Glu Glu Ser Thr
385                 390                 395                 400

TTC CAT CCA CTG GGC ATG TCT GGG GCA GGA AGC TGAAGGGACT CTAACCACTG      1253
Phe His Pro Leu Gly Met Ser Gly Ala Gly Ser
            405                 410

CCCTCCTGGA ACTGCTGTGC GTGGATCC                                         1281

(2) INFORMATION FOR SEQ ID NO:4:

(i) SEQUENCE CHARACTERISTICS:
        (A) LENGTH: 1313 base pairs
        (B) TYPE: nucleic acid
        (C) STRANDEDNESS: both
        (D) TOPOLOGY: linear (ii) MOLECULE TYPE: cDNA (ix) FEATURE:
```

```
          (A) NAME/KEY: CDS
          (B) LOCATION: 1..1311

(xi) SEQUENCE DESCRIPTION: SEQ ID NO:4:

ATG CTG CTG CTG CTG GCC AGA TGT TTT CTG GTG ATC CTT GCT TCC TCG      48
Met Leu Leu Leu Leu Ala Arg Cys Phe Leu Val Ile Leu Ala Ser Ser
 1               5                  10                  15

CTG CTG GTG TGC CCC GGG CTG GCC TGT GGG CCC GGC AGG GGG TTT GGA      96
Leu Leu Val Cys Pro Gly Leu Ala Cys Gly Pro Gly Arg Gly Phe Gly
             20                  25                  30

AAG AGG CGG CAC CCC AAA AAG CTG ACC CCT TTA GCC TAC AAG CAG TTT     144
Lys Arg Arg His Pro Lys Lys Leu Thr Pro Leu Ala Tyr Lys Gln Phe
         35                  40                  45

ATT CCC AAC GTA GCC GAG AAG ACC CTA GGG GCC AGC GGC AGA TAT GAA     192
Ile Pro Asn Val Ala Glu Lys Thr Leu Gly Ala Ser Gly Arg Tyr Glu
     50                  55                  60

GGG AAG ATC ACA AGA AAC TCC GAA CGA TTT AAG GAA CTC ACC CCC AAT     240
Gly Lys Ile Thr Arg Asn Ser Glu Arg Phe Lys Glu Leu Thr Pro Asn
 65                  70                  75                  80

TAC AAC CCC GAC ATC ATA TTT AAG GAT GAG GAA AAC ACG GGA GCA GAC     288
Tyr Asn Pro Asp Ile Ile Phe Lys Asp Glu Glu Asn Thr Gly Ala Asp
                 85                  90                  95

CGG CTG ATG ACT CAG AGG TGC AAA GAC AAG TTA AAT GCC TTG GCC ATC     336
Arg Leu Met Thr Gln Arg Cys Lys Asp Lys Leu Asn Ala Leu Ala Ile
            100                 105                 110

TCT GTG ATG AAC CAG TGG CCT GGA GTG AGG CTG CGA GTG ACC GAG GGC     384
Ser Val Met Asn Gln Trp Pro Gly Val Arg Leu Arg Val Thr Glu Gly
        115                 120                 125

TGG GAT GAG GAC GGC CAT CAT TCA GAG GAG TCT CTA CAC TAT GAG GGT     432
Trp Asp Glu Asp Gly His His Ser Glu Glu Ser Leu His Tyr Glu Gly
130                 135                 140

CGA GCA GTG GAC ATC ACC ACG TCC GAC CGG GAC CGC AGC AAG TAC GGC     480
Arg Ala Val Asp Ile Thr Thr Ser Asp Arg Asp Arg Ser Lys Tyr Gly
145                 150                 155                 160

ATG CTG GCT CGC CTG GCT GTG GAA GCA GGT TTC GAC TGG GTC TAC TAT     528
Met Leu Ala Arg Leu Ala Val Glu Ala Gly Phe Asp Trp Val Tyr Tyr
                165                 170                 175

GAA TCC AAA GCT CAC ATC CAC TGT TCT GTG AAA GCA GAG AAC TCC GTG     576
Glu Ser Lys Ala His Ile His Cys Ser Val Lys Ala Glu Asn Ser Val
            180                 185                 190

GCG GCC AAA TCC GGC GGC TGT TTC CCG GGA TCC GCC ACC GTG CAC CTG     624
Ala Ala Lys Ser Gly Gly Cys Phe Pro Gly Ser Ala Thr Val His Leu
        195                 200                 205

GAG CAG GGC GGC ACC AAG CTG GTG AAG GAC TTA CGT CCC GGA GAC CGC     672
Glu Gln Gly Gly Thr Lys Leu Val Lys Asp Leu Arg Pro Gly Asp Arg
    210                 215                 220

GTG CTG GCG GCT GAC GAC CAG GGC CGG CTG CTG TAC AGC GAC TTC CTC     720
Val Leu Ala Ala Asp Asp Gln Gly Arg Leu Leu Tyr Ser Asp Phe Leu
225                 230                 235                 240

ACC TTC CTG GAC CGC GAC GAA GGC GCC AAG AAG GTC TTC TAC GTG ATC     768
Thr Phe Leu Asp Arg Asp Glu Gly Ala Lys Lys Val Phe Tyr Val Ile
                245                 250                 255

GAG ACG CTG GAG CCG CGC GAG CGC CTG CTG CTC ACC GCC GCG CAC CTG     816
Glu Thr Leu Glu Pro Arg Glu Arg Leu Leu Leu Thr Ala Ala His Leu
            260                 265                 270

CTC TTC GTG GCG CCG CAC AAC GAC TCG GGG CCC ACG CCC GGG CCA AGC     864
Leu Phe Val Ala Pro His Asn Asp Ser Gly Pro Thr Pro Gly Pro Ser
        275                 280                 285

GCG CTC TTT GCC AGC CGC GTG CGC CCC GGG CAG CGC GTG TAC GTG GTG     912
Ala Leu Phe Ala Ser Arg Val Arg Pro Gly Gln Arg Val Tyr Val Val
```

```
                  290                 295                 300
GCT GAA CGC GGC GGG GAC CGC CGG CTG CTG CCC GCC GCG GTG CAC AGC        960
Ala Glu Arg Gly Gly Asp Arg Arg Leu Leu Pro Ala Ala Val His Ser
305                 310                 315                 320

GTG ACG CTG CGA GAG GAG GAG GCG GGC GCG TAC GCG CCG CTC ACG GCG       1008
Val Thr Leu Arg Glu Glu Glu Ala Gly Ala Tyr Ala Pro Leu Thr Ala
                325                 330                 335

CAC GGC ACC ATT CTC ATC AAC CGG GTG CTC GCC TCG TGC TAC GCT GTC       1056
His Gly Thr Ile Leu Ile Asn Arg Val Leu Ala Ser Cys Tyr Ala Val
                340                 345                 350

ATC GAG GAG CAC AGC TGG GCA CAC CGG GCC TTC GCG CCT TTC CGC CTG       1104
Ile Glu Glu His Ser Trp Ala His Arg Ala Phe Ala Pro Phe Arg Leu
                355                 360                 365

GCG CAC GCG CTG CTG GCC GCG CTG GCA CCC GCC CGC ACG GAC GGC GGG       1152
Ala His Ala Leu Leu Ala Ala Leu Ala Pro Ala Arg Thr Asp Gly Gly
370                 375                 380

GGC GGG GGC AGC ATC CCT GCA GCG CAA TCT GCA ACG GAA GCG AGG GGC       1200
Gly Gly Gly Ser Ile Pro Ala Ala Gln Ser Ala Thr Glu Ala Arg Gly
385                 390                 395                 400

GCG GAG CCG ACT GCG GGC ATC CAC TGG TAC TCG CAG CTG CTC TAC CAC       1248
Ala Glu Pro Thr Ala Gly Ile His Trp Tyr Ser Gln Leu Leu Tyr His
                405                 410                 415

ATT GGC ACC TGG CTG TTG GAC AGC GAG ACC ATG CAT CCC TTG GGA ATG       1296
Ile Gly Thr Trp Leu Leu Asp Ser Glu Thr Met His Pro Leu Gly Met
                420                 425                 430

GCG GTC AAG TCC AGC TG                                                1313
Ala Val Lys Ser Ser
                435

(2) INFORMATION FOR SEQ ID NO:5:

(i) SEQUENCE CHARACTERISTICS:
        (A) LENGTH: 1256 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..1254

(xi) SEQUENCE DESCRIPTION: SEQ ID NO:5:

ATG CGG CTT TTG ACG AGA GTG CTG CTG GTG TCT CTT CTC ACT CTG TCC         48
Met Arg Leu Leu Thr Arg Val Leu Leu Val Ser Leu Leu Thr Leu Ser
1               5                   10                  15

TTG GTG GTG TCC GGA CTG GCC TGC GGT CCT GGC AGA GGC TAC GGC AGA         96
Leu Val Val Ser Gly Leu Ala Cys Gly Pro Gly Arg Gly Tyr Gly Arg
                20                  25                  30

AGA AGA CAT CCG AAG AAG CTG ACA CCT CTC GCC TAC AAG CAG TTC ATA        144
Arg Arg His Pro Lys Lys Leu Thr Pro Leu Ala Tyr Lys Gln Phe Ile
                35                  40                  45

CCT AAT GTC GCG GAG AAG ACC TTA GGG GCC AGC GGC AGA TAC GAG GGC        192
Pro Asn Val Ala Glu Lys Thr Leu Gly Ala Ser Gly Arg Tyr Glu Gly
50                  55                  60

AAG ATA ACG CGC AAT TCG GAG AGA TTT AAA GAA CTT ACT CCA AAT TAC        240
Lys Ile Thr Arg Asn Ser Glu Arg Phe Lys Glu Leu Thr Pro Asn Tyr
65                  70                  75                  80

AAT CCC GAC ATT ATC TTT AAG GAT GAG GAG AAC ACG GGA GCG GAC AGG        288
Asn Pro Asp Ile Ile Phe Lys Asp Glu Glu Asn Thr Gly Ala Asp Arg
                85                  90                  95
```

```
CTC ATG ACA CAG AGA TGC AAA GAC AAG CTG AAC TCG CTG GCC ATC TCT         336
Leu Met Thr Gln Arg Cys Lys Asp Lys Leu Asn Ser Leu Ala Ile Ser
            100                 105                 110

GTA ATG AAC CAC TGG CCA GGG GTT AAG CTG CGT GTG ACA GAG GGC TGG         384
Val Met Asn His Trp Pro Gly Val Lys Leu Arg Val Thr Glu Gly Trp
        115                 120                 125

GAT GAG GAC GGT CAC CAT TTT GAA GAA TCA CTC CAC TAC GAG GGA AGA         432
Asp Glu Asp Gly His His Phe Glu Glu Ser Leu His Tyr Glu Gly Arg
    130                 135                 140

GCT GTT GAT ATT ACC ACC TCT GAC CGA GAC AAG AGC AAA TAC GGG ACA         480
Ala Val Asp Ile Thr Thr Ser Asp Arg Asp Lys Ser Lys Tyr Gly Thr
145                 150                 155                 160

CTG TCT CGC CTA GCT GTG GAG GCT GGA TTT GAC TGG GTC TAT TAC GAG         528
Leu Ser Arg Leu Ala Val Glu Ala Gly Phe Asp Trp Val Tyr Tyr Glu
                165                 170                 175

TCC AAA GCC CAC ATT CAT TGC TCT GTC AAA GCA GAA AAT TCG GTT GCT         576
Ser Lys Ala His Ile His Cys Ser Val Lys Ala Glu Asn Ser Val Ala
            180                 185                 190

GCG AAA TCT GGG GGC TGT TTC CCA GGT TCG GCT CTG GTC TCG CTC CAG         624
Ala Lys Ser Gly Gly Cys Phe Pro Gly Ser Ala Leu Val Ser Leu Gln
        195                 200                 205

GAC GGA GGA CAG AAG GCC GTG AAG GAC CTG AAC CCC GGA GAC AAG GTG         672
Asp Gly Gly Gln Lys Ala Val Lys Asp Leu Asn Pro Gly Asp Lys Val
    210                 215                 220

CTG GCG GCA GAC AGC GCG GGA AAC CTG GTG TTC AGC GAC TTC ATC ATG         720
Leu Ala Ala Asp Ser Ala Gly Asn Leu Val Phe Ser Asp Phe Ile Met
225                 230                 235                 240

TTC ACA GAC CGA GAC TCC ACG ACG CGA CGT GTG TTT TAC GTC ATA GAA         768
Phe Thr Asp Arg Asp Ser Thr Thr Arg Arg Val Phe Tyr Val Ile Glu
                245                 250                 255

ACG CAA GAA CCC GTT GAA AAG ATC ACC CTC ACC GCC GCT CAC CTC CTT         816
Thr Gln Glu Pro Val Glu Lys Ile Thr Leu Thr Ala Ala His Leu Leu
            260                 265                 270

TTT GTC CTC GAC AAC TCA ACG GAA GAT CTC CAC ACC ATG ACC GCC GCG         864
Phe Val Leu Asp Asn Ser Thr Glu Asp Leu His Thr Met Thr Ala Ala
        275                 280                 285

TAT GCC AGC AGT GTC AGA GCC GGA CAA AAG GTG ATG GTT GTT GAT GAT         912
Tyr Ala Ser Ser Val Arg Ala Gly Gln Lys Val Met Val Val Asp Asp
    290                 295                 300

AGC GGT CAG CTT AAA TCT GTC ATC GTG CAG CGG ATA TAC ACG GAG GAG         960
Ser Gly Gln Leu Lys Ser Val Ile Val Gln Arg Ile Tyr Thr Glu Glu
305                 310                 315                 320

CAG CGG GGC TCG TTC GCA CCA GTG ACT GCA CAT GGG ACC ATT GTG GTC        1008
Gln Arg Gly Ser Phe Ala Pro Val Thr Ala His Gly Thr Ile Val Val
                325                 330                 335

GAC AGA ATA CTG GCG TCC TGT TAC GCC GTA ATA GAG GAC CAG GGG CTT        1056
Asp Arg Ile Leu Ala Ser Cys Tyr Ala Val Ile Glu Asp Gln Gly Leu
            340                 345                 350

GCG CAT TTG GCC TTC GCG CCC GCC AGG CTC TAT TAT TAC GTG TCA TCA        1104
Ala His Leu Ala Phe Ala Pro Ala Arg Leu Tyr Tyr Tyr Val Ser Ser
        355                 360                 365

TTC CTG TCC CCC AAA ACT CCA GCA GTC GGT CCA ATG CGA CTT TAC AAC        1152
Phe Leu Ser Pro Lys Thr Pro Ala Val Gly Pro Met Arg Leu Tyr Asn
    370                 375                 380

AGG AGG GGG TCC ACT GGT ACT CCA GGC TCC TGT CAT CAA ATG GGA ACG        1200
Arg Arg Gly Ser Thr Gly Thr Pro Gly Ser Cys His Gln Met Gly Thr
385                 390                 395                 400

TGG CTT TTG GAC AGC AAC ATG CTT CAT CCT TTG GGG ATG TCA GTA AAC        1248
Trp Leu Leu Asp Ser Asn Met Leu His Pro Leu Gly Met Ser Val Asn
                405                 410                 415
```

```
TCA AGC TG                                                                    1256
Ser Ser
```

(2) INFORMATION FOR SEQ ID NO:6:

(i) SEQUENCE CHARACTERISTICS:
        (A) LENGTH: 1425 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..1425

(xi) SEQUENCE DESCRIPTION: SEQ ID NO:6:

```
ATG CTG CTG CTG GCG AGA TGT CTG CTG CTA GTC CTC GTC TCC TCG CTG            48
Met Leu Leu Leu Ala Arg Cys Leu Leu Leu Val Leu Val Ser Ser Leu
 1               5                  10                  15

CTG GTA TGC TCG GGA CTG GCG TGC GGA CCG GGC AGG GGG TTC GGG AAG            96
Leu Val Cys Ser Gly Leu Ala Cys Gly Pro Gly Arg Gly Phe Gly Lys
             20                  25                  30

AGG AGG CAC CCC AAA AAG CTG ACC CCT TTA GCC TAC AAG CAG TTT ATC           144
Arg Arg His Pro Lys Lys Leu Thr Pro Leu Ala Tyr Lys Gln Phe Ile
         35                  40                  45

CCC AAT GTG GCC GAG AAG ACC CTA GGC GCC AGC GGA AGG TAT GAA GGG           192
Pro Asn Val Ala Glu Lys Thr Leu Gly Ala Ser Gly Arg Tyr Glu Gly
     50                  55                  60

AAG ATC TCC AGA AAC TCC GAG CGA TTT AAG GAA CTC ACC CCC AAT TAC           240
Lys Ile Ser Arg Asn Ser Glu Arg Phe Lys Glu Leu Thr Pro Asn Tyr
 65                  70                  75                  80

AAC CCC GAC ATC ATA TTT AAG GAT GAA GAA AAC ACC GGA GCG GAC AGG           288
Asn Pro Asp Ile Ile Phe Lys Asp Glu Glu Asn Thr Gly Ala Asp Arg
                 85                  90                  95

CTG ATG ACT CAG AGG TGT AAG GAC AAG TTG AAC GCT TTG GCC ATC TCG           336
Leu Met Thr Gln Arg Cys Lys Asp Lys Leu Asn Ala Leu Ala Ile Ser
            100                 105                 110

GTG ATG AAC CAG TGG CCA GGA GTG AAA CTG CGG GTG ACC GAG GGC TGG           384
Val Met Asn Gln Trp Pro Gly Val Lys Leu Arg Val Thr Glu Gly Trp
        115                 120                 125

GAC GAA GAT GGC CAC CAC TCA GAG GAG TCT CTG CAC TAC GAG GGC CGC           432
Asp Glu Asp Gly His His Ser Glu Glu Ser Leu His Tyr Glu Gly Arg
    130                 135                 140

GCA GTG GAC ATC ACC ACG TCT GAC CGC GAC CGC AGC AAG TAC GGC ATG           480
Ala Val Asp Ile Thr Thr Ser Asp Arg Asp Arg Ser Lys Tyr Gly Met
145                 150                 155                 160

CTG GCC CGC CTG GCG GTG GAG GCC GGC TTC GAC TGG GTG TAC TAC GAG           528
Leu Ala Arg Leu Ala Val Glu Ala Gly Phe Asp Trp Val Tyr Tyr Glu
                165                 170                 175

TCC AAG GCA CAT ATC CAC TGC TCG GTG AAA GCA GAG AAC TCG GTG GCG           576
Ser Lys Ala His Ile His Cys Ser Val Lys Ala Glu Asn Ser Val Ala
            180                 185                 190

GCC AAA TCG GGA GGC TGC TTC CCG GGC TCG GCC ACG GTG CAC CTG GAG           624
Ala Lys Ser Gly Gly Cys Phe Pro Gly Ser Ala Thr Val His Leu Glu
        195                 200                 205

CAG GGC GGC ACC AAG CTG GTG AAG GAC CTG AGC CCC GGG GAC CGC GTG           672
Gln Gly Gly Thr Lys Leu Val Lys Asp Leu Ser Pro Gly Asp Arg Val
    210                 215                 220

CTG GCG GCG GAC GAC CAG GGC CGG CTG CTC TAC AGC GAC TTC CTC ACT           720
Leu Ala Ala Asp Asp Gln Gly Arg Leu Leu Tyr Ser Asp Phe Leu Thr
```

```
                225                 230                 235                 240
TTC CTG GAC CGC GAC GAC GGC GCC AAG AAG GTC TTC TAC GTG ATC GAG        768
Phe Leu Asp Arg Asp Asp Gly Ala Lys Lys Val Phe Tyr Val Ile Glu
                245                 250                 255

ACG CGG GAG CCG CGC GAG CGC CTG CTC ACC GCC GCG CAC CTG CTC            816
Thr Arg Glu Pro Arg Glu Arg Leu Leu Leu Thr Ala Ala His Leu Leu
                260                 265                 270

TTT GTG GCG CCG CAC AAC GAC TCG GCC ACC GGG GAG CCC GAG GCG TCC        864
Phe Val Ala Pro His Asn Asp Ser Ala Thr Gly Glu Pro Glu Ala Ser
                275                 280                 285

TCG GGC TCG GGG CCG CCT TCC GGG GGC GCA CTG GGG CCT CGG GCG CTG        912
Ser Gly Ser Gly Pro Pro Ser Gly Gly Ala Leu Gly Pro Arg Ala Leu
                290                 295                 300

TTC GCC AGC CGC GTG CGC CCG GGC CAG CGC GTG TAC GTG GTG GCC GAG        960
Phe Ala Ser Arg Val Arg Pro Gly Gln Arg Val Tyr Val Val Ala Glu
305                 310                 315                 320

CGT GAC GGG GAC CGC CGG CTC CTG CCC GCC GCT GTG CAC AGC GTG ACC       1008
Arg Asp Gly Asp Arg Arg Leu Leu Pro Ala Ala Val His Ser Val Thr
                325                 330                 335

CTA AGC GAG GAG GCC GCG GGC GCC TAC GCG CCG CTC ACG GCC CAG GGC       1056
Leu Ser Glu Glu Ala Ala Gly Ala Tyr Ala Pro Leu Thr Ala Gln Gly
                340                 345                 350

ACC ATT CTC ATC AAC CGG GTG CTG GCC TCG TGC TAC GCG GTC ATC GAG       1104
Thr Ile Leu Ile Asn Arg Val Leu Ala Ser Cys Tyr Ala Val Ile Glu
                355                 360                 365

GAG CAC AGC TGG GCG CAC CGG GCC TTC GCG CCC TTC CGC CTG GCG CAC       1152
Glu His Ser Trp Ala His Arg Ala Phe Ala Pro Phe Arg Leu Ala His
                370                 375                 380

GCG CTC CTG GCT GCA CTG GCG CCC GCG CGC ACG GAC CGC GGC GGG GAC       1200
Ala Leu Leu Ala Ala Leu Ala Pro Ala Arg Thr Asp Arg Gly Gly Asp
385                 390                 395                 400

AGC GGC GGC GGG GAC CGC GGG GGC GGC GGC AGA GTA GCC CTA ACC           1248
Ser Gly Gly Gly Asp Arg Gly Gly Gly Gly Arg Val Ala Leu Thr
                405                 410                 415

GCT CCA GGT GCT GCC GAC GCT CCG GGT GCG GGG GCC ACC GCG GGC ATC       1296
Ala Pro Gly Ala Ala Asp Ala Pro Gly Ala Gly Ala Thr Ala Gly Ile
                420                 425                 430

CAC TGG TAC TCG CAG CTG CTC TAC CAA ATA GGC ACC TGG CTC CTG GAC       1344
His Trp Tyr Ser Gln Leu Leu Tyr Gln Ile Gly Thr Trp Leu Leu Asp
                435                 440                 445

AGC GAG GCC CTG CAC CCG CTG GGC ATG GCG GTC AAG TCC AGC NNN AGC       1392
Ser Glu Ala Leu His Pro Leu Gly Met Ala Val Lys Ser Ser Xaa Ser
                450                 455                 460

CGG GGG GCC GGG GGA GGG GCG CGG GAG GGG GCC                           1425
Arg Gly Ala Gly Gly Gly Ala Arg Glu Gly Ala
465                 470                 475
```

(2) INFORMATION FOR SEQ ID NO:7:

(i) SEQUENCE CHARACTERISTICS:
        (A) LENGTH: 939 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..936

(xi) SEQUENCE DESCRIPTION: SEQ ID NO:7:

```
CGG CGC CTC ATG ACC CAG CGC TGC AAG GAC CGC CTG AAC TCG CTG GCT        48
Arg Arg Leu Met Thr Gln Arg Cys Lys Asp Arg Leu Asn Ser Leu Ala
 1               5                  10                  15

ATC TCG GTG ATG AAC CAG TGG CCC GGT GTG AAG CTG CGG GTG ACC GAG        96
Ile Ser Val Met Asn Gln Trp Pro Gly Val Lys Leu Arg Val Thr Glu
                20                  25                  30

GGC TGG GAC GAG GAC GGC CAC CAC TCA GAG GAG TCC CTG CAT TAT GAG       144
Gly Trp Asp Glu Asp Gly His His Ser Glu Glu Ser Leu His Tyr Glu
            35                  40                  45

GGC CGC GCG GTG GAC ATC ACC ACA TCA GAC CGC GAC CGC AAT AAG TAT       192
Gly Arg Ala Val Asp Ile Thr Thr Ser Asp Arg Asp Arg Asn Lys Tyr
 50                  55                  60

GGA CTG CTG GCG CGC TTG GCA GTG GAG GCC GGC TTT GAC TGG GTG TAT       240
Gly Leu Leu Ala Arg Leu Ala Val Glu Ala Gly Phe Asp Trp Val Tyr
 65                  70                  75                  80

TAC GAG TCA AAG GCC CAC GTG CAT TGC TCC GTC AAG TCC GAG CAC TCG       288
Tyr Glu Ser Lys Ala His Val His Cys Ser Val Lys Ser Glu His Ser
                85                  90                  95

GCC GCA GCC AAG ACG GGC GGC TGC TTC CCT GCC GGA GCC CAG GTA CGC       336
Ala Ala Ala Lys Thr Gly Gly Cys Phe Pro Ala Gly Ala Gln Val Arg
            100                 105                 110

CTG GAG AGT GGG GCG CGT GTG GCC TTG TCA GCC GTG AGG CCG GGA GAC       384
Leu Glu Ser Gly Ala Arg Val Ala Leu Ser Ala Val Arg Pro Gly Asp
        115                 120                 125

CGT GTG CTG GCC ATG GGG GAG GAT GGG AGC CCC ACC TTC AGC GAT GTG       432
Arg Val Leu Ala Met Gly Glu Asp Gly Ser Pro Thr Phe Ser Asp Val
130                 135                 140

CTC ATT TTC CTG GAC CGC GAG CCC CAC AGG CTG AGA GCC TTC CAG GTC       480
Leu Ile Phe Leu Asp Arg Glu Pro His Arg Leu Arg Ala Phe Gln Val
145                 150                 155                 160

ATC GAG ACT CAG GAC CCC CCA CGC CGC CTG GCA CTC ACA CCC GCT CAC       528
Ile Glu Thr Gln Asp Pro Pro Arg Arg Leu Ala Leu Thr Pro Ala His
                165                 170                 175

CTG CTC TTT ACG GCT GAC AAT CAC ACG GAG CCG GCA GCC CGC TTC CGG       576
Leu Leu Phe Thr Ala Asp Asn His Thr Glu Pro Ala Ala Arg Phe Arg
            180                 185                 190

GCC ACA TTT GCC AGC CAC GTG CAG CCT GGC CAG TAC GTG CTG GTG GCT       624
Ala Thr Phe Ala Ser His Val Gln Pro Gly Gln Tyr Val Leu Val Ala
        195                 200                 205

GGG GTG CCA GGC CTG CAG CCT GCC CGC GTG GCA GCT GTC TCT ACA CAC       672
Gly Val Pro Gly Leu Gln Pro Ala Arg Val Ala Ala Val Ser Thr His
210                 215                 220

GTG GCC CTC GGG GCC TAC GCC CCG CTC ACA AAG CAT GGG ACA CTG GTG       720
Val Ala Leu Gly Ala Tyr Ala Pro Leu Thr Lys His Gly Thr Leu Val
225                 230                 235                 240

GTG GAG GAT GTG GTG GCA TCC TGC TTC GCG GCC GTG GCT GAC CAC CAC       768
Val Glu Asp Val Val Ala Ser Cys Phe Ala Ala Val Ala Asp His His
                245                 250                 255

CTG GCT CAG TTG GCC TTC TGG CCC CTG AGA CTC TTT CAC AGC TTG GCA       816
Leu Ala Gln Leu Ala Phe Trp Pro Leu Arg Leu Phe His Ser Leu Ala
            260                 265                 270

TGG GGC AGC TGG ACC CCG GGG GAG GGT GTG CAT TGG TAC CCC CAG CTG       864
Trp Gly Ser Trp Thr Pro Gly Glu Gly Val His Trp Tyr Pro Gln Leu
        275                 280                 285

CTC TAC CGC CTG GGG CGT CTC CTG CTA GAA GAG GGC AGC TTC CAC CCA       912
Leu Tyr Arg Leu Gly Arg Leu Leu Glu Glu Gly Ser Phe His Pro
290                 295                 300

CTG GGC ATG TCC GGG GCA GGG AGC TGA                                   939
Leu Gly Met Ser Gly Ala Gly Ser
305                 310
```

(2) INFORMATION FOR SEQ ID NO:8:

(i) SEQUENCE CHARACTERISTICS:
        (A) LENGTH: 425 amino acids
        (B) TYPE: amino acid
        (D) TOPOLOGY: linear (ii) MOLECULE TYPE: protein (xi) SEQUENCE DESCRIPTION: SEQ ID NO:8:

```
Met Val Glu Met Leu Leu Leu Thr Arg Ile Leu Leu Val Gly Phe Ile
 1               5                  10                  15

Cys Ala Leu Leu Val Ser Ser Gly Leu Thr Cys Gly Pro Gly Arg Gly
             20                  25                  30

Ile Gly Lys Arg Arg His Pro Lys Lys Leu Thr Pro Leu Ala Tyr Lys
         35                  40                  45

Gln Phe Ile Pro Asn Val Ala Glu Lys Thr Leu Gly Ala Ser Gly Arg
 50                  55                  60

Tyr Glu Gly Lys Ile Thr Arg Asn Ser Glu Arg Phe Lys Glu Leu Thr
 65                  70                  75                  80

Pro Asn Tyr Asn Pro Asp Ile Ile Phe Lys Asp Glu Glu Asn Thr Gly
                 85                  90                  95

Ala Asp Arg Leu Met Thr Gln Arg Cys Lys Asp Lys Leu Asn Ala Leu
                100                 105                 110

Ala Ile Ser Val Met Asn Gln Trp Pro Gly Val Lys Leu Arg Val Thr
            115                 120                 125

Glu Gly Trp Asp Glu Asp Gly His His Ser Glu Glu Ser Leu His Tyr
130                 135                 140

Glu Gly Arg Ala Val Asp Ile Thr Thr Ser Asp Arg Asp Arg Ser Lys
145                 150                 155                 160

Tyr Gly Met Leu Ala Arg Leu Ala Val Glu Ala Gly Phe Asp Trp Val
                165                 170                 175

Tyr Tyr Glu Ser Lys Ala His Ile His Cys Ser Val Lys Ala Glu Asn
                180                 185                 190

Ser Val Ala Ala Lys Ser Gly Gly Cys Phe Pro Gly Ser Ala Thr Val
            195                 200                 205

His Leu Glu His Gly Gly Thr Lys Leu Val Lys Asp Leu Ser Pro Gly
210                 215                 220

Asp Arg Val Leu Ala Ala Asp Ala Asp Gly Arg Leu Leu Tyr Ser Asp
225                 230                 235                 240

Phe Leu Thr Phe Leu Asp Arg Met Asp Ser Ser Arg Lys Leu Phe Tyr
                245                 250                 255

Val Ile Glu Thr Arg Gln Pro Arg Ala Arg Leu Leu Leu Thr Ala Ala
                260                 265                 270

His Leu Leu Phe Val Ala Pro Gln His Asn Gln Ser Glu Ala Thr Gly
            275                 280                 285

Ser Thr Ser Gly Gln Ala Leu Phe Ala Ser Asn Val Lys Pro Gly Gln
290                 295                 300

Arg Val Tyr Val Leu Gly Glu Gly Gln Gln Leu Leu Pro Ala Ser
305                 310                 315                 320

Val His Ser Val Ser Leu Arg Glu Glu Ala Ser Gly Ala Tyr Ala Pro
                325                 330                 335

Leu Thr Ala Gln Gly Thr Ile Leu Ile Asn Arg Val Leu Ala Ser Cys
            340                 345                 350
```

```
Tyr Ala Val Ile Glu Glu His Ser Trp Ala His Trp Ala Phe Ala Pro
            355                 360                 365

Phe Arg Leu Ala Gln Gly Leu Leu Ala Ala Leu Cys Pro Asp Gly Ala
            370                 375                 380

Ile Pro Thr Ala Ala Thr Thr Thr Gly Ile His Trp Tyr Ser Arg
385                 390                 395                 400

Leu Leu Tyr Arg Ile Gly Ser Trp Val Leu Asp Gly Asp Ala Leu His
                405                 410                 415

Pro Leu Gly Met Val Ala Pro Ala Ser
            420                 425

(2) INFORMATION FOR SEQ ID NO:9:

(i) SEQUENCE CHARACTERISTICS:
        (A) LENGTH: 396 amino acids
        (B) TYPE: amino acid
        (D) TOPOLOGY: linear (ii) MOLECULE TYPE: protein (xi) SEQUENCE DESCRIPTION: SEQ ID NO:9:

Met Ala Leu Pro Ala Ser Leu Leu Pro Leu Cys Cys Leu Ala Leu Leu
1               5                   10                  15

Ala Leu Ser Ala Gln Ser Cys Gly Pro Gly Arg Gly Pro Val Gly Arg
            20                  25                  30

Arg Arg Tyr Val Arg Lys Gln Leu Val Pro Leu Leu Tyr Lys Gln Phe
        35                  40                  45

Val Pro Ser Met Pro Glu Arg Thr Leu Gly Ala Ser Gly Pro Ala Glu
    50                  55                  60

Gly Arg Val Thr Arg Gly Ser Glu Arg Phe Arg Asp Leu Val Pro Asn
65                  70                  75                  80

Tyr Asn Pro Asp Ile Ile Phe Lys Asp Glu Glu Asn Ser Gly Ala Asp
                85                  90                  95

Arg Leu Met Thr Glu Arg Cys Lys Glu Arg Val Asn Ala Leu Ala Ile
            100                 105                 110

Ala Val Met Asn Met Trp Pro Gly Val Arg Leu Arg Val Thr Glu Gly
        115                 120                 125

Trp Asp Glu Asp Gly His His Ala Gln Asp Ser Leu His Tyr Glu Gly
    130                 135                 140

Arg Ala Leu Asp Ile Thr Thr Ser Asp Arg Asp Arg Asn Lys Tyr Gly
145                 150                 155                 160

Leu Leu Ala Arg Leu Ala Val Glu Ala Gly Phe Asp Trp Val Tyr Tyr
                165                 170                 175

Glu Ser Arg Asn His Ile His Val Ser Val Lys Ala Asp Asn Ser Leu
            180                 185                 190

Ala Val Arg Ala Gly Gly Cys Phe Pro Gly Asn Ala Thr Val Arg Leu
        195                 200                 205

Arg Ser Gly Glu Arg Lys Gly Leu Arg Glu Leu His Arg Gly Asp Trp
    210                 215                 220

Val Leu Ala Ala Asp Ala Ala Gly Arg Val Val Pro Thr Pro Val Leu
225                 230                 235                 240

Leu Phe Leu Asp Arg Asp Leu Gln Arg Arg Ala Ser Phe Val Ala Val
                245                 250                 255

Glu Thr Glu Arg Pro Pro Arg Lys Leu Leu Leu Thr Pro Trp His Leu
            260                 265                 270

Val Phe Ala Ala Arg Gly Pro Ala Pro Ala Pro Gly Asp Phe Ala Pro
```

```
            275                 280                 285
Val Phe Ala Arg Arg Leu Arg Ala Gly Asp Ser Val Leu Ala Pro Gly
    290                 295                 300
Gly Asp Ala Leu Gln Pro Ala Arg Val Ala Arg Val Ala Arg Glu Glu
305                 310                 315                 320
Ala Val Gly Val Phe Ala Pro Leu Thr Ala His Gly Thr Leu Leu Val
                325                 330                 335
Asn Asp Val Leu Ala Ser Cys Tyr Ala Val Leu Glu Ser His Gln Trp
            340                 345                 350
Ala His Arg Ala Phe Ala Pro Leu Arg Leu Leu His Ala Leu Gly Ala
        355                 360                 365
Leu Leu Pro Gly Gly Ala Val Gln Pro Thr Gly Met His Trp Tyr Ser
    370                 375                 380
Arg Leu Leu Tyr Arg Leu Ala Glu Glu Leu Met Gly
385                 390                 395
```

(2) INFORMATION FOR SEQ ID NO:10:

(i) SEQUENCE CHARACTERISTICS:
        (A) LENGTH: 411 amino acids
        (B) TYPE: amino acid
        (D) TOPOLOGY: linear (ii) MOLECULE TYPE: protein (xi) SEQUENCE DESCRIPTION: SEQ ID NO:10:

```
Met Ser Pro Ala Trp Leu Arg Pro Arg Leu Arg Phe Cys Leu Phe Leu
1               5                   10                  15
Leu Leu Leu Leu Val Pro Ala Ala Arg Gly Cys Gly Pro Gly Arg
            20                  25                  30
Val Val Gly Ser Arg Arg Arg Pro Pro Arg Lys Leu Val Pro Leu Ala
                35                  40                  45
Tyr Lys Gln Phe Ser Pro Asn Val Pro Glu Lys Thr Leu Gly Ala Ser
        50                  55                  60
Gly Arg Tyr Glu Gly Lys Ile Ala Arg Ser Ser Glu Arg Phe Lys Glu
65                  70                  75                  80
Leu Thr Pro Asn Tyr Asn Pro Asp Ile Ile Phe Lys Asp Glu Glu Asn
                85                  90                  95
Thr Gly Ala Asp Arg Leu Met Thr Gln Arg Cys Lys Asp Arg Leu Asn
            100                 105                 110
Ser Leu Ala Ile Ser Val Met Asn Gln Trp Pro Gly Val Lys Leu Arg
        115                 120                 125
Val Thr Glu Gly Arg Asp Glu Asp Gly His His Ser Glu Glu Ser Leu
    130                 135                 140
His Tyr Glu Gly Arg Ala Val Asp Ile Thr Thr Ser Asp Arg Asp Arg
145                 150                 155                 160
Asn Lys Tyr Gly Leu Leu Ala Arg Leu Ala Val Glu Ala Gly Phe Asp
                165                 170                 175
Trp Val Tyr Tyr Glu Ser Lys Ala His Val His Cys Ser Val Lys Ser
            180                 185                 190
Glu His Ser Ala Ala Ala Lys Thr Gly Gly Cys Phe Pro Ala Gly Ala
        195                 200                 205
Gln Val Arg Leu Glu Asn Gly Glu Arg Val Ala Leu Ser Ala Val Lys
    210                 215                 220
Pro Gly Asp Arg Val Leu Ala Met Gly Glu Asp Gly Thr Pro Thr Phe
225                 230                 235                 240
```

-continued

```
Ser Asp Val Leu Ile Phe Leu Asp Arg Glu Pro Asn Arg Leu Arg Ala
                245                 250                 255

Phe Gln Val Ile Glu Thr Gln Asp Pro Pro Arg Arg Leu Ala Leu Thr
            260                 265                 270

Pro Ala His Leu Leu Phe Ile Ala Asp Asn His Thr Glu Pro Ala Ala
            275                 280                 285

His Phe Arg Ala Thr Phe Ala Ser His Val Gln Pro Gly Gln Tyr Val
            290                 295                 300

Leu Val Ser Gly Val Pro Gly Leu Gln Pro Ala Arg Val Ala Ala Val
305                 310                 315                 320

Ser Thr His Val Ala Leu Gly Ser Tyr Ala Pro Leu Thr Arg His Gly
                325                 330                 335

Thr Leu Val Val Glu Asp Val Val Ala Ser Cys Phe Ala Ala Val Ala
                340                 345                 350

Asp His His Leu Ala Gln Leu Ala Phe Trp Pro Leu Arg Leu Phe Pro
                355                 360                 365

Ser Leu Ala Trp Gly Ser Trp Thr Pro Ser Glu Gly Val His Ser Tyr
            370                 375                 380

Pro Gln Met Leu Tyr Arg Leu Gly Arg Leu Leu Leu Glu Glu Ser Thr
385                 390                 395                 400

Phe His Pro Leu Gly Met Ser Gly Ala Gly Ser
                405                 410
```

(2) INFORMATION FOR SEQ ID NO:11:

(i) SEQUENCE CHARACTERISTICS:
        (A) LENGTH: 437 amino acids
        (B) TYPE: amino acid
        (D) TOPOLOGY: linear (ii) MOLECULE TYPE: protein (xi) SEQUENCE DESCRIPTION: SEQ ID NO:11:

```
Met Leu Leu Leu Ala Arg Cys Phe Leu Val Ile Leu Ala Ser Ser
 1               5                  10                  15

Leu Leu Val Cys Pro Gly Leu Ala Cys Gly Pro Gly Arg Gly Phe Gly
                20                  25                  30

Lys Arg Arg His Pro Lys Lys Leu Thr Pro Leu Ala Tyr Lys Gln Phe
                35                  40                  45

Ile Pro Asn Val Ala Glu Lys Thr Leu Gly Ala Ser Gly Arg Tyr Glu
            50                  55                  60

Gly Lys Ile Thr Arg Asn Ser Glu Arg Phe Lys Glu Leu Thr Pro Asn
65                  70                  75                  80

Tyr Asn Pro Asp Ile Ile Phe Lys Asp Glu Glu Asn Thr Gly Ala Asp
                85                  90                  95

Arg Leu Met Thr Gln Arg Cys Lys Asp Lys Leu Asn Ala Leu Ala Ile
                100                 105                 110

Ser Val Met Asn Gln Trp Pro Gly Val Arg Leu Arg Val Thr Glu Gly
            115                 120                 125

Trp Asp Glu Asp Gly His His Ser Glu Glu Ser Leu His Tyr Glu Gly
130                 135                 140

Arg Ala Val Asp Ile Thr Thr Ser Asp Arg Asp Arg Ser Lys Tyr Gly
145                 150                 155                 160

Met Leu Ala Arg Leu Ala Val Glu Ala Gly Phe Asp Trp Val Tyr Tyr
                165                 170                 175
```

-continued

```
Glu Ser Lys Ala His Ile His Cys Ser Val Lys Ala Glu Asn Ser Val
            180                 185                 190

Ala Ala Lys Ser Gly Gly Cys Phe Pro Gly Ser Ala Thr Val His Leu
            195                 200                 205

Glu Gln Gly Gly Thr Lys Leu Val Lys Asp Leu Arg Pro Gly Asp Arg
            210                 215                 220

Val Leu Ala Ala Asp Asp Gln Gly Arg Leu Leu Tyr Ser Asp Phe Leu
225                 230                 235                 240

Thr Phe Leu Asp Arg Asp Glu Gly Ala Lys Lys Val Phe Tyr Val Ile
                245                 250                 255

Glu Thr Leu Glu Pro Arg Glu Arg Leu Leu Leu Thr Ala Ala His Leu
                260                 265                 270

Leu Phe Val Ala Pro His Asn Asp Ser Gly Pro Thr Pro Gly Pro Ser
            275                 280                 285

Ala Leu Phe Ala Ser Arg Val Arg Pro Gly Gln Arg Val Tyr Val Val
            290                 295                 300

Ala Glu Arg Gly Gly Asp Arg Arg Leu Leu Pro Ala Ala Val His Ser
305                 310                 315                 320

Val Thr Leu Arg Glu Glu Ala Gly Ala Tyr Ala Pro Leu Thr Ala
                325                 330                 335

His Gly Thr Ile Leu Ile Asn Arg Val Leu Ala Ser Cys Tyr Ala Val
            340                 345                 350

Ile Glu Glu His Ser Trp Ala His Arg Ala Phe Ala Pro Phe Arg Leu
            355                 360                 365

Ala His Ala Leu Leu Ala Ala Leu Ala Pro Ala Arg Thr Asp Gly Gly
            370                 375                 380

Gly Gly Gly Ser Ile Pro Ala Ala Gln Ser Ala Thr Glu Ala Arg Gly
385                 390                 395                 400

Ala Glu Pro Thr Ala Gly Ile His Trp Tyr Ser Gln Leu Leu Tyr His
                405                 410                 415

Ile Gly Thr Trp Leu Leu Asp Ser Glu Thr Met His Pro Leu Gly Met
                420                 425                 430

Ala Val Lys Ser Ser
            435

(2) INFORMATION FOR SEQ ID NO:12:

(i) SEQUENCE CHARACTERISTICS:
        (A) LENGTH: 418 amino acids
        (B) TYPE: amino acid
        (D) TOPOLOGY: linear (ii) MOLECULE TYPE: protein (xi) SEQUENCE DESCRIPTION: SEQ ID NO:12:

Met Arg Leu Leu Thr Arg Val Leu Leu Val Ser Leu Leu Thr Leu Ser
1               5                   10                  15

Leu Val Val Ser Gly Leu Ala Cys Gly Pro Gly Arg Gly Tyr Gly Arg
            20                  25                  30

Arg Arg His Pro Lys Lys Leu Thr Pro Leu Ala Tyr Lys Gln Phe Ile
            35                  40                  45

Pro Asn Val Ala Glu Lys Thr Leu Gly Ala Ser Gly Arg Tyr Glu Gly
            50                  55                  60

Lys Ile Thr Arg Asn Ser Glu Arg Phe Lys Glu Leu Thr Pro Asn Tyr
65              70                  75                  80

Asn Pro Asp Ile Ile Phe Lys Asp Glu Glu Asn Thr Gly Ala Asp Arg
```

```
                    85                  90                  95
Leu Met Thr Gln Arg Cys Lys Asp Lys Leu Asn Ser Leu Ala Ile Ser
            100                 105                 110

Val Met Asn His Trp Pro Gly Val Lys Leu Arg Val Thr Glu Gly Trp
            115                 120                 125

Asp Glu Asp Gly His His Phe Glu Glu Ser Leu His Tyr Glu Gly Arg
            130                 135                 140

Ala Val Asp Ile Thr Thr Ser Asp Arg Asp Lys Ser Lys Tyr Gly Thr
145                 150                 155                 160

Leu Ser Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
                180                 185                 190

Ala Lys Ser Gly Gly Cys Phe Pro Gly Ser Ala Leu Val Ser Leu Gln
                195                 200                 205

Asp Gly Gly Gln Lys Ala Val Lys Asp Leu Asn Pro Gly Asp Lys Val
            210                 215                 220

Leu Ala Ala Asp Ser Ala Gly Asn Leu Val Phe Ser Asp Phe Ile Met
225                 230                 235                 240

Phe Thr Asp Arg Asp Ser Thr Thr Arg Arg Val Phe Tyr Val Ile Glu
            245                 250                 255

Thr Gln Glu Pro Val Glu Lys Ile Thr Leu Thr Ala Ala His Leu Leu
            260                 265                 270

Phe Val Leu Asp Asn Ser Thr Glu Asp Leu His Thr Met Thr Ala Ala
            275                 280                 285

Tyr Ala Ser Ser Val Arg Ala Gly Gln Lys Val Met Val Val Asp Asp
            290                 295                 300

Ser Gly Gln Leu Lys Ser Val Ile Val Gln Arg Ile Tyr Thr Glu Glu
305                 310                 315                 320

Gln Arg Gly Ser Phe Ala Pro Val Thr Ala His Gly Thr Ile Val Val
                325                 330                 335

Asp Arg Ile Leu Ala Ser Cys Tyr Ala Val Ile Glu Asp Gln Gly Leu
                340                 345                 350

Ala His Leu Ala Phe Ala Pro Ala Arg Leu Tyr Tyr Tyr Val Ser Ser
            355                 360                 365

Phe Leu Ser Pro Lys Thr Pro Ala Val Gly Pro Met Arg Leu Tyr Asn
370                 375                 380

Arg Arg Gly Ser Thr Gly Thr Pro Gly Ser Cys His Gln Met Gly Thr
385                 390                 395                 400

Trp Leu Leu Asp Ser Asn Met Leu His Pro Leu Gly Met Ser Val Asn
                405                 410                 415

Ser Ser (2) INFORMATION FOR SEQ ID NO:13:

(i) SEQUENCE CHARACTERISTICS:
        (A) LENGTH: 475 amino acids
        (B) TYPE: amino acid
        (D) TOPOLOGY: linear (ii) MOLECULE TYPE: protein (xi) SEQUENCE DESCRIPTION: SEQ ID NO:13:

Met Leu Leu Leu Ala Arg Cys Leu Leu Leu Val Leu Val Ser Ser Leu
1               5                   10                  15
```

-continued

```
Leu Val Cys Ser Gly Leu Ala Cys Gly Pro Gly Arg Gly Phe Gly Lys
             20                  25                  30

Arg Arg His Pro Lys Lys Leu Thr Pro Leu Ala Tyr Lys Gln Phe Ile
         35                  40                  45

Pro Asn Val Ala Glu Lys Thr Leu Gly Ala Ser Gly Arg Tyr Glu Gly
     50                  55                  60

Lys Ile Ser Arg Asn Ser Glu Arg Phe Lys Glu Leu Thr Pro Asn Tyr
 65                  70                  75                  80

Asn Pro Asp Ile Ile Phe Lys Asp Glu Asn Thr Gly Ala Asp Arg
                 85                  90                  95

Leu Met Thr Gln Arg Cys Lys Asp Lys Leu Asn Ala Leu Ala Ile Ser
                100                 105                 110

Val Met Asn Gln Trp Pro Gly Val Lys Leu Arg Val Thr Glu Gly Trp
            115                 120                 125

Asp Glu Asp Gly His His Ser Glu Glu Ser Leu His Tyr Glu Gly Arg
        130                 135                 140

Ala Val Asp Ile Thr Thr Ser Asp Arg Asp Arg Ser Lys Tyr Gly Met
145                 150                 155                 160

Leu Ala Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Thr Val His Leu Glu
        195                 200                 205

Gln Gly Gly Thr Lys Leu Val Lys Asp Leu Ser Pro Gly Asp Arg Val
    210                 215                 220

Leu Ala Ala Asp Asp Gln Gly Arg Leu Leu Tyr Ser Asp Phe Leu Thr
225                 230                 235                 240

Phe Leu Asp Arg Asp Asp Gly Ala Lys Lys Val Phe Tyr Val Ile Glu
                245                 250                 255

Thr Arg Glu Pro Arg Glu Arg Leu Leu Leu Thr Ala Ala His Leu Leu
            260                 265                 270

Phe Val Ala Pro His Asn Asp Ser Ala Thr Gly Glu Pro Glu Ala Ser
        275                 280                 285

Ser Gly Ser Gly Pro Pro Ser Gly Gly Ala Leu Gly Pro Arg Ala Leu
    290                 295                 300

Phe Ala Ser Arg Val Arg Pro Gly Gln Arg Val Tyr Val Val Ala Glu
305                 310                 315                 320

Arg Asp Gly Asp Arg Arg Leu Leu Pro Ala Ala Val His Ser Val Thr
                325                 330                 335

Leu Ser Glu Glu Ala Ala Gly Ala Tyr Ala Pro Leu Thr Ala Gln Gly
            340                 345                 350

Thr Ile Leu Ile Asn Arg Val Leu Ala Ser Cys Tyr Ala Val Ile Glu
        355                 360                 365

Glu His Ser Trp Ala His Arg Ala Phe Ala Pro Phe Arg Leu Ala His
    370                 375                 380

Ala Leu Leu Ala Ala Leu Ala Pro Ala Arg Thr Asp Arg Gly Gly Asp
385                 390                 395                 400

Ser Gly Gly Gly Asp Arg Gly Gly Gly Arg Val Ala Leu Thr
                405                 410                 415

Ala Pro Gly Ala Ala Asp Ala Pro Gly Ala Gly Ala Thr Ala Gly Ile
            420                 425                 430

His Trp Tyr Ser Gln Leu Leu Tyr Gln Ile Gly Thr Trp Leu Leu Asp
```

```
              435                 440                 445
Ser Glu Ala Leu His Pro Leu Gly Met Ala Val Lys Ser Ser Xaa Ser
         450                 455                 460
Arg Gly Ala Gly Gly Ala Arg Glu Gly Ala
465                 470                 475
```

(2) INFORMATION FOR SEQ ID NO:14:

(i) SEQUENCE CHARACTERISTICS:
        (A) LENGTH: 312 amino acids
        (B) TYPE: amino acid
        (D) TOPOLOGY: linear (ii) MOLECULE TYPE: protein (xi) SEQUENCE DESCRIPTION: SEQ ID NO:14:

```
Arg Arg Leu Met Thr Gln Arg Cys Lys Asp Arg Leu Asn Ser Leu Ala
1               5                   10                  15
Ile Ser Val Met Asn Gln Trp Pro Gly Val Lys Leu Arg Val Thr Glu
                20                  25                  30
Gly Trp Asp Glu Asp Gly His His Ser Glu Glu Ser Leu His Tyr Glu
            35                  40                  45
Gly Arg Ala Val Asp Ile Thr Thr Ser Asp Arg Asp Arg Asn Lys Tyr
        50                  55                  60
Gly Leu Leu Ala Arg Leu Ala Val Glu Ala Gly Phe Asp Trp Val Tyr
65                  70                  75                  80
Tyr Glu Ser Lys Ala His Val His Cys Ser Val Lys Ser Glu His Ser
                85                  90                  95
Ala Ala Ala Lys Thr Gly Gly Cys Phe Pro Ala Gly Ala Gln Val Arg
                100                 105                 110
Leu Glu Ser Gly Ala Arg Val Ala Leu Ser Ala Val Arg Pro Gly Asp
            115                 120                 125
Arg Val Leu Ala Met Gly Glu Asp Gly Ser Pro Thr Phe Ser Asp Val
        130                 135                 140
Leu Ile Phe Leu Asp Arg Glu Pro His Arg Leu Arg Ala Phe Gln Val
145                 150                 155                 160
Ile Glu Thr Gln Asp Pro Pro Arg Arg Leu Ala Leu Thr Pro Ala His
                165                 170                 175
Leu Leu Phe Thr Ala Asp Asn His Thr Glu Pro Ala Ala Arg Phe Arg
            180                 185                 190
Ala Thr Phe Ala Ser His Val Gln Pro Gly Gln Tyr Val Leu Val Ala
        195                 200                 205
Gly Val Pro Gly Leu Gln Pro Ala Arg Val Ala Ala Val Ser Thr His
        210                 215                 220
Val Ala Leu Gly Ala Tyr Ala Pro Leu Thr Lys His Gly Thr Leu Val
225                 230                 235                 240
Val Glu Asp Val Val Ala Ser Cys Phe Ala Ala Val Ala Asp His His
                245                 250                 255
Leu Ala Gln Leu Ala Phe Trp Pro Leu Arg Leu Phe His Ser Leu Ala
            260                 265                 270
Trp Gly Ser Trp Thr Pro Gly Glu Gly Val His Trp Tyr Pro Gln Leu
        275                 280                 285
Leu Tyr Arg Leu Gly Arg Leu Leu Glu Glu Gly Ser Phe His Pro
    290                 295                 300
Leu Gly Met Ser Gly Ala Gly Ser
305                 310
```

(2) INFORMATION FOR SEQ ID NO:15:

(i) SEQUENCE CHARACTERISTICS:
        (A) LENGTH: 64 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:15:

Gln Arg Cys Lys Asp Lys Leu Asn Ser Leu Ala Ile Ser Val Met Asn
1               5                   10                  15

His Trp Pro Gly Val Lys Leu Arg Val Thr Glu Gly Trp Asp Glu Asp
            20                  25                  30

Gly His His Phe Glu Glu Ser Leu His Tyr Glu Gly Arg Ala Val Asp
        35                  40                  45

Ile Thr Thr Ser Asp Arg Asp Lys Ser Lys Tyr Gly Thr Leu Ser Arg
    50                  55                  60

(2) INFORMATION FOR SEQ ID NO:16:

(i) SEQUENCE CHARACTERISTICS:
        (A) LENGTH: 65 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:16:

Gln Arg Cys Lys Glu Lys Leu Asn Ser Leu Ala Ile Ser Val Met Asn
1               5                   10                  15

Met Trp Pro Gly Val Lys Leu Arg Val Thr Glu Gly Trp Asp Glu Asp
            20                  25                  30

Gly Asn His Phe Glu Asp Ser Leu His Tyr Glu Gly Arg Ala Val Asp
        35                  40                  45

Ile Thr Thr Ser Ser Asp Arg Asp Arg Asn Lys Tyr Gly Met Phe Ala
    50                  55                  60
Arg
65

(2) INFORMATION FOR SEQ ID NO:17:

(i) SEQUENCE CHARACTERISTICS:
        (A) LENGTH: 64 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:17:

Gln Arg Cys Lys Asp Lys Leu Asn Ser Leu Ala Ile Ser Val Met Asn
1               5                   10                  15

Leu Trp Pro Gly Val Lys Leu Arg Val Thr Glu Gly Trp Asp Glu Asp
            20                  25                  30

```
Gly Leu His Ser Glu Glu Ser Leu His Tyr Glu Gly Arg Ala Val Asp
         35                  40                  45

Ile Thr Thr Ser Asp Arg Asp Arg Asn Lys Tyr Arg Met Leu Ala Arg
 50                  55                  60
```

(2) INFORMATION FOR SEQ ID NO:18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

```
GGAATTCCCA GMGNTGYAAR GARMRNBNAA                                        30
```

(2) INFORMATION FOR SEQ ID NO:19:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

```
TCATCGATGG ACCCARTCRA ANCCNGCYTC                                        30
```

(2) INFORMATION FOR SEQ ID NO:20:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

```
GCTCTAGAGC TCNACNGCNA RNCKNGC                                           27
```

(2) INFORMATION FOR SEQ ID NO:21:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

```
AGCTGTCGAC GCGGCCGCTA CGTAGGTTAC CGACGTCAAG CTTAGATCTC                  50
```

(2) INFORMATION FOR SEQ ID NO:22:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

```
AGCTGAGATC TAAGCTTGAC GTCGGTAACC TACGTAGCGG CCGCGTCGAC                50
```

(2) INFORMATION FOR SEQ ID NO:23:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

```
GATCGGCCAG GCAGGCCTCG CGATATCGTC ACCGCGGTAT TCGAA                     45
```

(2) INFORMATION FOR SEQ ID NO:24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

```
AGTGCCAGTC GGGGCCCCCA GGGCCGCGCC                                      30
```

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

```
TACCACAGCG GATGGTTCGG                                                 20
```

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:26:

```
GTGGTGGTTA TGCCGATCGC                                                 20
```

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

```
TAAGAGGCCT ATAAGAGGCG G                                               21
```

(2) INFORMATION FOR SEQ ID NO:28:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:28:

AAGTCAGCCC AGAGGAGACT                                              20

(2) INFORMATION FOR SEQ ID NO:29:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:29:

Cys Gly Pro Gly Arg Gly
1               5

(2) INFORMATION FOR SEQ ID NO:30:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

AGMGNTGYAA RGARMRNBNA A                                            21

(2) INFORMATION FOR SEQ ID NO:31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

CTCNACNGCN ARNCKNGCNA                                              20

(2) INFORMATION FOR SEQ ID NO:32:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

CTGCAGGGAT CCACCATGCG GCTTTTGACG AG                                32

(2) INFORMATION FOR SEQ ID NO:33:

(i) SEQUENCE CHARACTERISTICS:
    (A) LENGTH: 31 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:33:

CTGCAGGGAT CCTTATTCCA CACGAGGGAT T           31

(2) INFORMATION FOR SEQ ID NO:34:

(i) SEQUENCE CHARACTERISTICS:
        (A) LENGTH: 471 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:34:

```
Met Asp Asn His Ser Ser Val Pro Trp Ala Ser Ala Ala Ser Val Thr
1               5                   10                  15

Cys Leu Ser Leu Asp Ala Lys Cys His Ser Ser Ser Ser Ser Ser Ser
            20                  25                  30

Ser Lys Ser Ala Ala Ser Ser Ile Ser Ala Ile Pro Gln Glu Glu Thr
        35                  40                  45

Gln Thr Met Arg His Ile Ala His Thr Gln Arg Cys Leu Ser Arg Leu
    50                  55                  60

Thr Ser Leu Val Ala Leu Leu Ile Val Leu Pro Met Val Phe Ser
65                  70                  75                  80

Pro Ala His Ser Cys Gly Pro Gly Arg Gly Leu Gly Arg His Arg Ala
                85                  90                  95

Arg Asn Leu Tyr Pro Leu Val Leu Lys Gln Thr Ile Pro Asn Leu Ser
            100                 105                 110

Glu Tyr Thr Asn Ser Ala Ser Gly Pro Leu Glu Gly Val Ile Arg Arg
        115                 120                 125

Asp Ser Pro Lys Phe Lys Asp Leu Val Pro Asn Tyr Asn Arg Asp Ile
    130                 135                 140

Leu Phe Arg Asp Glu Glu Gly Thr Gly Ala Asp Arg Leu Met Ser Lys
145                 150                 155                 160

Arg Cys Lys Glu Lys Leu Asn Val Leu Ala Tyr Ser Val Met Asn Glu
                165                 170                 175

Trp Pro Gly Ile Arg Leu Leu Val Thr Glu Ser Trp Asp Glu Asp Tyr
            180                 185                 190

His His Gly Gln Glu Ser Leu His Tyr Glu Gly Arg Ala Val Thr Ile
        195                 200                 205

Ala Thr Ser Asp Arg Asp Gln Ser Lys Tyr Gly Met Leu Ala Arg Leu
    210                 215                 220

Ala Val Glu Ala Gly Phe Asp Trp Val Ser Tyr Val Ser Arg Arg His
225                 230                 235                 240

Ile Tyr Cys Ser Val Lys Ser Asp Ser Ser Ile Ser Ser His Val His
                245                 250                 255

Gly Cys Phe Thr Pro Glu Ser Thr Ala Leu Leu Glu Ser Gly Val Arg
            260                 265                 270

Lys Pro Leu Gly Glu Leu Ser Ile Gly Asp Arg Val Leu Ser Met Thr
```

```
                    275                 280                 285
Ala Asn Gly Gln Ala Val Tyr Ser Glu Val Ile Leu Phe Met Asp Arg
290                 295                 300

Asn Leu Glu Gln Met Gln Asn Phe Val Gln Leu His Thr Asp Gly Gly
305                 310                 315                 320

Ala Val Leu Thr Val Thr Pro Ala His Leu Val Ser Val Trp Gln Pro
                325                 330                 335

Glu Ser Gln Lys Leu Thr Phe Val Phe Ala Asp Arg Ile Glu Glu Lys
                340                 345                 350

Asn Gln Val Leu Val Arg Asp Val Glu Thr Gly Glu Leu Arg Pro Gln
                355                 360                 365

Arg Val Val Lys Val Gly Ser Val Arg Ser Lys Gly Val Val Ala Pro
370                 375                 380

Leu Thr Arg Glu Gly Thr Ile Val Val Asn Ser Val Ala Ala Ser Cys
385                 390                 395                 400

Tyr Ala Val Ile Asn Ser Gln Ser Leu Ala His Trp Gly Leu Ala Pro
                405                 410                 415

Met Arg Leu Leu Ser Thr Leu Glu Ala Trp Leu Pro Ala Lys Glu Gln
                420                 425                 430

Leu His Ser Ser Pro Lys Val Val Ser Ala Gln Gln Gln Asn Gly
                435                 440                 445

Ile His Trp Tyr Ala Asn Ala Leu Tyr Lys Val Lys Asp Tyr Val Leu
450                 455                 460

Pro Gln Ser Trp Arg His Asp
465                 470

(2) INFORMATION FOR SEQ ID NO:35:

(i) SEQUENCE CHARACTERISTICS:
        (A) LENGTH: 73 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:35:

Arg Cys Lys Glu Arg Val Asn Ser Leu Ala Ile Ala Val Met His Met
1               5                   10                  15

Trp Pro Gly Val Arg Leu Arg Val Thr Glu Gly Trp Asp Glu Asp Gly
                20                  25                  30

His His Leu Pro Asp Ser Leu His Tyr Glu Gly Arg Ala Leu Asp Ile
            35                  40                  45

Thr Thr Ser Asp Arg Asp Arg His Lys Tyr Gly Met Leu Ala Arg Leu
        50                  55                  60

Ala Val Glu Ala Gly Phe Asp Trp Val
65                  70

(2) INFORMATION FOR SEQ ID NO:36:

(i) SEQUENCE CHARACTERISTICS:
        (A) LENGTH: 73 amino acids
        (B) TYPE: amino acid
        (C) STRANDEDNESS:
        (D) TOPOLOGY: linear (ii) MOLECULE TYPE: peptide
```

(v) FRAGMENT TYPE: internal (xi) SEQUENCE DESCRIPTION: SEQ ID NO:36:

```
Arg Cys Lys Asp Lys Leu Asn Ala Leu Ala Ile Ser Val Met Asn Gln
1               5                   10                  15

Trp Pro Gly Val Lys Leu Arg Val Thr Glu Gly Trp Asp Glu Asp Gly
            20                  25                  30

His His Ser Glu Glu Ser Leu His Tyr Glu Gly Arg Ala Val Asp Ile
        35                  40                  45

Thr Thr Ser Asp Arg Asp Arg Ser Lys Tyr Gly Met Leu Ala Arg Leu
    50                  55                  60

Ala Val Glu Ala Gly Phe Asp Trp Val
65                  70
```

(2) INFORMATION FOR SEQ ID NO:37:

(i) SEQUENCE CHARACTERISTICS:
        (A) LENGTH: 64 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:37:

```
Lys Arg Cys Lys Glu Lys Leu Asn Val Leu Ala Tyr Ser Val Met Asn
1               5                   10                  15

Glu Trp Pro Gly Ile Arg Leu Val Val Thr Glu Ser Trp Asp Glu Asp
            20                  25                  30

Tyr His His Gly Gln Glu Ser Leu His Tyr Glu Gly Arg Ala Val Thr
        35                  40                  45

Ile Ala Thr Ser Asp Arg Asp Gln Ser Lys Tyr Gly Met Leu Ala Arg
    50                  55                  60
```

(2) INFORMATION FOR SEQ ID NO:38:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:38:

AAAAGCTTTA YTGYTAYGTN GGNATHGG                    28

(2) INFORMATION FOR SEQ ID NO:39:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:39:

AAGAATTCTA NGCRTTRTAR TTRTTNGG                    28

(2) INFORMATION FOR SEQ ID NO:40:

```
        (i) SEQUENCE CHARACTERISTICS:
             (A) LENGTH: 221 amino acids
             (B) TYPE: amino acid
             (C) STRANDEDNESS:
             (D) TOPOLOGY: linear (ii) MOLECULE TYPE: peptide (v) FRAGMENT TYPE: internal (xi) SEQUENCE DESCRIPTION: SEQ ID NO:40:

Cys Gly Pro Gly Arg Gly Xaa Gly Xaa Arg Arg His Pro Lys Lys Leu
1               5                  10                  15

Thr Pro Leu Ala Tyr Lys Gln Phe Ile Pro Asn Val Ala Glu Lys Thr
             20                  25                  30

Leu Gly Ala Ser Gly Arg Tyr Glu Gly Lys Ile Xaa Arg Asn Ser Glu
         35                  40                  45

Arg Phe Lys Glu Leu Thr Pro Asn Tyr Asn Pro Asp Ile Ile Phe Lys
     50                  55                  60

Asp Glu Glu Asn Thr Gly Ala Asp Arg Leu Met Thr Gln Arg Cys Lys
65                  70                  75                  80

Asp Lys Leu Asn Xaa Leu Ala Ile Ser Val Met Asn Xaa Trp Pro Gly
                 85                  90                  95

Val Xaa Leu Arg Val Thr Glu Gly Trp Asp Glu Asp Gly His His Xaa
            100                 105                 110

Glu Glu Ser Leu His Tyr Glu Gly Arg Ala Val Asp Ile Thr Thr Ser
        115                 120                 125

Asp Arg Asp Xaa Ser Lys Tyr Gly Xaa Leu Xaa Arg Leu Ala Val Glu
    130                 135                 140

Ala Gly Phe Asp Trp Val Tyr Tyr Glu Ser Lys Ala His Ile His Cys
145                 150                 155                 160

Ser Val Lys Ala Glu Asn Ser Val Ala Ala Lys Ser Gly Gly Cys Phe
                165                 170                 175

Pro Gly Ser Ala Xaa Val Xaa Leu Xaa Xaa Gly Gly Xaa Lys Xaa Val
            180                 185                 190

Lys Asp Leu Xaa Pro Gly Asp Xaa Val Leu Ala Ala Asp Xaa Xaa Gly
        195                 200                 205

Xaa Leu Xaa Xaa Ser Asp Phe Xaa Xaa Phe Xaa Asp Arg
    210                 215                 220

(2) INFORMATION FOR SEQ ID NO:41:

(i) SEQUENCE CHARACTERISTICS:
             (A) LENGTH: 167 amino acids
             (B) TYPE: amino acid
             (C) STRANDEDNESS:
             (D) TOPOLOGY: linear (ii) MOLECULE TYPE: peptide (v) FRAGMENT TYPE: internal (xi) SEQUENCE DESCRIPTION: SEQ ID NO:41:

Cys Gly Pro Gly Arg Gly Xaa Xaa Xaa Arg Arg Xaa Xaa Xaa Pro Lys
1               5                  10                  15

Xaa Leu Xaa Pro Leu Xaa Tyr Lys Gln Phe Xaa Pro Xaa Xaa Xaa Glu
             20                  25                  30

Xaa Thr Leu Gly Ala Ser Gly Xaa Xaa Glu Gly Xaa Xaa Xaa Arg Xaa
         35                  40                  45

Ser Glu Arg Phe Xaa Xaa Leu Thr Pro Asn Tyr Asn Pro Asp Ile Ile
```

-continued

```
                50                  55                  60
Phe Lys Asp Glu Glu Asn Xaa Gly Ala Asp Arg Leu Met Thr Xaa Arg
 65                  70                  75                  80

Cys Lys Xaa Xaa Xaa Asn Xaa Leu Ala Ile Ser Val Met Asn Xaa Trp
                 85                  90                  95

Pro Gly Val Xaa Leu Arg Val Thr Glu Gly Xaa Asp Glu Asp Gly His
                100                 105                 110

His Xaa Xaa Xaa Ser Leu His Tyr Glu Gly Arg Ala Xaa Asp Ile Thr
            115                 120                 125

Thr Ser Asp Arg Asp Xaa Xaa Lys Tyr Gly Xaa Leu Xaa Arg Leu Ala
        130                 135                 140

Val Glu Ala Gly Phe Asp Trp Val Tyr Tyr Glu Ser Xaa Xaa His Xaa
145                 150                 155                 160

His Xaa Ser Val Lys Xaa Xaa
                165
```

(2) INFORMATION FOR SEQ ID NO:42:

(i) SEQUENCE CHARACTERISTICS:
      (A) LENGTH: 3900 base pairs
      (B) TYPE: nucleic acid
      (C) STRANDEDNESS: both
      (D) TOPOLOGY: linear (ii) MOLECULE TYPE: cDNA (ix) FEATURE:
      (A) NAME/KEY: CDS
      (B) LOCATION: 1..3897

(xi) SEQUENCE DESCRIPTION: SEQ ID NO:42:

```
ATG GAC CGC GAC AGC CTC CCA CGC GTT CCG GAC ACA CAC GGC GAT GTG        48
Met Asp Arg Asp Ser Leu Pro Arg Val Pro Asp Thr His Gly Asp Val
  1               5                  10                  15

GTC GAT GAG AAA TTA TTC TCG GAT CTT TAC ATA CGC ACC AGC TGG GTG        96
Val Asp Glu Lys Leu Phe Ser Asp Leu Tyr Ile Arg Thr Ser Trp Val
                 20                  25                  30

GAC GCC CAA GTG GCG CTC GAT CAG ATA GAT AAG GGC AAA GCG CGT GGC       144
Asp Ala Gln Val Ala Leu Asp Gln Ile Asp Lys Gly Lys Ala Arg Gly
             35                  40                  45

AGC CGC ACG GCG ATC TAT CTG CGA TCA GTA TTC CAG TCC CAC CTC GAA       192
Ser Arg Thr Ala Ile Tyr Leu Arg Ser Val Phe Gln Ser His Leu Glu
         50                  55                  60

ACC CTC GGC AGC TCC GTG CAA AAG CAC GCG GGC AAG GTG CTA TTC GTG       240
Thr Leu Gly Ser Ser Val Gln Lys His Ala Gly Lys Val Leu Phe Val
 65                  70                  75                  80

GCT ATC CTG GTG CTG AGC ACC TTC TGC GTC GGC CTG AAG AGC GCC CAG       288
Ala Ile Leu Val Leu Ser Thr Phe Cys Val Gly Leu Lys Ser Ala Gln
                 85                  90                  95

ATC CAC TCC AAG GTG CAC CAG CTG TGG ATC CAG GAG GGC GGC GGG CTG       336
Ile His Ser Lys Val His Gln Leu Trp Ile Gln Glu Gly Gly Gly Leu
                100                 105                 110

GAG GCG GAA CTG GCC TAC ACA CAG AAG ACG ATC GGC GAG GAC GAG TCG       384
Glu Ala Glu Leu Ala Tyr Thr Gln Lys Thr Ile Gly Glu Asp Glu Ser
            115                 120                 125

GCC ACG CAT CAG CTG CTC ATT CAG ACG ACC CAC GAC CCG AAC GCC TCC       432
Ala Thr His Gln Leu Leu Ile Gln Thr Thr His Asp Pro Asn Ala Ser
        130                 135                 140

GTC CTG CAT CCG CAG GCG CTG CTT GCC CAC CTG GAG GTC CTG GTC AAG       480
Val Leu His Pro Gln Ala Leu Leu Ala His Leu Glu Val Leu Val Lys
145                 150                 155                 160
```

```
GCC ACC GCC GTC AAG GTG CAC CTC TAC GAC ACC GAA TGG GGG CTG CGC      528
Ala Thr Ala Val Lys Val His Leu Tyr Asp Thr Glu Trp Gly Leu Arg
            165                 170                 175

GAC ATG TGC AAC ATG CCG AGC ACG CCC TCC TTC GAG GGC ATC TAC TAC      576
Asp Met Cys Asn Met Pro Ser Thr Pro Ser Phe Glu Gly Ile Tyr Tyr
                180                 185                 190

ATC GAG CAG ATC CTG CGC CAC CTC ATT CCG TGC TCG ATC ATC ACG CCG      624
Ile Glu Gln Ile Leu Arg His Leu Ile Pro Cys Ser Ile Ile Thr Pro
                195                 200                 205

CTG GAC TGT TTC TGG GAG GGA AGC CAG CTG TTG GGT CCG GAA TCA GCG      672
Leu Asp Cys Phe Trp Glu Gly Ser Gln Leu Leu Gly Pro Glu Ser Ala
    210                 215                 220

GTC GTT ATA CCA GGC CTC AAC CAA CGA CTC CTG TGG ACC ACA CTG AAT      720
Val Val Ile Pro Gly Leu Asn Gln Arg Leu Leu Trp Thr Thr Leu Asn
225                 230                 235                 240

CCC GCC TCT GTG ATG CAG TAT ATG AAG CAG AAG ATG TCC GAG GAA AAG      768
Pro Ala Ser Val Met Gln Tyr Met Lys Gln Lys Met Ser Glu Glu Lys
                245                 250                 255

ATC AGC TTC GAC TTC GAG ACC GTG GAG CAG TAC ATG AAG CGT GCG GCC      816
Ile Ser Phe Asp Phe Glu Thr Val Glu Gln Tyr Met Lys Arg Ala Ala
                260                 265                 270

ATT GCG AGT GGC TAC ATG GAG AAG CCC TGC CTG AAC CCA CTG AAT CCC      864
Ile Ala Ser Gly Tyr Met Glu Lys Pro Cys Leu Asn Pro Leu Asn Pro
                275                 280                 285

AAT TGC CCG GAC ACG GCA CCG AAC AAG AAC AGC ACC CAG CCG CCG GAT      912
Asn Cys Pro Asp Thr Ala Pro Asn Lys Asn Ser Thr Gln Pro Pro Asp
    290                 295                 300

GTG GGA GCC ATC CTG TCC GGA GGC TGC TAC GGT TAT GCC GCG AAG CAC      960
Val Gly Ala Ile Leu Ser Gly Gly Cys Tyr Gly Tyr Ala Ala Lys His
305                 310                 315                 320

ATG CAC TGG CCG GAG GAG CTG ATT GTG GGC GGA GCG AAG AGG AAC CGC     1008
Met His Trp Pro Glu Glu Leu Ile Val Gly Gly Ala Lys Arg Asn Arg
                325                 330                 335

AGC GGA CAC TTG AGG AAG GCC CAG GCC CTG CAG TCG GTG GTG CAG CTG     1056
Ser Gly His Leu Arg Lys Ala Gln Ala Leu Gln Ser Val Val Gln Leu
            340                 345                 350

ATG ACC GAG AAG GAA ATG TAC GAC CAG TGG CAG GAC AAC TAC AAG GTG     1104
Met Thr Glu Lys Glu Met Tyr Asp Gln Trp Gln Asp Asn Tyr Lys Val
    355                 360                 365

CAC CAT CTT GGA TGG ACG CAG GAG AAG GCA GCG GAG GTT TTG AAC GCC     1152
His His Leu Gly Trp Thr Gln Glu Lys Ala Ala Glu Val Leu Asn Ala
370                 375                 380

TGG CAG CGC AAC TTT TCG CGG GAG GTG GAA CAG CTG CTA CGT AAA CAG     1200
Trp Gln Arg Asn Phe Ser Arg Glu Val Glu Gln Leu Leu Arg Lys Gln
385                 390                 395                 400

TCG AGA ATT GCC ACC AAC TAC GAT ATC TAC GTG TTC AGC TCG GCT GCA     1248
Ser Arg Ile Ala Thr Asn Tyr Asp Ile Tyr Val Phe Ser Ser Ala Ala
                405                 410                 415

CTG GAT GAC ATC CTG GCC AAG TTC TCC CAT CCC AGC GCC TTG TCC ATT     1296
Leu Asp Asp Ile Leu Ala Lys Phe Ser His Pro Ser Ala Leu Ser Ile
            420                 425                 430

GTC ATC GGC GTG GCC GTC ACC GTT TTG TAT GCC TTC TGC ACG CTC CTC     1344
Val Ile Gly Val Ala Val Thr Val Leu Tyr Ala Phe Cys Thr Leu Leu
            435                 440                 445

CGC TGG AGG GAC CCC GTC CGT GGA CAG AGC AGT GTC GGC GTG GCC GGA     1392
Arg Trp Arg Asp Pro Val Arg Gly Gln Ser Ser Val Gly Val Ala Gly
    450                 455                 460

GTT CTG CTC ATG TGC TTT AGT ACC GCC GCC GGA TTG GGA TTG TCA GCC     1440
Val Leu Leu Met Cys Phe Ser Thr Ala Ala Gly Leu Gly Leu Ser Ala
```

```
                465                 470                 475                 480
CTG CTC GGT ATC GTT TTC AAT GCC GCC AGC ACC CAG GTG GTT CCG TTT           1488
Leu Leu Gly Ile Val Phe Asn Ala Ala Ser Thr Gln Val Val Pro Phe
                        485                 490                 495

TTG GCC CTT GGT CTG GGC GTC GAT CAC ATC TTC ATG CTG ACC GCT GCC           1536
Leu Ala Leu Gly Leu Gly Val Asp His Ile Phe Met Leu Thr Ala Ala
                500                 505                 510

TAT GCG GAG AGC AAT CGG CGG GAG CAG ACC AAG CTG ATT CTC AAG AAA           1584
Tyr Ala Glu Ser Asn Arg Arg Glu Gln Thr Lys Leu Ile Leu Lys Lys
                515                 520                 525

GTG GGA CCA AGC ATC CTG TTC AGT GCC TGC AGC ACC GCA GGA TCC TTC           1632
Val Gly Pro Ser Ile Leu Phe Ser Ala Cys Ser Thr Ala Gly Ser Phe
        530                 535                 540

TTT GCG GCC GCC TTT ATT CCG GTG CCG GCT TTG AAG GTA TTC TGT CTG           1680
Phe Ala Ala Ala Phe Ile Pro Val Pro Ala Leu Lys Val Phe Cys Leu
545                 550                 555                 560

CAG GCT GCC ATC GTA ATG TGC TCC AAT TTG GCA GCG GCT CTA TTG GTT           1728
Gln Ala Ala Ile Val Met Cys Ser Asn Leu Ala Ala Ala Leu Leu Val
                565                 570                 575

TTT CCG GCC ATG ATT TCG TTG GAT CTA CGG AGA CGT ACC GCC GGC AGG           1776
Phe Pro Ala Met Ile Ser Leu Asp Leu Arg Arg Arg Thr Ala Gly Arg
                580                 585                 590

GCG GAC ATC TTC TGC TGC TGT TTT CCG GTG TGG AAG GAA CAG CCG AAG           1824
Ala Asp Ile Phe Cys Cys Cys Phe Pro Val Trp Lys Glu Gln Pro Lys
                595                 600                 605

GTG GCA CCA CCG GTG CTG CCG CTG AAC AAC AAC AAC GGG CGC GGG GCC           1872
Val Ala Pro Pro Val Leu Pro Leu Asn Asn Asn Asn Gly Arg Gly Ala
        610                 615                 620

CGG CAT CCG AAG AGC TGC AAC AAC AAC AGG GTG GCG CTG CCC GCC CAG           1920
Arg His Pro Lys Ser Cys Asn Asn Asn Arg Val Ala Leu Pro Ala Gln
625                 630                 635                 640

AAT CCT CTG CTG GAA CAG AGG GCA GAC ATC CCT GGG AGC AGT CAC TCA           1968
Asn Pro Leu Leu Glu Gln Arg Ala Asp Ile Pro Gly Ser Ser His Ser
                645                 650                 655

CTG GCG TCC TTC TCT CTG GCA ACA TTC GCC TTT CAG CAC TAC ACT CCC           2016
Leu Ala Ser Phe Ser Leu Ala Thr Phe Ala Phe Gln His Tyr Thr Pro
                660                 665                 670

TTC CTC ATG CGC AGC TGG GTG AAG TTC CTG ACC GTT ATG GGT TTC CTG           2064
Phe Leu Met Arg Ser Trp Val Lys Phe Leu Thr Val Met Gly Phe Leu
                675                 680                 685

GCG GCC CTC ATA TCC AGC TTG TAT GCC TCC ACG CGC CTT CAG GAT GGC           2112
Ala Ala Leu Ile Ser Ser Leu Tyr Ala Ser Thr Arg Leu Gln Asp Gly
                690                 695                 700

CTG GAC ATT ATT GAT CTG GTG CCC AAG GAC AGC AAC GAG CAC AAG TTC           2160
Leu Asp Ile Ile Asp Leu Val Pro Lys Asp Ser Asn Glu His Lys Phe
705                 710                 715                 720

CTG GAT GCT CAA ACT CGG CTC TTT GGC TTC TAC AGC ATG TAT GCG GTT           2208
Leu Asp Ala Gln Thr Arg Leu Phe Gly Phe Tyr Ser Met Tyr Ala Val
                725                 730                 735

ACC CAG GGC AAC TTT GAA TAT CCC ACC CAG CAG CAG TTG CTC AGG GAC           2256
Thr Gln Gly Asn Phe Glu Tyr Pro Thr Gln Gln Gln Leu Leu Arg Asp
                740                 745                 750

TAC CAT GAT TCC TTT GTG CGG GTG CCA CAT GTG ATC AAG AAT GAT AAT           2304
Tyr His Asp Ser Phe Val Arg Val Pro His Val Ile Lys Asn Asp Asn
                755                 760                 765

GGT GGA CTG CCG GAC TTC TGG CTG CTC CTC TTC AGC GAG TGG CTG GGT           2352
Gly Gly Leu Pro Asp Phe Trp Leu Leu Leu Phe Ser Glu Trp Leu Gly
        770                 775                 780

AAT CTG CAA AAG ATA TTC GAC GAG GAA TAC CGC GAC GGA CGG CTG ACC           2400
```

```
                                                            -continued

Asn Leu Gln Lys Ile Phe Asp Glu Glu Tyr Arg Asp Gly Arg Leu Thr
785                 790                 795                 800

AAG GAG TGC TGG TTC CCA AAC GCC AGC AGC GAT GCC ATC CTG GCC TAC      2448
Lys Glu Cys Trp Phe Pro Asn Ala Ser Ser Asp Ala Ile Leu Ala Tyr
                    805                 810                 815

AAG CTA ATC GTG CAA ACC GGC CAT GTG GAC AAC CCC GTG GAC AAG GAA      2496
Lys Leu Ile Val Gln Thr Gly His Val Asp Asn Pro Val Asp Lys Glu
                820                 825                 830

CTG GTG CTC ACC AAT CGC CTG GTC AAC AGC GAT GGC ATC ATC AAC CAA      2544
Leu Val Leu Thr Asn Arg Leu Val Asn Ser Asp Gly Ile Ile Asn Gln
            835                 840                 845

CGC GCC TTC TAC AAC TAT CTG TCG GCA TGG GCC ACC AAC GCG TCT TCG      2592
Arg Ala Phe Tyr Asn Tyr Leu Ser Ala Trp Ala Thr Asn Ala Ser Ser
        850                 855                 860

CCT ACG GAG CTT CTC AGG GCA AAT TGT ATC CGG AAC CGC GCC AAC GGA      2640
Pro Thr Glu Leu Leu Arg Ala Asn Cys Ile Arg Asn Arg Ala Asn Gly
865                 870                 875                 880

GCT TCT CAG GGC AAA TTG TAT CCG GAA CCG CGC CAG TAT TTT CAC CAA      2688
Ala Ser Gln Gly Lys Leu Tyr Pro Glu Pro Arg Gln Tyr Phe His Gln
                    885                 890                 895

CCC AAC GAG TAC GAT CTT AAG ATA CCC AAG AGT CTG CCA TTG GTC TAC      2736
Pro Asn Glu Tyr Asp Leu Lys Ile Pro Lys Ser Leu Pro Leu Val Tyr
                900                 905                 910

GCT CAG ATG CCC TTT TAC CTC CAC GGA CTA ACA GAT ACC TCG CAG ATC      2784
Ala Gln Met Pro Phe Tyr Leu His Gly Leu Thr Asp Thr Ser Gln Ile
            915                 920                 925

AAG ACC CTG ATA GGT CAT ATT CGC GAC CTG AGC GTC AAG TAC GAG GGC      2832
Lys Thr Leu Ile Gly His Ile Arg Asp Leu Ser Val Lys Tyr Glu Gly
        930                 935                 940

TTC GGC CTG CCC AAC TAT CCA TCG GGC ATT CCC TTC ATC TTC TGG GAG      2880
Phe Gly Leu Pro Asn Tyr Pro Ser Gly Ile Pro Phe Ile Phe Trp Glu
945                 950                 955                 960

CAG TAC ATG ACC CTG CGC TCC TCA CTG GCC ATG ATC CTG GCC TGC GTG      2928
Gln Tyr Met Thr Leu Arg Ser Ser Leu Ala Met Ile Leu Ala Cys Val
                    965                 970                 975

CTA CTC GCC GCC CTG GTG CTG GTC TCC CTG CTC CTG CTC TCC GTT TGG      2976
Leu Leu Ala Ala Leu Val Leu Val Ser Leu Leu Leu Leu Ser Val Trp
                980                 985                 990

GCC GCC GTT CTC GTG ATC CTC AGC GTT CTG GCC TCG CTG GCC CAG ATC      3024
Ala Ala Val Leu Val Ile Leu Ser Val Leu Ala Ser Leu Ala Gln Ile
            995                 1000                1005

TTT GGG GCC ATG ACT CTG CTG GGC ATC AAA CTC TCG GCC ATT CCG GCA      3072
Phe Gly Ala Met Thr Leu Leu Gly Ile Lys Leu Ser Ala Ile Pro Ala
        1010                1015                1020

GTC ATA CTC ATC CTC AGC GTG GGC ATG ATG CTG TGC TTC AAT GTG CTG      3120
Val Ile Leu Ile Leu Ser Val Gly Met Met Leu Cys Phe Asn Val Leu
1025                1030                1035                1040

ATA TCA CTG GGC TTC ATG ACA TCC GTT GGC AAC CGA CAG CGC CGC GTC      3168
Ile Ser Leu Gly Phe Met Thr Ser Val Gly Asn Arg Gln Arg Arg Val
                    1045                1050                1055

CAG CTG AGC ATG CAG ATG TCC CTG GGA CCA CTT GTC CAC GGC ATG CTG      3216
Gln Leu Ser Met Gln Met Ser Leu Gly Pro Leu Val His Gly Met Leu
                1060                1065                1070

ACC TCC GGA GTG GCC GTG TTC ATG CTC TCC ACG TCG CCC TTT GAG TTT      3264
Thr Ser Gly Val Ala Val Phe Met Leu Ser Thr Ser Pro Phe Glu Phe
            1075                1080                1085

GTG ATC CGG CAC TTC TGC TGG CTT CTG CTG GTG GTC TTA TGC GTT GGC      3312
Val Ile Arg His Phe Cys Trp Leu Leu Leu Val Val Leu Cys Val Gly
        1090                1095                1100
```

```
GCC TGC AAC AGC CTT TTG GTG TTC CCC ATC CTA CTG AGC ATG GTG GGA      3360
Ala Cys Asn Ser Leu Leu Val Phe Pro Ile Leu Leu Ser Met Val Gly
1105                1110                1115                1120

CCG GAG GCG GAG CTG GTG CCG CTG GAG CAT CCA GAC CGC ATA TCC ACG      3408
Pro Glu Ala Glu Leu Val Pro Leu Glu His Pro Asp Arg Ile Ser Thr
            1125                1130                1135

CCC TCT CCG CTG CCC GTG CGC AGC AGC AAG AGA TCG GGC AAA TCC TAT      3456
Pro Ser Pro Leu Pro Val Arg Ser Ser Lys Arg Ser Gly Lys Ser Tyr
        1140                1145                1150

GTG GTG CAG GGA TCG CGA TCC TCG CGA GGC AGC TGC CAG AAG TCG CAT      3504
Val Val Gln Gly Ser Arg Ser Ser Arg Gly Ser Cys Gln Lys Ser His
            1155                1160                1165

CAC CAC CAC CAC AAA GAC CTT AAT GAT CCA TCG CTG ACG ACG ATC ACC      3552
His His His His Lys Asp Leu Asn Asp Pro Ser Leu Thr Thr Ile Thr
        1170                1175                1180

GAG GAG CCG CAG TCG TGG AAG TCC AGC AAC TCG TCC ATC CAG ATG CCC      3600
Glu Glu Pro Gln Ser Trp Lys Ser Ser Asn Ser Ser Ile Gln Met Pro
1185                1190                1195                1200

AAT GAT TGG ACC TAC CAG CCG CGG GAA CAG CGA CCC GCC TCC TAC GCG      3648
Asn Asp Trp Thr Tyr Gln Pro Arg Glu Gln Arg Pro Ala Ser Tyr Ala
            1205                1210                1215

GCC CCG CCC CCC GCC TAT CAC AAG GCC GCC GCC CAG CAG CAC CAC CAG      3696
Ala Pro Pro Pro Ala Tyr His Lys Ala Ala Ala Gln Gln His His Gln
        1220                1225                1230

CAT CAG GGC CCG CCC ACA ACG CCC CCG CCG CCC TTC CCG ACG GCC TAT      3744
His Gln Gly Pro Pro Thr Thr Pro Pro Pro Pro Phe Pro Thr Ala Tyr
        1235                1240                1245

CCG CCG GAG CTG CAG AGC ATC GTG GTG CAG CCG GAG GTG ACG GTG GAG      3792
Pro Pro Glu Leu Gln Ser Ile Val Val Gln Pro Glu Val Thr Val Glu
1250                1255                1260

ACG ACG CAC TCG GAC AGC AAC ACC ACC AAG GTG ACG GCC ACG GCC AAC      3840
Thr Thr His Ser Asp Ser Asn Thr Thr Lys Val Thr Ala Thr Ala Asn
1265                1270                1275                1280

ATC AAG GTG GAG CTG GCC ATG CCC GGC AGG GCG GTG CGC AGC TAT AAC      3888
Ile Lys Val Glu Leu Ala Met Pro Gly Arg Ala Val Arg Ser Tyr Asn
            1285                1290                1295

TTT ACG AGT TAG                                                      3900
Phe Thr Ser (2) INFORMATION FOR SEQ ID NO:43:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:43:

ACCGAGGGCT GGGACGAAGA TGGC                                           24

(2) INFORMATION FOR SEQ ID NO:44:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:44:
```

CGCTCGGTCG TACGGCATGA ACGAC                                         25

(2) INFORMATION FOR SEQ ID NO:45:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:45:

ATGGGGATGT GTGTGTGGTC AAGTGTA                                       27

(2) INFORMATION FOR SEQ ID NO:46:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:46:

TTCACAGACT CTCAAAGTGT ATTTT                                         25

(2) INFORMATION FOR SEQ ID NO:47:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:47:

Met Gly Ser Ser His His His His His His Leu Val Pro Arg Gly Ser
1               5                   10                  15

His Met (2) INFORMATION FOR SEQ ID NO:48:

(i) SEQUENCE CHARACTERISTICS:
        (A) LENGTH: 1299 amino acids
        (B) TYPE: amino acid
        (D) TOPOLOGY: linear (ii) MOLECULE TYPE: protein (xi) SEQUENCE DESCRIPTION: SEQ ID NO:48:

Met Asp Arg Asp Ser Leu Pro Arg Val Pro Asp Thr His Gly Asp Val
1               5                   10                  15

Val Asp Glu Lys Leu Phe Ser Asp Leu Tyr Ile Arg Thr Ser Trp Val
                20                  25                  30

Asp Ala Gln Val Ala Leu Asp Gln Ile Asp Lys Gly Lys Ala Arg Gly
            35                  40                  45

Ser Arg Thr Ala Ile Tyr Leu Arg Ser Val Phe Gln Ser His Leu Glu
        50                  55                  60

Thr Leu Gly Ser Ser Val Gln Lys His Ala Gly Lys Val Leu Phe Val
65                  70                  75                  80

-continued

```
Ala Ile Leu Val Leu Ser Thr Phe Cys Val Gly Leu Lys Ser Ala Gln
             85                  90                  95

Ile His Ser Lys Val His Gln Leu Trp Ile Gln Glu Gly Gly Gly Leu
            100                 105                 110

Glu Ala Glu Leu Ala Tyr Thr Gln Lys Thr Ile Gly Glu Asp Glu Ser
            115                 120                 125

Ala Thr His Gln Leu Leu Ile Gln Thr Thr His Asp Pro Asn Ala Ser
        130                 135                 140

Val Leu His Pro Gln Ala Leu Leu Ala His Leu Glu Val Leu Val Lys
145                 150                 155                 160

Ala Thr Ala Val Lys Val His Leu Tyr Asp Thr Glu Trp Gly Leu Arg
                165                 170                 175

Asp Met Cys Asn Met Pro Ser Thr Pro Ser Phe Glu Gly Ile Tyr Tyr
            180                 185                 190

Ile Glu Gln Ile Leu Arg His Leu Ile Pro Cys Ser Ile Ile Thr Pro
            195                 200                 205

Leu Asp Cys Phe Trp Glu Gly Ser Gln Leu Leu Gly Pro Glu Ser Ala
        210                 215                 220

Val Val Ile Pro Gly Leu Asn Gln Arg Leu Leu Trp Thr Thr Leu Asn
225                 230                 235                 240

Pro Ala Ser Val Met Gln Tyr Met Lys Gln Lys Met Ser Glu Glu Lys
                245                 250                 255

Ile Ser Phe Asp Phe Glu Thr Val Glu Gln Tyr Met Lys Arg Ala Ala
            260                 265                 270

Ile Ala Ser Gly Tyr Met Glu Lys Pro Cys Leu Asn Pro Leu Asn Pro
        275                 280                 285

Asn Cys Pro Asp Thr Ala Pro Asn Lys Asn Ser Thr Gln Pro Pro Asp
    290                 295                 300

Val Gly Ala Ile Leu Ser Gly Gly Cys Tyr Gly Tyr Ala Ala Lys His
305                 310                 315                 320

Met His Trp Pro Glu Glu Leu Ile Val Gly Gly Ala Lys Arg Asn Arg
                325                 330                 335

Ser Gly His Leu Arg Lys Ala Gln Ala Leu Gln Ser Val Val Gln Leu
            340                 345                 350

Met Thr Glu Lys Glu Met Tyr Asp Gln Trp Gln Asp Asn Tyr Lys Val
        355                 360                 365

His His Leu Gly Trp Thr Gln Glu Lys Ala Ala Glu Val Leu Asn Ala
    370                 375                 380

Trp Gln Arg Asn Phe Ser Arg Glu Val Glu Gln Leu Leu Arg Lys Gln
385                 390                 395                 400

Ser Arg Ile Ala Thr Asn Tyr Asp Ile Tyr Val Phe Ser Ser Ala Ala
                405                 410                 415

Leu Asp Asp Ile Leu Ala Lys Phe Ser His Pro Ser Ala Leu Ser Ile
            420                 425                 430

Val Ile Gly Val Ala Val Thr Val Leu Tyr Ala Phe Cys Thr Leu Leu
        435                 440                 445

Arg Trp Arg Asp Pro Val Arg Gly Gln Ser Ser Val Gly Val Ala Gly
    450                 455                 460

Val Leu Leu Met Cys Phe Ser Thr Ala Ala Gly Leu Gly Leu Ser Ala
465                 470                 475                 480

Leu Leu Gly Ile Val Phe Asn Ala Ala Ser Thr Gln Val Val Pro Phe
                485                 490                 495

Leu Ala Leu Gly Leu Gly Val Asp His Ile Phe Met Leu Thr Ala Ala
```

-continued

```
              500                 505                 510
Tyr Ala Glu Ser Asn Arg Arg Glu Gln Thr Lys Leu Ile Leu Lys Lys
        515                 520                 525

Val Gly Pro Ser Ile Leu Phe Ser Ala Cys Ser Thr Ala Gly Ser Phe
530                 535                 540

Phe Ala Ala Ala Phe Ile Pro Val Pro Ala Leu Lys Val Phe Cys Leu
545                 550                 555                 560

Gln Ala Ala Ile Val Met Cys Ser Asn Leu Ala Ala Leu Leu Val
            565                 570                 575

Phe Pro Ala Met Ile Ser Leu Asp Leu Arg Arg Thr Ala Gly Arg
            580                 585                 590

Ala Asp Ile Phe Cys Cys Cys Phe Pro Val Trp Lys Glu Gln Pro Lys
        595                 600                 605

Val Ala Pro Pro Val Leu Pro Leu Asn Asn Asn Gly Arg Gly Ala
        610                 615                 620

Arg His Pro Lys Ser Cys Asn Asn Asn Arg Val Ala Leu Pro Ala Gln
625                 630                 635                 640

Asn Pro Leu Leu Glu Gln Arg Ala Asp Ile Pro Gly Ser Ser His Ser
            645                 650                 655

Leu Ala Ser Phe Ser Leu Ala Thr Phe Ala Phe Gln His Tyr Thr Pro
            660                 665                 670

Phe Leu Met Arg Ser Trp Val Lys Phe Leu Thr Val Met Gly Phe Leu
            675                 680                 685

Ala Ala Leu Ile Ser Ser Leu Tyr Ala Ser Thr Arg Leu Gln Asp Gly
        690                 695                 700

Leu Asp Ile Ile Asp Leu Val Pro Lys Asp Ser Asn Glu His Lys Phe
705                 710                 715                 720

Leu Asp Ala Gln Thr Arg Leu Phe Gly Phe Tyr Ser Met Tyr Ala Val
                725                 730                 735

Thr Gln Gly Asn Phe Glu Tyr Pro Thr Gln Gln Leu Leu Arg Asp
            740                 745                 750

Tyr His Asp Ser Phe Val Arg Val Pro His Val Ile Lys Asn Asp Asn
            755                 760                 765

Gly Gly Leu Pro Asp Phe Trp Leu Leu Phe Ser Glu Trp Leu Gly
770                 775                 780

Asn Leu Gln Lys Ile Phe Asp Glu Tyr Arg Asp Gly Arg Leu Thr
785                 790                 795                 800

Lys Glu Cys Trp Phe Pro Asn Ala Ser Ser Asp Ala Ile Leu Ala Tyr
                805                 810                 815

Lys Leu Ile Val Gln Thr Gly His Val Asp Asn Pro Val Asp Lys Glu
            820                 825                 830

Leu Val Leu Thr Asn Arg Leu Val Asn Ser Asp Gly Ile Ile Asn Gln
            835                 840                 845

Arg Ala Phe Tyr Asn Tyr Leu Ser Ala Trp Ala Thr Asn Ala Ser Ser
850                 855                 860

Pro Thr Glu Leu Leu Arg Ala Asn Cys Ile Arg Asn Arg Ala Asn Gly
865                 870                 875                 880

Ala Ser Gln Gly Lys Leu Tyr Pro Glu Pro Arg Gln Tyr Phe His Gln
                885                 890                 895

Pro Asn Glu Tyr Asp Leu Lys Ile Pro Lys Ser Leu Pro Leu Val Tyr
                900                 905                 910

Ala Gln Met Pro Phe Tyr Leu His Gly Leu Thr Asp Thr Ser Gln Ile
            915                 920                 925
```

-continued

```
Lys Thr Leu Ile Gly His Ile Arg Asp Leu Ser Val Lys Tyr Glu Gly
    930             935                 940
Phe Gly Leu Pro Asn Tyr Pro Ser Gly Ile Pro Phe Ile Phe Trp Glu
945             950                 955                 960
Gln Tyr Met Thr Leu Arg Ser Ser Leu Ala Met Ile Leu Ala Cys Val
            965                 970                 975
Leu Leu Ala Ala Leu Val Leu Val Ser Leu Leu Leu Ser Val Trp
            980                 985                 990
Ala Ala Val Leu Val Ile Leu Ser Val Leu Ala Ser Leu Ala Gln Ile
            995                 1000                1005
Phe Gly Ala Met Thr Leu Leu Gly Ile Lys Leu Ser Ala Ile Pro Ala
            1010                1015                1020
Val Ile Leu Ile Leu Ser Val Gly Met Met Leu Cys Phe Asn Val Leu
1025            1030                1035                1040
Ile Ser Leu Gly Phe Met Thr Ser Val Gly Asn Arg Gln Arg Arg Val
            1045                1050                1055
Gln Leu Ser Met Gln Met Ser Leu Gly Pro Leu Val His Gly Met Leu
            1060                1065                1070
Thr Ser Gly Val Ala Val Phe Met Leu Ser Thr Ser Pro Phe Glu Phe
            1075                1080                1085
Val Ile Arg His Phe Cys Trp Leu Leu Leu Val Val Leu Cys Val Gly
            1090                1095                1100
Ala Cys Asn Ser Leu Leu Val Phe Pro Ile Leu Leu Ser Met Val Gly
1105            1110                1115                1120
Pro Glu Ala Glu Leu Val Pro Leu Glu His Pro Asp Arg Ile Ser Thr
            1125                1130                1135
Pro Ser Pro Leu Pro Val Arg Ser Ser Lys Arg Ser Gly Lys Ser Tyr
            1140                1145                1150
Val Val Gln Gly Ser Arg Ser Ser Arg Gly Ser Cys Gln Lys Ser His
            1155                1160                1165
His His His His Lys Asp Leu Asn Asp Pro Ser Leu Thr Thr Ile Thr
            1170                1175                1180
Glu Glu Pro Gln Ser Trp Lys Ser Ser Asn Ser Ser Ile Gln Met Pro
1185            1190                1195                1200
Asn Asp Trp Thr Tyr Gln Pro Arg Glu Gln Arg Pro Ala Ser Tyr Ala
            1205                1210                1215
Ala Pro Pro Pro Ala Tyr His Lys Ala Ala Ala Gln Gln His His Gln
            1220                1225                1230
His Gln Gly Pro Pro Thr Thr Pro Pro Pro Phe Pro Thr Ala Tyr
            1235                1240                1245
Pro Pro Glu Leu Gln Ser Ile Val Val Gln Pro Glu Val Thr Val Glu
            1250                1255                1260
Thr Thr His Ser Asp Ser Asn Thr Thr Lys Val Thr Ala Thr Ala Asn
1265            1270                1275                1280
Ile Lys Val Glu Leu Ala Met Pro Gly Arg Ala Val Arg Ser Tyr Asn
            1285                1290                1295
Phe Thr Ser
```

COMPOSITIONS COMPRISING HEDGEHOG PROTEINS

RELATED APPLICATIONS

This application is a continuation of application Ser. No. 08/462,386, filed Jun. 5, 1995, which is a continuation-in-part of application Ser. No. 08/435,093, filed May 4, 1995, now abandoned, which is a continuation-in-part of application Ser. No. 08/356,060, filed Dec. 14, 1994, now U.S. Pat. No. 5,844,079, which is a continuation-in-part of application Ser. No. 08/176,427 filed Dec. 30, 1993, now U.S. Pat. No. 5,789,543, the teachings of each of which are incorporated herein by reference.

FUNDING

Work described herein was supported by Grant Number HD 27222-01 awarded by the National Institutes of Health. The United States Government has certain rights in the invention.

BACKGROUND OF THE INVENTION

Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are essential to embryonic patterning in vertebrate development from the earliest establishment of the body plan, to the patterning of the organ systems, to the generation of diverse cell types during tissue differentiation (Davidson, E., (1990) *Development.* 108: 365–389; Gurdon, J. B., (1992) *Cell* 68: 185–199; Jessell, T. M. et al., (1992) *Cell* 68: 257–270). The effects of developmental cell interactions are varied. Typically, responding cells are diverted from one route of cell differentiation to another by inducing cells that differ from both the uninduced and induced states of the responding cells (inductions). Sometimes cells induce their neighbors to differentiate like themselves (homoiogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation (J. B. Gurdon (1992) *Cell* 68:185–199).

The origin of the nervous system in all vertebrates can be traced to the end of gastrulation. At this time, the ectoderm in the dorsal side of the embryo changes its fate from epidermal to neural. The newly formed neuroectoderm thickens to form a flattened structure called the neural plate which is characterized, in some vertebrates, by a central groove (neural groove) and thickened lateral edges (neural folds). At its early stages of differentiation, the neural plate already exhibits signs of regional differentiation along its anterior posterior (A-P) and mediolateral axis (M-L). The neural folds eventually fuse at the dorsal midline to form the neural tube which will differentiate into brain at its anterior end and spinal cord at its posterior end. Closure of the neural tube creates dorsal/ventral differences by virtue of previous mediolateral differentiation. Thus, at the end of neurulation, the neural tube has a clear anterior-posterior (A-P), dorsal ventral (D-V) and mediolateral (M-L) polarities (see, for example, *Principles in Neural Science* (3rd), eds. Kandel, Schwartz and Jessell, Elsevier Science Publishing Company: NY, 1991; and *Developmental Biology* (3rd), ed. S. F. Gilbert, Sinauer Associates: Sunderland Mass., 1991). Inductive interactions that define the fate of cells within the neural tube establish the initial pattern of the embryonic vertebrate nervous system. In the spinal cord, the identify of cell types is controlled, in part, by signals from two midline cell groups, the notochord and floor plate, that induce neural plate cells to differentiate into floor plate, motor neurons, and other ventral neuronal types (van Straaten et al. (1988) *Anat. Embryol.* 177:317–324; Placzek et al. (1993) *Development* 117:205–218; Yamada et al. (1991) *Cell* 64:035–647; and Hatta et al. (1991) *Nature* 350:339–341). In addition, signals from the floor plate are responsible for the orientation and direction of commissural neuron outgrowth (Placzek, M. et al., (1990) *Development* 110: 19–30). Besides patterning the neural tube, the notochord and floor-plate are also responsible for producing signals which control the patterning of the somites by inhibiting differentiation of dorsal somite derivatives in the ventral regions (Brand-Saberi, B. et al., (1993) *Anat. Embryol.* 188: 239–245; Porquie, O. et al., (1993) *Proc. Natl. Acad. Sci. USA* 90: 5242–5246).

Another important signaling center exists in the posterior mesenchyme of developing limb buds, called the Zone of Polarizing Activity, or "ZPA". When tissue from the posterior region of the limb bud is grafted to the anterior border of a second limb bud, the resultant limb will develop with additional digits in a mirror-image sequence along the anteroposterior axis (Saunders and Gasseling, (1968) *Epithelial-Mesenchymal Interaction,* pp. 78–97). This finding has led to the model that the ZPA is responsible for normal anteroposterior patterning in the limb. The ZPA has been hypothesized to function by releasing a signal, termed a "morphogen", which forms a gradient across the early embryonic bud. According to this model, the fate of cells at different distances from the ZPA is determined by the local concentration of the morphogen, with specific thresholds of the morphogen inducing successive structures (Wolpert, (1969) *Theor. Biol.* 25:1–47). This is supported by the finding that the extent of digit duplication is proportional to the number of implanted ZPA cells (Tickle, (1981) *Nature* 254:199–202).

A candidate for the putative ZPA morphogen was identified by the discovery that a source of retinoic acid can result in the same type of mirror-image digit duplications when placed in the anterior of a limb bud (Tickle et al., (1982) *Nature* 296:564–565; Summerbell, (1983) *J. Embryol* 78:269–289). The response to exogenous retinoic acid is concentration dependent as the morphogen model demands (Tickle et al., (1985) *Dev. Biol.* 109:82–95). Moreover, a differential distribution of retinoic acid exists across the limb bud, with a higher concentration in the ZPA region (Thaller and Eichele, (1987) *Nature* 327:625–628).

Recent evidence, however, has indicated that retinoic acid is unlikely to be the endogenous factor responsible for ZPA activity (reviewed in Brockes, (1991) *Nature* 350:15; Tabin, (1991) *Cell* 66:199–217). It is now believed that rather than directly mimicking an endogenous signal, retinoic acid implants act by inducing an ectopic ZPA. The anterior limb tissue just distal to a retinoic acid implant and directly under the ectoderm has been demonstrated to acquire ZPA activity by serially transplanting that tissue to another limb bud (Summerbell and Harvey, (1983) *Limb Development and Regeneration* pp. 109–118; Wanek et al., (1991) *Nature* 350:81–83). Conversely, the tissue next to a ZPA graft does not gain ZPA activity (Smith, (1979) *J. Embryol* 52:105–113). Exogenous retinoic acid would thus appear to act upstream of the ZPA in limb patterning.

The immediate downstream targets of ZPA action are not known. However, one important set of genes which are ectopically activated during ZPA-induced pattern duplications are the 5' genes of the Hoxd cluster. These genes are normally expressed in a nested pattern emanating from the posterior margin of the limb bud (Dolle et al., (1989) *Nature* 342:767–772; Izpisua-Belmonte et al., (1991) *Nature* 350:585–589). This nested pattern of Hox gene expression has been directly demonstrated to determine the identity of the structures produced along the anteroposterior axis of the limb (Morgan et al., (1993) *Nature* 358:236–239). As this would predict, ZPA grafts which produce mirror-image duplication of structures at an anatomical level first lead to the ectopic activation of the Hoxd genes in a mirror-image duplication at the molecular level. (Nohno et al., (1991) *Cell* 64:1197–1205; Izpisua-Belmonte et al., (1991) *Nature* 350:585–589). The molecular signals which regulate the expression of these important genes are currently not understood.

SUMMARY OF THE INVENTION

The present invention relates to the discovery of a novel family of genes, and gene products, expressed in vertebrate organisms, which genes referred to hereinafter as the "hedgehog" gene family, the products of which are referred to as hedgehog proteins. The products of the hedgehog gene have apparent broad involvement in the formation and maintenance of ordered spatial arrangements of differentiated tissues in vertebrates, both adult and embryonic, and can be used to generate and/or maintain an array of different vertebrate tissue both in vitro and in vivo.

In general, the invention features hedgehog polypeptides, preferably substantially pure preparations of one or more of the subject hedgehog polypeptides. The invention also provides recombinantly produced hedgehog polypeptides. In preferred embodiments the polypeptide has a biological activity including: an ability to modulate proliferation, survival and/or differentiation of mesodermally-derived tissue, such as tissue derived from dorsal mesoderm; the ability to modulate proliferation, survival and/or differentiation of ectodermally-derived tissue, such as tissue derived from the neural tube, neural crest, or head mesenchyme; the ability to modulate proliferation, survival and/or differentiation of endodermally-derived tissue, such as tissue derived from the primitive gut. Moreover, in preferred embodiments, the subject hedgehog proteins have the ability to induce expression of secondary signaling molecules, such as members of the Transforming Growth Factor β family, as well as members of the fibroblast growth factor (FGF) family.

In a preferred embodiment, the polypeptide is identical with or homologous to a Sonic hedgehog (Shh) polypeptide, such as a mammalian Shh represented by SEQ ID Nos:13 or 11, an avian Shh represented by SEQ ID No:8, or a fish Shh represented by SEQ ID No:12. For instance, the Shh polypeptide preferably has an amino acid sequence at least 60% homologous to a polypeptide represented by any of SEQ ID Nos: 8, 11, 12 or 13, though polypeptides with higher sequence homologies of, for example, 80%, 90% or 95% are also contemplated. Exemplary Shh proteins are represented by SEQ ID No. 40. The Shh polypeptide can comprise a full length protein, such as represented in the sequence listings, or it can comprise a fragment of, for instance, at least 5, 10, 20, 50, 100, 150 or 200 amino acids in length. Preferred hedgehog polypeptides include Shh sequences corresponding approximately to the natural proteolytic fragments of the hedgehog proteins, such as from about Cys-24 through about the region that contains the proteolytic processing site, e.g., Ala-194 to Gly-203, or from about Cys-198 through Ala-475 of the human Shh protein, or analogous fragments thereto.

In another preferred embodiment, the polypeptide is identical with or homologous to an Indian hedgehog (Ihh) polypeptide, such as a human Ihh represented by SEQ ID No:14, or a mouse Ihh represented by SEQ ID No:10. For instance, the Ihh polypeptide preferably has an amino acid sequence at least 60% homologous to a polypeptide represented by either of SEQ ID Nos: 10 or 14, though Ihh polypeptides with higher sequence homologies of, for example, 80%, 90% or 95% are also contemplated. The polypeptide can comprise the full length protein represented by in part by these sequences, or it can comprise a fragment of, for instance, at least 5, 10, 20, 50, 100, 150 or 200 amino acids in length. Preferred Ihh polypeptides comprise an N-terminal fragment from Cys-28 through the region that contains the proteolytic processing site, e.g., Ala-198 to Gly-207, or a C-terminal fragment from about Cys-203 through Ser-411 of the mouse Ihh represented by SEQ ID No:10, or analogous fragments thereto.

In still a further preferred embodiment, the polypeptide is identical with or homologous to a Desert hedgehog (Dhh) polypeptide, such as a mouse Dhh represented by SEQ ID No:9. For instance, the Dhh polypeptide preferably has an amino acid sequence at least 60% homologous to a polypeptide represented by SEQ ID No:9, though Dhh polypeptides with higher sequence homologies of, for example, 80%, 90% or 95% are also contemplated. The polypeptide can comprise the full length protein represented by this sequence, or it can comprise a fragment of, for instance, at least 5, 10, 20, 50, 100, 150 or 200 amino acids in length. Preferred Dhh polypeptides comprise Dhh sequences corresponding to the N-terminal portion of the protein from about Cys-23 through about the region that contains the proteolytic processing site, e.g., Val-124 to Asn-203 or C-terminal fragment from about Cys-199 through Gly-396 of SEQ ID No:9, or analogous fragments thereto.

In another preferred embodiment, the invention features a purified or recombinant polypeptide fragment of a hedgehog protein, which polypeptide has the ability to modulate, e.g., mimic or antagonize, a the activity of a wild-type hedgehog protein. Preferably, the polypeptide fragment comprises a sequence identical or homologous to an amino acid sequence designated in one of SEQ ID No:8, SEQ ID No:9, SEQ ID No:10, SEQ ID No:11, SEQ ID No:12, SEQ ID No:13, or SEQ ID No:14. More preferably, the polypeptide fragment comprises an amino acid sequence designated in SEQ ID No:40, e.g., includes the fragment of Cys-1 to Gly-174.

In yet another preferred embodiment, the invention features a purified or recombinant polypeptide, which polypeptide has a molecular weight of approximately 19 kDa and has the ability to modulate, e.g., mimic or antagonize, a the activity of a wild-type hedgehog protein. Preferably, the polypeptide comprises an amino acid sequence identical or homologous to an sequence designated in one of SEQ ID No:8, SEQ ID No:9, SEQ ID No:10, SEQ ID No:11, SEQ ID No:12, SEQ ID No:13, or SEQ ID No:14. More preferably, the polypeptide comprises an amino acid sequence designated in SEQ ID No:40.

In still another preferred embodiment, the invention features a purified or recombinant hedgehog polypeptide comprising an amino acid sequence represented by the formula A-B wherein, A represents all or the portion of the amino acid sequence designated by residues 1–168 of SEQ ID No:40; and B represents at least one amino acid residue of the amino acid sequence designated by residues 169–221 of SEQ ID No:40; wherein A and B together represent a contiguous polypeptide sequence represented by SEQ ID No:40, and the polypeptide modulates, e.g., mimics or antagonizes, the biological activity of a hedgehog protein. Preferably, B can represent at least 5, 10 or 20 amino acid residues of the amino acid sequence designated by residues 169–221 of SEQ ID No:40.

In another embodiment, the invention features a purified or recombinant polypeptide comprising an amino acid sequence represented by the formula A-B, wherein A represents all or the portion of the amino acid sequence designated by residues 24–193 of SEQ ID No:13; and B represents at least one amino acid residue of the amino acid sequence designated by residues 194–250 of SEQ ID No:13; wherein A and B together represent a contiguous polypeptide sequence designated in SEQ ID No:13, and the polypeptide modulates, e.g., mimics or antagonizes, the biological activity of a hedgehog protein.

In yet another preferred embodiment, the invention features a purified or recombinant polypeptide comprising an amino acid sequence represented by the formula A-B, wherein A represents all or the portion of the amino acid sequence designated by residues 25–193, or analogous residues thereof, of a vertebrate hedgehog polypeptide identical or homologous to SEQ ID No:11; and B represents at least one amino acid residue of the amino acid sequence designated by residues 194–250, or analogous residues thereof, of a vertebrate hedgehog polypeptide identical or homologous to SEQ ID No:11; wherein A and B together represent a contiguous polypeptide sequence designated in SEQ ID No:11, and the polypeptide modulates, e.g., agonizes or antagonizes, the biological activity of a hedgehog protein.

In another embodiment, the invention features a purified or recombinant polypeptide comprising an amino acid sequence represented by the formula A-B, wherein A represents all or the portion of the amino acid sequence designated by residues 23–193 of SEQ ID No:9; and B represents at least one amino acid residue of the amino acid sequence designated by residues 194–250 of SEQ ID No:9; wherein A and B together represent a contiguous polypeptide sequence designated in SEQ ID No:9, and the polypeptide modulates, e.g., agonizes or antagonizes, the biological activity of a hedgehog protein.

In yet another embodiment, the invention features a purified or recombinant polypeptide comprising an amino acid sequence represented by the formula A-B, wherein A represents all or the portion of the amino acid sequence designated by residues 28–197 of SEQ ID No:10; and B represents at least one amino acid residue of the amino acid sequence designated by residues 198–250 of SEQ ID No:10; wherein A and B together represent a contiguous polypeptide sequence designated in SEQ ID No:10, and the polypeptide modulates, e.g., agonizes or antagonizes, the biological activity of a hedgehog protein.

In yet a further preferred embodiment, the invention features a purified or recombinant polypeptide comprising an amino acid sequence represented by the formula A-B, wherein A represents all or the portion of the amino acid sequence designated by residues 1–98, or analogous residues thereof, of a vertebrate hedgehog polypeptide identical or homologous to SEQ ID No:14; and B represents at least one amino acid residue of the amino acid sequence designated by residues 99–150, or analogous residues thereof, of a vertebrate hedgehog polypeptide identical or homologous to SEQ ID No:14; wherein A and B together represent a contiguous polypeptide sequence designated in SEQ ID No:14, and the polypeptide modulates, e.g., agonizes or antagonizes, the biological activity of a hedgehog protein.

In another preferred embodiment, the invention features a nucleic acid encoding a polypeptide fragment of a hedgehog protein, e.g. a fragment described above. Preferably, the polypeptide fragment comprises an amino acid sequence identical or homologous with a sequence designated in one of SEQ ID No:8, SEQ ID No:9; SEQ ID No:10, SEQ ID No:11, SEQ ID No:12, SEQ ID No:13, or SEQ ID No:14. More preferably, the polypeptide fragment comprises an amino acid sequence designated in SEQ ID No:40.

In yet another preferred embodiment, the invention features a nucleic acid encoding a polypeptide, which polypeptide has a molecular weight of approximately 19 kDa and has the ability to modulate, e.g., either mimic or antagonize, atleast a portion of the activity of a wild-type hedgehog protein. Preferably, the polypeptide comprises an amino acid sequence identical or homologous with a sequence designated in one of SEQ ID No:8, SEQ ID No:9, SEQ ID No:10, SEQ ID No:11, SEQ ID No:12, SEQ ID No:13, or SEQ ID No:14. More preferably, the polypeptide comprises an amino acid sequence designated in the general formula SEQ ID No:40.

In another preferred embodiment, the invention feature a nucleic acid which encodes a polypeptide that modulates, e.g., mimics or antagonizes, the biological activity of a hedgehog protein, which nucleic acid comprises all or a portion of the nucleotide sequence of the coding region of a gene identical or homologous to the nucleotide sequence designated by one of SEQ ID No:1, SEQ ID No:2, SEQ ID No:3, SEQ ID No:4, SEQ ID No:5, SEQ ID No:6 or SEQ ID No:7. Preferably, the nucleic acid comprises a hedgehog-encoding portion that hybridizes under stringent conditions to a coding portion of one or more of the nucleic acids designated by SEQ ID No:1–7.

Moreover, as described below, the hedgehog polypeptide can be either an agonist (e.g. mimics), or alternatively, an antagonist of a biological activity of a naturally occurring form of the protein, e.g., the polypeptide is able to modulate differentiation and/or growth and/or survival of a cell responsive to authentic hedgehog proteins. Homologs of the subject hedgehog proteins include versions of the protein which are resistant to proteolytic cleavage, as for example, due to mutations which alter potential cleavage sequences or which inactivate an enzymatic activity associated with the protein. Other forms are secreted and isolatable from a cell with no further proteolytic cleavage required beyond cleavage of a signal sequence, e.g., truncated forms of the protein, such as corresponding to the natural proteolytic fragments described below.

The hedgehog polypeptides of the present invention can be glycosylated, or conversely, by choice of the expression system or by modification of the protein sequence to preclude glycosylation, reduced carbohydrate analogs can also be provided. Glycosylated forms include derivatization with glycosaminoglycan chains. Likewise, hedgehog polypeptides can be generated which lack an endogenous signal sequence (though this is typically cleaved off even if present in the pro-form of the protein).

The subject proteins can also be provided as chimeric molecules, such as in the form of fusion proteins. For instance, the hedgehog protein can be provided as a recombinant fusion protein which includes a second polypeptide portion, e.g., a second polypeptide having an amino acid sequence unrelated (heterologous) to the hedgehog polypeptide, e.g. the second polypeptide portion is glutathione-S-transferase, e.g. the second polypeptide portion is an enzymatic activity such as alkaline phosphatase, e.g. the second polypeptide portion is an epitope tag.

Yet another aspect of the present invention concerns an immunogen comprising a hedgehog polypeptide in an immunogenic preparation, the immunogen being capable of eliciting an immune response specific for a hedgehog polypeptide; e.g. a humoral response, e.g. an antibody response; e.g. a cellular response. In preferred embodiments, the immunogen comprising an antigenic determinant, e.g. a unique determinant, from a protein represented by one of SEQ ID Nos. 8–14.

A still further aspect of the present invention features antibodies and antibody preparations specifically reactive with an epitope of the hedgehog immunogen.

In another preferred embodiment, the invention features a nucleic acid encoding a polypeptide fragment of a hedgehog protein, e.g. a fragment described above. Preferably, the polypeptide fragment comprises an amino acid sequence identical or homologous with a sequence designated in one of SEQ ID No:8, SEQ ID No:9, SEQ ID No:10, SEQ ID No:11, SEQ ID No:12, SEQ ID No:13, or SEQ ID No:14. More preferably, the polypeptide fragment comprises an amino acid sequence designated in SEQ ID No:40.

In yet another preferred embodiment, the invention features a nucleic acid encoding a polypeptide, which polypeptide has a molecular weight of approximately 19 kDa and has the ability to modulate, e.g., either mimic or antagonize, atleast a portion of the activity of a wild-type hedgehog protein. Preferably, the polypeptide comprises an amino acid sequence identical or homologous with a sequence designated in one of SEQ ID No:8, SEQ ID No:9, SEQ ID No:10, SEQ ID No:11, SEQ ID No:12, SEQ ID No:13, or SEQ ID No:14. More preferably, the polypeptide comprises an amino acid sequence designated in the general formula SEQ ID No:40.

In another preferred embodiment, the invention feature a nucleic acid which encodes a polypeptide that modulates, e.g., mimics or antagonizes, the biological activity of a hedgehog protein, which nucleic acid comprises all or a portion of the nucleotide sequence of the coding region of a gene identical or homologous to the nucleotide sequence designated by one of SEQ ID No:1, SEQ ID No:2, SEQ ID No:3, SEQ ID No:4, SEQ ID No:5, SEQ ID No:6 or SEQ ID No:7. Preferably, the nucleic acid comprises a hedgehog-encoding portion that hybridizes under stringent conditions to a coding portion of one or more of the nucleic acids designated by SEQ ID No:1–7.

Another aspect of the present invention provides a substantially isolated nucleic acid having a nucleotide sequence which encodes a hedgehog polypeptide. In preferred embodiments, the encoded polypeptide specifically mimics or antagonizes inductive events mediated by wild-type hedgehog proteins. The coding sequence of the nucleic acid can comprise a sequence which is identical to a coding sequence represented in one of SEQ ID Nos: 1–7, or it can merely be homologous to one or more of those sequences. For instance, the hedgehog encoding sequence preferably has a sequence at least 60% homologous to a nucleotide sequence in one or more of SEQ ID Nos: 1–7, though higher sequence homologies of, for example, 80%, 90% or 95% are also contemplated. The polypeptide encoded by the nucleic acid can comprise an amino acid sequence represented in one of SEQ ID Nos: 8–14 such as one of those full length proteins, or it can comprise a fragment of that nucleic acid, which fragment may, for instance, encode a fragment which is, for example, at least 5, 10, 20, 50 or 100 or 200 amino acids in length. The polypeptide encoded by the nucleic acid can be either an agonist (e.g. mimics), or alternatively, an antagonist of a biological activity of a naturally occurring form of a hedgehog protein.

Furthermore, in certain preferred embodiments, the subject hedgehog nucleic acid will include a transcriptional regulatory sequence, e.g. at least one of a transcriptional promoter or transcriptional enhancer sequence, which regulatory sequence is operably linked to the hedgehog gene sequence. Such regulatory sequences can be used in to render the hedgehog gene sequence suitable for use as an expression vector.

In yet a further preferred embodiment, the nucleic acid hybridizes under stringent conditions to a nucleic acid probe corresponding to at least 12 consecutive nucleotides of either sense or antisense sequence of one or more of SEQ ID Nos:1–7; though preferably to at least 20 consecutive nucleotides; and more preferably to at least 40, 50 or 75 consecutive nucleotides of either sense or antisense sequence of one or more of SEQ ID Nos:1–7.

The invention also features transgenic non-human animals, e.g. mice, rats, rabbits, chickens, frogs or pigs, having a transgene, e.g., animals which include (and preferably express) a heterologous form of a hedgehog gene described herein, or which misexpress an endogenous hedgehog gene, e.g., an animal in which expression of one or more of the subject hedgehog proteins is disrupted. Such a transgenic animal can serve as an animal model for studying cellular and tissue disorders comprising mutated or mis-expressed hedgehog alleles or for use in drug screening.

The invention also provides a probe/primer comprising a substantially purified oligonucleotide, wherein the oligonucleotide comprises a region of nucleotide sequence which hybridizes under stringent conditions to at least 10 consecutive nucleotides of sense or antisense sequence of SEQ ID No:1, or naturally occurring mutants thereof. Nucleic acid probes which are specific for each of the classes of vertebrate hedgehog proteins are contemplated by the present invention, e.g. probes which can discern between nucleic acid encoding an Shh versus an Ihh versus a Dhh versus an Mhh. In preferred embodiments, the probe/primer further includes a label group attached thereto and able to be detected. The label group can be selected, e.g., from a group consisting of radioisotopes, fluorescent compounds, enzymes, and enzyme co-factors. Probes of the invention can be used as a part of a diagnostic test kit for identifying dysfunctions associated with mis-expression of a hedgehog protein, such as for detecting in a sample of cells isolated from a patient, a level of a nucleic acid encoding a subject hedgehog protein; e.g. measuring a hedgehog mRNA level in a cell, or determining whether a genomic hedgehog gene has been mutated or deleted. These so called "probes/primers" of the invention can also be used as a part of "antisense" therapy which refers to administration or in situ generation of oligonucleotide probes or their derivatives which specifically hybridize (e.g. bind) under cellular conditions, with the cellular mRNA and/or genomic DNA encoding one or more of the subject hedgehog proteins so as to inhibit expression of that protein, e.g. by inhibiting transcription and/or translation. Preferably, the oligonucleotide is at least 10 nucleotides in length, though primers of 20, 30, 50, 100, or 150 nucleotides in length are also contemplated.

In yet another aspect, the invention provides an assay for screening test compounds for inhibitors, or alternatively, potentiators, of an interaction between a hedgehog protein and a hedgehog receptor. An exemplary method includes the steps of (i) combining a hedgehog receptor, either soluble or membrane bound (including whole cells), a hedgehog polypeptide, and a test compound, e.g., under conditions wherein, but for the test compound, the hedgehog protein and the hedgehog receptor are able to interact; and (ii) detecting the formation of a complex which includes the hedgehog protein and the receptor either by directly quantitating the complex or by measuring inductive effects of the hedgehog protein. A statistically significant change, such as a decrease, in the formation of the complex in the presence of a test compound (relative to what is seen in the absence of the test compound) is indicative of a modulation, e.g., inhibition, of the interaction between the hedgehog protein and the receptor.

Yet another aspect of the present invention concerns a method for modulating one or more of growth, differentiation, or survival of a mammalian cell responsive to hedgehog induction. In general, whether carries out in vivo, in vitro, or in situ, the method comprises treating the cell with an effective amount of a hedgehog polypeptide so as to alter, relative to the cell in the absence of hedgehog treatment, at least one of (i) rate of growth, (ii) differentiation, or (iii) survival of the cell. Accordingly, the method can be carried out with polypeptides mimics the effects of a naturally-occurring hedgehog protein on the cell, as well as with polypeptides which antagonize the effects of a naturally-occurring hedgehog protein on said cell. In preferred embodiments, the hedgehog polypeptide provided in the subject method are derived from verterbrate sources, e.g., are vertebrate hedgehog polypeptides. For instance, preferred polypeptides includes an amino acid sequence identical or homologous to an amino acid sequence (e.g., including bioactive fragments) designated in one of SEQ ID No:8, SEQ ID No:9, SEQ ID No:10, SEQ ID No:11, SEQ ID No:12, SEQ ID No:13 or SEQ ID No:14. Furthermore, the present invention contemplates the use of invertebrate hedgehog polypeptides, such as the Dros-HH polypeptide designated by SEQ ID No:34, or bioactive fragments thereof equivalent to the subject vertebrate fragments.

In one embodiment, the subject method includes the treatment of testicular cells, so as modulate spermatogenesis. In another embodiment, the subject method is used to modulate osteogenesis, comprising the treatment of osteogenic cells with a hedgehog polypeptide. Liekwise, where the treated cell is a chondrogenic cell, the present method is used to modulate chondrogenesis. In still another embodiment, hedgehog polypeptides can be used to modulate the differentiation of neural cells, e.g., the method can be used to cause differentiation of a neuronal cell, to maintain a neuronal cell in a differentiated state, and/or to enhance the survival of a neuronal cell, e.g., to prevent apoptosis or other forms of cell death. For instance, the present method can be used to affect the differentiation of such neuronal cells as motor neurons, cholinergic neurons, dopanergic neurons, serotenergic neurons, and peptidergic neurons.

The present method is applicable, for example, to cell culture technique, such as in the culturing of neural and other cells whose survival or differentiative state is dependent on hedgehog function. Moreover, hedgehog agonists and antagonists can be used for therapeutic intervention, such as to enhance survival and maintenance of neurons and other neural cells in both the central nervous system and the peripheral nervous system, as well as to influence other vertebrate organogenic pathways, such as other ectodermal patterning, as well as certain mesodermal and endodermal differentiation processes. In an exemplary embodiment, the method is practiced for modulating, in an animal, cell growth, cell differentiation or cell survival, and comprises administering a therapeutically effective amount of a hedgehog polypeptide to alter, relative the absence of hedgehog treatment, at least one of (i) rate of growth, (ii) differentiation, or (iii) survival of one or more cell-types in the animal.

Another aspect of the present invention provides a method of determining if a subject, e.g. a human patient, is at risk for a disorder characterized by unwanted cell proliferation or aberrant control of differentiation. The method includes detecting, in a tissue of the subject, the presence or absence of a genetic lesion characterized by at least one of (i) a mutation of a gene encoding a hedgehog protein, e.g. represented in SEQ ID No:2, or a homolog thereof; or (ii) the mis-expression of a hedgehog gene. In preferred embodiments, detecting the genetic lesion includes ascertaining the existence of at least one of: a deletion of one or more nucleotides from a hedgehog gene; an addition of one or more nucleotides to the gene, a substitution of one or more nucleotides of the gene, a gross chromosomal rearrangement of the gene; an alteration in the level of a messenger RNA transcript of the gene; the presence of a non-wild type splicing pattern of a messenger RNA transcript of the gene; or a non-wild type level of the protein.

For example, detecting the genetic lesion can include (i) providing a probe/primer including an oligonucleotide containing a region of nucleotide sequence which hybridizes to a sense or antisense sequence of a hedgehog gene, e.g. a nucleic acid represented in one of SEQ ID Nos: 1–7, or naturally occurring mutants thereof, or 5' or 3' flanking sequences naturally associated with the hedgehog gene; (ii) exposing the probe/primer to nucleic acid of the tissue; and (iii) detecting, by hybridization of the probe/primer to the nucleic acid, the presence or absence of the genetic lesion; e.g. wherein detecting the lesion comprises utilizing the probe/primer to determine the nucleotide sequence of the hedgehog gene and, optionally, of the flanking nucleic acid sequences. For instance, the probe/primer can be employed in a polymerase chain reaction (PCR) or in a ligation chain reaction (LCR). In alternate embodiments, the level of a hedgehog protein is detected in an immunoassay using an antibody which is specifically immunoreactive with the hedgehog protein.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And*

*Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

Other features and advantages of the invention will be apparent from the following detailed description, and from the claims.

BRIEF DESCRIPTION OF THE DRAWINGS

FIG. 1 represents the amino acid sequences of two chick hh clones, chicken hedgehog-A (pCHA; SEQ ID No:35) and chicken hedgehog-B (pCHB; SEQ ID No:36). These clones were obtained using degenerate primers corresponding to the underlined amino acid residues of the Drosophila sequence (corresponding to residues 161–232 of SEQ ID No:34) also shown in FIG. 1, followed by nested PCR using chicken genomic DNA.

FIG. 2 is an alignment comparing the amino acid sequences of chick Shh (SEQ ID No:8) with its Drosophila homolog (SEQ ID No:34). Shh residues 1–26 correspond to the proposed signal peptide. Identical residues are enclosed by boxes and gaps in order to highlight similarity. The nucleotide sequence of Shh has been submitted to Genbank.

FIGS. 5A-1 and 5A-2 are a "pileup" alignment of predicted amino acid sequences which compares Drosophila hh (D-hh; SEQ ID No:34), mouse hh (M-Dhh; SEQ ID No:9); M-Ihh; SEQ ID No:10; M-Shh; SEQ ID No:11), chicken hh (C-Shh; SEQ ID No:8), and zebrafish hh (Z-Shh; SEQ ID No:12). The predicted hydrophobic transmembrane/signal sequences are indicated in italics and the predicted signal sequence processing site is arrowed. The positions of introns interrupting the Drosophila hh and M-Dhh open reading frames are indicated by arrowheads. All amino acids shared among the six predicted hh proteins are indicated in bold. FIG. 5B is a sequence alignment of the N-terminal portion of vertebrate hedgehog proteins, and the predicted degenerate sequence "CON" (SEQ ID No:41).

FIG. 6 is an inter- and cross-species comparison of amino acid identities among the predicted processed hh proteins shown in FIGS. 5A-1 and 5A-2. All values are percentages. Figures in parentheses represent similarities allowing for conservative amino acid substitutions.

FIGS. 9A and 9B illustrate the comparison of zebrafish Shh (Z-Shh) and Drosophila hh (hh) amino acid sequences. FIG. 9A (SEQ ID NOS: 34 and 12) is an alignment of zebrafish Shh and Drosophila hh amino acid sequences. Identical amino acids are linked by vertical bars. Dots indicate gaps introduced for optimal alignment. Putative transmembrane/signal peptide sequences are underlined (Kyte and Doolittle (1982) *J Mol Biol* 157:133–148). The position of exon boundaries in the Drosophila gene are indicated by arrowheads. The region of highest similarity between Z-Shh and hh overlaps exon 2. FIG. 9B is a schematic comparison of Z-Shh and drosophila hh. Black boxes indicate the position of the putative transmembrane/signal peptide sequences. relative to the amino-terminus. Sequence homologies were scored by taking into account the alignment of chemically similar amino acids and percentage of homology in the boxed regions is indicated.

FIG. 10 (SEQ ID NOS: 37, 15, 16, and 17) is an alignment of partial predicted amino acid sequences from three different zebrafish hh homologs. One of these sequences corresponds to Shh, while the other two define additional hh homologs in zebrafish, named hh(a) and hh(b). Amino acid identities among the three partial homologs are indicated by vertical bars.

Expression of Fgf-4 in the AER can be induced by Sonic providing an indirect signaling pathway from Sonic to the mesoderm. FGFs also maintain expression of Sonic in the ZPA, thereby completing a positive feedback loop which controls the relative positions of the signaling centers. While Fgf-4 provides competence signals to the mesoderm, it also promotes mesodermal proliferation. Thus patterning of the mesoderm is dependent on the same signals which promote its proliferation. This mechanism inextricably integrates limb patterning with outgrowth.

Figure 15A:
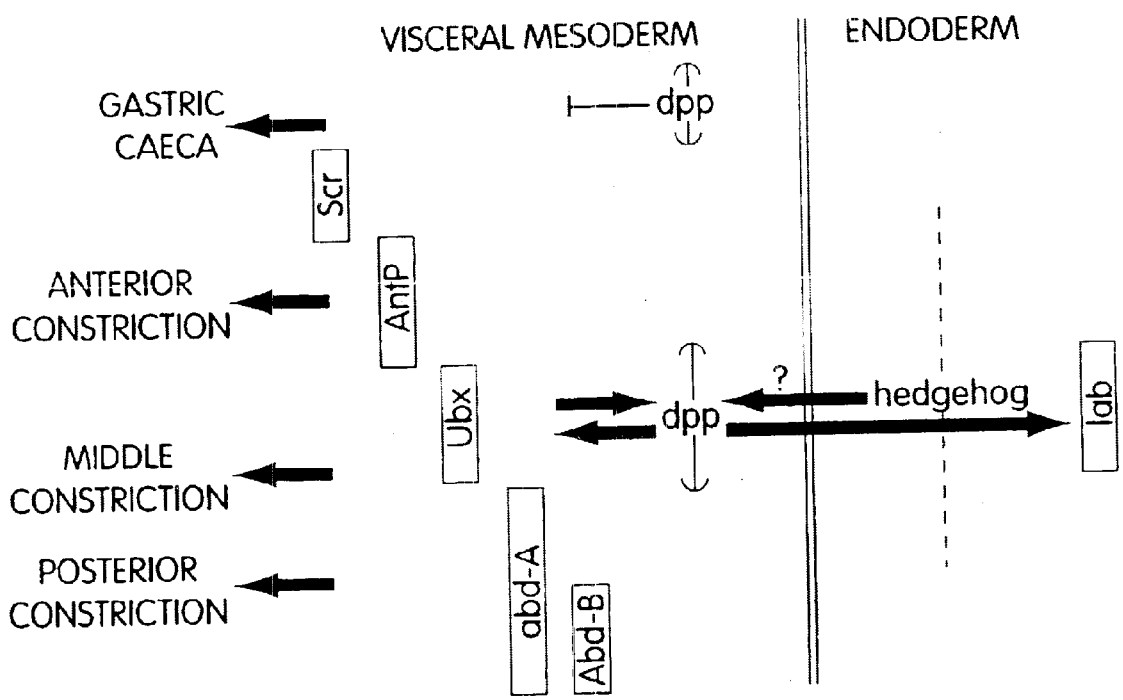
Figure 15B:
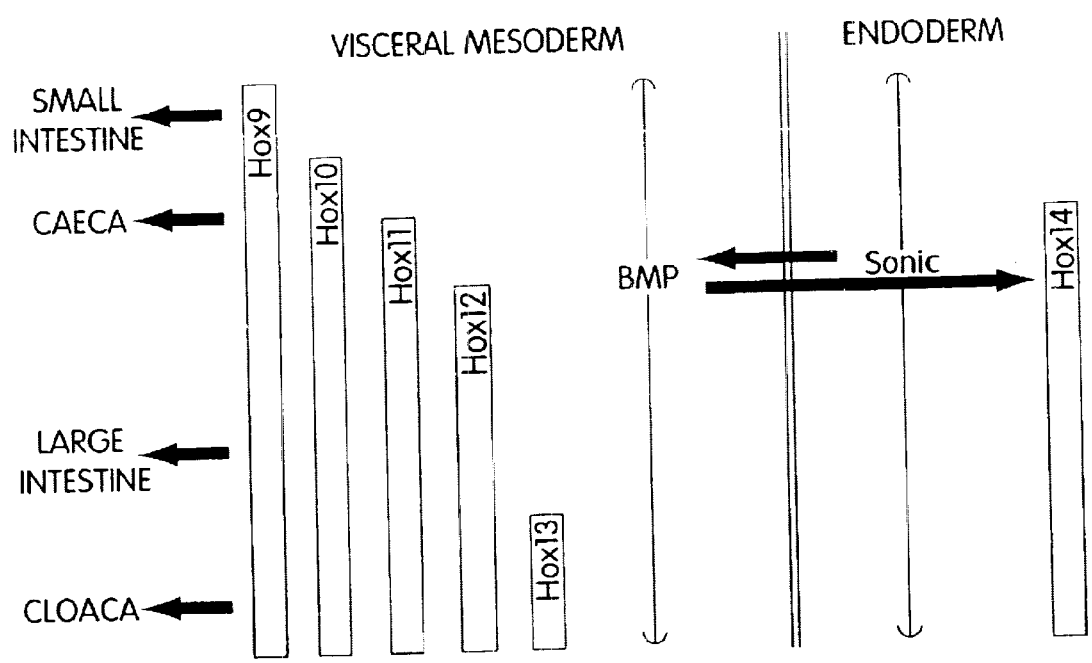

FIG. 15 is a schematic diagram of patterning of the Drosophila and vertebrate gut. Regulatory interactions responsible for patterning of Drosophila midgut (A) are compared to a model for patterning of the vertebrate hindgut (B) based on expression data. Morphologic regional distinctions are indicated to the left (A and B), genes expressed in the visceral mesoderm are in the center panel, those in the gut lumenal endoderm are on the right. HOM/Hox gene expression domains are boxed. Regionally expressing secreted gene products are indicated by lines. Arrows indicate activating interactions, barred lines, inhibiting interactions. Regulatory interactions in Drosophila gut (A) have been established by genetic studies except for the relationship between dpp and hedgehog, which is hypothesized based on their interactions in the Drosophila imaginal discs, hedgehog appears to be a signal from the endoderm to the mesoderm, and that dpp is expressed in the mesoderm.

Figure 16:
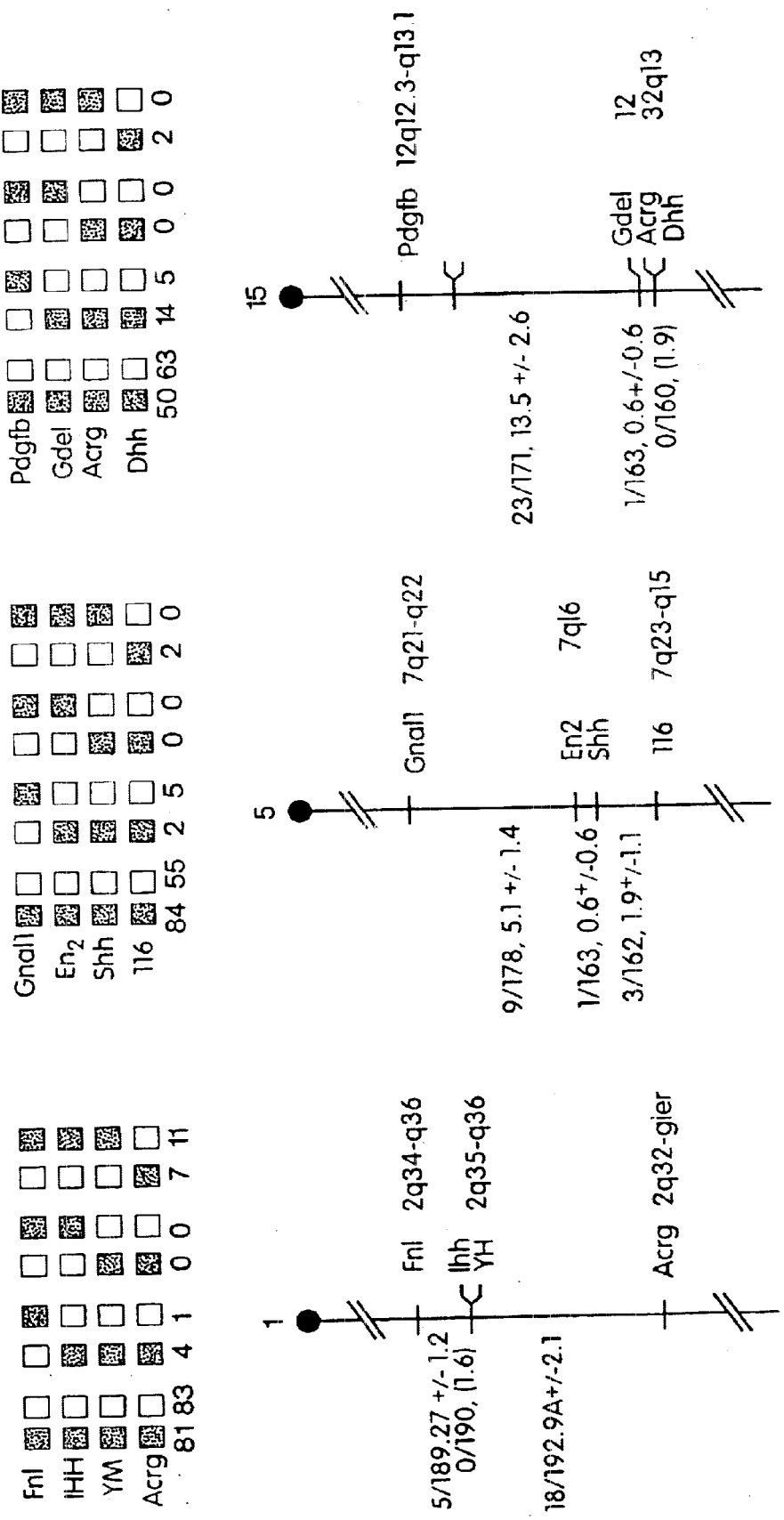

FIG. 16 is a schematic diagram of chromosomal locations of Ihh, Shh and Dhh in the mouse genome. The loci were mapped by interspecific backcross analysis. The segregation patterns of the loci and flanking genes in backcross animals that were typed for all loci are shown above the chromosome maps. For individual pairs of loci more animals were typed. Each column represents the chromosome identified in the backcross progeny that was inherited from the (C57BL/6J x M. spretus) F1 parent. The shaded boxes represent the presence of a C57BL/6J allele and white boxes represent the presence of a M. spretus allele. The number of the offsprings inheriting each type of chromosome is listed at the bottom of each column. Partial chromosome linkage maps showing location of Ihh, Shh and Dhh in relation too linked genes is shown. The number of recombinant $N_2$ animals is presented over total number of $N_2$ animals typed to the left of the chromosome maps between each pair of loci. The recombinant frequencies, expressed as genetic distance in centimorgans (± one standard error) are also shown. When no recombination between loci was detected, the upper 95% confidence limit of the recombination distance is indicated in parentheses. Gene order was determined by minimizing the number of recombinant events required to explain the allele distribution patterns. The position of loci in human chromosomes can be obtained from GDB (Genome Data Base), a computerized database of human linkage information maintained by the William H. Welch Medical Library of the John Hopkins University (Baltimore, Md.).

DETAILED DESCRIPTION OF THE INVENTION

Of particular importance in the development and maintenance of tissue in vertebrate animals is a type of extracellular communication called induction, which occurs between neighboring cell layers and tissues (Saxen et al. (1989) *Int J Dev Biol* 33:21–48; and Gurdon et al. (1987) *Development* 99:285–306). In inductive interactions, chemical signals secreted by one cell population influence the developmental fate of a second cell population. Typically, cells responding to the inductive signals are diverted from one cell fate to another, neither of which is the same as the fate of the signaling cells.

Inductive signals are key regulatory proteins that function in vertebrate pattern formation, and are present in important signaling centers known to operatex embryonically, for example, to define the organization of the vertebrate embryo. For example, these signaling structures include the notochord, a transient structure which initiates the formation of the nervous system and helps to define the different types of neurons within it. The notochord also regulates mesodermal patterning along the body axis. Another distinct group of cells having apparent signaling activity is the floorplate of the neural tube (the precursor of the spinal cord and brain) which also signals the differentiation of different nerve cell types. It is also generally believed that the region of mesoderm at the bottom of the buds which form the limbs (called the Zone of Polarizing Activity or ZPA) operates as a signaling center by secreting a morphogen which ultimately produces the correct patterning of the developing limbs.

The present invention concerns the discovery that polypeptides encoded by a family of vertebrate genes, termed here hedgehog genes, comprise the signals produced by these embryonic patterning centers. As described herein, each of the disclosed vertebrate hedgehog (hh) homologs exhibits spatially and temporally restricted expression domains indicative of important roles in embryonic patterning. For instance, the results provided below indicate that vertebrate hh genes are expressed in the posterior limb bud, Hensen's node, the early notochord, the floor plate of the neural tube, the fore- and hindgut and their derivatives. These are all important signaling centers known to be required for proper patterning of surrounding embryonic tissues.

The hedgehog family of vertebrate inter-cellular signaling molecules provided by the present invention consists of at least four members. Three of these members, herein referred to as Desert hedgehog (Dhh), Sonic hedgehog (Shh) and Indian hedgehog (Ihh), apparently exist in all vertebrates, including fish, birds, and mammals. A fourth member, herein referred to as Moonrat hedgehog (Mhh), appears specific to fish. According to the appended sequence listing, (see also Table 1) a chicken Shh polypeptide is encoded by SEQ ID No:1; a mouse Dhh polypeptide is encoded by SEQ ID No:2; a mouse Ihh polypeptide is encoded by SEQ ID No:3; a mouse Shh polypeptide is encoded by SEQ ID No:4 a zebrafish Shh polypeptide is encoded by SEQ ID No:5; a human Shh polypeptide is encoded by SEQ ID No:6; and a human Ihh polypeptide is encoded by SEQ ID No:7.

TABLE 1

| Guide to hedgehog sequences in Sequence Listing | | |
|---|---|---|
| | Nucleotide | Amino Acid |
| Chicken Shh | SEQ ID No. 1 | SEQ ID No. 8 |
| Mouse Dhh | SEQ ID No. 2 | SEQ ID No. 9 |
| Mouse Ihh | SEQ ID No. 3 | SEQ ID No. 10 |
| Mouse Shh | SEQ ID No. 4 | SEQ ID No. 11 |
| Zebrafish Shh | SEQ ID No. 5 | SEQ ID No. 12 |
| Human Shh | SEQ ID No. 6 | SEQ ID No. 13 |
| Human Ihh | SEQ ID No. 7 | SEQ ID No. 14 |

Certain of the vertebrate hedgehog (hh) proteins of the present invention are defined by SEQ ID Nos:8–14 and can be cloned from vertebrate organisms including fish, avian and mammalian sources. These proteins are distinct from the drosophila hedgehog protein which, for clarity, will be referred to hereinafter as "Dros-HH". In addition to the sequence variation between the various hh homologs, the vertebrate hedgehog proteins are apparently present naturally in a number of different forms, including a pro-form, a full-length mature form, and several processed fragments thereof. The pro-form includes an N-terminal signal peptide for directed secretion of the extracellular domain, while the full-length mature form lacks this signal sequence. Further processing of the mature form apparently occurs in some instances to yield biologically active fragments of the protein. For instance, sonic hedgehog undergoes additional proteolytic processing to yield two peptides of approximately 19 kDa and 27 kDa, both of which are secreted. In addition to proteolytic fragmentation, the vertebrate hedgehog proteins can also be modified post-translationally, such as by glycosylation, though bacterially produced (e.g. unglycosylated) forms of the proteins apparently still maintain some of the activity of the native protein.

As described in the following examples, the cDNA clones provided by the present invention were first obtained by screening a mouse genomic library with a partial Drosophila hh cDNA clone (0.7 kb). Positive plaques were identified and one mouse clone was selected. This clone was then used as a probe to obtain a genomic clone containing the full coding sequence of the Mouse Dhh gene. As described in the attached Examples, Northern blots and in situ hybridization demonstrated that Mouse Dhh is expressed in the testes, and potentially the ovaries, and is also associated with sensory neurons of the head and trunk. Interestingly, no expression was detected on the nerve cell bodies themselves (only the axons), indicating that Dhh is likely produced by the Shwann cells.

In order to obtain cDNA clones encoding chicken hh genes, degenerate oligonucleotides were designed corresponding to the amino and carboxy ends of Drosophila hh exon 2. As described in the Examples below, these oligonucleotides were used to isolate PCR fragments from chicken genomic DNA. These fragments were then cloned and sequenced. Ten clones yielded two different hh homologs, chicken Dhh and chicken Shh. The chicken Shh clone was then used to screen a stage 21/22 limb bud cDNA library which yielded a full length Shh clone.

In order to identify other vertebrate hedgehog homologs, the chicken clones (Dhh and Shh) were used to probe a genomic southern blot containing chicken DNA. As described below, genomic DNA was cut with various enzymes which do not cleave within the probe sequences. The DNA was run on a gel and transferred to a nylon filter. Probes were derived by ligating each 220 bp clone into a concatomer and then labeling with a random primer kit. The blots were hybridized and washed at low stringency. In each case, three hybridizing bands were observed following autoradiography, one of which was significantly more intense (a different band with each probe), indicating that there are at least three vertebrate hh genes. Additional cDNA and genomic screens carried out have yielded clones of three hh homologs from chickens and mice (Shh, Dhh and Ihh), and four hh homologs from zebrafish (Shh, Dhh, Ihh and Mhh). Weaker hybridization signals suggested that the gene family may be even larger. Moreover, a number of weakly hybridizing genomic clones have been isolated. Subsequently, the same probes derived from chicken hedgehog homologs have been utilized to screen a human genomic library. PCR fragments derived from the human genomic library were then sequenced, and PCR probes derived from the human sequences were used to screen human fetal cDNA libraries. Full-length cDNA encoding human sonic hedgehog protein (Shh) and partial cDNA encoding human Indian hedgehog protein (Ihh) were isolated from the fetal library, and represent a source of recombinant human hedgehog proteins.

To order to determine the expression patterns of the various vertebrate hh homologs, in situ hybridizations were performed in developing embryos of chicken, mice and fish. As described in the Examples below, the resulting expression patterns of each hh homolog were similar across each species and revealed that hh genes are expressed in a number of important embryonic signaling centers. For example, Shh is expressed in Hensen's node, the notochord, the ventral floorplate of the developing neural tube, and the ZPA at the base of the limb buds; Ihh is expressed in the embryonic yolksac and hindgut, and appear also to be involved in chondrogenesis; Dhh is expressed in the testes; and Mhh (only in zebrafish) is expressed in the notochord and in certain cranial nerves.

Furthermore, experimental evidence indicates that certain hedgehog proteins initiate expression of secondary signaling molecules, including Bmp-2 (a TGF-β relative) in the mesoderm and Fgf-4 in the ectoderm. The mesoderm requires ectodermally-derived competence factor(s), which include Fgf-4, to activate target gene expression in response to hedgehog signaling. The expression of, for example, Sonic and Fgf4 is coordinately regulated by a positive feedback loop operating between the posterior mesoderm and the overlying AER, which is the ridge of pseudostratified epithelium extending antero-posteriorly along the distal margin of the bud. These data provide a basis for understanding the integration of growth and patterning in the developing limb which can have important implications in the treatment of bone disorders described in greater detail herein.

To determine the role hedgehog proteins plays in inductive interactions between the endoderm and mesoderm, which are critical to gut morphogenesis, in situ hybridizations and recombinant retroviral injections were performed in developing chick embryos. The ventral mesoderm is induced to undergo gut-specific differentiation by the adjacent endoderm. As described in Examples below, at the earliest stages of chick gut formation Shh is expressed by the endoderm, and BMP-4 (a TGF-β relative) is expressed in the adjacent visceral mesoderm. Ectopic expression of Sonic is sufficient to induce expression of BMP-4 in visceral mesoderm, suggesting that Sonic serves as an inductive signal from the endoderm to the mesoderm. Subsequent organ-specific endodermal differentiation depends on regional inductive signal from the visceral mesoderm. Hox genes are expressed in the undifferentiated chick hind gut mesoderm with boundaries corresponding to morphologic borders, suggesting a role in regulating gut morphogenesis.

Bioactive fragments of hedgehog polypeptides of the present invention have been generated and are described in great detail in U.S. Ser. No. 08/435,093, filed May 4, 1995, herein incorporated by reference.

Accordingly, certain aspects of the present invention relate to nucleic acids encoding vertebrate hedgehog proteins, the hedgehog proteins themselves, antibodies immunoreactive with hh proteins, and preparations of such compositions. Moreover, the present invention provides diagnostic and therapeutic assays and reagents for detecting and treating disorders involving, for example, aberrant expression of vertebrate hedgehog homologs. In addition, drug discovery assays are provided for identifying agents which can modulate the binding of vertebrate hedgehog homologues to hedgehog-binding moieties (such as hedgehog receptors, ligands, or other extracellular matrix components). Such agents can be useful therapeutically to alter the growth and/or differentiation of a cell. Other aspects of the invention are described below or will be apparent to those skilled in the art in light of the present disclosure.

For convenience, certain terms employed in the specification, examples, and appended claims are collected here.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "gene" or "recombinant gene" refers to a nucleic acid comprising an open reading frame encoding one of the vertebrate hh polypeptides of the present invention, including both exon and (optionally) intron sequences. A "recombinant gene" refers to nucleic acid encoding a vertebrate hh polypeptide and comprising vertebrate hh-encoding exon sequences, though it may optionally include intron sequences which are either derived from a chromosomal vertebrate hh gene or from an unrelated chromosomal gene. Exemplary recombinant genes encoding the subject vertebrate hh polypeptide are represented by SEQ ID No:1, SEQ ID No:2, SEQ ID No:3, SEQ ID No:4, SEQ ID No:5, SEQ ID No:6 or SEQ ID No:7. The term "intron" refers to a DNA sequence present in a given vertebrate hh gene which is not translated into protein and is generally found between exons.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a vertebrate hh polypeptide or, where anti-sense expression occurs from the transferred gene, the expression of a naturally-occurring form of the vertebrate hh protein is disrupted.

As used herein the term "bioactive fragment of a hedgehog protein" refers to a fragment of a hedgehog polypeptide, wherein the encoded polypeptide specifically agonizes or antagonizes inductive events mediated by wild-type hedgehog proteins. The hedgehog biactive fragment preferably is, for example, at least 5, 10, 20, 50, 100, 150 or 200 amino acids in length.

An "effective amount" of a hedgehog polypeptide, or a bioactive fragment thereof, with respect to the subject method of treatment, refers to an amount of agonist or antagonist in a preparation which, when applied as part of a desired dosage regimen, provides modulation of growth, differentiation or survival of cells, e.g., modulation of spermatogenesis, skeletogenesis, e.g., osteogenesis, chondrogenesis, or limb patterning, or neuronal differentiation.

As used herein, "phenotype" refers to the entire physical, biochemical, and physiological makeup of a cell, e.g., having any one trait or any group of traits.

The terms "induction" or "induce", as relating to the biological activity of a hedgehog protein, refers generally to the process or act of causing to occur a specific effect on the phenotype of cell. Such effect can be in the form of causing a change in the phenotype, e.g., differentiation to another cell phenotype, or can be in the form of maintaining the cell in a particular cell, e.g., preventing dedifferentiation or promoting survival of a cell.

As used herein the term "animal" refers to mammals, preferably mammals such as live stock or humans. Likewise, a "patient" or "subject" to be treated by the subject method can mean either a human or non-human animal.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of one of the recombinant vertebrate hedgehog genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of hedgehog proteins.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of neural origin, e.g. neuronal cells. The term also covers so-called "leaky" promoters, which regulate expression of a selected DNA primarily in one tissue, but cause expression in other tissues as well.

As used herein, the term "target tissue" refers to connective tissue, cartilage, bone tissue or limb tissue, which is either present in an animal, e.g., a mammal, e.g., a human or is present in in vitro culture, e.g, a cell culture.

As used herein, a "transgenic animal" is any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of the vertebrate hh proteins, e.g. either agonistic or antagonistic forms. However, transgenic animals in which the recombinant vertebrate hh gene is silent are also contemplated, as for example, the FLP or CRE recombinase dependent constructs described below. The "non-human animals" of the invention include vertebrates such as rodents, non-human primates, sheep, dog, cow, chickens, amphibians, reptiles, etc. Preferred non-human animals are selected from the rodent family including rat and mouse, most preferably mouse, though transgenic amphibians, such as members of the Xenopus genus, and transgenic chickens can also provide important tools for understanding and identifying agents which can affect, for example, embryogenesis and tissue formation. The term "chimeric animal" is used herein to refer to animals in which the recombinant gene is found, or in which the recombinant is expressed in some but not all cells of the animal. The term "tissue-specific chimeric animal" indicates that one of the recombinant vertebrate Ah genes is present and/or expressed in some tissues but not others.

As used herein, the term "transgene" means a nucleic acid sequence (encoding, e.g., one of the vertebrate hh polypeptides), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a vertebrate hh polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a protein with the same biological activity.

"Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40 percent identity, though preferably less than 25 percent identity, with one of the vertebrate hh sequences of the present invention.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding one of the subject vertebrate hh polypeptides with a second amino acid sequence defining a domain foreign to and not substantially homologous with any domain of one of the vertebrate hh proteins. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula X-hh-Y, wherein hh represents a portion of the protein which is derived from one of the vertebrate hh proteins, and X and Y are independently absent or represent amino acid sequences which are not related to one of the vertebrate hh sequences in an organism, including naturally occurring mutants.

As used herein, the terms "transforming growth factor-beta" and "TGF-β" denote a family of structurally related paracrine polypeptides found ubiquitously in vertebrates, and prototypic of a large family of metazoan growth, differentiation, and morphogenesis factors (see, for review, Massaque et al. (1990) *Ann Rev Cell Biol* 6:597–641; and Sporn et al. (1992) *J Cell Biol* 119:1017–1021). Included in this family are the "bone morphogenetic proteins" or "BMPs", which refers to proteins isolated from bone, and fragments thereof and synthetic peptides which are capable of inducing bone deposition alone or when combined with appropriate cofactors. Preparation of BMPs, such as BMP-1, -2, -3, and -4, is described in, for example, PCT publication WO 88/00205. Wozney (1989) *Growth Fact Res* 1:267–280 describes additional BMP proteins closely related to BMP-2, and which have been designated BMP-5, -6, and -7. PCT publications WO89/09787 and WO89/09788 describe a protein called "OP-1," now known to be BMP-7. Other BMPs are known in the art.

The term "isolated" as also used herein with respect to nucleic acids, such as DNA or RNA, refers to molecules separated from other DNAs, or RNAs, respectively, that are present in the natural source of the macromolecule. For example, an isolated nucleic acid encoding one of the subject vertebrate hh polypeptides preferably includes no more than 10 kilobases (kb) of nucleic acid sequence which naturally immediately flanks the vertebrate hh gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

As used herein the term "approximately 19 kDa" with respect to N-terminal bioactive fragments of a hedgehog protein, refers to a polypeptide which can range in size from 16 kDa to 22 kDa, more preferably 18–20 kDa. In a preferred embodiment, "approximately 19 kDa" refers to a mature form of the peptide after the cleavage of the signal sequence and proteolysis to release an N-terminal portion of the mature protein. For instance, in the case of the Sonic hedgehog polypeptide, a fragment of approximately 19 kDa is generated when the mature polypeptide is cleaved at a proteolytic processing site which is located in the region between Ala-169 and Gly-178 of SEQ ID No:40, e.g., a fragment from Cys-1 to Gly-174 of SEQ ID No:40.

Likewise, the term "approximately 27 kDa" with respect to C-terminal fragments of a hedgehog protein, refers to a polypeptide which can range in size from 24 kDa to 30 kDa, more preferably 26–29 kDa. In a preferred embodiment, "approximately 27 kDa" refers to a mature form of the C-terminal polypeptide after proteolysis to release an N-terminal portion of the mature protein.

As described below, one aspect of the invention pertains to isolated nucleic acids comprising the nucleotide inducing sequences encoding vertebrate hh homologues, and/or equivalents of such nucleic acids. The term nucleic acid as used herein is intended to include fragments as equivalents. The term equivalent is understood to include nucleotide sequences encoding functionally equivalent hedgehog polypeptides or functionally equivalent peptides having an activity of a vertebrate hedgehog protein such as described herein. Equivalent nucleotide sequences will include sequences that differ by one or more nucleotide substitutions, additions or deletions, such as allelic variants; and will, therefore, include sequences that differ from the nucleotide sequence of the vertebrate hedgehog cDNAs shown in SEQ ID Nos:1–7 due to the degeneracy of the genetic code. Equivalents will also include nucleotide sequences that hybridize under stringent conditions (i.e., equivalent to about 20–27° C. below the melting temperature ($T_m$) of the DNA duplex formed in about 1M salt) to the nucleotide sequences represented in one or more of SEQ ID Nos:1–7. In one embodiment, equivalents will further include nucleic acid sequences derived from and evolutionarily related to, a nucleotide sequences shown in any of SEQ ID Nos:1–7.

Moreover, it will be generally appreciated that, under certain circumstances, it may be advantageous to provide homologs of one of the subject hedgehog polypeptides which function in a limited capacity as one of either a hedgehog agonist (mimetic) or a hedgehog antagonist, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of the biological activities of naturally occurring forms of hedgehog proteins.

Homologs of one of the subject hedgehog proteins can be generated by mutagenesis, such as by discrete point mutation(s), or by truncation. For instance, mutation can give rise to homologs which retain substantially the same, or merely a subset, of the biological activity of the hh polypeptide from which it was derived. Alternatively, antagonistic forms of the protein can be generated which are able to inhibit the function of the naturally occurring form of the protein, such as by competitively binding to an hh receptor.

In general, polypeptides referred to herein as having an activity (e.g., are "bioactive") of a vertebrate hh protein are defined as polypeptides which include an amino acid sequence corresponding (e.g., identical or homologous) to all or a portion of the amino acid sequences of a vertebrate hh proteins shown in any of SEQ ID No:8, SEQ ID No:9, SEQ ID No:10, SEQ ID No:11, SEQ ID No:12, SEQ ID No:13 or SEQ ID No:14 and which mimic or antagonize all or a portion of the biological/biochemical activities of a naturally occuring hedgehog protein. Examples of such biological activity include the ability to induce (or otherwise modulate) formation and differentiation of the head, limbs, lungs, central nervous system (CNS), digestive tract or other gut components, or mesodermal patterning of developing vertebrate embryos. As set out in U.S. Ser. Nos. 08/356,060 and 08/176,427, the vertebrate hedgehog proteins, especially Shh, can constitute a general ventralizing activity. For instance, the subject polypeptides can be characterized by an ability to induce and/or maintain differentiation of neurons, e.g., motorneurons, cholinergic neurons, dopanergic neurons, serotenergic neurons, peptidergic neurons and the like. In preferred embodiments, the biological activity can comprise an ability to regulate neurogenesis, such as a motor neuron inducing activity, a neuronal differentiation inducing activity, or a neuronal survival promoting activity. Hedgehog proteins of the present invention can also have biological activities which include an ability to regulate organogensis, such as through the ability to influence limb patterning, by, for example, skeletogenic activity. The biological activity associated with the hedgehog proteins of the present invention can also include the ability to induce stem cell or germ cell differentiation, including the ability to induce differentiation of chondrocytes or an involvement in spermatogenesis.

Hedgehog proteins of the present invention can also be characterized in terms of biological activities which include: an ability to modulate proliferation, survival and/or differentiation of mesodermally-derived tissue, such as tissue derived from dorsal mesoderm; the ability to modulate proliferation, survival and/or differentiation of ectodermally-derived tissue, such as tissue derived from the neural tube, neural crest, or head mesenchyme; the ability to modulate proliferation, survival and/or differentiation of endodermally-derived tissue, such as tissue derived from the primitive gut. Moreover, as described in the Examples below, the subject hedgehog proteins have the ability to induce expression of secondary signaling molecules, such as members of the Transforming Growth Factor β (TGFβ) family, including bone morphogenic proteins, e.g. BMP-2 and BMP-4, as well as members of the fibroblast growth factor (FGF) family, such as Fgf-4. Other biological activities of the subject hedgehog proteins are described herein or will be reasonably apparent to those skilled in the art. According to the present invention, a polypeptide has biological activity if it is a specific agonist or antagonist of a naturally-occurring form of a vertebrate hedgehog protein.

Preferred nucleic acids encode a vertebrate hedgehog polypeptide comprising an amino acid sequence at least 60% homologous, more preferably 70% homologous and most preferably 80% homologous with an amino acid sequence selected from the group consisting of SEQ ID Nos:8–14. Nucleic acids which encode polypeptides at least about 90%, more preferably at least about 95%, and most preferably at least about 98–99% homology with an amino acid sequence represented in one of SEQ ID Nos:8–14 are also within the scope of the invention. In one embodiment, the nucleic acid is a cDNA encoding a peptide having at least one activity of the subject vertebrate hh polypeptide. Preferably, the nucleic acid includes all or a portion of the nucleotide sequence corresponding to the coding region of SEQ ID Nos:1–7.

Preferred nucleic acids encode a bioactive fragment of a vertebrate hedgehog polypeptide comprising an amino acid sequence at least 60% homologous, more preferably 70% homologous and most preferably 80% homologous with an amino acid sequence selected from the group consisting of SEQ ID Nos:8–14. Nucleic acids which encode polypeptides at least about 90%, more preferably at least about 95%, and most preferably at least about 98–99% homology, or identical, with an amino acid sequence represented in one of SEQ ID Nos:8–14 are also within the scope of the invention.

With respect to bioctive fragments of sonic clones, a preferred nucleic acid encodes a polypeptide including a hedgehog portion having molecular weight of approximately 19 kDa and which polyptide can modulate, e.g., mimic or antagonize, a hedgehog biological activity. Preferably, the polypeptide encoded by the nucleic acid comprises an amino acid sequence identical or homologous to an amino acid sequence designated in one of SEQ ID No:8, SEQ ID No:9, SEQ ID No:10, SEQ ID No:11, SEQ ID No:12, SEQ ID No:13, or SEQ ID No:14. More preferably, the polypeptide comprises an amino acid sequence designated in SEQ ID No:40.

A preferred nucleic acid encodes a hedgehog polypeptide comprising an amino acid sequence represented by the formula A-B wherein, A represents all or the portion of the amino acid sequence designated by residues 1–168 of SEQ ID No:40; and B represents at least one amino acid residue of the amino acid sequence designated by residues 169–221 of SEQ ID No:40; wherein A and B together represent a contiguous polypeptide sequence designated by SEQ ID No:40. Preferably, B can represent at least five, ten or twenty amino acid residues of the amino acid sequence designated by residues 169–221 of SEQ ID No:40.

To further illustrate, another preferred nucleic acid encodes a polypeptide comprising an amino acid sequence represented by the formula A-B, wherein A represents all or the portion of the amino acid sequence designated by residues 24–193 of SEQ ID No:13; and B represents at least one amino acid residue of the amino acid sequence designated by residues 194–250 of SEQ ID No:13; wherein A and B together represent a contiguous polypeptide sequence designated in SEQ ID No:13, and the polypeptide modulates, e.g., agonizes or antagonizes, the biological activity of a hedgehog protein.

Yet another preferred nucleic acid encodes a polypeptide comprising an amino acid sequence represented by the formula A-B, wherein A represents all or the portion, e.g., 25, 50, 75 or 100 residues, of the amino acid sequence designated by residues 25–193, or analogous residues thereof, of a vertebrate hedgehog polypeptide identical or homologous to SEQ ID No:11; and B represents at least one amino acid residue of the amino acid sequence designated by residues 194–250, or analogous residues thereof, of a vertebrate hedgehog polypeptide identical or homologous to SEQ ID No:11; wherein A and B together represent a contiguous polypeptide sequence designated in SEQ ID No:11.

Another preferred nucleic acid encodes a polypeptide comprising an amino acid sequence represented by the formula A-B, wherein A represents all or the portion, e.g., 25, 50, 75 or 100 residues, of the amino acid sequence designated by residues 23–193 of SEQ ID No:9; and B represents at least one amino acid residue of the amino acid sequence designated by residues 194–250 of SEQ ID No:9; wherein A and B together represent a contiguous polypeptide sequence designated in SEQ ID No:9, and the polypeptide modulates, e.g., agonizes or antagonizes, the biological activity of a hedgehog protein.

Another preferred nucleic acid encodes a polypeptide comprising an amino acid sequence represented by the formula A-B, wherein A represents all or the portion, e.g., 25, 50, 75 or 100 residues, of the amino acid sequence designated by residues 28–197 of SEQ ID No:10; and B represents at least one amino acid residue of the amino acid sequence designated by residues 198–250 of SEQ ID No:10; wherein A and B together represent a contiguous polypeptide sequence designated in SEQ ID No:10, and the polypeptide modulates, e.g., agonizes or antagonizes, the biological activity of a hedgehog protein.

Yet another preferred nucleic acid encodes a polypeptide comprising an amino acid sequence represented by the formula A-B, wherein A represents all or the portion, e.g., 25, 50 or 75 residues, of the amino acid sequence designated by residues 1–98, or analogous residues thereof, of a vertebrate hedgehog polypeptide identical or homologous to SEQ ID No:14; and B represents at least one amino acid residue of the amino acid sequence designated by residues 99–150, or analogous residues thereof, of a vertebrate hedgehog polypeptide identical or homologous to SEQ ID No:14; wherein A and B together represent a contiguous polypeptide sequence designated in SEQ ID No:14.

Another aspect of the invention provides a nucleic acid which hybridizes under high or low stringency conditions to a nucleic acid represented by one of SEQ ID Nos:1–7. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Nucleic acids, having a sequence that differs from the nucleotide sequences shown in one of SEQ ID No:1, SEQ ID No:2, SEQ ID No:3, SEQ ID No:4, SEQ ID No:5, SEQ ID No:6 or SEQ ID No:7 due to degeneracy in the genetic code are also within the scope of the invention. Such nucleic acids encode functionally equivalent peptides (i.e., a peptide having a biological activity of a vertebrate hh polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of a vertebrate hh polypeptide. However, it is expected that DNA sequence polymorphisms that do lead to changes in the amino acid sequences of the subject hh polypeptides will exist among vertebrates. One skilled in the art will appreciate that these variations in one or more nucleotides (up to about 3–5% of the nucleotides) of the nucleic acids encoding polypeptides having an activity of a vertebrate hh polypeptide may exist among individuals of a given species due to natural allelic variation.

As used herein, a hedgehog gene fragment refers to a nucleic acid having fewer nucleotides than the nucleotide sequence encoding the entire mature form of a vertebrate hh protein yet which (preferably) encodes a polypeptide which retains some biological activity of the full length protein.

As indicated by the examples set out below, hedgehog protein-encoding nucleic acids can be obtained from mRNA present in any of a number of eukaryotic cells. It should also be possible to obtain nucleic acids encoding vertebrate hh polypeptides of the present invention from genomic DNA obtained from both adults and embryos. For example, a gene encoding a hh protein can be cloned from either a cDNA or a genomic library in accordance with protocols described herein, as well as those generally known to persons skilled in the art. A cDNA encoding a hedgehog protein can be obtained by isolating total mRNA from a cell, e.g. a mammalian cell, e.g. a human cell, including embryonic cells. Double stranded cDNAs can then be prepared from the total mRNA, and subsequently inserted into a suitable plasmid or bacteriophage vector using any one of a number of known techniques. The gene encoding a vertebrate hh protein can also be cloned using established polymerase chain reaction techniques in accordance with the nucleotide sequence information provided by the invention. The nucleic acid of the invention can be DNA or RNA. A preferred nucleic acid is a cDNA represented by a sequence selected from the group consisting of SEQ ID Nos:1–7.

Another aspect of the invention relates to the use of the isolated nucleic acid in "antisense" therapy. As used herein, "antisense" therapy refers to administration or in situ generation of oligonucleotide probes or their derivatives which specifically hybridizes (e.g. binds) under cellular conditions, with the cellular mRNA and/or genomic DNA encoding one or more of the subject hedgehog proteins so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a vertebrate hh protein. Alternatively, the antisense construct is an oligonucleotide probe which is generated ex vivo and which, when introduced into the cell causes inhibition of expression by hybridizing with the mRNA and/or genomic sequences of a vertebrate hh gene. Such oligonucleotide probes are preferably modified oligonucleotide which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *Biotechniques* 6:958–976; and Stein et al. (1988) *Cancer Res* 48:2659–2668.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of loads of administration, including systemic and topical or localized administration. Techniques and formulations generally may be found in *Remmington's Pharmaceutical Sciences,* Meade Publishing Co., Easton, Pa. For systemic administration, injection is preferred, including intramuscular, intravenous, intraperitoneal, and subcutaneous for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as generally known in the art.

In addition to use in therapy, the oligomers of the invention may be used as diagnostic reagents to detect the presence or absence of the target DNA or RNA sequences to which they specifically bind. Such diagnostic tests are described in further detail below.

Likewise, the antisense constructs of the present invention, by antagonizing the normal biological activity of one of the hedgehog proteins, can be used in the manipulation of tissue, e.g. tissue differentiation, both in vivo and in ex vivo tissue cultures.

Also, the anti-sense techniques (e.g. microinjection of antisense molecules, or transfection with plasmids whose transcripts are anti-sense with regard to an hh mRNA or gene sequence) can be used to investigate role of hh in developmental events, as well as the normal cellular function of hh in adult tissue. Such techniques can be utilized in cell culture, but can also be used in the creation of transgenic animals.

This invention also provides expression vectors containing a nucleic acid encoding a vertebrate hh polypeptide, operably linked to at least one transcriptional regulatory sequence. Operably linked is intended to mean that the nucleotide sequence is linked to a regulatory sequence in a manner which allows expression of the nucleotide sequence. Regulatory sequences are art-recognized and are selected to direct expression of the subject vertebrate hh proteins. Accordingly, the term transcriptional regulatory sequence includes promoters, enhancers and other expression control elements. Such regulatory sequences are described in Goeddel; *Gene Expression Technology: Methods in Enzymology* 185, Academic Press, San Diego, Calif. (1990). For instance, any of a wide variety of expression control sequences, sequences that control the expression of a DNA sequence when operatively linked to it, may be used in these vectors to express DNA sequences encoding vertebrate hh polypeptides of this invention. Such useful expression control sequences, include, for example, a viral LTR, such as the LTR of the Moloney murine leukemia virus, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage λ, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered. In one embodiment, the expression vector includes a recombinant gene encoding a peptide having an agonistic activity of a subject hedgehog polypeptide, or alternatively, encoding a peptide which is an antagonistic form of the hh protein. Such expression vectors can be used to transfect cells and thereby produce polypeptides, including fusion proteins, encoded by nucleic acids as described herein.

Moreover, the gene constructs of the present invention can also be used as a part of a gene therapy protocol to deliver nucleic acids encoding either an agonistic or antagonistic form of one of the subject vertebrate hedgehog proteins. Thus, another aspect of the invention features expression vectors for in vivo or in vitro transfection and expression of a vertebrate hh polypeptide in particular cell types so as to reconstitute the function of, or alternatively, abrogate the function of hedgehog-induced signaling in a tissue in which the naturally-occurring form of the protein is misexpressed; or to deliver a form of the protein which alters differentiation of tissue, or which inhibits neoplastic transformation.

Expression constructs of the subject vertebrate hh polypeptide, and mutants thereof, may be administered in any biologically effective carrier, e.g. any formulation or composition capable of effectively delivering the recombinant gene to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically. Furthermore, it will be recognized that the particular gene construct provided for in vivo transduction of hedgehog expression are also useful for in vitro transduction of cells, such as for use in the ex vivo tissue culture systems described below.

A preferred approach for in vivo introduction of nucleic acid into a cell is by use of a viral vector containing nucleic acid, e.g. a cDNA, encoding the particular form of the hedgehog polypeptide desired. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller; A. D. (1990) *Blood* 76:271). Thus, recombinant retrovirus can be constructed in which part of the retroviral coding sequence (gag, pol, env) has been replaced by nucleic acid encoding one of the subject proteins rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including neuronal cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci.* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115; U.S. Pat. Nos. 4,868,116; 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al. (1989) *PNAS* 86:9079–9083; Julan et al. (1992) *J. Gen Virol* 73:3251–3255; and Goud et al. (1983) *Virology* 163:251–254); or coupling cell surface receptor ligands to the viral env proteins (Neda et al. (1991) *J Biol Chem* 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector in to an amphotropic vector.

Moreover, use of retroviral gene delivery can be further enhanced by the use of tissue- or cell-specific transcriptional regulatory sequences which control expression of the hh gene of the retroviral vector.

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they can be used to infect a wide variety of cell types, including airway epithelium (Rosenfeld et al. (1992) cited supra), endothelial cells (Lemarchand et al. (1992) *Proc. Natl. Acad. Sci. USA* 89:6482–6486), hepatocytes (Herz and Gerard (1993) *Proc. Natl. Acad. Sci. USA* 90:2812–2816) and muscle cells (Quantin et al. (1992) *Proc. Natl. Acad. Sci. USA* 89:2581–2584). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol* 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) *Cell* 16:683; Berkner et al., supra; and Graham et al. in *Methods in Molecular Biology*, E. J. Murray, Ed. (Humana, Clifton, N.J., 1991) vol. 7. pp. 109–127). Expression of the inserted hedgehog gene can be under control of, for example, the E1A promoter, the major late promoter (MLP) and associated leader sequences, the E3 promoter, or exogenously added promoter sequences.

Yet another viral vector system useful for delivery of one of the subject vertebrate hh genes is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

In addition to viral transfer methods, such as those illustrated above, non-viral methods can also be employed to cause expression of a subject hedgehog polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject hh polypeptide gene by the targeted cell. Exemplary gene delivery systems of this type include liposomal derived systems, poly-lysine conjugates, and artificial viral envelopes.

In clinical settings, the gene delivery systems for the therapeutic hedgehog gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *PNAS* 91: 3054–3057). A vertebrate hh gene, such as any one of the clones represented in the group consisting of SEQ ID NO: 1–7, can be delivered in a gene therapy construct by electroporation using techniques described, for example, by Dev et al. ((1994) *Cancer Treat Rev* 20:105–115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

Another aspect of the present invention concerns recombinant forms of the hedgehog proteins. Recombinant polypeptides preferred by the present invention, in addition to native hedgehog proteins, are at least 60% homologous, more preferably 70% homologous and most preferably 80% homologous with an amino acid sequence represented by any of SEQ ID Nos:8–14. Polypeptides which possess an activity of a hedgehog protein (i.e. either agonistic or antagonistic), and which are at least 90%, more preferably at least 95%, and most preferably at least about 98–99% homologous with a sequence selected from the group consisting of SEQ ID Nos:8–14 are also within the scope of the invention.

The term "recombinant protein" refers to a polypeptide of the present invention which is produced by recombinant DNA techniques, wherein generally, DNA encoding a vertebrate hh polypeptide is inserted into a suitable expression vector which is in turn used to transform a host cell to produce the heterologous protein. Moreover, the phrase "derived from", with respect to a recombinant hedgehog gene, is meant to include within the meaning of "recombinant protein" those proteins having an amino acid sequence of a native hedgehog protein, or an amino acid sequence similar thereto which is generated by mutations including substitutions and deletions (including truncation) of a naturally occurring form of the protein.

The present invention further pertains to recombinant forms of one of the subject hedgehog polypeptides which are encoded by genes derived from a vertebrate organism, particularly a mammal (e.g. a human), and which have amino acid sequences evolutionarily related to the hedgehog proteins represented in SEQ ID Nos:8–14. Such recombinant hh polypeptides preferably are capable of functioning in one of either role of an agonist or antagonist of at least one biological activity of a wild-type ("authentic") hedgehog protein of the appended sequence listing. The term "evolutionarily related to", with respect to amino acid sequences of vertebrate hedgehog proteins, refers to both polypeptides having amino acid sequences which have arisen naturally, and also to mutational variants of vertebrate hh polypeptides which are derived, for example, by combinatorial mutagenesis. Such evolutionarily derived hedgehog proteins polypeptides preferred by the present invention are at least 60% homologous, more preferably 70% homologous and most preferably 80% homologous with the amino acid sequence selected from the group consisting of SEQ ID Nos:8–14. Polypeptides having at least about 90%, more preferably at least about 95%, and most preferably at least about 98–99% homology with a sequence selected from the group consisting of SEQ ID Nos:8–14 are also within the scope of the invention.

The present invention further pertains to methods of producing the subject hedgehog polypeptides. For example, a host cell transfected with a nucleic acid vector directing expression of a nucleotide sequence encoding the subject polypeptides can be cultured under appropriate conditions to allow expression of the peptide to occur. The polypeptide hedgehog may be secreted and isolated from a mixture of cells and medium containing the recombinant vertebrate hh polypeptide. Alternatively, the peptide may be retained cytoplasmically by removing the signal peptide sequence from the recombinant hh gene and the cells harvested, lysed and the protein isolated. A cell culture includes host cells, media and other byproducts. Suitable media for cell culture are well known in the art. The recombinant hh polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant hh polypeptide is a fusion protein containing a domain which facilitates its purification, such as an hh/GST fusion protein.

This invention also pertains to a host cell transfected to express a recombinant form of the subject hedgehog polypeptides. The host cell may be any prokaryotic or eukaryotic cell. Thus, a nucleotide sequence derived from the cloning of vertebrate hedgehog proteins, encoding all or a selected portion of the full-length protein, can be used to produce a recombinant form of a vertebrate hh polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. insulin, interferons, human growth hormone, IL-1, IL-2, and the like. Similar procedures, or modifications thereof, can be employed to prepare recombinant hedgehog polypeptides by microbial means or tissue-culture technology in accord with the subject invention.

The recombinant hedgehog genes can be produced by ligating nucleic acid encoding an hh protein, or a portion thereof, into a vector suitable for expression in either prokaryotic cells, eukaryotic cells, or both. Expression vectors for production of recombinant forms of the subject hh polypeptides include plasmids and other vectors. For instance, suitable vectors for the expression of a hedgehog polypeptide include plasmids of the types: pBR322-derived plasmids, pEMBL-derived plasmids, pEX-derived plasmids, pBTac-derived plasmids and pUC-derived plasmids for expression in prokaryotic cells, such as $E.$ $coli.$ A number of vectors exist for the expression of recombinant proteins in yeast. For instance, YEP24, YIP5, YEP51, YEP52, pYES2, and YRP17 are cloning and expression vehicles useful in the introduction of genetic constructs into $S.$ $cerevisiae$ (see, for example, Broach et al. (1983) in $Experimental$ $Manipulation$ $of$ $Gene$ $Expression,$ ed. M. Inouye Academic Press, p. 83, incorporated by reference herein). These vectors can replicate in $E.$ $coli$ due the presence of the pBR322 ori, and in $S.$ $cerevisiae$ due to the replication determinant of the yeast 2 micron plasmid. In addition, drug resistance markers such as ampicillin can be used. In an illustrative embodiment, an hh polypeptide is produced recombinantly utilizing an expression vector generated by sub-cloning the coding sequence of one of the hedgehog genes represented in SEQ ID Nos:1–7.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see $Molecular$ $Cloning$ $A$ $Laboratory$ $Manual,$ 2nd Ed., ed. by Sambrook, Fritsch and Maniatis (Cold Spring Harbor Laboratory Press: 1989) Chapters 16 and 17.

In some instances, it may be desirable to express the recombinant hedgehog polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When it is desirable to express only a portion of an hh protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from $E.$ $coli$ (Ben-Bassat et al. (1987) $J.$ $Bacteriol.$ 169:751–757) and $Salmonella$ $typhimurium$ and its in vitro activity has been demonstrated on recombinant proteins (Miller et al. (1987) $PNAS$ 84:2718–1722). Therefore, removal of an N-terminal methionine, if desired, can be achieved either in vivo by expressing hedgehog-derived polypeptides in a host which produces MAP (e.g., $E.$ $coli$ or CM89 or $S.$ $cerevisiae$), or in vitro by use of purified MAP (e.g., procedure of Miller et al., supra).

Alternatively, the coding sequences for the polypeptide can be incorporated as a part of a fusion gene including a nucleotide sequence encoding a different polypeptide. This type of expression system can be useful under conditions where it is desirable to produce an immunogenic fragment of a hedgehog protein. For example, the VP6 capsid protein of rotavirus can be used as an immunologic carrier protein for portions of the hh polypeptide, either in the monomeric form or in the form of a viral particle. The nucleic acid sequences corresponding to the portion of a subject hedgehog protein to which antibodies are to be raised can be incorporated into a fusion gene construct which includes coding sequences for a late vaccinia virus structural protein to produce a set of recombinant viruses expressing fusion proteins comprising hh epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of an hh protein and the poliovirus capsid protein can be created to enhance immunogenicity of the set of polypeptide antigens (see, for example, EP Publication No:0259149; and Evans et al. (1989) *Nature* 339:385; Huang et al. (1988) *J. Virol.* 62:3855; and Schlienger et al. (1992) *J. Virol.* 66:2).

The Multiple Antigen Peptide system for peptide-based immunization can also be utilized to generate an immunogen, wherein a desired portion of an hh polypeptide is obtained directly from organo-chemical synthesis of the peptide onto an oligomeric branching lysine core (see, for example, Posnett et al. (1988) *JBC* 263:1719 and Nardelli et al. (1992) *J. Immunol.* 148:914). Antigenic determinants of hh proteins can also be expressed and presented by bacterial cells.

In addition to utilizing fusion proteins to enhance immunogenicity, it is widely appreciated that fusion proteins can also facilitate the expression of proteins, and accordingly, can be used in the expression of the vertebrate hh polypeptides of the present invention. For example, hedgehog polypeptides can be generated as glutathione-S-transferase (GST-fusion) proteins. Such GST-fusion proteins can enable easy purification of the hedgehog polypeptide, as for example by the use of glutathione-derivatized matrices (see, for example, *Current Protocols in Molecular Biology*, eds. Ausubel et al. (N.Y.: John Wiley & Sons, 1991)). In another embodiment, a fusion gene coding for a purification leader sequence, such as a poly-(His)/enterokinase cleavage site sequence, can be used to replace the signal sequence which naturally occurs at the N-terminus of the hh protein (e.g.of the pro-form, in order to permit purification of the poly(His)-hh protein by affinity chromatography using a $Ni^{2+}$ metal resin. The purification leader sequence can then be subsequently removed by treatment with enterokinase (e.g., see Hochuli et al. (1987) *J. Chromatography* 411:177; and Janknecht et al. *PNAS* 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

Hedgehog polypeptides may also be chemically modified to create hh derivatives by forming covalent or aggregate conjugates with other chemical moieties, such as glycosyl groups, lipids, phosphate, acetyl groups and the like. Covalent derivatives of hedgehog proteins can be prepared by linking the chemical moieties to functional groups on amino acid sidechains of the protein or at the N-terminus or at the C-terminus of the polypeptide.

For instance, hedgehog proteins can be generated to include a moiety, other than sequence naturally associated with the protein, that binds a component of the extracellular matrix and enhances localization of the analog to cell surfaces. For example, sequences derived from the fibronectin "type-III repeat", such as a tetrapeptide sequence R-G-D-S (Pierschbacher et al. (1984) *Nature* 309:30–3; and Kornblihtt et al. (1985) *EMBO* 4:1755–9) can be added to the hh polypeptide to support attachment of the chimeric molecule to a cell through binding ECM components (Ruoslahti et al. (1987) *Science* 238:491–497; Pierschbacheret al. (1987) *J. Biol. Chem.* 262:17294–8.; Hynes (1987) *Cell* 48:549–54; and Hynes (1992) *Cell* 69:11–25).

The present invention also makes available isolated hedgehog polypeptides which are isolated from, or otherwise substantially free of other cellular and extracellular proteins, especially morphogenic proteins or other extracellular or cell surface associated proteins which may normally be associated with the hedgehog polypeptide. The term "substantially free of other cellular or extracellular proteins" (also referred to herein as "contaminating proteins") or "substantially pure or purified preparations" are defined as encompassing preparations of hh polypeptides having less than 20% (by dry weight) contaminating protein, and preferably having less than 5% contaminating protein. Functional forms of the subject polypeptides can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins. The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions. In preferred embodiments, purified hedgehog preparations will lack any contaminating proteins from the same animal from that hedgehog is normally produced, as can be accomplished by recombinant expression of, for example, a human hedgehog protein in a non-human cell.

As described above for recombinant polypeptides, isolated hh polypeptides can include all or a portion of the amino acid sequences represented in SEQ ID No:8, SEQ ID No:9, SEQ ID No:10, SEQ ID No:11, SEQ ID No:12, SEQ ID No:13 or SEQ ID No:14, or a homologous sequence thereto. Preferred fragments of the subject hedgehog proteins correspond to the N-terminal and C-terminal proteolytic fragments of the mature protein (see, for instance, Examples 6 and 9). Bioactive fragments of hedgehog polypeptides are described in great detail in U.S. Ser. No. 08/435,093, filed May 4, 1995, herein incorporated by reference.

Isolated peptidyl portions of hedgehog proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a hedgehog polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") hedgehog protein.

The recombinant hedgehog polypeptides of the present invention also include homologs of the authentic hedgehog proteins, such as versions of those protein which are resistant to proteolytic cleavage, as for example, due to mutations which alter potential cleavage sequences or which inactivate an enzymatic activity associated with the protein. Hedgehog homologs of the present invention also include proteins which have been post-translationally modified in a manner different than the authentic protein. Exemplary derivatives of vertebrate hedgehog proteins include polypeptides which lack N-glycosylation sites (e.g. to produce an unglycosylated protein), or which lack N-terminal and/or C-terminal sequences.

Modification of the structure of the subject vertebrate hh polypeptides can be for such purposes as enhancing therapeutic or prophylactic efficacy, or stability (e.g., ex vivo shelf life and resistance to proteolytic degradation in vivo). Such modified peptides, when designed to retain at least one activity of the naturally-occurring form of the protein, are considered functional equivalents of the hedgehog polypeptides described in more detail herein. Such modified peptides can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine, histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing= cysteine and methionine. (see, for example, *Biochemistry*, 2nd ed., Ed. by L. Stryer, W H Freeman and Co.: 1981). Whether a change in the amino acid sequence of a peptide results in a functional hedgehog homolog (e.g. functional in the sense that it acts to mimic or antagonize the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

This invention further contemplates a method for generating sets of combinatorial mutants of the subject hedgehog proteins as well as truncation mutants, and is especially useful for identifying potential variant sequences (e.g. homologs) that are functional in binding to a receptor for hedgehog proteins. The purpose of screening such combinatorial libraries is to generate, for example, novel hh homologs which can act as either agonists or antagonist, or alternatively, possess novel activities all together. To illustrate, hedgehog homologs can be engineered by the present method to provide more efficient binding to a cognate receptor, yet still retain at least a portion of an activity associated with hh. Thus, combinatorially-derived homologs can be generated to have an increased potency relative to a naturally occurring form of the protein. Likewise, hedgehog homologs can be generated by the present combinatorial approach to act as antagonists, in that they are able to mimic, for example, binding to other extracellular matrix components (such as receptors), yet not induce any biological response, thereby inhibiting the action of authentic hedgehog or hedgehog agonists. Moreover, manipulation of certain domains of hh by the present method can provide domains more suitable for use in fusion proteins, such as one that incorporates portions of other proteins which are derived from the extracellular matrix and/or which bind extracellular matrix components.

In one aspect of this method, the amino acid sequences for a population of hedgehog homologs or other related proteins are aligned, preferably to promote the highest homology possible. Such a population of variants can include, for example, hh homologs from one or more species. Amino acids which appear at each position of the aligned sequences are selected to create a degenerate set of combinatorial sequences. In a preferred embodiment, the variegated library of hedgehog variants is generated by combinatorial mutagenesis at the nucleic acid level, and is encoded by a variegated gene library. For instance, a mixture of synthetic oligonucleotides can be enzymatically ligated into gene sequences such that the degenerate set of potential hh sequences are expressible as individual polypeptides, or alternatively, as a set of larger fusion proteins (e.g. for phage display) containing the set of hh sequences therein.

Figure 2:
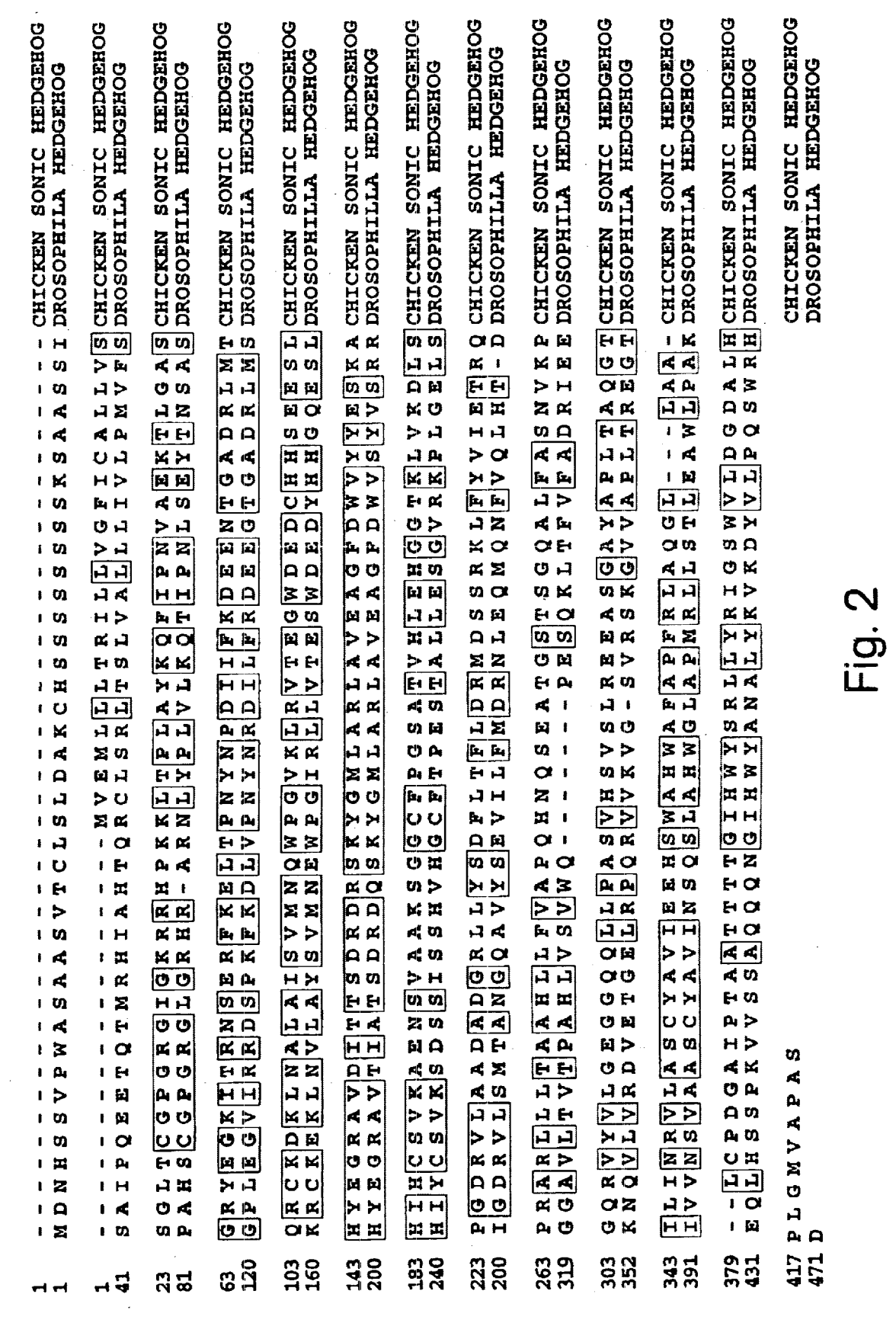

As illustrated in FIGS. 5A-1 and 5A-2,to analyze the sequences of a population of variants, the amino acid sequences of interest can be aligned relative to sequence homology. The presence or absence of amino acids from an aligned sequence of a particular variant is relative to a chosen consensus length of a reference sequence, which can be real or artificial. In order to maintain the highest homology in alignment of sequences, deletions in the sequence of a variant relative to the reference sequence can be represented by an amino acid space (● or *), while insertional mutations in the variant relative to the reference sequence can be disregarded and left out of the sequence of the variant when aligned. For instance, FIGS. 5A-1 and 5A-2 include the alignment of several cloned forms of hh from different species. Analysis of the alignment of the hh clones shown in FIGS. 5A-1 and 5A-2 can give rise to the generation of a degenerate library of polypeptides comprising potential hh sequences.

In an illustrative embodiment, alignment of exons 1, 2 and a portion of exon 3 encoded sequences (e.g. the N-terminal approximately 221 residues of the mature protein) of each of the Shh clones produces a degenerate set of Shh polypeptides represented by the general formula:

C-G-P-G-R-G-X(1)-G -X(2)-R-R-H-P-K-K-L-T-P-L-A-Y-K-Q-F-I-P-N-V-A-E-K-T-L-G-A-S-G-R-Y-E-G-K-I-X(

3)-R-N-S-E-R-F-K-E-L-T-P-N-Y-N-P-D-I-I-F-K-D-E-E-N-T-G-A-D-R-L-M-T-Q-R-C-K-D-K-L-N-X(

4)-L-A-I-S-V-M-N-X(

5)-W-P-G-V-X(6)-L-R-V-T-E-G-W-D-E-D-G-H-H-X(7)-E-E-S-L-H-Y-E-G-R-A-V-D-I-T-T-S-D-R-D-X(

8)-S-K-Y-G -X(9)-L-X(10)-R-L-A-V-E-A-G-F-D-W-V-Y-Y-E-S-K-A-H-I-H-C-S-V-K-A-E-N-S-V-A-A-K-S-G-G-C-F-P-G-S-A-X(

11)-V-X(12)-L-X(13)-X(14)-G-G-X(15)-K-X-(16)-V-K-D-L-X(

17)-P-G-D-X(18)-V-L-A-A-D-X(19)-X(20)-G-X(21)-L-X(

22)-X(23)-S-D-F-X(24)-X(25)-F-X(26)-D-R     (SEQ ID No:40), wherein each of the degenerate positions "X" can be an amino acid which occurs in that position in one of the human, mouse, chicken or zebrafish Shh clones, or, to expand the library, each X can also be selected from amongst amino acid residue which would be conservative substitutions for the amino acids which appear naturally in each of those positions. For instance, Xaa(1) represents Gly, Ala, Val, Leu, Ile, Phe, Tyr or Trp; Xaa(2) represents Arg, His or Lys; Xaa(3) represents Gly, Ala, Val, Leu, Ile, Ser or Thr; Xaa(4) represents Gly, Ala, Val, Leu, Ile, Ser or Thr; Xaa(5) represents Lys, Arg, His, Asn or Gln; Xaa(6) represents Lys, Arg or His; Xaa(7) represents Ser, Thr, Tyr, Trp or Phe; Xaa(8) represents Lys, Arg or His; Xaa(9) represents Met, Cys, Ser or Thr; Xaa(10) represents Gly, Ala, Val, Leu, Ile, Ser or Thr; Xaa(11) represents Leu, Val, Met, Thr or Ser; Xaa(12) represents His, Phe, Tyr, Ser, Thr, Met or Cys; Xaa(13) represents Gin, Asn, Glu, or Asp; Xaa(14) represents His, Phe, Tyr, Thr, Gin, Asn, Glu or Asp; Xaa(15) represents Gin, Asn, Glu, Asp, Thr, Ser, Met or Cys; Xaa(16) represents Ala, Gly, Cys, Leu, Val or Met; Xaa(17) represents Arg, Lys, Met, Ile, Asn, Asp, Glu, Gin, Ser, Thr or Cys; Xaa(18) represents Arg, Lys, Met or Ile; Xaa(19) represents Ala, Gly, Cys, Asp, Glu, Gin, Asn, Ser, Thr or Met; Xaa(20) represents Ala, Gly, Cys, Asp, Asn, Glu or Gln; Xaa(21) represents Arg, Lys, Met, Ile, Asn, Asp, Glu or Gin; Xaa(22) represent Leu, Val, Met or Ile; Xaa(23) represents Phe, Tyr, Thr, His or Trp; Xaa(24) represents Ile, Val, Leu or Met; .Xaa(25) represents Met, Cys, Ile, Leu, Val, Thr or Ser; Xaa(26) represents Leu, Val, Met, Thr or Ser. In an even more expansive library, each X can be selected from any amino acid.

In similar fashion, alignment of each of the human, mouse, chicken and zebrafish hedgehog clones (FIG. 5B), can provide a degenerate polypeptide sequence represented by the general formula:

C-G-P-G-R-G-X(1)-X(2)-X(3)-R-R-X(4)-X(5)-X(6) -P-K-X(7)-L-X(8)-P-L-X(

9)-Y-K-Q-F-X(10)-P-X(11)-X(12)-X(13)-E-X(14)-T-L-G-A-S-G-X(

15)-X(16)-E-G-X(17)-X(18)-X(19)-R-X(20)-S-E-R-F-X(21)-X(22)-L-T-P-N-Y-N-P-D-I-I-F-K-D-E-E-N-X(

23)-G-A-D-R-L-M-T-X(24)-R-C-K-X(

25)-X(26)-X(27)-N-X(28)-L-A-I-S-V-M-N-X(29)-W-P-G-V-X(30)-L-R-V-T-E-G-X(

31)-D-E-D-G-H-H-X(32)-X(33)-X(34)-S-L-H-Y-E-G-R-A-X(

35)-D-I-T-T-S-D-R-D-X(36)-X(37)-K-Y-G-X(38)-L-X(39)-R-L-A-V-E-A-G-F-D-W-V-Y-Y-E-S-X(

40)-X(41)-H-X(42)-H-X(43)-S-V-K-X(44)-X( 45)                             (SEQ ID No:41), wherein, as above, each of the degenerate positions "X" can be an amino acid which occurs in a corresponding position in one of the wild-type clones, and may also include amino acid residue which would be conservative substitutions, or each X can be any amino acid residue. In an exemplary embodiment, Xaa(1) represents Gly, Ala, Val, Leu, Ile, Pro, Phe or Tyr; Xaa(2) represents Gly, Ala, Val, Leu or Ile; Xaa(3) represents Gly, Ala, Val, Leu, Ile, Lys, His or Arg; Xaa(4) represents Lys, Arg or His; Xaa(5) represents Phe, Trp, Tyr or an amino acid gap; Xaa(6) represents Gly, Ala, Val, Leu, Ile or an amino acid gap; Xaa(7) represents Asn, Gln, His, Arg or Lys; Xaa(8) represents Gly, Ala, Val, Leu, Ile, Ser or Thr; Xaa(9) represents Gly, Ala, Val, Leu, Ile, Ser or Thr; Xaa(10) represents Gly, Ala, Val, Leu, Ile, Ser or Thr; Xaa(11) represents Ser, Thr, Gln or Asn; Xaa(12) represents Met, Cys, Gly, Ala, Val, Leu, Ile, Ser or Thr; Xaa(13) represents Gly, Ala, Val, Leu, Ile or Pro; Xaa(14) represents Arg, His or Lys; Xaa(15) represents Gly, Ala, Val, Leu, Ile, Pro, Arg, His or Lys; Xaa(16) represents Gly, Ala, Val, Leu, Ile, Phe or Tyr; Xaa(17) represents Arg, His or Lys; Xaa(18) represents Gly, Ala, Val, Leu, Ile, Ser or Thr; Xaa(19) represents Thr or Ser; Xaa(20) represents Gly, Ala, Val, Leu, Ile, Asn or Gln; Xaa(21) represents Arg, His or Lys; Xaa(22) represents Asp or Glu; Xaa(23) represents Ser or Thr; Xaa(24) represents Glu, Asp, Gln or Asn; Xaa(25) represents Glu or Asp; Xaa(26) represents Arg, His or Lys; Xaa(27) represents Gly, Ala, Val, Leu or Ile; Xaa(28) represents Gly, Ala, Val, Leu, Ile, Thr or Ser; Xaa(29) represents Met, Cys, Gln, Asn, Arg, Lys or His; Xaa(30) represents Arg, His or Lys; Xaa(31) represents Trp, Phe, Tyr, Arg, His or Lys; Xaa(32) represents Gly, Ala, Val, Leu, Ile, Ser, Thr, Tyr or Phe; Xaa(33) represents Gln, Asn, Asp or Glu; Xaa(34) represents Asp or Glu; Xaa(35) represents Gly, Ala, Val, Leu, or Ile; Xaa(36) represents Arg, His or Lys; Xaa(37) represents Asn, Gln, Thr or Ser; Xaa(38) represents Gly, Ala, Val, Leu, Ile, Ser, Thr, Met or Cys; Xaa(39) represents Gly, Ala, Val, Leu, Ile, Thr or Ser; Xaa(40) represents Arg, His or Lys; Xaa(41) represents Asn, Gln, Gly, Ala, Val, Leu or Ile; Xaa(42) represents Gly, Ala, Val, Leu or Ile; Xaa(43) represents Gly, Ala, Val, Leu, Ile, Ser, Thr or Cys; Xaa(44) represents Gly, Ala, Val, Leu, Ile, Thr or Ser; and Xaa(45) represents Asp or Glu.

There are many ways by which the library of potential hh homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential hh sequences. The synthesis of degenerate oligonucleotides is well known in the art (see for example, Narang, S A (1983) *Tetrahedron* 39:3; Itakura et al. (1981) *Recombinant DNA,*

*Proc 3rd Cleveland Sympos. Macromolecules,* ed. A G Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis of hedgehog homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate hedgehog sequences created by combinatorial mutagenesis techniques.

In one embodiment, the combinatorial library is designed to be secreted (e.g. the polypeptides of the library all include a signal sequence but no transmembrane or cytoplasmic domains), and is used to transfect a eukaryotic cell that can be co-cultured with embryonic cells. A functional hedgehog protein secreted by the cells expressing the combinatorial library will diffuse to neighboring embryonic cells and induce a particular biological response, such as to illustrate, neuronal differentiation. Using antibodies directed to epitopes of particular neuronal cells (e.g. Islet-1 or Pax-1), the pattern of detection of neuronal induction will resemble a gradient function, and will allow the isolation (generally after several repetitive rounds of selection) of cells producing active hedgehog homologs. Likewise, hh antagonists can be selected in similar fashion by the ability of the cell producing a functional antagonist to protect neighboring cells from the effect of wild-type hedgehog added to the culture media.

To illustrate, target cells are cultured in 24-well microtitre plates. Other eukaryotic cells are transfected with the combinatorial hh gene library and cultured in cell culture inserts (e.g. Collaborative Biomedical Products, Catalog #40446) that are able to fit into the wells of the microtitre plate. The cell culture inserts are placed in the wells such that recombinant hh homologs secreted by the cells in the insert can diffuse through the porous bottom of the insert and contact the target cells in the microtitre plate wells. After a period of time sufficient for functional forms of a hedgehog protein to produce a measurable response in the target cells, the inserts are removed and the effect of the variant hedgehog proteins on the target cells determined. For example, where the target cell is a neural crest cell and the activity desired from the hh homolog is the induction of neuronal differentiation, then fluorescently-labeled antibodies specific for Islet-1 or other neuronal markers can be used to score for induction in the target cells as indicative of a functional hh in that well. Cells from the inserts corresponding to wells which score positive for activity can be split and re-cultured on several inserts, the process being repeated until the active clones are identified.

In yet another screening assay, the candidate hedgehog gene products are displayed on the surface of a cell or viral particle, and the ability of particular cells or viral particles to associate with a hedgehog-binding moiety (such as an hedgehog receptor or a ligand which binds the hedgehog protein) via this gene product is detected in a "panning assay". Such panning steps can be carried out on cells cultured from embryos. For instance, the gene library can be cloned into the gene for a surface membrane protein of a bacterial cell, and the resulting fusion protein detected by panning (Ladner et al., WO 88/06630; Fuchs et al. (1991) *Bio/Technology* 9:1370–1371; and Goward et al. (1992) *TIBS* 18:136–140). In a similar fashion, fluorescently labeled molecules which bind hh can be used to score for potentially functional hh homologs. Cells can be visually inspected and separated under a fluorescence microscope, or, where the morphology of the cell permits, separated by a fluorescence-activated cell sorter.

In an alternate embodiment, the gene library is expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, large number of phage can be screened at one time. Second, since each infectious phage displays the combinatorial gene product on its surface, if a particular phage is recovered from an affinity matrix in low yield, the phage can be amplified by another round of infection. The group of almost identical *E.coli* filamentous phages M13, fd, and f1 are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) *J. Biol. Chem.* 267:16007–16010; Griffths et al. (1993) *EMBO J* 12:725–734; Clackson et al. (1991) *Nature* 352:624–628; and Barbas et al. (1992) *PNAS* 89:4457–4461).

In an illustrative embodiment, the recombinant phage antibody system (RPAS, Pharamacia Catalog number 27-9400-01) can be easily modified for use in expressing and screening hh combinatorial libraries. For instance, the pCANTAB 5 phagemid of the RPAS kit contains the gene which encodes the phage gIII coat protein. The hh combinatorial gene library can be cloned into the phagemid adjacent to the gIII signal sequence such that it will be expressed as a gIII fusion protein. After ligation, the phagemid is used to transform competent *E. coli* TG1 cells. Transformed cells are subsequently infected with M13KO7 helper phage to rescue the phagemid and its candidate hh gene insert. The resulting recombinant phage contain phagemid DNA encoding a specific candidate hh, and display one or more copies of the corresponding fusion coat protein. The phage-displayed candidate hedgehog proteins which are capable of binding an hh receptor are selected or enriched by panning. For instance, the phage library can be applied to cultured embryonic cells and unbound phage washed away from the cells. The bound phage is then isolated, and if the recombinant phage express at least one copy of the wild type gill coat protein, they will retain their ability to infect *E. coli.* Thus, successive rounds of reinfection of *E. coli,* and panning will greatly enrich for hh homologs, which can then be screened for further biological activities in order to differentiate agonists and antagonists.

Combinatorial mutagenesis has a potential to generate very large libraries of mutant proteins, e.g., in the order of $10^{26}$ molecules. Combinatorial libraries of this size may be technically challenging to screen even with high throughput screening assays such as phage display. To overcome this problem, a new technique has been developed recently, recursive ensembel mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, *PNAS USA* 89:7811–7815; Yourvan et al., 1992, *Parallel Problem Solving from Nature,* 2., In Maenner and Manderick, eds., Elsevir Publishing Co., Amsterdam, pp. 401–410; Delgrave et al., 1993, *Protein Engineering* 6(3):327–331).

The invention also provides for reduction of the vertebrate hh protein to generate mimetics, e.g. peptide or non-peptide agents, which are able to disrupt binding of a vertebrate hh polypeptide of the present invention with an hh receptor. Thus, such mutagenic techniques as described above are also useful to map the determinants of the hedgehog proteins which participate in protein-protein interactions involved in, for example, binding of the subject vertebrate hh polypeptide to other extracellular matrix components. To illustrate, the critical residues of a subject hh polypeptide or hh ligand which are involved in molecular recognition of an hh receptor can be determined and used to generate hedgehog-derived peptidomimetics which competitively inhibit binding of the authentic hedgehog protein with that moiety. By employing, for example, scanning mutagenesis to map the amino acid residues of each of the subject hedgehog proteins which are involved in binding other extracellular proteins, peptidomimetic compounds can be generated which mimic those residues of the hedgehog protein which facilitate the interaction. Such mimetics may then be used to interfere with the normal function of a hedgehog protein. For instance, non-hydrolyzable peptide analogs of such residues can be generated using benzodiazepine (e.g., see Freidinger et al. in *Peptides: Chemistry and Biology,* G. R. Marshall ed., ESCOM Publisher: Leiden, Netherlands, 1988), azepine (e.g., see Huffman et al. in *Peptides: Chemistry and Biology,* G. R. Marshall ed., ESCOM Publisher: Leiden, Netherlands, 1988), substituted gama lactam rings (Garvey et al. in *Peptides: Chemistry and Biology,* G. R. Marshall ed., ESCOM Publisher:Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134:71).

Another aspect of the invention pertains to an antibody specifically reactive with a vertebrate hedgehog protein. For example, by using immunogens derived from hedgehog protein, e.g. based on the cDNA sequences, anti-protein/anti-peptide antisera or monoclonal antibodies can be made by standard protocols, (See, for example, *Antibodies: A Laboratory Manual* ed. by Harlow and Lane (Cold Spring Harbor Press: 1988)). A mammal, such as a mouse, a hamster or rabbit can be immunized with an immunogenic form of the peptide (e.g., a vertebrate hh polypeptide or an antigenic fragment which is capable of eliciting an antibody response). Techniques for conferring immunogenicity on a protein or peptide include conjugation to carriers or other techniques well known in the art. An immunogenic portion of a hedgehog protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immuno-specific for antigenic determinants of a hedgehog protein of a vertebrate organism, such as a mammal, e.g. antigenic determinants of a protein represented by SEQ ID Nos:8–14 or a closely related homolog (e.g. at least 85% homologous, preferably at least 90% homologous, and more preferably at least 95% homologous). In yet a further preferred embodiment of the present invention, in order to provide, for example, antibodies which are immuno-selective for discrete hedgehog homologs, e.g. Shh versus Dhh versus Ihh, the anti-hh polypeptide antibodies do not substantially cross react (i.e. does not react specifically) with a protein which is, for example, less than 85% homologous to any of SEQ ID Nos:8–14; e.g., less than 95% homologous with one of SEQ ID Nos:8–14; e.g., less than 98–99% homologous with one of SEQ ID Nos:8–14. By "not substantially cross react", it is meant that the antibody has a binding affinity for a non-homologous protein which is at least one order of magnitude, more preferably at least 2 orders of magnitude, and even more preferably at least 3 orders of magnitude less than the binding affinity of the antibody for one or more of the proteins of SEQ ID Nos:8–14.

Following immunization of an animal with an antigenic preparation of a hedgehog protein, anti-hh antisera can be obtained and, if desired, polyclonal anti-hh antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) *Nature,* 256: 495–497), the human B cell hybridoma technique (Kozbar et al., (1983) *Immunology Today,* 4:72), and the EBV-hybridoma technique to produce human monoclonal antibodies (Cole et al., (1985) *Monoclonal Antibodies and Cancer Therapy,* Alan R. Liss, Inc. pp. 77–96). Hybridoma cells can be screened immunochemically for production of antibodies specifically reactive with a vertebrate hh polypeptide of the present invention and monoclonal antibodies isolated from a culture comprising such hybridoma cells.

The term antibody as used herein is intended to include fragments thereof which are also specifically reactive with one of the subject vertebrate hh polypeptides. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific and chimeric molecules having affinity for a hedgehog protein conferred by at least one CDR region of the antibody.

Both monoclonal and polyclonal antibodies (Ab) directed against authentic hedgehog polypeptides, or hedgehog variants, and antibody fragments such as Fab and $F(ab)_2$, can be used to block the action of one or more hedgehog proteins and allow the study of the role of these proteins in, for example, embryogenesis and/or maintenance of differential tissue. For example, purified monoclonal Abs can be injected directly into the limb buds of chick or mouse embryos. It is demonstrated in the examples below that hh is expressed in the limb buds of, for example, day 10.5 embryos. Thus, the use of anti-hh Abs during this developmental stage can allow assessment of the effect of hh on the formation of limbs in vivo. In a similar approach, hybridomas producing anti-hh monoclonal Abs, or biodegradable gels in which anti-hh Abs are suspended, can be implanted at a site proximal or within the area at which hh action is intended to be blocked. Experiments of this nature can aid in deciphering the role of this and other factors that may be involved in limb patterning and tissue formation.

Antibodies which specifically bind hedgehog epitopes can also be used in immunohistochemical staining of tissue samples in order to evaluate the abundance and pattern of expression of each of the subject hh polypeptides. Anti-hedgehog antibodies can be used diagnostically in immuno-precipitation and immuno-blotting to detect and evaluate hedgehog protein levels in tissue as part of a clinical testing procedure. For instance, such measurements can be useful in predictive valuations of the onset or progression of neurological disorders, such as those marked by denervation-like or disuse-like symptoms. Likewise, the ability to monitor hh levels in an individual can allow determination of the efficacy of a given treatment regimen for an individual afflicted with such a disorder. The level of hh polypeptides may be measured in bodily fluid, such as in samples of cerebral spinal fluid or amniotic fluid, or can be measured in tissue, such as produced by biopsy. Diagnostic assays using anti-hh antibodies can include, for example, immunoassays designed to aid in early diagnosis of a neurodegenerative disorder, particularly ones which are manifest at birth. Diagnostic assays using anti-hh polypeptide antibodies can also include immunoassays designed to aid in early diagnosis and phenotyping of a differentiative disorder, as well as neoplastic or hyperplastic disorders.

Another application of anti-hh antibodies of the present invention is in the immunological screening of cDNA libraries constructed in expression vectors such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of an hh protein, e.g. other orthologs of a particular hedgehog protein or other homologs from the same species, can then be detected with antibodies, as, for example, reacting nitrocellulose filters lifted from infected plates with anti-hh antibodies. Positive phage detected by this assay can then be isolated from the infected plate. Thus, the presence of hedgehog homologs can be detected and cloned from other animals, as can alternate isoforms (including splicing variants) from humans.

Moreover, the nucleotide sequences determined from the cloning of hh genes from vertebrate organisms will further allow for the generation of probes and primers designed for use in identifying and/or cloning hedgehog homologs in other cell types, e.g. from other tissues, as well as hh homologs from other vertebrate organisms. For instance, the present invention also provides a probe/primer comprising a substantially purified oligonucleotide, which oligonucleotide comprises a region of nucleotide sequence that hybridizes under stringent conditions to at least 10 consecutive nucleotides of sense or anti-sense sequence selected from the group consisting of SEQ ID No:1, SEQ ID No:2, SEQ ID No:3, SEQ ID No:4, SEQ ID No:5, SEQ ID No:6 and SEQ ID No:7, or naturally occurring mutants thereof. For instance, primers based on the nucleic acid represented in SEQ ID Nos:1–7 can be used in PCR reactions to clone hedgehog homologs. Likewise, probes based on the subject hedgehog sequences can be used to detect transcripts or genomic sequences encoding the same or homologous proteins. In preferred embodiments, the probe further comprises a label group attached thereto and able to be detected, e.g. the label group is selected from the group consisting of radioisotopes, fluorescent compounds, enzymes, and enzyme co-factors.

Such probes can also be used as a part of a diagnostic test kit for identifying cells or tissue which misexpress a hedgehog protein, such as by measuring a level of a hedgehog encoding nucleic acid in a sample of cells from a patient; e.g. detecting hh mRNA levels or determining whether a genomic hh gene has been mutated or deleted.

To illustrate, nucleotide probes can be generated from the subject hedgehog genes which facilitate histological screening of intact tissue and tissue samples for the presence (or absence) of hedgehog-encoding transcripts. Similar to the diagnostic uses of anti-hedgehog antibodies, the use of probes directed to hh messages, or to genomic hh sequences, can be used for both predictive and therapeutic evaluation of allelic mutations which might be manifest in, for example, neoplastic or hyperplastic disorders (e.g. unwanted cell growth) or abnormal differentiation of tissue. Used in conjunction with immunoassays as described above, the oligonucleotide probes can help facilitate the determination of the molecular basis for a developmental disorder which may involve some abnormality associated with expression (or lack thereof) of a hedgehog protein. For instance, variation in polypeptide synthesis can be differentiated from a mutation in a coding sequence.

Accordingly, the present method provides a method for determining if a subject is at risk for a disorder characterized by aberrant control of differentiation or unwanted cell proliferation. For instance, the subject assay can be used in the screening and diagnosis of genetic and acquired disorders which involve alteration in one or more of the hedgehog genes. In preferred embodiments, the subject method can be generally characterized as comprising: detecting, in a tissue sample of the subject (e.g. a human patient), the presence or absence of a genetic lesion characterized by at least one of (i) a mutation of a gene encoding a hedgehog protein or (ii) the mis-expression of a hedgehog gene. To illustrate, such genetic lesions can be detected by ascertaining the existence of at least one of (i) a deletion of one or more nucleotides from a hedgehog gene, (ii) an addition of one or more nucleotides to a hedgehog gene, (iii) a substitution of one or more nucleotides of a hedgehog gene, (iv) a gross chromosomal rearrangement of a hedgehog gene, (v) a gross alteration in the level of a messenger RNA transcript of an hh gene, (vi) the presence of a non-wild type splicing pattern of a messenger RNA transcript of a vertebrate hh gene, and (vii) a non-wild type level of a hedgehog protein. In one aspect of the invention there is provided a probe/primer comprising an oligonucleotide containing a region of nucleotide sequence which is capable of hybridizing to a sense or antisense sequence selected from the group consisting of SEQ ID Nos:1–7, or naturally occurring mutants thereof, or 5' or 3' flanking sequences or intronic sequences naturally associated with a vertebrate hh gene. The probe is exposed to nucleic acid of a tissue sample; and the hybridization of the probe to the sample nucleic acid is detected. In certain embodiments, detection of the lesion comprises utilizing the probe/primer in a polymerase chain reaction (PCR) (see, e.g., U.S. Pat. Nos.:4,683,195 and 4,683,202) or, alternatively, in a ligation chain reaction (LCR) (see, e.g., Landegran et al. (1988) *Science,* 241:1077–1080; and NaKazawa et al. (1944) *PNAS* 91:360–364) the later of which can be particularly useful for detecting point mutations in hedgehog genes. Alternatively, immunoassays can be employed to determine the level of hh proteins, either soluble or membrane bound.

Yet another diagnostic screen employs a source of hedgehog protein directly. As described herein, hedgehog proteins of the present invention are involved in the induction of differentiation. Accordingly, the pathology of certain differentiative and/or proliferative disorders can be marked by loss of hedgehog sensitivity by the afflicted tissue. Consequently, the response of a tissue or cell sample to an inductive amount of a hedgehog protein can be used to detect and characterize certain cellular transformations and degenerative conditions. For instance, tissue/cell samples from a patient can be treated with a hedgehog agonist and the response of the tissue to the treatment determined. Response can be qualified and/or quantified, for example, on the basis of phenotypic change as result of hedgehog induction. For example, expression of gene products induced by hedgehog treatment can be scored for by immunoassay. The patched protein, for example, is upregulated in drosophila in response to Dros-HH, and, in light of the findings herein, a presumed vertebrate homolog will similarly be upregulated. Thus, detection of patched expression on the cells of the patient sample can permit detection of tissue that is not hedgehog-responsive. Likewise, scoring for other phenotypic markers provides a means for determining the response to hedgehog.

Furthermore, by making available purified and recombinant hedgehog polypeptides, the present invention facilitates the development of assays which can be used to screen for drugs, including hedgehog homologs, which are either agonists or antagonists of the normal cellular function of the subject hedgehog polypeptides, or of their role in the pathogenesis of cellular differentiation and/or proliferation and disorders related thereto. In one embodiment, the assay evaluates the ability of a compound to modulate binding between a hedgehog polypeptide and a hedgehog receptor. A variety of assay formats will suffice and, in light of the present inventions, will be comprehended by skilled artisan.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with receptor proteins. Accordingly, in an exemplary screening assay of the present invention, the compound of interest is contacted with a hedgehog receptor polypeptide which is ordinarily capable of binding a hedgehog protein. To the mixture of the compound and receptor is then added a composition containing a hedgehog polypeptide. Detection and quantification of receptor/hedgehog complexes provides a means for determining the compound's efficacy at inhibiting (or potentiating) complex formation between the receptor protein and the hedgehog polypeptide. The efficacy of the compound can be assessed by generating dose response curves from data obtained using various concentrations of the test compound. Moreover, a control assay can also be performed to provide a baseline for comparison. In the control assay, isolated and purified hedgehog polypeptide is added to a composition containing the receptor protein, and the formation of receptor/hedgehog complex is quantitated in the absence of the test compound.

In an illustrative embodiment, the polypeptide utilized as a hedgehog receptor can be generated from the drosophila patched protein or a vertebrate homolog thereof. In light of the ability of, for example, Shh to activate HH pathways in transgenic drosophila (see Example 4), it may be concluded that vertebrate hedgehog proteins are capable of binding to drosophila HH receptors. Accordingly, an exemplary screening assay includes a suitable portion of the patched protein (SEQ ID No. 42), such as one or both of the substantial extracellular domains (e.g. residues Lys-93 to His-426 and Arg-700 to Arg-966). For instance, the patched protein can be provided in soluble form, as for example a preparation of one of the extracellular domains, or a preparation of both of the extracellular domains which are covalently connected by an unstructured linker (see, for example, Huston et al. (1988) PNAS 85:4879; and U.S. Pat. No. 5,091,513), or can be provided as part of a liposomal preparation or expressed on the surface of a cell.

Complex formation between the hedgehog polypeptide and a hedgehog receptor may be detected by a variety of techniques. For instance, modulation of the formation of complexes can be quantitated using, for example, detectably labelled proteins such as radiolabelled, fluorescently labelled, or enzymatically labelled hedgehog polypeptides, by immunoassay, or by chromatographic detection.

Typically, it will be desirable to immobilize either the hedgehog receptor or the hedgehog polypeptide to facilitate separation of receptor/hedgehog complexes from uncomplexed forms of one of the proteins, as well as to accommodate automation of the assay. In one embodiment, a fusion protein can be provided which adds a domain that allows the protein to be bound to a matrix. For example, glutathione-S-transferase/receptor (GST/receptor) fusion proteins can be adsorbed onto glutathione sepharose beads (Sigma Chemical, St. Louis, Mo.) or glutathione derivatized microtitre plates, which are then combined with the hedgehog polypeptide, e.g. an $^{35}$S-labeled hedgehog polypeptide, and the test compound and incubated under conditions conducive to complex formation, e.g. at physiological conditions for salt and pH, though slightly more stringent conditions may be desired. Following incubation, the beads are washed to remove any unbound hedgehog polypeptide, and the matrix bead-bound radiolabel determined directly (e.g. beads placed in scintillant), or in the supernatant after the receptor/hedgehog complexes are dissociated. Alternatively, the complexes can dissociated from the bead, separated by SDS-PAGE gel, and the level of hedgehog polypeptide found in the bead fraction quantitated from the gel using standard electrophoretic techniques.

Other techniques for immobilizing proteins on matrices are also available for use in the subject assay. For instance, soluble portions of the hedgehog receptor protein can be immobilized utilizing conjugation of biotin and streptavidin. For instance, biotinylated receptor molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the hedgehog receptor but which do not interfere with hedgehog binding can be derivatized to the wells of the plate, and the receptor trapped in the wells by antibody conjugation. As above, preparations of a hedgehog polypeptide and a test compound are incubated in the receptor-presenting wells of the plate, and the amount of receptor/hedgehog complex trapped in the well can be quantitated. Exemplary methods for detecting such complexes, in addition to those described above for the GST-immobilized complexes, include immunodetection of complexes using antibodies reactive with the hedgehog polypeptide, or which are reactive with the receptor protein and compete for binding with the hedgehog polypeptide; as well as enzyme-linked assays which rely on detecting an enzymatic activity associated with the hedgehog polypeptide. In the instance of the latter, the enzyme can be chemically conjugated or provided as a fusion protein with the hedgehog polypeptide. To illustrate, the hedgehog polypeptide can be chemically cross-linked or genetically fused with alkaline phosphatase, and the amount of hedgehog polypeptide trapped in the complex can be assessed with a chromogenic substrate of the enzyme, e.g. paranitrophenylphosphate. Likewise, a fusion protein comprising the hedgehog polypeptide and glutathione-S-transferase can be provided, and complex formation quantitated by detecting the GST activity using 1-chloro-2,4-dinitrobenzene (Habig et al (1974) *J Biol Chem* 249:7130).

For processes which rely on immunodetection for quantitating one of the proteins trapped in the complex, antibodies against the protein, such as the anti-hedgehog antibodies described herein, can be used. Alternatively, the protein to be detected in the complex can be "epitope tagged" in the form of a fusion protein which includes, in addition to the hedgehog polypeptide or hedgehog receptor sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) *J Biol Chem* 266:21150–21157) which includes a 10-residue sequence from c-myc, as well as the pFLAG system (International Biotechnologies, Inc.) or the pEZZ-protein A system (Pharamacia, N.J.).

Where the desired portion of the hh receptor (or other hedgehog binding molecule) cannot be provided in soluble form, liposomal vesicles can be used to provide manipulatable and isolatable sources of the receptor. For example, both authentic and recombinant forms of the patched protein can be reconstituted in artificial lipid vesicles (e.g. phosphatidylcholine liposomes) or in cell membrane-derived vesicles (see, for example, Bear et al. (1992) *Cell* 68:809–818; Newton et al. (1983) *Biochemistry* 22:6110–6117; and Reber et al. (1987) *J Biol Chem* 262:11369–11374).

In addition to cell-free assays, such as described above, the readily available source of vertebrate hedgehog proteins provided by the present invention also facilitates the generation of cell-based assays for identifying small molecule agonists/antagonists and the like. Analogous to the cell-based assays described above for screening combinatorial libraries, cells which are sensitive to hedgehog induction can be contacted with a hedgehog protein and a test agent of interest, with the assay scoring for modulation in hedgehog inductive responses by the target cell in the presence and absence of the test agent. As with the cell-free assays, agents which produce a statistically significant change in hedgehog activities (either inhibition or potentiation) can be identified.

In an illustrative embodiment, motor neuron progenitor cells, such as from neural plate explants, can be used as target cells. Treatment of such explanted cells with, for example, Shh causes the cells to differentiate into motor neurons. By detecting the co-expression of the LIM homeodomain protein Islet-1 (Thor et al. (1991) *Neuron* 7:881–889; Ericson et al. (1992) *Science* 256:1555–1560) and the immunoglobulin-like protein SC1 (Tanaka et al. (1984) *Dev Biol* 106:26–37), the ability of a candidate agent to potentiate or inhibit Shh induction of motor neuron differentiation can be measured. The hedgehog protein can be provided as a purified source, or in the form of cells/tissue which express the protein and which are co-cultured with the target cells.

In yet another embodiment, the method of the present invention can be used to isolate and clone hedgehog receptors. For example, purified hedgehog proteins of the present invention can be employed to precipitate hedgehog receptor proteins from cell fractions prepared from cells which are responsive to a hedgehog protein. For instance, purified hedgehog protein can be derivatized with biotin (using, for instance, NHS-Biotin, Pierce Chemical catalog no. 21420G), and the biotinylated protein utilized to saturate membrane bound hh receptors. The hedgehog bound receptors can subsequently be adsorbed or immobilized on streptavidin. If desired, the hedgehog-receptor complex can be cross-linked with a chemical cross-linking agent. In such as manner, hh receptors can be purified, preferably to near homogeneity. The isolated hh receptor can then be partially digested with, for example, trypsin, and the resulting peptides separated by reverse-phase chromatography. The chromatography fragments are then analyzed by Edman degradation to obtain single sequences for two or more of the proteolytic fragments. From the chemically determined amino acid sequence for each of these tryptic fragments, a set of oligonucleotide primers can be designed for PCR. These primers can be used to screen both genomic and cDNA libraries. Similar strategies for cloning receptors have been employed, for example, to obtain the recombinant gene for somatostatin receptors (Eppler et al. (1992) *J Biol Chem* 267:15603–15612).

Other techniques for identifying hedgehog receptors by expression cloning will be evident in light of the present disclosure. For instance, purified hh polypeptides can be immobilized in wells of micro titre plates and contacted with, for example, COS cells transfected with a cDNA library (e.g., from tissue expected to be responsive to hedgehog induction). From this panning assay, cells which express hedgehog receptor molecules can be isolated on the basis of binding to the immobilized hedgehog protein. Another cloning system, described in PCT publications WO 92/06220 of Flanagan and Leder, involves the use of an expression cloning system whereby a hedgehog receptor is stored on the basis of binding to a hedgehog/alkaline phosphatase fusion protein (see also Cheng et al. (1994) *Cell* 79:157–168)

Another aspect of the present invention relates to a method of inducing and/or maintaining a differentiated state, enhancing survival, and/or promoting proliferation of a cell responsive to a vertebrate hedgehog protein, by contacting the cells with an hh agonist or an hh antagonist as the circumstances may warrant. For instance, it is contemplated by the invention that, in light of the present finding of an apparently broad involvement of hedgehog proteins in the formation of ordered spatial arrangements of differentiated tissues in vertebrates, the subject method could be used to generate and/or maintain an array of different vertebrate tissue both in vitro and in vivo. The hh agent, whether inductive or anti-inductive, can be, as appropriate, any of the preparations described above, including isolated polypeptides, gene therapy constructs, antisense molecules, peptidomimetics or agents identified in the drug assays provided herein. Moreover, it is contemplated that, based on the observation of activity of the vertebrate hedgehog proteins in drosophila, hh agents, for purposes of therapeutic and diagnostic uses, can include the Dros-HH protein and homologs thereof. Moreover, the source of hedgehog protein can be, in addition to purified protein or recombinant cells, cells or tissue explants which naturally produce one or more hedgehog proteins. For instance, as described in Example 2, neural tube explants from embryos, particularly floorplate tissue, can provide a source for Shh polypeptide, which source can be implanted in a patient or otherwise provided, as appropriate, for induction or maintenance of differentiation.

For example, the present method is applicable to cell culture techniques. In vitro neuronal culture systems have proved to be fundamental and indispensable tools for the study of neural development, as well as the identification of neurotrophic factors such as nerve growth factor (NGF), ciliary trophic factors (CNTF), and brain derived neurotrophic factor (BDNF). Once a neuronal cell has become terminally-differentiated it typically will not change to another terminally differentiated cell-type. However, neuronal cells can nevertheless readily lose their differentiated state. This is commonly observed when they are grown in culture from adult tissue, and when they form a blastema during regeneration. The present method provides a means for ensuring an adequately restrictive environment in order to maintain neuronal cells at various stages of differentiation, and can be employed, for instance, in cell cultures designed to test the specific activities of other trophic factors. In such embodiments of the subject method, the cultured cells can be contacted with an hh polypeptide, or an agent identified in the assays described above, in order to induce neuronal differentiation (e.g. of a stem cell), or to maintain the integrity of a culture of terminally-differentiated neuronal cells by preventing loss of differentiation. The source of hedgehog protein in the culture can be derived from, for example, a purified or semi-purified protein composition added directly to the cell culture media, or alternatively, supported and/or released from a polymeric device which supports the growth of various neuronal cells and which has been doped with the protein. The source of the hedgehog protein can also be a cell that is co-cultured with the intended neuronal cell and which produces a recombinant hh. Alternatively, the source can be the neuronal cell itself which has been engineered to produce a recombinant hedgehog protein. In an exemplary embodiment, a naive neuronal cell (e.g. a stem cell) is treated with an hh agonist in order to induce differentiation of the cells into, for example, sensory neurons or, alternatively, motorneurons. Such neuronal cultures can be used as convenient assay systems as well as sources of implantable cells for therapeutic treatments. For example, hh polypeptides may be useful in establishing and maintaining the olfactory neuron cultures described in U.S. Pat. No. 5,318,907 and the like.

According to the present invention, large numbers of non-tumorigenic neural progenitor cells can be perpetuated in vitro and induced to differentiate by contact with hedgehog proteins. Generally, a method is provided comprising the steps of isolating neural progenitor cells from an animal, perpetuating these cells in vitro or in vivo, preferably in the presence of growth factors, and differentiating these cells into particular neural phenotypes, e.g., neurons and glia, by contacting the cells with a hedgehog agonist.

Progenitor cells are thought to be under a tonic inhibitory influence which maintains the progenitors in a suppressed state until their differentiation is required. However, recent techniques have been provided which permit these cells to be proliferated, and unlike neurons which are terminally differentiated and therefore non-dividing, they can be produced in unlimited number and are highly suitable for transplantation into heterologous and autologous hosts with neurodegenerative diseases.

By "progenitor" it is meant an oligopotent or multipotent stem cell which is able to divide without limit and, under specific conditions, can produce daughter cells which terminally differentiate such as into neurons and glia. These cells can be used for transplantation into a heterologous or autologous host. By heterologous is meant a host other than the animal from which the progenitor cells were originally derived. By autologous is meant the identical host from which the cells were originally derived.

Cells can be obtained from embryonic, post-natal, juvenile or adult neural tissue from any animal. By any animal is meant any multicellular animal which contains nervous tissue. More particularly, is meant any fish, reptile, bird, amphibian or mammal and the like. The most preferable donors are mammals, especially mice and humans.

In the case of a heterologous donor animal, the animal may be euthanized, and the brain and specific area of interest removed using a sterile procedure. Brain areas of particular interest include any area from which progenitor cells can be obtained which will serve to restore function to a degenerated area of the host's brain. These regions include areas of the central nervous system (CNS) including the cerebral cortex, cerebellum, midbrain, brainstem, spinal cord and ventricular tissue, and areas of the peripheral nervous system (PNS) including the carotid body and the adrenal medulla. More particularly, these areas include regions in the basal ganglia, preferably the striatum which consists of the caudate and putamen, or various cell groups such as the globus pallidus, the subthalamic nucleus, the nucleus basalis which is found to be degenerated in Alzheimer's Disease patients, or the substantia nigra pars compacta which is found to be degenerated in Parkinson's Disease patients.

Human heterologous neural progenitor cells may be derived from fetal tissue obtained from elective abortion, or from a post-natal, juvenile or adult organ donor. Autologous neural tissue can be obtained by biopsy, or from patients undergoing neurosurgery in which neural tissue is removed, in particular during epilepsy surgery, and more particularly during temporal lobectomies and hippocampalectomies.

Cells can be obtained from donor tissue by dissociation of individual cells from the connecting extracellular matrix of the tissue. Dissociation can be obtained using any known procedure, including treatment with enzymes such as trypsin, collagenase and the like, or by using physical methods of dissociation such as with a blunt instrument. Dissociation of fetal cells can be carried out in tissue culture medium, while a preferable medium for dissociation of juvenile and adult cells is artificial cerebral spinal fluid (aCSF). Regular aCSF contains 124 mM NaCl, 5 mM KCl, 1.3 mM $MgCl_2$, 2 mM $CaCl_2$, 26 mM $NaHCO_3$, and 10 mM D-glucose. Low $Ca^{2+}$ aCSF contains the same ingredients except for $MgCl_2$ at a concentration of 3.2 mM and $CaCl_2$ at a concentration of 0.1 mM.

Dissociated cells can be placed into any known culture medium capable of supporting cell growth, including MEM, DMEM, RPMI, F-12, and the like, containing supplements which are required for cellular metabolism such as glutamine and other amino acids, vitamins, minerals and useful proteins such as transferrin and the like. Medium may also contain antibiotics to prevent contamination with yeast, bacteria and fungi such as penicillin, streptomycin, gentamicin and the like. In some cases, the medium may contain serum derived from bovine, equine, chicken and the like. A particularly preferable medium for cells is a mixture of DMEM and F-12.

Conditions for culturing should be close to physiological conditions. The pH of the culture media should be close to physiological pH, preferably between pH 6–8, more preferably close to pH 7, even more particularly about pH 7.4. Cells should be cultured at a temperature close to physiological temperature, preferably between 30° C.–40° C., more preferably between 32° C.–38° C., and most preferably between 35° C.–37° C.

Cells can be grown in suspension or on a fixed substrate, but proliferation of the progenitors is preferably done in suspension to generate large numbers of cells by formation of "neurospheres" (see, for example, Reynolds et al. (1992) *Science* 255:1070–1709; and PCT Publications WO93/01275, WO94/09119, WO94/10292, and WO94/16718). In the case of propagating (or splitting) suspension cells, flasks are shaken well and the neurospheres allowed to settle on the bottom corner of the flask. The spheres are then transferred to a 50 ml centrifuge tube and centrifuged at low speed. The medium is aspirated, the cells resuspended in a small amount of medium with growth factor, and the cells mechanically dissociated and resuspended in separate aliquots of media.

Cell suspensions in culture medium are supplemented with any growth factor which allows for the proliferation of progenitor cells and seeded in any receptacle capable of sustaining cells, though as set out above, preferably in culture flasks or roller bottles. Cells typically proliferate within 3–4 days in a 37° C. incubator, and proliferation can be reinitiated at any time after that by dissociation of the cells and resuspension in fresh medium containing growth factors.

In the absence of substrate, cells lift off the floor of the flask and continue to proliferate in suspension forming a hollow sphere of undifferentiated cells. After approximately 3–10 days in vitro, the proliferating clusters (neurospheres) are fed every 2–7 days, and more particularly every 2–4 days by gentle centrifugation and resuspension in medium containing growth factor.

After 6–7 days in vitro, individual cells in the neurospheres can be separated by physical dissociation of the neurospheres with a blunt instrument, more particularly by triturating the neurospheres with a pipette. Single cells from the dissociated neurospheres are suspended in culture medium containing growth factors, and differentiation of the cells can be induced by plating (or resuspending) the cells in the presence of a hedgehog agonist, and (optionally) any other factor capable of sustaining differentiation, such as bFGF and the like.

To further illustrate other uses of hedgehog agonists and antagonists, it is noted that intracerebral grafting has emerged as an additional approach to central nervous system therapies. For example, one approach to repairing damaged brain tissues involves the transplantation of cells from fetal or neonatal animals into the adult brain (Dunnett et al. (1987) *J Exp Biol* 123:265–289; and Freund et al. (1985) *J Neurosci* 5:603–616). Fetal neurons from a variety of brain regions can be successfully incorporated into the adult brain, and such grafts can alleviate behavioral defects. For example, movement disorder induced by lesions of dopaminergic projections to the basal ganglia can be prevented by grafts of embryonic dopaminergic neurons. Complex cognitive functions that are impaired after lesions of the neocortex can also be partially restored by grafts of embryonic cortical cells. The use of hedgehog proteins or mimetics, such as Shh or Dhh, in the culture can prevent loss of differentiation, or where fetal tissue is used, especially neuronal stem cells, can be used to induce differentiation.

Stem cells useful in the present invention are generally known. For example, several neural crest cells have been identified, some of which are multipotent and likely represent uncommitted neural crest cells, and others of which can generate only one type of cell, such as sensory neurons, and likely represent committed progenitor cells. The role of hedgehog proteins employed in the present method to culture such stem cells can be to induce differentiation of the uncommitted progenitor and thereby give rise to a committed progenitor cell, or to cause further restriction of the developmental fate of a committed progenitor cell towards becoming a terminally-differentiated neuronal cell. For example, the present method can be used in vitro to induce and/or maintain the differentiation of neural crest cells into glial cells, schwann cells, chromaffin cells, cholinergic sympathetic or parasympathetic neurons, as well as peptidergic and serotonergic neurons. The hedgehog protein can be used alone, or can be used in combination with other neurotrophic factors which act to more particularly enhance a particular differentiation fate of the neuronal progenitor cell. In the later instance, an hh polypeptide might be viewed as ensuring that the treated cell has achieved a particular phenotypic state such that the cell is poised along a certain developmental pathway so as to be properly induced upon contact with a secondary neurotrophic factor. In similar fashion, even relatively undifferentiated stem cells or primitive neuroblasts can be maintained in culture and caused to differentiate by treatment with hedgehog agonists. Exemplary primitive cell cultures comprise cells harvested from the neural plate or neural tube of an embryo even before much overt differentiation has occurred.

In addition to the implantation of cells cultured in the presence of a functional hedgehog activity and other in vitro uses described above, yet another aspect of the present invention concerns the therapeutic application of a hedgehog protein or mimetic to enhance survival of neurons and other neuronal cells in both the central nervous system and the peripheral nervous system. The ability of hedgehog protein to regulate neuronal differentiation during development of the nervous system and also presumably in the adult state indicates that certain of the hedgehog proteins can be reasonably expected to facilitate control of adult neurons with regard to maintenance, functional performance, and aging of normal cells; repair and regeneration processes in chemically or mechanically lesioned cells; and prevention of degeneration and premature death which result from loss of differentiation in certain pathological conditions. In light of this understanding, the present invention specifically contemplates applications of the subject method to the treatment of (prevention and/or reduction of the severity of) neurological conditions deriving from: (i) acute, subacute, or chronic injury to the nervous system, including traumatic injury, chemical injury, vasal injury and deficits (such as the ischemia resulting from stroke), together with infectious/inflammatory and tumor-induced injury; (ii) aging of the nervous system including Alzheimer's disease; (iii) chronic neurodegenerative diseases of the nervous system, including Parkinson's disease, Huntington's chorea, amylotrophic lateral sclerosis and the like, as well as spinocerebellar degenerations; and (iv) chronic immunological diseases of the nervous system or affecting the nervous system, including multiple sclerosis.

Many neurological disorders are associated with degeneration of discrete populations of neuronal elements and may be treatable with a therapeutic regimen which includes a hedgehog agonist. For example, Alzheimer's disease is associated with deficits in several neurotransmitter systems, both those that project to the neocortex and those that reside with the cortex. For instance, the nucleus basalis in patients with Alzheimer's disease have been observed to have a profound (75%) loss of neurons compared to age-matched controls. Although Alzheimer's disease is by far the most common form of dementia, several other disorders can produce dementia. Several of these are degenerative diseases characterized by the death of neurons in various parts of the central nervous system, especially the cerebral cortex. However, some forms of dementia are associated with degeneration of the thalamus or the white matter underlying the cerebral cortex. Here, the cognitive dysfunction results from the isolation of cortical areas by the degeneration of efferents and afferents. Huntington's disease involves the degeneration of intrastraital and cortical cholinergic neurons and GABAergic neurons. Pick's disease is a severe neuronal degeneration in the neocortex of the frontal and anterior temporal lobes, sometimes accompanied by death of neurons in the striatum. Treatment of patients suffering from such degenerative conditions can include the application of hedgehog polypeptides, or agents which mimic their effects, in order to control, for example, differentiation and apoptotic events which give rise to loss of neurons (e.g. to enhance survival of existing neurons) as well as promote differentiation and repopulation by progenitor cells in the area affected. In preferred embodiments, a source of a hedgehog agent is stereotactically provided within or proximate the area of degeneration. In addition to degenerative-induced dementias, a pharmaceutical preparation of one or more of the subject hedgehog proteins can be applied opportunely in the treatment of neurodegenerative disorders which have manifestations of tremors and involuntary movements. Parkinson's disease, for example, primarily affects subcortical structures and is characterized by degeneration of the nigrostriatal pathway, raphe nuclei, locus cereleus, and the motor nucleus of vagus. Ballism is typically associated with damage to the subthalmic nucleus, often due to acute vascular accident. Also included are neurogenic and myopathic diseases which ultimately affect the somatic division of the peripheral nervous system and are manifest as neuromuscular disorders. Examples include chronic atrophies such as amyotrophic lateral sclerosis, Guillain-Barre syndrome and chronic peripheral neuropathy, as well as other diseases which can be manifest as progressive bulbar palsies or spinal muscular atrophies. The present method is amenable to the treatment of disorders of the cerebellum which result in hypotonia or ataxia, such as those lesions in the cerebellum which produce disorders in the limbs ipsilateral to the lesion. For instance, a preparation of a hedgehog homolog can used to treat a restricted form of cerebellar cortical degeneration involving the anterior lobes (vermis and leg areas) such as is common in alcoholic patients.

In an illustrative embodiment, the subject method is used to treat amyotrophic lateral sclerosis. ALS is a name given to a complex of disorders that comprise upper and lower motor neurons. Patients may present with progressive spinal muscular atrophy, progressive bulbar palsy, primary lateral sclerosis, or a combination of these conditions. The major pathological abnormality is characterized by a selective and progressive degeneration of the lower motor neurons in the spinal cord and the upper motor neurons in the cerebral cortex. The therapeutic application of a hedgehog agonist, particularly Dhh, can be used alone, or in conjunction with other neurotrophic factors such as CNTF, BDNF or NGF to prevent and/or reverse motor neuron degeneration in ALS patients.

Hedgehog proteins of the present invention can also be used in the treatment of autonomic disorders of the peripheral nervous system, which include disorders affecting the innervation of smooth muscle and endocrine tissue (such as glandular tissue). For instance, the subject method can be used to treat tachycardia or atrial cardiac arrythmias which may arise from a degenerative condition of the nerves innervating the striated muscle of the heart.

Furthermore, a potential role for certain of the hedgehog proteins, which is apparent from the appended examples, mainly the data of respecting hedgehog expression in sensory and motor neurons of the head and trunk (including limb buds), concerns the role of hedgehog proteins in development and maintenance of dendritic processes of axonal neurons. Potential roles for hedgehog proteins consequently include guidance for axonal projections and the ability to promote differentiation and/or maintenance of the innervating cells to their axonal processes. Accordingly, compositions comprising hedgehog agonists or other hedgehog agents described herein, may be employed to support, or alternatively antagonize the survival and reprojection of several types of ganglionic neurons sympathetic and sensory neurons as well as motor neurons. In particular, such therapeutic compositions may be useful in treatments designed to rescue, for example, various neurons from lesion-induced death as well as guiding reprojection of these neurons after such damage. Such diseases include, but are not limited to, CNS trauma infarction, infection (such as viral infection with varicella-zoster), metabolic disease, nutritional deficiency, toxic agents (such as cisplatin treatment). Moreover, certain of the hedgehog agents (such as antagonistic form) may be useful in the selective ablation of sensory neurons, for example, in the treatment of chronic pain syndromes.

As appropriate, hedgehog agents can be used in nerve prostheses for the repair of central and peripheral nerve damage. In particular, where a crushed or severed axon is intubulated by use of a prosthetic device, hedgehog polypeptides can be added to the prosthetic device to increase the rate of growth and regeneration of the dendridic processes. Exemplary nerve guidance channels are described in U.S. Pat. Nos. 5,092,871 and 4,955,892. Accordingly, a severed axonal process can be directed toward the nerve ending from which it was severed by a prosthesis nerve guide which contains, e.g. a semi-solid formulation containing hedgehog polypeptide or mimetic, or which is derivatized along the inner walls with a hedgehog protein.

In another embodiment, the subject method can be used in the treatment of neoplastic or hyperplastic transformations such as may occur in the central nervous system. For instance, certain of the hedgehog proteins (or hh agonists) which induce differentiation of neuronal cells can be utilized to cause such transformed cells to become either post-mitotic or apoptotic. Treatment with a hedgehog agent may facilitate disruption of autocrine loops, such as TGF-$\beta$ or PDGF autostimulatory loops, which are believed to be involved in the neoplastic transformation of several neuronal tumors. Hedgehog agonists may, therefore, thus be of use in the treatment of, for example, malignant gliomas, medulloblastomas, neuroectodermal tumors, and ependymonas.

Yet another aspect of the present invention concerns the application of the discovery that hedgehog proteins are morphogenic signals involved in other vertebrate organogenic pathways in addition to neuronal differentiation as described above, having apparent roles in other endodermal patterning, as well as both mesodermal and endodermal differentiation processes. As described in the Examples below, Shh clearly plays a role in proper limb growth and patterning by initiating expression of signaling molecules, including Bmp-2 in the mesoderm and Fgf-4 in the ectoderm. Thus, it is contemplated by the invention that compositions comprising hedgehog proteins can also be utilized for both cell culture and therapeutic methods involving generation and maintenance of non-neuronal tissue.

In one embodiment, the present invention makes use of the discovery that hedgehog proteins, such as Shh, are apparently involved in controlling the development of stem cells responsible for formation of the digestive tract, liver, lungs, and other organs which derive from the primitive gut. As described in the Examples below, Shh serves as an inductive signal from the endoderm to the mesoderm, which is critical to gut morphogenesis. Therefore, for example, hedgehog agonists can be employed in the development and maintenance of an artificial liver which can have multiple metabolic functions of a normal liver. In an exemplary embodiment, hedgehog agonists can be used to induce differentiation of digestive tube stem cells to form hepatocyte cultures which can be used to populate extracellular matrices, or which can be encapsulated in biocompatible polymers, to form both implantable and extracorporeal artificial livers.

In another embodiment, therapeutic compositions of hedgehog agonists can be utilized in conjunction with transplantation of such artificial livers, as well as embryonic liver structures, to promote intraperitoneal implantation, vascularization, and in vivo differentiation and maintenance of the engrafted liver tissue.

In yet another embodiment, hedgehog agonists can be employed therapeutically to regulate such organs after physical, chemical or pathological insult. For instance, therapeutic compositions comprising hedgehog agonists can be utilized in liver repair subsequent to a partial hepatectomy. Similarly, therapeutic compositions containing hedgehog agonists can be used to promote regeneration of lung tissue in the treatment of emphysema.

In still another embodiment of the present invention, compositions comprising hedgehog agonists can be used in the in vitro generation of skeletal tissue, such as from skeletogenic stem cells, as well as the in vivo treatment of skeletal tissue deficiencies. The present invention particularly contemplates the use of hedgehog agonists which maintain a skeletogenic activity, such as an ability to induce chondrogenesis and/or osteogenesis. By "skeletal tissue deficiency", it is meant a deficiency in bone or other skeletal connective tissue at any site where it is desired to restore the bone or connective tissue, no matter how the deficiency originated, e.g. whether as a result of surgical intervention, removal of tumor, ulceration, implant, fracture, or other traumatic or degenerative conditions.

For instance, the present invention makes available effective therapeutic methods and compositions for restoring cartilage function to a connective tissue. Such methods are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a Taxation of a joint by a torn ligament, malignment of joints, bone fracture, or by hereditary disease. The present reparative method is also useful for remodeling cartilage matrix, such as in plastic or reconstructive surgery, as well as periodontal surgery. The present method may also be applied to improving a previous reparative procedure, for example, following surgical repair of a meniscus, ligament, or cartilage. Furthermore, it may prevent the onset or exacerbation of degenerative disease if applied early enough after trauma.

In one embodiment of the present invention, the subject method comprises treating the afflicted connective tissue with a therapeutically sufficient amount of a hedgehog agonist, particularly an Ihh agonist, to generate a cartilage repair response in the connective tissue by stimulating the differentiation and/or proliferation of chondrocytes embedded in the tissue. Induction of chondrocytes by treatment with a hedgehog agonist can subsequently result in the synthesis of new cartilage matrix by the treated cells. Such connective tissues as articular cartilage, interarticular cartilage (menisci), costal cartilage (connecting the true ribs and the sternum), ligaments, and tendons are particularly amenable to treatment in reconstructive and/or regenerative therapies using the subject method. As used herein, regenerative therapies include treatment of degenerative states which have progressed to the point of which impairment of the tissue is obviously manifest, as well as preventive treatments of tissue where degeneration is in its earliest stages or imminent. The subject method can further be used to prevent the spread of mineralisation into fibrotic tissue by maintaining a constant production of new cartilage.

In an illustrative embodiment, the subject method can be used to treat cartilage of a diarthroidal joint, such as a knee, an ankle, an elbow, a hip, a wrist, a knuckle of either a finger or toe, or a temperomandibular joint. The treatment can be directed to the meniscus of the joint, to the articular cartilage of the joint, or both. To further illustrate, the subject method can be used to treat a degenerative disorder of a knee, such as which might be the result of traumatic injury (e.g., a sports injury or excessive wear) or osteoarthritis. An injection of a hedgehog agonist into the joint with, for instance, an arthroscopic needle, can be used to treat the afflicted cartilage. In some instances, the injected agent can be in the form of a hydrogel or other slow release vehicle described above in order to permit a more extended and regular contact of the agent with the treated tissue.

The present invention further contemplates the use of the subject method in the field of cartilage transplantation and prosthetic device therapies. To date, the growth of new cartilage from either transplantation of autologous or allogenic cartilage has been largely unsuccessful. Problems arise, for instance, because the characteristics of cartilage and fibrocartilage varies between different tissue: such as between articular, meniscal cartilage, ligaments, and tendons, between the two ends of the same ligament or tendon, and between the superficial and deep parts of the tissue. The zonal arrangement of these tissues may reflect a gradual change in mechanical properties, and failure occurs when implanted tissue, which has not differentiated under those conditions, lacks the ability to appropriately respond. For instance, when meniscal cartilage is used to repair anterior cruciate ligaments, the tissue undergoes a metaplasia to pure fibrous tissue. By promoting chondrogenesis, the subject method can be used to particularly addresses this problem, by causing the implanted cells to become more adaptive to the new environment and effectively resemble hypertrophic chondrocytes of an earlier developmental stage of the tissue. Thus, the action of chondrogenesis in the implanted tissue, as provided by the subject method, and the mechanical forces on the actively remodeling tissue can synergize to produce an improved implant more suitable for the new function to which it is to be put.

In similar fashion, the subject method can be applied to enhancing both the generation of prosthetic cartilage devices and to their implantation. The need for improved treatment has motivated research aimed at creating new cartilage that is based on collagen-glycosaminoglycan templates (Stone et al. (1990) *Clin Orthop Relat Red* 252:129), isolated chondrocytes (Grande et al. (1989) *J Orthop Res* 7:208; and Takigawa et al. (1987) *Bone Miner* 2:449), and chondrocytes attached to natural or synthetic polymers (Walitani et al. (1989) *J Bone Jt Surg* 71B:74; Vacanti et al. (1991) *Plast Reconstr Surg* 88:753; von Schroeder et al. (1991) *J Biomed Mater Res* 25:329; Freed et al. (1993) *J Biomed Mater Res* 27:11; and the Vacanti et al. U.S. Pat. No. 5,041,138). For example, chondrocytes can be grown in culture on biodegradable, biocompatible highly porous scaffolds formed from polymers such as polyglycolic acid, polylactic acid, agarose gel, or other polymers which degrade over time as function of hydrolysis of the polymer backbone into innocuous monomers. The matrices are designed to allow adequate nutrient and gas exchange to the cells until engraftment occurs. The cells can be cultured in vitro until adequate cell volume and density has developed for the cells to be implanted. One advantage of the matrices is that they can be cast or molded into a desired shape on an individual basis, so that the final product closely resembles the patient's own ear or nose (by way of example), or flexible matrices can be used which allow for manipulation at the time of implantation, as in a joint.

In one embodiment of the subject method, the implants are contacted with a hedgehog agonist during the culturing process, such as an Ihh agonist, in order to induce and/or maintain differentiated chondrocytes in the culture in order as to further stimulate cartilage matrix production within the implant. In such a manner, the cultured cells can be caused to maintain a phenotype typical of a chondrogenic cell (i.e. hypertrophic), and hence continue the population of the matrix and production of cartilage tissue.

In another embodiment, the implanted device is treated with a hedgehog agonist in order to actively remodel the implanted matrix and to make it more suitable for its intended function. As set out above with respect to tissue transplants, the artificial transplants suffer from the same deficiency of not being derived in a setting which is comparable to the actual mechanical environment in which the matrix is implanted. The activation of the chondrocytes in the matrix by the subject method can allow the implant to acquire characteristics similar to the tissue for which it is intended to replace.

In yet another embodiment, the subject method is used to enhance attachment of prosthetic devices. To illustrate, the subject method can be used in the implantation of a periodontal prosthesis, wherein the treatment of the surrounding connective tissue stimulates formation of periodontal ligament about the prosthesis, as well as inhibits formation of fibrotic tissue proximate the prosthetic device.

In still further embodiments, the subject method can be employed for the generation of bone (osteogenesis) at a site in the animal where such skeletal tissue is deficient. Indian hedgehog is particularly associated with the hypertrophic chondrocytes that are ultimately replaced by osteoblasts. For instance, administration of a hedgehog agent of the present invention can be employed as part of a method for treating bone loss in a subject, e.g. to prevent and/or reverse osteoporosis and other osteopenic disorders, as well as to regulate bone growth and maturation. For example, preparations comprising hedgehog agonists can be employed, for example, to induce endochondral ossification, at least so far as to facilitate the formation of cartilaginous tissue precursors to form the "model" for ossification. Therapeutic compositions of hedgehog agonists can be supplemented, if required, with other osteoinductive factors, such as bone growth factors (e.g. TGF-β factors, such as the bone morphogenetic factors BMP-2 and BMP-4, as well as activin), and may also include, or be administered in combination with, an inhibitor of bone resorption such as estrogen, bisphosphonate, sodium fluoride, calcitonin, or tamoxifen, or related compounds. However, it will be appreciated that hedgehog proteins, such as Ihh and Shh are likely to be upstream of BMPs, e.g. hh treatment will have the advantage of initiating endogenous expression of BMPs along with other factors.

In yet another embodiment of the present invention, a hedgehog antagonist can be used to inhibit spermatogenesis. Thus, in light of the present finding that hedgehog proteins are involved in the differentiation and/or proliferation and maintenance of testicular germ cells, hedgehog antagonist can be utilized to block the action of a naturally-occurring hedgehog protein. In a preferred embodiment, the hedgehog antagonist inhibits the biological activity of Dhh with respect to spermatogenesis, by competitively binding hedgehog receptors in the testis. In similar fashion, hedgehog agonists and antagonists are potentially useful for modulating normal ovarian function.

The hedgehog protein, or a pharmaceutically acceptable salt thereof, may be conveniently formulated for administration with a biologically acceptable medium, such as water, buffered saline, polyol (for example, glycerol, propylene glycol, liquid polyethylene glycol and the like) or suitable mixtures thereof. The optimum concentration of the active. ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the hedgehog protein, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations". Based on the above, such pharmaceutical formulations include, although not exclusively, solutions or freeze-dried powders of a hedgehog homolog (such as a Shh, Dhh or Mhh) in association with one or more pharmaceutically acceptable vehicles or diluents, and contained in buffered media at a suitable pH and isosmotic with physiological fluids. For illustrative purposes only and without being limited by the same, possible compositions or formulations which may be prepared in the form of solutions for the treatment of nervous system disorders with a hedgehog protein are given in U.S. Pat. No. 5,218,094. In the case of freeze-dried preparations, supporting excipients such as, but not exclusively, mannitol or glycine may be used and appropriate buffered solutions of the desired volume will be provided so as to obtain adequate isotonic buffered solutions of the desired pH. Similar solutions may also be used for the pharmaceutical compositions of hh in isotonic solutions of the desired volume and include, but not exclusively, the use of buffered saline solutions with phosphate or citrate at suitable concentrations so as to obtain at all times isotonic pharmaceutical preparations of the desired pH, (for example, neutral pH).

Pharmaceutical formulations of the present invention can also include veterinary compositions, e.g., pharmaceutical preparations of the hedgehog proteins, or bioactive fragments thereof, suitable for veterinary uses, e.g., for the treatment of live stock or domestic animals, e.g., dogs.

Methods of introduction of exogenous hh at the site of treatment include, but are not limited to, intradermal, intramuscular, intraperitoneal, intravenous, subcutaneous, oral, intranasal and topical. In addition, it may be desirable to introduce the pharmaceutical compositions of the invention into the central nervous system by any suitable route, including intraventricular and intrathecal injection. Intraventricular injection may be facilitated by an intraventricular catheter, for example, attached to a reservoir, such as an Ommaya reservoir.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of an hh at a particular target site. Such embodiments of the present invention can be used for the delivery of an exogenously purified hedgehog protein, which has been incorporated in the polymeric device, or for the delivery of hedgehog produced by a cell encapsulated in the polymeric device.

An essential feature of certain embodiments of the implant can be the linear release of the hh, which can be achieved through the manipulation of the polymer composition and form. By choice of monomer composition or polymerization technique, the amount of water, porosity and consequent permeability characteristics can be controlled. The selection of the shape, size, polymer, and method for implantation can be determined on an individual basis according to the disorder to be treated and the individual patient response. The generation of such implants is generally known in the art. See, for example, *Concise Encylopedia of Medical & Dental Materials,* ed. by David Williams (MIT Press: Cambridge, Mass., 1990); and the Sabel et al. U.S. Pat. No. 4,883,666. In another embodiment of an implant, a source of cells producing a hedgehog protein, or a solution of hydogel matrix containing purified hh, is encapsulated in implantable hollow fibers. Such fibers can be pre-spun and subsequently loaded with the hedgehog source (Aebischer et al. U.S. Pat. No. 4,892,538; Aebischer et al. U.S. Pat. No. 5,106,627; Hoffman et al. (1990) *Expt. Neurobiol.* 110:39–44; Jaeger et al. (1990) *Prog. Brain Res.* 82:41–46; and Aebischer et al. (1991) *J Biomech. Eng.* 113:178–183), or can be co-extruded with a polymer which acts to form a polymeric coat about the hh source (Lim U.S. Pat. No. 4,391,909; Sefton U.S. Pat. No. 4,353,888; Sugamori et al. (1989) *Trans. Am. Artif. Intern. Organs* 35:791–799; Sefton et al. (1987) *Biotehnol. Bioeng.* 29:1135–1143; and Aebischer et al. (1991) *Biomaterials* 12:50–55).

In yet another embodiment of the present invention, the pharmaceutical hedgehog protein can be administered as part of a combinatorial therapy with other agents. For example, the combinatorial therapy can include a hedgehog protein with at least one trophic factor. Exemplary trophic factors include nerve growth factor, cilliary neurotrophic growth factor, schwanoma-derived growth factor, glial growth factor, stiatal-derived neuronotrophic factor, platelet-derived growth factor, and scatter factor (HGF-SF). Antimitogenic agents can also be used, for example, when proliferation of surrounding glial cells or astrocytes is undesirable in the regeneration of nerve cells. Examples of such antimitotic agents include cytosine, arabinoside, 5-fluorouracil, hydroxyurea, and methotrexate.

Another aspect of the invention features transgenic non-human animals which express a heterologous hedgehog gene of the present invention, or which have had one or more genomic hedgehog genes disrupted in at least one of the tissue or cell-types of the animal. Accordingly, the invention features an animal model for developmental diseases, which animal has hedgehog allele which is mis-expressed. For example, a mouse can be bred which has one or more hh alleles deleted or otherwise rendered inactive. Such a mouse model can then be used to study disorders arising from mis-expressed hedgehog genes, as well as for evaluating potential therapies for similar disorders.

Another aspect of the present invention concerns transgenic animals which are comprised of cells (of that animal) which contain a transgene of the present invention and which preferably (though optionally) express an exogenous hedgehog protein in one or more cells in the animal. A hedgehog transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of a hedgehog protein can be essential for many forms of lineage analysis and can additionally provide a means to assess the effects of, for example, lack of hedgehog expression which might grossly alter development in small patches of tissue within an otherwise normal embryo. Toward this and, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of one of the subject hedgehog proteins. For example, excision of a target sequence which interferes with the expression of a recombinant hh gene, such as one which encodes an antagonistic homolog or an antisense transcript, can be designed to activate expression of that gene. This interference with expression of the protein can result from a variety of mechanisms, such as spatial separation of the hh gene from the promoter element or an internal stop codon.

Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

In an illustrative embodiment, either the cre/loxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J. Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of a recombinant hedgehog protein can be regulated via control of recombinase expression.

Use of the crel/oxP recombinase system to regulate expression of a recombinant hh protein requires the construction of a transgenic animal containing transgenes encoding both the Cre recombinase and the subject protein. Animals containing both the Cre recombinase and a recombinant hedgehog gene can be provided through the construction of "double" transgenic animals. A convenient method for providing such animals is to mate two transgenic animals each containing a transgene, e.g., an hh gene and recombinase gene.

One advantage derived from initially constructing transgenic animals containing a hedgehog transgene in a recombinase-mediated expressible format derives from the likelihood that the subject protein, whether agonistic or antagonistic, can be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues and/or a desired temporal pattern. Thus, the creation of a founder population in which, for example, an antagonistic hh transgene is silent will allow the study of progeny from that founder in which disruption of hedgehog mediated induction in a particular tissue or at certain developmental stages would result in, for example, a lethal phenotype.

Similar conditional transgenes can be provided using prokaryotic promoter sequences which require prokaryotic proteins to be simultaneous expressed in order to facilitate expression of the hedgehog transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, a hedgehog transgene could remain silent into adulthood until "turned on" by the introduction of the trans-activator.

In an exemplary embodiment, the "transgenic non-human animals" of the invention are produced by introducing transgenes into the germline of the non-human animal. Embryonic target cells at various developmental stages can be used to introduce transgenes. Different methods are used depending on the stage of development of the embryonic target cell. The zygote is the best target for micro-injection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

Retroviral infection can also be used to introduce hedgehog transgenes into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J.* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonic stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *PNAS* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

Methods of making hedgehog knock-out or disruption transgenic animals are also generally known. See, for example, *Manipulating the Mouse Embryo*, (Cold Spring Harbor Laboratory Press, Cold Spring Harbor, N.Y., 1986). Recombinase dependent knockouts can also be generated, e.g. by homologous recombination to insert recombinase target sequences flanking portions of an endogenous hh gene, such that tissue specific and/or temporal control of inactivation of a hedgehog allele can be controlled as above.

EXEMPLIFICATION

The invention, now being generally described, will be more readily understood by reference to the following examples, which are included merely for purposes of illustration of certain aspects and embodiments of the present invention and are not intended to limit the invention.

EXAMPLE 1

Cloning and Expression of Chick Sonic Hedgehog
(i) Experimental Procedures

Using degenerate PCR primers, vHH50 (SEQ ID No:18), vHH30 (SEQ ID No:19) and vHH31 (SEQ ID No:20) corresponding to a sequence conserved between Drosophila hedgehog (SEQ ID No:34) (Lee, J. J. et al. (1992) *Cell* 71: 33–50; Mohler, J. et al., (1992) *Development* 115: 957–971) and mouse Indian hedgehog (Ihh) (SEQ ID No:10), a 220 base pair (bp) fragment was amplified from chicken genomic DNA. From 15 isolates, two distinct sequences were cloned, pCHA (SEQ ID No:35) and pCHB (SEQ ID No:36), each highly homologous to mouse Ihh (FIG. 1). A probe made from isolate pCHA did not detect expression in embryonic tissues. Isolate pCHB, however, detected a 4 kb message in RNA prepared from embryonic head, trunk, or limb bud RNA. This cloned PCR fragment was therefore used as a probe to screen an unamplified cDNA library prepared from Hamburger Hamilton stage 22 (Hamburger, W. et al., (1951) *J. Morph.* 88: 49–92) limb bud RNA as described below.

A single 1.6 kilobase (kb) cDNA clone, pHH-2, was selected for characterization and was used in all subsequent analyses. The gene encoding for this cDNA was named Sonic Hedgehog (after the Sega computer game cartoon character). Sequencing of the entire cDNA confirmed the presence of a single long open reading frame potentially encoding for a protein of 425 amino acids (aa). The clone extends 220 bp upstream of the predicted initiator methionine and approximately 70 bp beyond the stop codon. No consensus polyadenylation signal could be identified in the 3' untranslated region. A second potential initiator methionine occurs at amino acid residue 4. The putative translation initiation signals surrounding both methionines are predicted to be equally efficient (Kozak, M., (1987) *Nuc. Acids Res.* 15: 8125–8132). When the pHH-2 Sonic cDNA is used to probe a northern blot of stage 24 embryonic chick RNA, a single MRNA species of approximately 4 kb is detected in both limb and trunk tissue. The message size was predicted by comparing it to the position of 18S and 28S ribosomal RNA. Hybridized mRNA was visualized after a two day exposure to a phosphoscreen. Because the Sonic cDNA clone pHH-2 is only 1.6 kb, it is likely to be missing approximately 2.4 kb of untranslated sequence.

PCR Cloning

All standard cloning techniques were performed according to Ausubel et. al. (1989), and all enzymes were obtained from Boehringer Mannheim Biochemicals. Degenerate oligonucleotides corresponding to amino acid residues 161 to 237 of the Drosophila hedgehog protein (SEQ ID No:34) (Lee, J. J. et. al., (1992) *Cell* 71: 33–50) were synthesized. These degenerate oligonucleotides, vHH50 (SEQ ID No:18), vHH30 (SEQ ID No:19), and vHH3I (SEQ ID No:20) also contained Eco RI, Cla I, and Xba I sites, respectively, on their 5' ends to facilitate subcloning. The nucleotide sequence of these oligos is given below:

vHH50: 5'-GGAATTCCCAG(CA)GITG(CT)AA(AG)GA(AG)(CA)(AG)I(GCT)IAA-3' vHH30: 5'-TCATCGATGGACCCA(GA)TC(GA)AAIC-CIGC(TC)TC-3' vHH3I: 5'-GCTCTAGAGCTCIACIGCIA(GA)IC(GT)IGC-3' where I represents inosine. Nested PCR was performed by first amplifying chicken genomic DNA using the vHH50 and vHH30 primer pair and then further amplifying that product using the vHH50 and vHH3I primer pair. In each case the reaction conditions were: initial denaturation at 93° C. for 2.5 min., followed by 30 cycles of 94° C. for 45 s, 50° C. for 1 min 72° C. for 1, and a final incubation of 72° C. for 5 min. The 220 bp PCR product was subcloned into pGEM7zf (Promega). Two unique clones, pCHA (SEQ ID No:35) and pCHB (SEQ ID No:36) were identified.

DNA Sequence Analysis

Nucleotide sequences were determined by the dideoxy chain termination method (Sanger, F. et al., (1977) *Proc. Natl. Acad. Sci. USA* 74: 5463–5467) using Sequenase v2.0 T7 DNA polymerase (US Biochemicals). 5' and 3' nested deletions of pHH-2 were generated by using the nucleases Exo III and S1 (Erase a Base, Promega) and individual subclones sequenced. DNA and amino acid sequences were analyzed using both GCG (Devereux, J. et al., (1984) *Nuc. Acids Res.* 12: 387–394) and DNAstar software. Searches for related sequences were done through the BLAST network service (Altschul, S. F. et al., (1990) *J. Mol. Biol.* 215: 403–410) provided by the National Center for Biotechnology Information.

Southern Blot Analysis

Five (5) µg of chick genomic DNA was digested with Eco RI and/or Bam HI, fractionated on a 1% agarose gel, and transferred to a nylon membrane (Genescreen, New England Nuclear). The filters were probed with $^{32}$P-labeled hha or hhb at 42° C. in hybridization buffer (0.5% BSA, 500 mM NaHPO$_4$, 7% SDS, 1 mM EDTA, pH 7.2; Church, G. M. et al., (1984) *Proc. Natl. Acad. Sci. USA* 81: 1991–1995). The blots were washed at 63° C. once in 0.5% bovine serum albumin, 50 mM NaHPO$_4$ (pH 7.2), 5% SDS, 1 mM EDTA and twice in 40 mM NaHPO$_4$ (pH 7.2), 1% SDS, 1 mM EDTA, and visualized on Kodak XAR-5 film.

Isolation of Chicken Sonic cDNA Clones

A stage 22 limb bud cDNA library was constructed in λgt10 using Eco RI/NotI linkers. Unamplified phage plaques (10$^6$) were transferred to nylon filters (Colony/Plaque screen, NEN) and screened with α$^{32}$P-labelled pooled inserts from PCR clones pCHA (SEQ ID No:35) and pCHB (SEQ ID No:36). Hybridization was performed at 42° C. in 50% formamide 2×SSC, 10% dextran sulfate, 1% SDS and washing as described in the Southern Blot procedure. Eight positive plaques were identified, purified and their cDNA inserts excised with EcoRI and subcloned into pBluescript SK+ (Stratagene). All eight had approximately 1.7 kb inserts with identical restriction patterns. One, pHH-2, was chosen for sequencing and used in all further manipulations.

Preparation of Digoxigenin-Labeled Riboprobes

Plasmid pHH-2 was linearized with Hind III and transcribed with T3 RNA polymerase (for antisense probes) or with Bam HI and transcribed with T7 RNA polymerase according to the manufacturers instructions for the preparation of non-radioactive digoxigenin transcripts. Following the transcription reaction, RNA was precipitated, and resuspended in RNAse-free water.

Whole Mount In Situ Hybridization

Whole-mount in situ hybridization was performed using protocols modified from Parr, B. A. et al. (1993) *Development* 119: 247–261; Sasaki, H. et al. (1993) *Development* 118: 47–59; Rosen, B. et al. (1993) *Trends Genet.* 9: 162–167. Embryos from incubated fertile White Leghorn eggs (Spafas) were removed from the egg and extra-embryonic membranes dissected in calcium/magnesium-free phosphate-buffered saline (PBS) at room temperature. Unless otherwise noted, all washes are for five minutes at room temperature. Embryos were fixed overnight at 4° C. with 4% paraformaldehyde in PBS, washed twice with PBT (PBS with 0.1% Tween-20) at 4° C., and dehydrated through an ascending methanol series in PBT (25%, 50%, 75%, 2×100% methanol). Embryos were stored at −20° C. until further use.

Both pre-limb bud and limb bud stage embryos were rehydrated through an descending methanol series followed by two washes in PBT. Limb bud stage embryos were bleached in 6% hydrogen peroxide in PBT, washed three times with PBT, permeabilized with proteinase K (Boehringer, 2 $\mu$g/ml) for 15 minutes, washed with 2 mg/ml glycine in PBT for 10 minutes, and twice with PBT. Pre-limb bud stage embryos were permealibized (without prior incubation with hydrogen peroxide) by three 30 minute washes in RIPA buffer (150 mM NaCl, 1% NP-40, 0.5% Deoxycholate, 0.1% SDS, 1 mM EDTA, 50 mM Tris-HCl, pH 8.0). In all subsequent steps, pre-limb bud and limb bud stage embryos were treated equivalently. Embryos were fixed with 4% paraformaldehyde/0.2% gluteraldehyde in PBT, washed four times with PBT, once with pre-hybridization buffer (50% formamide, 5×SSC, 1% SDS, 50 $\mu$g/ml total yeast RNA, 50 $\mu$g/ml heparin, pH 4.5), and incubated with fresh pre-hybridization buffer for one hour at 70° C. The pre-hybridization buffer was then replaced with hybridization buffer (pre-hybridization buffer with digoxigenin labeled riboprobe at 1 $\mu$g/ml) and incubated overnight at 70° C.

Following hybridization, embryos were washed 3×30 minutes at 70° C. with solution 1 (50% formamide, 5×SSC, 1% SDS, pH 4.5), 3×30 minutes at 70° C. with solution 3 (50% formamide, 2×SSC, pH 4.5), and three times at room temperature with TBS (Tris-buffered saline with 2 mM levamisole) containing 0.1% Tween-20. Non-specific binding of antibody was prevented by preblocking embryos in TBS/0.1% Tween-20 containing 10% heat-inactivated sheep serum for 2.5 hours at room temperature and by pre-incubating anti-digoxigenin Fab alkaline-phosphatase conjugate (Boehringer) in TBS/0.1% Tween-20 containing heat inactivated 1% sheep serum and approximately 0.3% heat inactivated chick embryo powder. After an overnight incubation at 4° C. with the pre-adsorbed antibody in TBS/0.1% Tween-20 containing 1% sheep serum, embryos were washed 3×5 minutes at room temperature with TBS/0.1% Tween-20, 5×1.5 hour room temperature washes with TBS/1% Tween-20, and overnight with TBS/1% Tween-20 at 4° C. The buffer was exchanged by washing 3×10 minutes with NTMT (100 mM NaCl, 100 mM Tris-HCl, 50 mM MgCl2, 0.1% Tween-20, 2 mM levamisole). The antibody detection reaction was performed by incubating embryos with detection solution (NTMT with 0.25 mg/ml NBT and 0.13 mg/ml X-Phos). In general, pre-limb bud stage embryos were incubated for 5–15 hours and limb bud stage embryos 1–5 hours. After the detection reaction was deemed complete, embryos were washed twice with NTMT, once with PBT (pH 5.5), postfixed with 4% paraformaldehyde/0.1% gluteraldehyde in PBT, and washed several times with PBT. In some cases embryos were cleared through a series of 30%, 50%, 70%, and 80% glycerol in PBT. Whole embryos were photographed under transmitted light using a Nikon zoom stereo microscope with Kodak Ektar 100 ASA film. Selected embryos were processed for frozen sections by dehydration in 30% sucrose in PBS followed by embedding in gelatin and freezing. 25 $\mu$m cryostat sections were collected on superfrost plus slides (Fisher), rehydrated in PBS, and mounted with gelvatol. Sections were photographed with Nomarski optics using a Zeiss Axiophot microscope and Kodak Ektar 25 ASA film.

Figure 3:
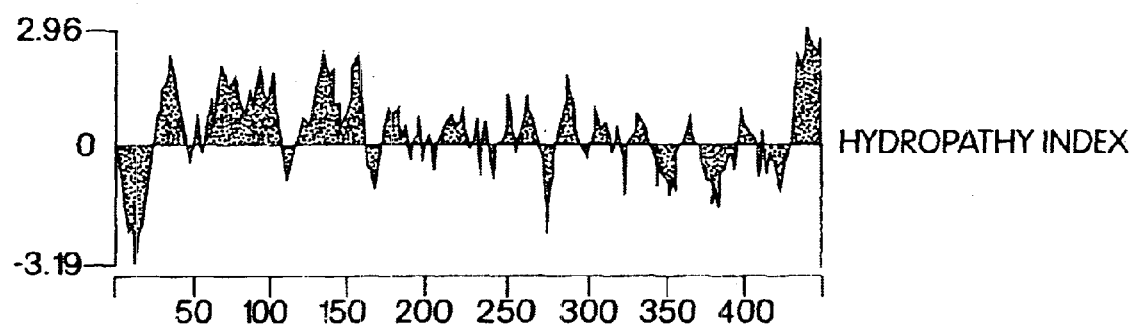
FIG. 3 is a hydropathy plot for the predicted chick Shh protein, generated by the methods of Kyte and Doolittle (1982). The values of hydrophobicity are plotted against the amino acid positions. Negative values predict a hydrophobic domain of the protein.

(ii) Sequence Homolgy Comparison between Chicken Sonic hh and Drosophila hh and Other Vertebrate Sonic hh Proteins The deduced Sonic amino acid sequence (SEQ ID No:8) is shown and compared to the Drosophila hedgehog protein (SEQ ID No:34) in FIG. 2. Over the entire open reading frame the two proteins are 48% homologous at the amino acids level. The predicted Drosophila protein extends 62 aa beyond that of Sonic at its amino terminus. This N-terminal extension precedes the putative signal peptide (residues 1–26) of the fly protein (SEQ ID No:34), and has been postulated to be removed during processing of the secreted form of Drosophila hedgehog (Lee, J. J. et al., (1992) *Cell* 71: 33–50). The sequence of residues 1–26 of the Sonic protein (SEQ ID No:8) matches well with consensus sequences for eukaryotic signal peptides (Landry, S. J. et al., (1993) *Trends. Biochem. Sci.* 16: 159–163) and is therefore likely to serve that function for Sonic. Furthermore, FIG. 3 shows a hydropathy plot (Kyte, J. et al., (1982) *J. Mol Biol.*157: 133–148) indicating that residues 1–26 of the Sonic protein (SEQ ID No:8) exhibit a high hydrophobic moment in accord with identified eukaryotic signal peptides. Cleavage of the putative signal sequence should occur C-terminal to residue 26 according to the predictive method of von Henjie, G. (1986) *Nucl. Acid. Res.* 11: 1986. A single potential N-linked glycosylation site is located at amino acid residue 282 of the Sonic protein (SEQ ID No:8). The predicted Sonic protein does not contain any other strong consensus motifs, and is not homologous to any other proteins outside of the Hedgehog family.

Figure 4:
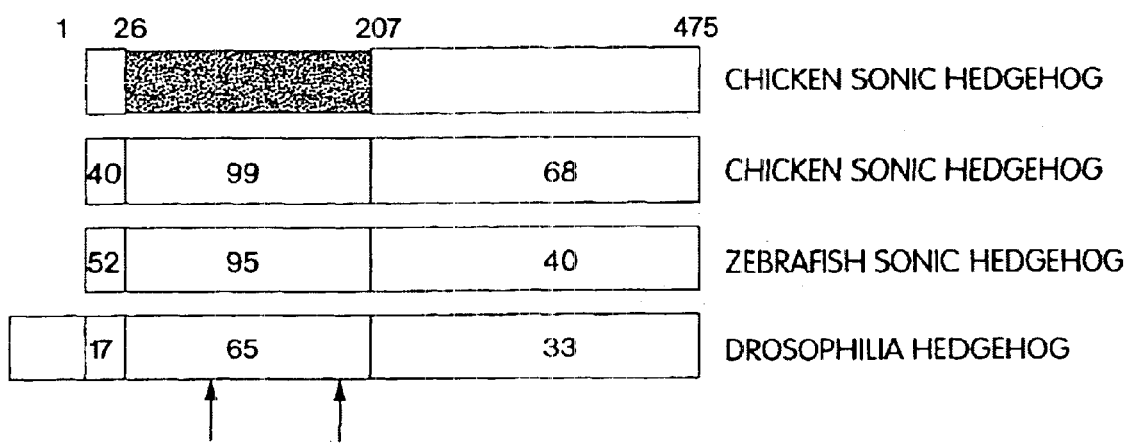
FIG. 4 is an alignment comparing the amino acid sequences of various hh proteins. The white region on the amino terminus of chicken Shh corresponds to the putative signal peptide. The black box refers to a highly conserved region from aa residues 26–207 of SEQ ID No:8). The arrows point to exon boundaries in the Drosophila gene (Lee et al. (1992) *Cell* 71: 33–50). In each case, the proteins are compared to chicken Shh (SEQ ID No:8) and the percent amino acid identity is indicated in each region's box.

The mouse (SEQ ID No:11) and zebrafish (SEQ ID No:12) homologs of Sonic have also been isolated. A comparison of these and the Drosophila sequence is shown schematically in FIG. 4. All of the vertebrate proteins have a similar predicted structure: a putative signal peptide at their amino terminus, followed by an extraordinarily similar 182 amino acid region (99% identity in chicken versus mouse and 95% identity in chicken versus zebrafish) and a less well conserved carboxy-terminal region.

(iii) At Least Three Hedgehog Homologues Are Present in the Chicken Genome

Since two distinct PCR products encoding for chicken hedgehogs were amplified from genomic DNA, the total number of genes in the chicken hedgehog family needed to be estimated. The two PCR clones pCHA (SEQ ID No:35) and pCHB (SEQ ID No:36) were used to probe a genomic Southern blot under moderately stringent conditions as described in the above Experimental Procedures. The blot was generated by digesting 5 μg of chick chromosomal DNA with EcoRI and BamHI alone and together. Each probe reacted most strongly with a distinct restriction fragment. For example, the blot probed with pCHA, shows three bands in each of the Bam HI lanes, one strong at 6.6 kb and two weak at 3.4 and 2.7 kb. The blot probed with pCHB, shows the 2.7 kb band as the most intense, while the 3.4 and 6.6 kb bands are weaker. A similar variation of intensities can also be seen in the Bam HI/Eco RI and EcoRI lanes. Exposure times were 72 hr. This data indicates that each probe recognizes a distinct chicken hedgehog gene, and that a third as yet uncharacterized chicken hedgehog homolog exists in the chicken genome.

(iv) Northern Analysis Defining Sites of Sonic Transcription

Northern analysis was performed which confirmed that Sonic is expressed during chick development. The spatial and temporal expression of Sonic in the chick embryo from gastrulation to early organogenesis was determined by whole mount in situ hybridization using a riboprobe corresponding to the full-length Sonic cDNA (SEQ ID No:1).

20 μg total RNA isolated from stage 24 chick leg buds or bodies (without heads or limbs) was fractionated on a 0.8% agarose formaldehyde gel and transferred to a nylon membrane (Hybond N, Amersham). The blot was probed with the 1.6 kb EcoRI insert from pHH-2. Random-primed $\alpha^{32}P$-labelled insert was hybridized at 42° C. hybridization buffer (1% BSA, 500 mM $NaHPO_4$, 7% SDS, 1 mM EDTA, pH 7.2) and washed at 63° C. once in 0.5% bovine serum albumin, 50 mM $NaHPO_4$ (pH 7.2), 5% SDS, 1 mM EDTA and once in 40 mM $NaHPO_4$ (pH 7.2), 1% SDS, 1 mM EDTA. The image was visualized using a phosphoimager (Molecular Dynamics) and photographed directly from the video monitor.

(v) Expression of Sonic During Mid-Gastrulation

Sonic message is detected in the gastrulating blastoderm at early stage 4, the earliest stage analyzed. Staining is localized to the anterior end of the primitive streak in a region corresponding to Hensen's node. As gastrulation proceeds, the primitive streak elongates to its maximal cranial-caudal extent, after which Hensen's node regresses caudally and the primitive streak shortens. At an early point of node regression, Sonic mRNA can be detected at the node and in midline cells anterior to the node. By late stage 5, when the node has migrated approximately one-third of the length of the fully elongated primitive streak, prominent Sonic expression is seen at the node and in the midline of the embryo, reaching its anterior limit at the developing head process. Sections at a cranial level show that Sonic mRNA is confined to invaginated axial mesendoderm, tissue which contributes to foregut and notochord. More caudally, but still anterior to Hensen's node, staining of axial mesoderm is absent and Sonic expression is confined to the epiblast. At the node itself, high levels of Sonic message are observed in an asymmetric distribution extending to the left of and posterior to the primitive pit. This asymmetric distribution is consistently observed (6/6 embryos from stages 5–7) and is always located to the left of the primitive pit. At the node, and just posterior to the node, Sonic expression is restricted to the epiblast and is not observed in either mesoderm or endoderm. The expression of Sonic in the dorsal epiblast layer without expression in underlying axial mesoderm contrasts markedly with later stages where Sonic expression in underlying mesoderm always precedes midline neural tube expression.

(vi) Expression of Sonic During Head Fold Stages

During the formation and differentiation of the head process, Sonic mRNA is detected in midline cells of the neural tube, the foregut, and throughout most of the axial mesoderm. At stage 7, Sonic message is readily detected asymmetrically at the node and in ventral midline cells anterior to the node. The rostral limit of Sonic expression extends to the anterior-most portions of the embryo where it is expressed in the foregut and prechordal mesoderm (Adelmann, H. B., (1932) Am. J. Anat. 31, 55–101). At stage 8, expression of Sonic persists along the entire ventral midline anterior to Hensen's node, while the node region itself no longer expresses Sonic. Transverse sections at different axial levels reveal that at stage 8 Sonic is coexpressed in the notochord and the overlying ventromedial neuroectoderm from anterior to Hensen's node to the posterior foregut. The levels of Sonic message are not uniform in the neural tube: highest levels are found at the presumptive mid- and hindbrain regions with progressively lower levels anterior and posterior. The increasing graded expression in the neural tube from Hensen's node to the rostral brain may reflect the developmental age of the neuroectoderm as differentiation proceeds from posterior to anterior. At the anterior-most end of the embryo, expression is observed in midline cells of the dorsal and ventral foregut as well as in prechordal mesoderm. Although the prechordal mesoderm is in intimate contact with the overlying ectoderm, the latter is devoid of Sonic expression.

(vii) Expression of Sonic During Early CNS Differentiation

At stages 10 through 14, Sonic expression is detected in the notochord, ventral neural tube (including the floor plate), and gut precursors. By stage 10, there is a marked expansion of the cephalic neuroectoderm, giving rise to the fore- mid- and hind-brain. At stage 10, Sonic mRNA is abundantly expressed in the ventral midline of the hindbrain and posterior midbrain. This expression expands laterally in the anterior midbrain and posterior forebrain. Expression does not extend to the rostral forebrain at this or later stages. Sections reveal that Sonic is expressed in the notochord, the prechordal mesoderm, and the anterior midline of the foregut. Expression in the neuroepithelium extends from the forebrain caudally. In the posterior-most regions of the embryo which express Sonic, staining is found only in the notochord and not in the overlying neurectoderm. This contrasts with earlier expression in which the posterior domains of Sonic expression contain cells are located in the dorsal epiblast, but not in underlying mesoderm or endoderm. Midgut precursors at the level of the anterior intestinal portal also show weak Sonic expression.

At stage 14, expression continues in all three germ layers. The epithelium of the closing midgut expresses Sonic along with portions of the pharyngeal endoderm and anterior foregut. Ectoderm lateral and posterior to the tail bud also exhibits weak expression. At this stage, Sonic is also expressed along entire length of the notochord which now extends rostrally only to the midbrain region and no longer contacts the neuroepithelium at the anterior end of the embryo. Expression in head mesenchyme anterior to the notochord is no longer observed. In the neural tube Sonic is found along the ventral midline of the fore- mid- and hindbrain and posteriorly in the spinal cord. In the forebrain, expression is expanded laterally relative to the hindbrain. At midgut levels, expression of Sonic in the neural tube appears to extend beyond the floor plate into more lateral regions. As observed at stage 10, Sonic at stage 14 is found in the notochord, but not in the ventral neural tube in posterior-most regions of the embryo. When neuroectodermal expression is first observed in the posterior embryo, it is located in midline cells which appear to be in contact with the notochord. At later stages, expression continues in areas which show expression at stage 14, namely the CNS, gut epithelium including the allantoic stalk, and axial mesoderm.

(viii) Sonic Is Expressed in Posterior Limb Bud Mesenchyme

The limb buds initially form as local thickenings of the lateral plate mesoderm. As distal outgrowth occurs during stage 17, Sonic expression becomes apparent in posterior regions of both the forelimb and the hindlimb. Sections through a stage 21 embryo at the level of the forelimbs reveal that expression of Sonic in limb buds is limited to mesenchymal tissue. A more detailed expression profile of Sonic during limb development is discussed below in Example 3. Briefly, as the limb bud grows out, expression of Sonic narrows along the anterior-posterior axis to become a thin stripe along the posterior margin closely apposed to the ectoderm. Expression is not found at more proximal regions of the bud. High levels of Sonic expression are maintained until around stage 25/26 when staining becomes weaker. Expression of Sonic is no longer observed in wing buds or leg buds after stage 28.

EXAMPLE 2

Mouse Sonic Hedgehog Is Implicated in the Regulation of CNS and Limb Polarity (i) Experimental Procedures Isolation of Hedgehog Phage Clones The initial screen for mammalian hh genes was performed, as above, using a 700 bp PCR fragment encompassing exons 1 and 2 of the Drosophila hh gene. Approximately one million plaques of a 129/Sv Lambda Fix II genomic library (Stratagene) were hybridized with an $\alpha^{32}$P-dATP labeled probe at low stringency (55° C. in 6×SSC, 0.5%SDS, 5×Denhardt's; final wash at 60° C. in 0.5×SSC, 0.1% SDS for 20'). Five cross hybridizing phage plaques corresponding to the Dhh gene were purified. Restriction enzyme analysis indicated that all clones were overlapping. Selected restriction enzyme digests were then performed to map and subclone one of these. Subclones in pGEM (Promega) or Bluescript (Stratagene) which crosshybridized with the Drosophila hh fragment where sequenced using an ABI automatic DNA sequencer.

Mouse Ihh and Shh were identified by low stringency hybridization (as described above) with a chick Shh cDNA clone to one million plaques of an 8.5 day λgt10 mouse embryo cDNA library (Fahrner, K. et al., (1987) *EMBO J.* 6: 1265–1271). Phage plaques containing a 1.8 kb Ihh and 0.64 and 2.8 kb Shh inserts were identified. Inserts were excised and subcloned into Bluescript (Stratagene) for dideoxy chain termination sequencing using modified T7 DNA polymerase (USB). The larger Shh clone contained a partially processed cDNA in which intron splicing at the exon ½ junction had not occurred.

To screen for additional Ihh and Shh cDNA clones, an 8.5 day λZAPII cDNA library was probed at high stringency (at 65° C. in 6×SSC, 0.5% SDS, 5×Denhardt's; final wash at 65° C. in 0.1×SSC, 0.1% SDS for 30') with the Ihh and Shh mouse cDNA clones. No additional Ihh clones were identified. However several 2.6 kb, apparently full length, Shh clones were isolated. The DNA sequence of the additional 5' coding region not present in the original 0.64 and 2.8 kb Shh clones was obtained by analysis of one of the 2.6 kb inserts.

Northern Blot Analysis

Expression of Shh was investigated by RNA blot analysis using 20 μg of total RNA from adult brain, spleen, kidney, liver, lung, 16.5 dpc brain, liver and lung; 9.5 dpc to 17.5 dpc whole embryo; 9.5 dpc forebrain, midbrain and 10.5 dpc brain. RNA samples were electrophoretically separated on a 1.2% agarose gel, transferred and u.v. crosslinked to Genescreen (DuPont) and probed with $2 \times 10^6$ cpm/ml of an $\alpha^{32}$P-dATP labeled mouse Shh probe (2.8 kb insert from λgt 10 screen). Hybridization was performed at 42° C. in 50% formamide 5×Denhardt's, 5×SSPE, 0.1%SDS, 6.5% dextran, 200 μg/ml salmon sperm DNA. Final wash was at 55° C. in 0.1×SSC, 0.1%SDS. The blot was exposed for 6 days in the presence of an intensifying screen.

In Situ Hybridization, β-Galactosidase Staining and Histological Analysis

Embryos from 7.25 to 14.5 dpc were analyzed for either Shh or HNF-3β expression by whole mount in situ hybridization to digoxygenin labeled RNA probes as described in Wilkinson, (1992) *In situ Hybridization: A Practical Approach.* Oxford; Parr et al., (1993) *Development* 119:247–261. The mouse Shh probe was either a 2.8 kb or 0.6 kb RNA transcript generated by T7 (2.8 kb) or T3 (0.6 kb) transcription of XbaI and HindIII digests of Bluescript (Stratagene) subclones of the original Shh cDNA inserts. The HNF-3β probe was generated by HindIII linearization of a HNF-3β cDNA clone (Sasaki, H. et al., (1993) *Development* 118: 47–59) and T7 polymerase transcription of 1.6 kb transcript. Embryos were photographed on an Olympus-SZH photomicroscope using Kodak Ektachrome EPY 64T color slide film.

Sections through wild type and WEXP2-CShh transgenic embryos were prepared and hybridized with $^{35}$S-UIP labeled RNA probes (Wilkinson, D. G. et al., (1987) *Development* 99: 493–500). Sections were photographed as described in McMahon, A. P. et al., (1992) *Cell* 69: 581–595.

β Staining of WEXP2-lacZ embryos with βwas performed according to Whiting, J. et al., (1991) *Genes & Dev.* 5: 2048–2059. General histological analysis of wildtype and WEXP2-CShh transgenic embryos was performed on paraffin sections of Bouin's fixed embryos counterstained with haematoxylin and eosin. Histological procedures were as described by Kaufman, M. H. (1992) *The Atlas of Mouse Development,* London: Academic Press. Sections were photographed on a Leitz Aristoplan compound microscope using Kodak EPY 64T color slide film.

DNA Constructs for Transgenics

Genomic Wnt-1 fragments were obtained by screening a λGEM12 (Promega) 129/Sv mouse genomic library with a 375 bp MluI-BglII fragment derived from the fourth exon of the murine Wnt-1 gene. One of the clones (W1-15.1) was used in this study.

As an initial step towards the generation of the pWEXP2 expression vector, W1-15.1 was digested to completion with restriction enzymes AatII and ClaI, and a 2774 bp AatII-ClaI fragment isolated. This fragment was ligated into AatII and ClaI cut pGEM-7Zf vector (Promega), generating pW1-18. This plasmid was digested with HindII and ligated to annealed oligonucleotides lacl (SEQ ID No:21) and lac2 (SEQ ID No:22) generating pW1-18S* which has a modified polylinker downstream of the ClaI restriction site. This construct (pW1-18S*) was digested with ClaI and BglII and ligated with both the 2.5 kb 3' ClaI-BglII exon-intron region and 5.5 kb 3' BglII-BglII Wnt-1 enhancer, generating pWRES4. This construct contains a 10.5 kb genomic region which starts upstream of the Wnt-1 translation initiation codon (at an AatII site approximately 1.0 kb from the ATG) and extends to a BglII site 5.5 kb downstream of the Wnt-1 polyadenylation signal. This plasmid also contains a 250 bp region of the neomycin phosphotransferase (neo) gene inserted in inverse orientation in the 3' transcribed but untranslated region. Finally, to generate the WEXP2 expression vector, a 2 kb Sfi I fragment was amplified from pWRES4 using Sf-1 (SEQ ID No:23) and Sf-2 (SEQ ID No:24) oligonucleotides. This amplified fragment was digested with Sfi I and inserted into Sfi I linearised pWRES4, generating pWEXP2. This destroys the Wnt-1 translation initiation codon, and replaces it by a polylinker containing Nru I, Eco RV, Sac II, and Bst BI restriction sites, which are unique in pWEXP2.

The WEXP2-lacZ construct was obtained by inserting an end-filled BglII-Xho I lacZ fragment isolated from the pSDKlacZpA vector in the Nru I cut pWEXP2 expression vector. Similarly, the WEXP2-CShh construct was obtained by inserting an end-filled XbaI cDNA fragment containing the full Chick Shh coding sequence (SEQ ID No:1) into the Nru I cut WEXP2 expression vector.

Oligonucleotide sequences are as follows:

lac1: 5'-AGCTGTCGACGCGGCCGCTACGTAGGT-
TACCGACGTCAAGCTTAGATCTC-3' lac2: 5'-AGCTGAGATCTAAGCTTGACGTCGG-
TAACCTACGTAGCGGCCGCGTCGAC-3'

Sf-1: 5'-GATCGGCCAGGCAGGCCTCGC-
GATATCGTCACCGCGGTATTCGAA-3'

Sf-2: 5'-AGTGCCAGTCGGGGCCCCCAGGGCCGCGCC-3'

Production and Genotyping of Transgenic Embryos

Transgenic mouse embryos were generated by microinjection of linear DNA fragments into the male pronucleus of B6CBAF1/J (C57BL/6J X CBA/J) zygotes. CD-1 or B6CBAF1/J females were used as recipients for injected embryos. $G_o$ mice embryos were collected at 9.5, 10.5, and 11.5 dpc, photographed using an Olympus SZH stereophotomicroscope on Kodak EPY-64T color slide film, then processed as described earlier.

WEXP2-lacZ and WEXP2-CShh transgenic embryos were identified by PCR analysis of proteinase-K digests of yolk sacs. Briefly, yolk sacs were carefully dissected free from maternal and embryonic tissues, avoiding cross-contamination between littermates, then washed once in PBS. After overnight incubation at 55° C. in 50 µl of PCR proteinase-K digestion buffer (McMahon, A. P. et al., (1990) Cell 62: 1073–1085). 1 µl of heat-inactivated digest was subjected to polymerase chain reaction (PCR) in a 20 µl volume for 40 cycles as follows: 94° C. for 30 seconds, 55° C. for 30 seconds, 72° C. for 1 minute, with the reaction ingredients described previously (McMahon, A. P. et al., (1990) Cell 62: 1073–1085)). In the case of the WEXP2-lacZ transgenic embryos, oligonucleotides 137 (SEQ ID No:25) and 138 (SEQ ID No:26) amplify a 352 bp lacZ specific product. In the case of the WEXP2-CShh embryos, oligonucleotides WPR2 (Wnt-1-specific) (SEQ ID No:27) and 924 (Chick Shh-specific) (SEQ ID No:28) amplify a 345 bp fragment spanning the insertion junction of the Chick-Shh cDNA in the WEXP2 expression vector. Table 2 summarizes the results of WEXP2-C-Shh transgenic studies.

Oligonucleotide sequences are as follows:

137: 5'-TACCACAGCGGATGGTTCGG-3'

138: 5'-GTGGTGGTTATGCCGATCGC-3'

WPR2: 5'-TAAGAGGCCTATAAGAGGCGG-3'

924: 5'-AAGTCAGCCCAGAGGAGACT-3'

(ii) Mouse hh Genes

The combined screening of mouse genomic and 8.5 day post coitum (dpc) cDNA libraries identified three mammalian hh counterparts (FIGS. 5A-1 and 5A-2) which herein will be referred to as Desert, Indian and Sonic hedgehog (Dhh, Ihh and Shh, respectively). Sequences encoding Dhh (SEQ ID No:2) were determined from analysis of clones identified by low stringency screening of a mouse genomic library. DNA sequencing of one of five overlapping lambda phage clones identified three homologous regions encoding a single open reading frame interrupted by introns in identical position to those of the Drosophila hh gene (FIGS. 5A-1 and 5A-2). Splicing across the exon ½ boundary was confirmed by polymerase chain reaction (PCR) amplification of first strand cDNA generated from adult testicular RNA. The partial sequence of Ihh (SEQ ID No:3) and the complete sequence of Shh (SEQ ID No:4) coding regions were determined from the analysis of overlapping cDNA clones isolated from 8.5 dpc cDNA libraries. The longest Shh clone, 2.6 kb, appears to be full length when compared with the Shh transcript present in embryonic RNAs. The 1.8 kb partial length Ihh cDNA is complete at the 3' end, as evidenced by the presence of a polyadenylation consensus sequence and short poly A tail.

Alignment of the predicted Drosophila hh protein sequence (SEQ ID No:34) with those of the mouse Dhh (SEQ ID No:9), Ihh (SEQ ID No:10) and Shh (SEQ ID No:11), and chick Shh (SEQ ID No:8) and zebrafish Shh (SEQ ID No:12), reveals several interesting features of the hh-family (FIGS. 5A-1 and 5A-2). All the vertebrate hh-proteins contain an amino terminal hydrophobic region of approximately 20 amino acids immediately downstream of the initiation methionine. Although the properties of these new hh proteins have not been investigated, it is likely that this region constitutes a signal peptide and vertebrate hhs are secreted proteins. Signal peptide cleavage is predicted to occur (von Heijne, G., (1986) Nucleic Acids Research 14: 4683–4690) just before an absolutely conserved six amino acid stretch, CGPGRG (SEQ ID No:29) (corresponding to residues 85–90) (FIGS. 5A-1 and 5A-2), in all hh proteins. This generates processed mouse Dhh (SEQ ID No:9) and Shh (SEQ ID No:11) proteins of 41 and 44 kd, respectively. Interestingly, Drosophila hh (SEQ ID No:34) is predicted to contain a substantial amino terminal extension beyond the hydrophobic domain suggesting that the Drosophila protein enters the secretory pathway by a type II secretory mechanism. This would generate a transmembrane tethered protein which would require subsequent cleavage to release a 43 kd secreted form of the protein. In vitro analysis of Drosophila hh is consistent with this interpretation (Lee, J. J. et al., (1992) Cell 71: 33–50). However, there also appears to be transitional initiation at a second methionine (position 51 of SEQ ID No:34) just upstream of the hydrophobic region (Lee, J. J. et al., (1992) Cell 71: 33–50), suggesting that Drosophila hh, like its vertebrate counterparts, may also be secreted by recognition of a conventional amino terminal signal peptide sequence.

Data base searches for protein sequences related to vertebrate hh's failed to identify any significant homologies, excepting Drosophila hh. In addition, searching the "PROSITE" data bank of protein motifs did not reveal any peptide motifs which are conserved in the different hh proteins. Thus, the hhs represent a novel family of putative cell signaling molecules.

One feature of the amino acid alignment is the high conservation of hh sequences. Vertebrate hhs share 47 to 51% amino acid identity with Drosophila hh throughout the predicted processed polypeptide sequence (FIG. 6). Dhh has a slightly higher identity than that of Ihh and Shh suggesting that Dhh may be the orthologue of Drosophila hh. Conservation is highest in the amino terminal half of the proteins, indeed, from position 85 (immediately after the predicted shared cleavage site) to 249, 62% of the amino acids are completely invariant amongst the Drosophila and vertebrate proteins. Comparison of mouse Dhh, Ihh and Shh where their sequences overlap in this more conserved region, indicates that Ihh and Shh are more closely related (90% amino acid identity; residues 85 to 266) than with the Dhh sequence (80% amino acid identity; residues 85 to 266). Thus, Ihh and Shh presumably resulted from a more recent gene duplication event.

Comparison of cross species identity amongst Shh proteins reveals an even more striking sequence conservation. Throughout the entire predicted processed sequence mouse and chick Shh share 84% of amino acid residues (FIG. 6). However, in the amino terminal half (positions 85 to 266) mouse and chick are 99% and mouse and zebrafish 94% identical in an 180 amino acid stretch. Conservation falls off rapidly after position 266 (FIGS. 5A-1 and 5A-2). SEQ ID No:40 shows the consensus sequence in the amino terminal half of all vertebrate Shh genes (human, mouse, chicken and zebrafish) identified to date. SEQ ID No:41 shows the consensus sequence in the amino terminal half of vertebrate hedgehog genes (Shh, Ihh, and Dhh) identified to date in different species (mouse, chicken, human and zebrafish).

In summary, hh family members are likely secreted proteins consisting of a highly conserved amino terminal and more divergent carboxyl terminal halves. The extreme interspecies conservation of the vertebrate Shh protein points to likely conservation of Shh function across vertebrate species.

(iii) Expression of Mouse Shh at the Axial Midline

Expression of Shh in the mouse was examined in order to explore the role of mouse Shh (SEQ ID No:11) in vertebrate development. Northern blots of embryonic and adult RNA samples were probed with a radiolabelled mouse Shh cDNA probe. An Shh transcript of approximately 2.6 kb was detected in 9.5 dpc whole embryo RNA, and 9.5 and 10.5 dpc brain RNA fractions. No expression was detected in total RNA samples from later embryonic stages. Of the late fetal and adult tissue RNAs examined Shh expression was only detected in 16.5 dpc and adult lung.

To better define the precise temporal and spatial expression of Shh an extensive series of whole mount and serial section in situ hybridizations were performed using digoxygenin and $^{35}$S-radiolabelled RNA probes, respectively, to mouse embryo samples from 7.25 dpc (mid streak egg cylinder stage of gastrulation) to 13.5 dpc. No Shh expression is detected at mid-gastrulation stages (7.25 dpc) prior to the appearance of the node, the mouse counterpart of the amphibian organizer and chick Hensen's node. When the primitive streak is fully extended and the midline mesoderm of the head process is emerging from the node (7.5 to 7.75 dpc), Shh is expressed exclusively in the head process. At late head fold stages, Shh is expressed in the node and midline mesoderm of the head process extending anteriorly under the presumptive brain. Just prior to somite formation, Shh extends to the anterior limit of the midline mesoderm, underlying the presumptive midbrain. As somites are formed, the embryonic axis extends caudally. The notochord, which represents the caudal extension of the head process, also expresses Shh, and expression is maintained in the node.

Interestingly, by 8 somites (8.5 dpc) strong Shh expression appears in the CNS. Expression is initiated at the ventral midline of the midbrain, above the rostral limit of the head process. By 10 somites CNS expression in the midline extends rostrally in the forebrain and caudally into the hindbrain and rostral spinal cord. Expression is restricted in the hindbrain to the presumptive floorplate, whereas midbrain expression extends ventro-laterally. In the forebrain, there is no morphological floor plate, however ventral Shh expression here is continuous with the midbrain. By 15 somites ventral CNS expression is continuous from the rostral limit of the diencephalon to the presumptive spinal cord in somitic regions. Over the next 18 to 24 hrs, to the 25–29 somite stage, CNS expression intensifies and forebrain expression extends rostral to the optic stalks. In contrast to all other CNS regions, in the rostral half of the diencephalon, Shh is not expressed at the ventral midline but in two strips immediately lateral to this area which merge again in the floor of the forebrain at its rostral limit. Expression of Shh in both the notochord and floorplate is retained until at least 13.5 dpc.

Several groups have recently reported the cloning and expression of vertebrate members of a family of transcription factors, related to the Drosophila forkhead gene. One of these, HNF-3β shows several similarities in expression to Shh (Sasaki, H. et al., (1993) *Development* 118: 47–59) suggesting that HNF-3β may be a potential regulator of Shh. To investigate this possibility, direct comparison of HNF-3β and Shh expression was undertaken. HNF-3β transcripts are first detected in the node (as previously reported by Sasaki, H. et al., (1993) supra), prior to the emergence of the head process and before Shh is expressed. From the node, expression proceeds anteriorly in the head process, similar to Shh expression. Activation of HNF-3β within the CNS is first observed at 2–3 somites, in the presumptive mid and hindbrain, prior to the onset of Shh expression. By 5 somites, expression in the midbrain broadens ventrolaterally, extends anteriorly into the forebrain and caudally in the presumptive floor plate down much of the neuraxis in the somitic region. Strong expression is maintained at this time in the node and notochord. However, by 10 somites expression in the head process is lost and by 25–29 somites notochordal expression is only present in the most extreme caudal notochord. In contrast to the transient expression of HNF-3β in the midline mesoderm, expression in the floor plate is stably retained until at least 11.5 dpc. Thus, there are several spatial similarities between the expression of HNF-3β and Shh in both the midline mesoderm and ventral CNS and it is likely that both genes are expressed in the same cells. However, in both regions, HNF-3β expression precedes that of Shh. The main differences are in the transient expression of HNF-3β in the head process and notochord and Shh expression in the forebrain. Whereas HNF-3β and Shh share a similar broad ventral and ventral lateral midbrain and caudal diencephalic expression, only Shh extends more rostrally into the forebrain. In general, these results are consistent with a model in which initial activation of Shh expression may be regulated by HNF-3β.

The similarity in Shh and HNF-3β expression domains is also apparent in the definitive endoderm which also lies at the midline. Broad HNF-3β expression in the foregut pocket is apparent at 5 somites as previously reported by Sasaki, H. et al., (1993) supra. Shh is also expressed in the endoderm, immediately beneath the forebrain. Both genes are active in the rostral and caudal endoderm from 8 to 11 somites. Whereas HNF-3β is uniformly expressed, Shh expression is initially restricted to two ventro-lateral strips of cells. Ventral restricted expression of Shh is retained in the most caudal region of the presumptive gut until at least 9.5 dpc whereas HNF-3β is uniformly expressed along the dorso-ventral axis. Both genes are expressed in the pharyngeal ectoderm at 9.5 dpc and expression is maintained in the gut until at least 11.5 dpc. Moreover, expression of Shh in the embryonic and adult lung RNA suggests that endodermal expression of Shh may continue in, at least some endoderm derived organs.

(iv) Expression of Shh in the Limb

Expression of Shh is not confined to midline structures. By 30–35 somites (9.75 dpc), expression is detected in a small group of posterior cells in the forelimb bud. The forelimb buds form as mesenchymal outpocketings on the flanks, opposite somites 8 to 12, at approximately the 17 to 20 somite stage. Shh expression is not detectable in the forelimbs until about 30–35 somites, over 12 hours after the initial appearance of the limbs. Expression is exclusively posterior and restricted to mesenchymal cells. By 10.5 dpc, both the fore and hindlimbs have elongated substantially from the body flank. At this time Shh is strongly expressed in the posterior, distal aspect of both limbs in close association with the overlying ectoderm. Analysis of sections at this stage detects Shh expression in an approximately six cell wide strip of posterior mesenchymal cells. In the forelimb, Shh expression ceases by 11.5 dpc. However, posterior, distal expression is still detected in the hindlimb. No limb expression is detected beyond 12.5 dpc.

(v) Ectopic Expression of Shh

Grafting studies carried out principally in the chick demonstrate that cell signals derived from the notochord and floor plate pattern the ventral aspect of the CNS (as described above). In the limb, a transient signal produced by a group of posterior cells in both limb buds, the zone of polarizing activity (ZPA), is thought to regulate patterning across the anterior-posterior axis. Thus, the sequence of Shh, which predicts a secreted protein and the expression profile in midline mesoderm, the floor plate and in the limb, suggest that Shh signaling may mediate pattern regulation in the ventral CNS and limb.

To determine whether Shh may regulate ventral development in the early mammalian CNS, a Wnt-1 enhancer was used to alter its normal domain of expression. Wnt-1 shows a dynamic pattern of expression which is initiated in the presumptive midbrain just prior to somite formation. As the neural folds elevate and fuse to enclose the neural tube, Wnt-1 expression in the midbrain becomes restricted to a tight circle, just anterior of the midbrain, the ventral midbrain and the dorsal midline of the diencephalon, midbrain, myelencephalon and spinal cord (Wilkinson, D. G. et al., (1987) *Cell* 50: 79–88; McMahon, A. P. et al., (1992) *Cell* 69: 581–595; Parr, B. A. et al., (1993) *Development* 119: 247–261).

It was determined that essentially normal expression of lacZ reporter constructs within the Wnt-1 expression domain is dependent upon a 5.5 kb enhancer region which lies downstream of the Wnt-1 polyadenylation sequence. A construct was generated for ectopic expression of cDNA clones in the Wnt-1 domain and tested in transgenics using a lacZ reporter (pWEXP-lacZ; FIG. 9). Two of the four $G_O$ transgenic embryos showed readily detectable β-galactosidase activity, and in both expression occurred throughout the normal Wnt-1 expression domain. More extensive studies with a similar construct also containing the 5.5 kb enhancer gave similar frequencies. Some ectopic expression was seen in newly emerging neural crest cells, probably as a result of perdurance of β-galactosidase RNA or protein in the dorsally derived crest. Thus, the Wnt-1 expression construct allows the efficient ectopic expression of cDNA sequences in the midbrain and in the dorsal aspect of much of the CNS.

Figure 7:
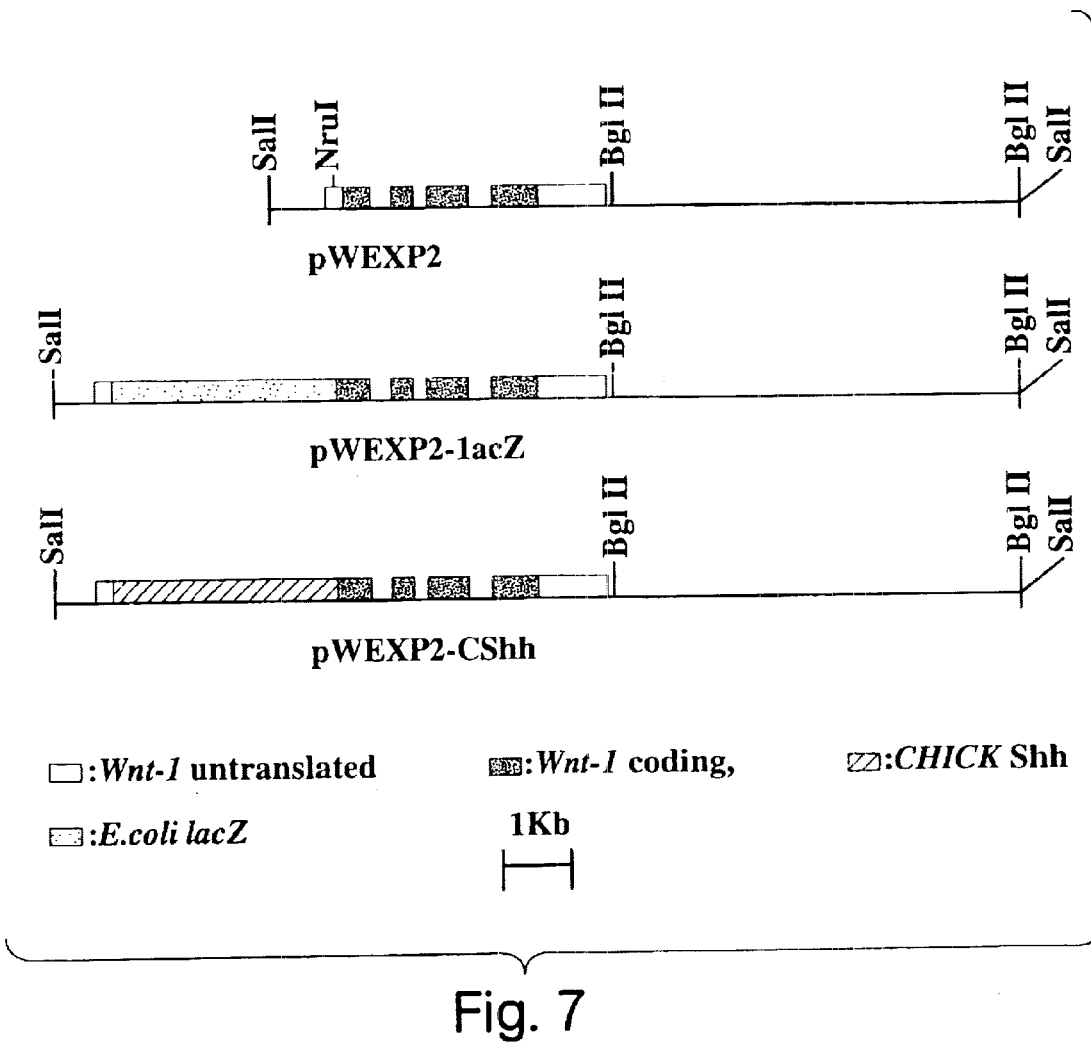
FIG. 7 is a representation of the DNA constructs used in transgenic studies to study ectopic expression of chick Shh in mouse embryos. Constructs were generated for ectopic expression of cDNA clones in the Wnt-1 expression domain and tested in transgenic mice embryos using a lac-Z reporter (pWEXP-lacZ (used as a control)) and a chick Shh reporter (pWEXP-CShh). The pWEXP-CShh construct contained two tandem head to tail copies of a chick Shh cDNA. The results of WEXP2-CShh transgenic studies are shown in Table 1.

An Shh ectopic expression construct (pWEXP-CShh) containing two tandem head to tail copies of a chick Shh cDNA was generated (FIG. 7). By utilizing this approach, ectopic expression of the chick Shh is distinguishable from that of the endogenous mouse Shh gene. Chick Shh shows a high degree of sequence identity and similar expression to the mouse gene. Thus, it is highly likely that Shh function is widely conserved amongst vertebrates, a conclusion further supported by studies of the same gene in zebrafish.

Table 2 shows the results of several transgenic experiments in which the $G_O$ population was collected at 9.5 to 11.5 dpc. Approximately half of the transgenic embryos identified at each stage of development had a clear, consistent CNS phenotype. As we expect, on the basis of control studies using the 5.5 kb Wnt-1 enhancer, that only half the transgenics will express the transgene, it is clear that in most embryos ectopically expressing chick Shh, an abnormal phenotype results.

TABLE 2

Summary of WEXP2-Chick Shh transgenic studies

| Age (dpc) | Number of Embryos | Number of Transgenics | Number of Embryos with CNS phenotype[a] |
|---|---|---|---|
| 9.5 | 37 | 11 | 6 (54.5%) |
| 10.5 | 59 | 16 | 8 (50%) |
| 11.5 | 33 | 7 | 3 (42.9%) |

FIGS. in parentheses, refer to the percentage of transgenic embryos with a CNS phenotype
[a]In addition one 9.5 pc and two 10.5 pc transgenic embryos showed non-specific growth retardation, as occurs at low frequency in transgenic studies. These embryos were excluded from further analysis.

At 9.5 dpc, embryos with a weaker phenotype show an open neural plate from the mid diencephalon to the myelencephalon. In embryos with a stronger phenotype at the same stage, the entire diencephalon is open and telencephalic and optic development is morphologically abnormal. As the most anterior diencephalic expression of Wnt-1 is lower than that in more caudal regions, the differences in severity may relate to differences in the level of chick Shh expression in different $G_O$ embryos. At the lateral margins of the open neural folds, where Wnt-1 is normally expressed, there is a thickening of the neural tissue extending from the diencephalon to myelencephalon. The cranial phenotype is similar at 10.5 and 11.5 dpc. However, there appears to be a retardation in cranial expansion of the CNS at later stages.

In addition to the dorsal cranial phenotype, there is a progressive dorsal phenotype in the spinal cord. At 9.5 dpc, the spinal cord appears morphologically normal, except at extreme rostral levels. However by 10.5 dpc, there is a dorsal dysmorphology extending to the fore or hindlimbs. By 11.5 dpc, all transgenic embryos showed a dorsal phenotype along almost the entire spinal cord. Superficially, the spinal cord had a rippled, undulating appearance suggestive of a change in cell properties dorsally. This dorsal phenotype, and the cranial phenotype were examined by histological analysis of transgenic embryos.

Sections through a 9.5 dpc embryo with an extreme CNS phenotype show a widespread dorsal perturbation in cranial CNS development. The neural/ectodermal junction in the diencephalon is abnormal. Neural tissue, which has a columnar epithelial morphology quite distinct from the squamous epithelium of the surface ectoderm, appears to spread dorsolaterally. The myelencephalon, like the diencephalon and midbrain, is open rostrally. Interestingly, there are discontinuous dorso-lateral regions in the myelencephalon with a morphology distinct from the normal roof plate regions close to the normal site of Wnt-1 expression. These cells form a tight, polarized epithelium with basely located nuclei, a morphology similar to the floor plate and distinct from other CNS regions. Differentiation of dorsally derived neural crest occurs in transgenic embryos as can be seen from the presence of cranial ganglia. In the rostral spinal cord, the neural tube appeared distended dorso-laterally which may account for the superficial dysmorphology.

By 11.5 dpc, CNS development is highly abnormal along the entire dorsal spinal cord to the hindlimb level. The dorsal half of the spinal cord is enlarged and distended. Dorsal sensory innervation occurs, however, the neuronal trajectories are highly disorganized. Most obviously, the morphology of dorsal cells in the spinal cord, which normally are elongated cells with distinct lightly staining nuclei and cytoplasm, is dramatically altered. Most of the dorsal half of the spinal cord consists of small tightly packed cells with darkly staining nuclei and little cytoplasm. Moreover, there appears to be many more of these densely packed cells, leading to abnormal outgrowth of the dorsal CNS. In contrast, ventral development is normal, as are dorsal root ganglia, whose origins lie in neural cells derived from the dorsal spinal cord.

(vi) Ectopic Shh Expression Activates Floor Plate Gene Expression

To determine whether ectopic expression of chick Shh results in inappropriate activation of a ventral midline development in the dorsal CNS, expression of two floor plate expressed genes, HNF-3β and mouse Shh, were examined. Whole mounts of 9.5 dpc transgenic embryos show ectopic expression of HNF-3β throughout the cranial Wnt-1 expression domain. In addition to normal expression at the ventral midline, HNF-3β transcripts are expressed at high levels, in a circle just rostral to the mid/hindbrain junction, along the dorsal (actually lateral in unfused brain folds) aspects of the midbrain and, more weakly, in the roof plate of the myelencephalon. No expression is observed in the metencephalon which does not express Wnt-1. Thus, ectopic expression of Shh leads to the activation of HNF-3β throughout the cranial Wnt-1 expression domain.

The relationship between chick Shh expression and the expression of HNF-3β in serial sections was also examined. Activation of HNF-3β in the brain at 9.5 and 10.5 dpc is localized to the dorsal aspect in good agreement with the observed ectopic expression of chick Shh. Interestingly mouse Shh is also activated dorsally. Thus, two early floor plate markers are induced in response to chick Shh.

From 9.5 dpc to 11.5 dpc, the spinal cord phenotype becomes more severe. The possibility that activation of a floor plate pathway may play a role in the observed phenotype was investigated. In contrast to the brain, where ectopic HNF-3β and Shh transcripts are still present, little or no induction of these floor plate markers is observed. Thus, although the dorsal spinal cord shows a widespread transformation in cellular phenotype, this does not appear to result from the induction of floor plate development.

EXAMPLE 3

Chick Sonic Hedgehog Mediates ZPA Activity
(i) Experimental Procedures
Retinoic Acid Bead Implants Fertilized white Leghorn chicken eggs were incubated to stage 20 and then implanted with AG1-X2 ion exchange beads (Biorad) soaked in 1 mg/ml retinoic acid (RA, Sigma) as described by Tickle, C. et al., (1985) *Dev. Biol* 109: 82–95. Briefly, the beads were soaked for 15 min in 1 mg/ml RA in DMSO, washed twice and implanted under the AER on the anterior margin of the limb bud. After 24 or 36 hours, some of the implanted embryos were harvested and fixed overnight in 4% paraformaldehyde in PBS and then processed for whole mount in situ analysis as previously described. The remainder of the animals were allowed to develop to embryonic day 10 to confirm that the dose of RA used was capable of inducing mirror image duplications. Control animals were implanted with DMSO soaked beads and showed no abnormal phenotype or gene expression.

Plasmids

Unless otherwise noted, all standard cloning techniques were performed according to Ausubel, F. M. et al., (1989) *Current Protocols in Molecular Biology* (N.Y.: Greene Publishing Assoc. and Wiley Inerscience), and all enzymes were obtained from Boehringer Mannheim Biochemicals. pHH-2 is a cDNA contain the entire coding region of chicken Sonic hedgehog (SEQ ID No:1). RCASBP(A) and RCASBP(E) are replication-competent retroviral vectors which encode viruses with differing host ranges. RCANBP(A) is a variant of RCASBP(A) from which the second splice acceptor has been removed. This results in a virus which can not express the inserted gene and acts as a control for the effects of viral infection (Hughes, S. H. et al., (1987) *J. Virol.* 61: 3004–3012; Fekete, D. et al., (1993) *Mol. Cell. Biol.* 13: 2604–2613). RCASBP/AP(E) is version of RCASBP(E) containing a human placental alkaline phosphatase cDNA (Fekete, D. et al., (1993b) *Proc. Natl. Acad Sci. USA* 90: 2350–2354). SLAX13 is a pBluescript SK+ derived plasmid with a second Cla I restriction site and the 5' untranslated region of v-src (from the adaptor plasmid CLA12-Nco, Hughes, S. H. et al., (1987) *J. Virol.* 61: 3004–3012) cloned 5' of the EcoRI (and ClaI) site in the pBluescript polylinker. RCASBP plasmids encoding Sonic from either the first (M1) or second (M2) methionine (at position 4) were constructed by first shuttling the 1.7 kb Sonic fragment of pHH-2 into SLAX-13 using oligonucleotides to modify the 5' end of the cDNA such that either the first or second methionine is in frame with the NcoI site of SLAX-13. The amino acid sequence of Sonic is not mutated in these constructs. The M1 and M2 Sonic ClaI fragments (v-src 5'UTR:Sonic) were each then subcloned into RCASBP(A), RCANBP(A) and RCASBP(E), generating Sonic/RCAS-A1, Sonic/RCAS-A2, Sonic/RCAN-A1, Sonic/RCAN-A2, Sonic/RCAS-E1 and Sonic/RCAS-E2.

Chick Embryos, Cell Lines and Virus Production

All experimental manipulations were performed on standard specific-pathogen free White Leghorn chick embryos (S-SPF) from closed flocks provided fertilized by SPAFAS (Norwich, Conn.). Eggs were incubated at 37.5° C. and staged according to Hamburger, V. et al., (1951) *J. Exp. Morph.* 88: 49–92. All chick embryo fibroblasts (CEF) were provided by C. Cepko. S-SPF embryos and CEFs have previously been shown to be susceptible to RCASBP(A) infection but resistant to RCASBP(E) infection (Fekete, D. et al., (1993b) *Proc. Natl. Acad. Sci. USA* 90: 2350–2354). Line 15b CEFs are susceptible to infection by both RCASBP (A) and (E). These viral host ranges were confirmed in control experiments. CEF cultures were grown and transfected with retroviral vector DNA as described (Morgan, B. A. et al., (1993) *Nature* 358: 236–239; Fekete, D. et al., (1993b) *Proc. Natl. Acad. Sci. USA* 90: 2350–2354). All viruses were harvested and concentrated as previously described (Morgan, B. A. et al., (1993) *Nature* 358: 236–239; Fekete, D. et al., (1993b) *Proc. Natl Acad. Sci. USA* 90: 2350–2354) and had titers of approximately $10^8$ cfu/ml.

Cell Implants

A single 60 mm dish containing line 15b CEFs which had been infected with either RCASBP/AP(E), Sonic/RCAS-E1 or Sonic/RCAS-E2 were grown to 50–90% confluence, lightly trypsinized and then spun at 1000 rpm for 5 min in a clinical centrifuge. The pellet was resuspended in 1 ml media, transferred to a microcentrifuge tube and then microcentrifuged for 2 min at 2000 rpm. Following a 30 min incubation at 37° C., the pellet was respun for 2 min at 2000 rpm and then lightly stained in media containing 0.01% nile blue sulfate. Pellet fragments of approximately 300 μm×100 μm×50 μm were implanted as a wedge to the anterior region of hh stage 19–23 wing buds (as described by Riley, B. B. et al., (1993) *Development* 118: 95–104). At embryonic day 10, the embryos were harvested, fixed in 4% paraformaldehyde in PBS, stained with alcian green, and cleared in methyl salicylate (Tickle, C. et al., (1985) *Dev. Biol* 109: 82–95).

Viral Infections

Concentrated Sonic/RCAS-A2 or Sonic/RCAN-A2 was injected under the AER on the anterior margin of stage 20–22 wing buds. At 24 or 36 hours post-infection, the embryos were harvested, fixed in 4% paraformaldehyde in PBS and processed for whole mount in situ analysis as previously described.

(ii) Co-Localization of Sonic Expression and Zpa Activity

ZPA activity has been carefully mapped both spatially and temporally within the limb bud (Honig, L. S. et al., (1985) *J. Embryol. exp. Morph.* 87: 163–174). In these experiments small blocks of limb bud tissue from various locations and stages of chick embryogenesis (Hamburger, V et al., (1951) *J. Exp. Morph.* 88: 49–92) were grafted to the anterior of host limb buds and the strength of ZPA activity was quantified according to degrees of digit duplication. Activity is first weakly detected along the flank prior to limb bud outgrowth. The activity first reaches a maximal strength at stage 19 in the proximal posterior margin of the limb bud. By stage 23 the activity extends the full length of the posterior border of the limb bud. The activity then shifts distally along the posterior margin so that by stage 25 it is no longer detectable at the base of the flank. The activity then fades distally until it is last detected at stage 29.

This detailed map of endogenous polarizing activity provided the opportunity to determine the extent of the correlation between the spatial pattern of ZPA activity and Sonic expression over a range of developmental stages. Whole mount in situ hybridization was used to assay the spatial and temporal pattern of Sonic expression in the limb bud. Sonic expression is not detected until stage 17, at the initiation of limb bud formation, at which time it is weakly observed in a punctate pattern reflecting a patchy expression in a few cells. From that point onwards the Sonic expression pattern exactly matches the location of the ZPA, as determined by Honig, L. S. et al., (1985) *J. Embryol. exp. Morph.* 87: 163–174, both in position and in intensity of expression.

(iii) Induction of Sonic Expression by Retinoic Acid

A source of retinoic acid placed at the anterior margin of the limb bud will induce ectopic tissue capable causing mirror-image duplications (Summerbell, D. et al., (1983) *In Limb Development and Regeneration* (N.Y.: Ala R. Liss) pp. 109–118; Wanek, N. et al., (1991) *Nature* 350: 81–83). The induction of this activity is not an immediate response to retinoic acid but rather takes approximately 18 hours to develop (Wanek, N. et al., (1991) *Nature* 350: 81–83). When it does develop, the polarizing activity is not found surrounding the implanted retinoic acid source, but rather is found distal to it in the mesenchyme along the margin of the limb bud (Wanek, N. et al., (1991) *Nature* 350: 81–83).

If Sonic expression is truly indicative of ZPA tissue, then it should be induced in the ZPA tissue which is ectopically induced by retinoic acid. To test this, retinoic acid-soaked beads were implanted in the anterior of limb buds and the expression of Sonic after various lengths of time using whole-mount in situ hybridization was assayed. As the limb bud grows, the bead remains imbedded proximally in tissue which begins to differentiate. Ectopic Sonic expression is first detected in the mesenchyme 24 hours after bead implantation. This expression is found a short distance from the distal edge of the bead. By 36 hours Sonic is strongly expressed distal to the bead in a stripe just under the anterior ectoderm in a mirror-image pattern relative to the endogenous Sonic expression in the posterior of the limb bud.

(iv) Effects of Ectopic Expression of Sonic on Limb Patterning

The normal expression pattern of Sonic, as well as that induced by retinoic acid, is consistent with Sonic being a signal produced by the ZPA. To determine whether Sonic expression is sufficient for ZPA activity, the gene was ectopically expressed within the limb bud. In most of the experiments we have utilized a variant of a replication-competent retroviral vector called RCAS (Hughes, S. H. et al., (1987) *J. Virol.* 61: 3004–3012)) both as a vehicle to introduce the Sonic sequences into chick cells and to drive their expression. The fact that there exists subtypes of avian retroviruses which have host ranges restricted to particular strains of chickens was taken advantage of to control the region infected with the Sonic/RCAS virus (Weiss, R. (et al.) (1984) *RNA Tumor Viruses,* Vol. 1 Weiss et al. eds., (N.Y.: Cold Spring Harbor Laboratories) pp. 209–260); Fekete, D. et al., (1993a) *Mol. Cell. Biol.* 13: 2604–2613). Thus a vector with a type E envelope protein (RCAS-E, Fekete, D. et al., (1993b) *Proc. Natl. Acad. Sci. USA* 90: 2350–2354) is unable to infect the cells of the SPAFAS outbred chick embryos routinely used in our lab. However, RCAS-E is able to infect cells from chick embryos of line 15b. In the majority of experiments, primary chick embryo fibroblasts (CEFs) prepared from line 15b embryos in vitro were infected. The infected cells were pelleted and implanted into a slit made in the anterior of S-SPF host limb buds. Due to the restricted host range of the vector, the infection was thus restricted to the graft and did not spread through the host limb bud.

To determine the fate of cells implanted and to control for any effect of the implant procedure, a control RCAS-E vector expressing human placental alkaline phosphatase was used. Alkaline phosphatase expression can be easily monitored histochemically and the location of infected cells can thus be conveniently followed at any stage. Within 24 hours following implantation the cells are dispersed proximally and distally within the anterior margin of the limb bud. Subsequently, cells are seen to disperse throughout the anterior portion of the limb and into the flank of the embryo.

Figure 8:
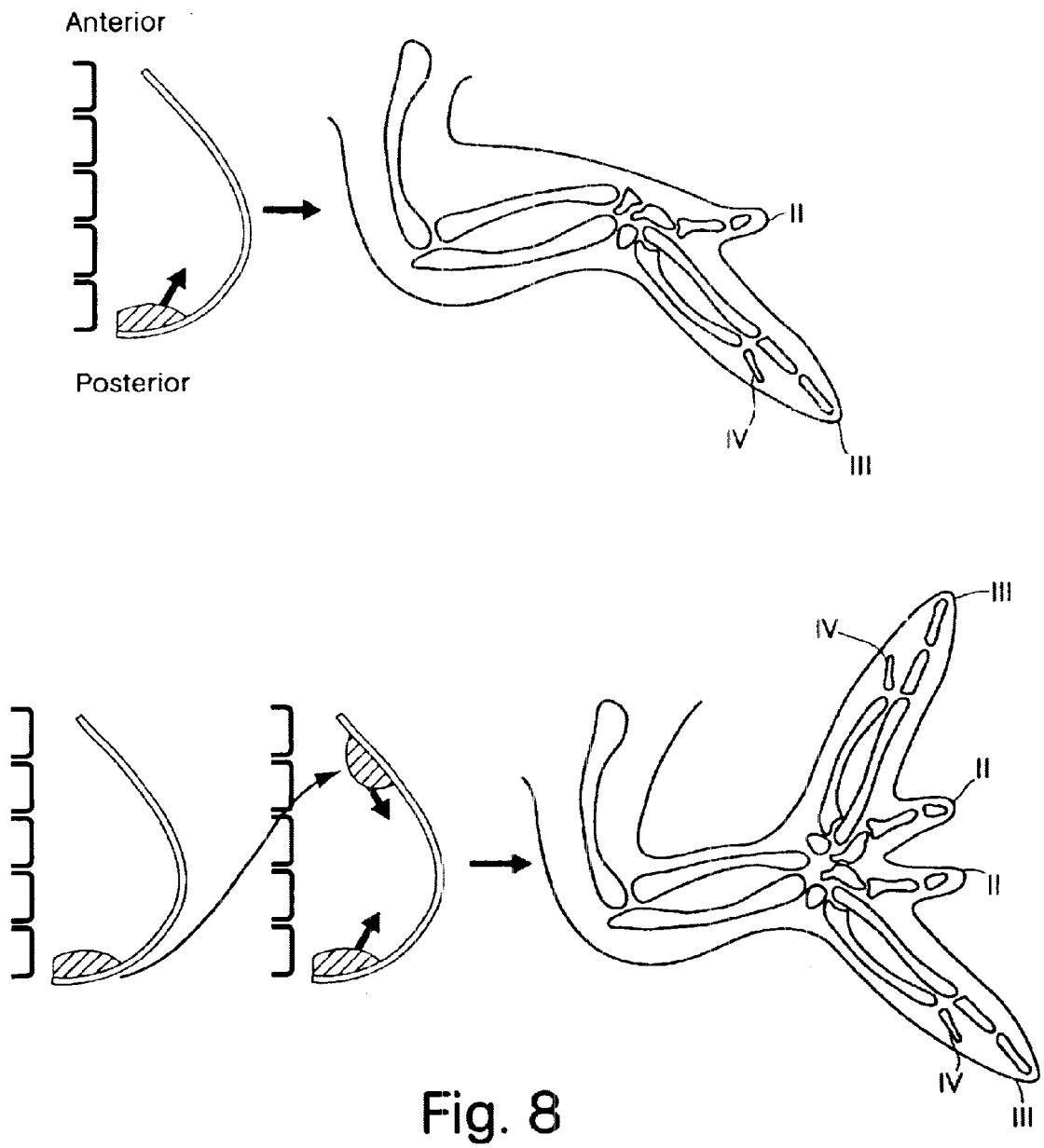
FIG. 8 is a model for anterioposterior limb patterning and the Zone of Polarizing Activity (ZPA), based on Saunders and Gasseling (1968). The left portion of the diagram schematizes a stage 20 limb bud. The somites are illustrated as blocks along the left margin of the limb bud; right portion of the same panel illustrates the mature wing. The hatched region on the posterior limb is the ZPA. Normally, the developed wing contains three digits II, III, and IV. The figure further shows the result of transplanting a ZPA from one limb bud to the anterior margin of another. The mature limb now contains six digits IV, III, II, II, III, and IV in a mirror-image duplication of the normal pattern. The large arrows in both panels represent the signal produced by the ZPA which acts to specify digit identity.

Limb buds grafted with alkaline phosphatase expressing cells or uninfected cells give rise to limbs with structures indistinguishable from unoperated wild type limbs. Such limbs have the characteristic anterior-to-posterior digit pattern 2-3-4. ZPA grafts give rise to a variety of patterns of digits depending on the placement of the graft within the bud (Tickle, C. et al., (1975) *Nature* 254: 199–202) and the amount of tissue engrafted (Tickle, C. (1981) *Nature* 289: 295–298). In some instances the result can be as weak as the duplication of a single digit 2. However, in optimal cases the ZPA graft evokes the production of a full mirror image duplication of digits 4-3-2-2-3-4 or 4-3-2-3-4 (see FIG. 8). A scoring system has been devised which rates the effectiveness of polarizing activity on the basis of the most posterior digit duplicated: any graft which leads to the development of a duplication of digit 4 has been defined as reflecting 100% polarizing activity (Honig, L. S. et al., (1985) *J. Embryol. Exp. Morph.* 87:163–174).

Grafts of 15b fibroblasts expressing Sonic resulted in a range of ZPA-like phenotypes. In some instances the resultant limbs deviate from the wild type solely by the presence of a mirror-image duplication of digit 2. The most common digit phenotype resulting from grafting Sonic-infected CEF cells is a mirror-image duplication of digits 4 and 3 with digit 2 missing: 4-3-3-4. In many such cases the two central digits appear fused in a 4-3/3-4 pattern. In a number of the cases the grafts induced full mirror-image duplications of the digits equivalent to optimal ZPA grafts 4-3-2-2-3-4. Besides the digit duplications, the ectopic expression of Sonic also gave rise to occasional duplications of proximal elements including the radius or ulna, the humerus and the coracoid. While these proximal phenotypes are not features of ZPA grafts, they are consistent with an anterior-to-posterior respecification of cell fate. In some instances, most commonly when the radius or ulna was duplicated, more complex digit patterns were observed. Typically, an additional digit 3 was formed distal to a duplicated radius.

The mirror-image duplications caused by ZPA grafts are not limited to skeletal elements. For example, feather buds are normally present only along the posterior edge of the limb. Limbs exhibiting mirror-image duplications as a result of ectopic Sonic expression have feather buds on both their anterior and posterior edges, similar to those observed in ZPA grafts.

While ZPA grafts have a powerful ability to alter limb pattern when placed at the anterior margin of a limb bud, they have no effect when placed at the posterior margin (Saunders, J. W. et al., (1968) *Epithelial-Mesenchymal Interaction,* Fleischmayer and Billingham, eds. (Baltimore: Williams and Wilkins) pp. 78–97). Presumably, the lack of posterior effect is a result of polarizing activity already being present in that region of the bud. Consistent with this, grafts of Sonic expressing cells placed in the posterior of limb buds never result in changes in the number of digits. Some such grafts did produce distortions in the shape of limb elements, the most common being a slight posterior curvature in the distal tips of digits 3 and 4 when compared to wild type wings.

(v) Effect of Ectopic Sonic Expression on Hoxd Gene Activity

The correct expression of Hoxd genes is part of the process by which specific skeletal elements are determined (Morgan, B. A. et al., (1993) *Nature* 358: 236–239). A transplant of a ZPA into the anterior of a chick limb bud ectopically activates sequential transcription of Hoxd genes in a pattern which mirrors the normal sequence of Hoxd gene expression (Nohno, T. et al., (1991) *Cell* 64: 1197–1205; Izpisua-Belmonte, J. C. et al., (1991) *Nature* 350: 585–589). Since ectopic Sonic expression leads to the same pattern duplications as a ZPA graft, we reasoned that Sonic would also lead to sequential activation of Hoxd genes.

To test this hypothesis, anterior buds were injected with Sonic/RCAS-A2, a virus which is capable of directly infecting the host strains of chicken embryos. This approach does not strictly limit the region expressing Sonic (being only moderately controlled by the timing, location and titer of viral injection), and thus might be expected to give a more variable result. However, experiments testing the kinetics of viral spread in infected limb buds indicate that infected cells remain localized near the anterior margin of the bud for at least 48 hours. Hoxd gene expression was monitored at various times post infection by whole mount in situ hybridization. As expected, these genes are activated in a mirror-image pattern relative their expression in the posterior of control limbs. For example, after 36 hours Hoxd-13 is expressed in a mirror-image symmetrical pattern in the broadened distal region of infected limb buds. Similar results were obtained with other Hoxd genes (manuscript in preparation).

EXAMPLE 4

A Functionally Conserved Homolog of Drosophila Hedgehog is Expressed in Tissues with Polarizing Activity in Zebrafish Embryos (i) Experimental Procedures Cloning and Sequencing Approximately $1.5 \times 10^6$ plaques of a 33 h zebrafish embryonic λgt11 cDNA library were screened by plaque hybridization at low stringency (McGinnis, W. et al., (1984) *Nature* 308: 428–433) using a mix of two hh sequences as a probe: a Drosophila hh 400 bp EcoRI fragment and a murine Ihh 264 bp BamHI-EcoRI exon 2 fragment. Four clones were isolated and subcloned into the EcoRI sites of pUC18 T3T7 (Pharmacia). Both strands of clone 8.3 were sequenced using nested deletions (Pharmacia) and internal oligonucleotide primers. DNA sequences and derived amino acid sequences were analyzed using "Geneworks" (Intelligenetics) and the GCG software packages.

PCR Amplification

Degenerate oligonucleotides hh5.1 (SEQ ID No:30) and hh3.3 (SEQ ID No:31) were used to amplify genomic zebrafish DNA hh 5.1: AG(CA)GITG(CT)AA(AG)GA(AG)(CA)(AG)I(GCT)IAA hh 3.3: CTCIACIGCIA(GA)ICK=(GT)IGCIA PCR was performed with an initial denaturation at 94° C. followed by 35 cycles of 47° C. for 1 min, 72° C. for 2 min and 94° C. for 1 min with a final extension at 72° C. Products were subcloned in pUC 18 (Pharmacia).

In Situ Hybridization

In situ hybridizations of zebrafish embryos were performed as described in Oxtoby, E. et al., (1993) *Nuc. Acids REs.* 21: 1087–1095 with the following modifications: Embryos were rehydrated in ethanol rather than methanol series; the proteinase K digestion was reduced to 5 min and subsequent washes were done in PBTw without glycine; the antibody was preadsorbed in PBTw, 2mg/ml BSA without sheep serum; and antibody incubation was performed in PBTw, 2mg/ml BSA. Drosophila embryos were processed and hybridized as previously described.

Histology

Stained embryos were dehydrated through ethanol:butanol series, as previously described (Godsave, S. F. et al., (1988) *Development* 102: 555–566), and embedded in Fibrowax. 8 μm sections were cut on an Anglian rotary microtome RNA Probe Synthesis For analysis of Shh expression, two different templates were used with consistent results; (i) phh[c] 8.3 linearized with Bgl II to transcribe an antisense RNA probe that excludes the conserved region, and (ii) phh[c] 8.3 linearized with Hind III to transcribe an antisense RNA that covers the complete cDNA. All in situ hybridizations were performed with the latter probe which gives better signal. Other probes were as follows: Axial DraI-linearised p6TIN (Strähle, U. et al., (1993) *Genes & Dev.* 7: 1436–1446) using T3 RNA polymerase. gsc linearized with EcoRI and transcribed with T7: pax 2 Bam HI-linearized pcF16 (Krauss, S. et al., (1991) *Development* 113: 1193–1206) using T7 RNA polymerase. In situ hybridizations were performed using labelled RNA at a concentration of 1 ng/ml final concentration. Antisense RNA probes were transcribed according to the manufacturer's protocol (DIG RNA Labelling Kit, BCL).

Zebrafish Strains

Wild type fish were bred from a founder population obtained from the Goldfish Bowl, Oxford. The mutant cyclops strain b16 and the mutant notail strains b160 and b195 were obtained from Eugene, Oregon. Fish were reared at 28° C. on a 14 h light/10 h dark cycle.

RNA Injections

The open reading frame of Shh was amplified by PCR, using oligonucleotides 5'-CTGCAGGGATCCACCATGCGGCTTTTGACGAG-3' (SEQ ID No:32), which contains a consensus Kozak sequence for translation initiation, and 5'-CTGCAGGGATC-CTTATTCCACACGAGGGATT-3' (SEQ ID No:33), and subcloned into the BglII site of pSP64T (Kreig, P.A. et al., (1984) *Nuc.Acids Res.* 12: 7057–7070). This vector includes 5' and 3' untranslated Xenopus β-Globin sequences for RNA stabilization and is commonly used for RNA injections experiments in Xenopus. In vitro transcribed Shh RNA at a concentration of approximately 100 µg/ml was injected into a single cell of naturally spawned zebrafish embryos at one-cell to 4-cell stages using a pressure-pulsed Narishige microinjector. The injected volume was within the picolitre range. Embryos were fixed 20 to 27 hrs after injection in BT-Fix (Westerfield, M. (1989) *The Zebrafish Book,* (Eugene: The University of Oregon Press)) and processed as described above for whole-mount in situ hybridizations with the axial probe.

Transgenic Drosophila

An EcoR1 fragment, containing the entire Shh ORF, was purified from the plasmid phh[c]8.3 and ligated with phosphatased EcoR1 digested transformation vector pCaSpeRhs (Thummel, C. S. et al., (1988) *Gene* 74: 445–456). The recombinant plasmid, pHS Shh containing the Shh ORF in the correct orientation relative to the heat shock promoter, was selected following restriction enzyme analysis of miniprep DNA from transformed colonies and used to transform Drosophila embryos using standard microinjection procedures (Roberts, D. B. (1986), *Drosophila, A Practical Approach,* Roberts, D. B., ed., (Oxford: IRL Press) pp. 1–38).

Ectopic Expression in Drosophila Embryos

Embryos carrying the appropriate transgenes were collected over 2 hr intervals, transferred to thin layers of 1% agarose on glass microscope slides and incubated in a plastic Petri dish floating in a water bath at 37° C. for 30 min intervals. Following heat treatment, embryos were returned to 25° C. prior to being fixed for in situ hybridization with DIG labelled single stranded Shh, wg or ptc RNA probes as previously described (Ingham et al., (1991) *Curr. Opin. Genet. Dev.* 1: 261–267).

(ii) Molecular Cloning of Zebrafish Hedgehog Homologues

In an initial attempt to isolate sequences homologous to Drosophila hh, a zebrafish genomic DNA library was screened at reduced stringency with a partial cDNA, hhPCR4.1, corresponding to the first and second exons of the Drosophila gene (Mohler, J. et al., (1992) *Development* 115: 957–971). This screen proved unsuccessful; however, a similar screen of a mouse genomic library yielded a single clone with significant homology to hh., subsequently designated Ihh. A 264 bp BamHI-EcoRI fragment from this lambda clone containing sequences homologous to the second exon of the Drosophila gene was subcloned and, together with the Drosophila partial cDNA fragment, used to screen a λ.gt11 I zebrafish cDNA library that was prepared from RNA extracted from 33 h old embryos. This screen yielded four clones with overlapping inserts the longest of which is 1.6 kb in length, herein referred to as Shh (SEQ ID No:5).

(iii) A Family of Zebrafish Genes Homologous to the Drosophila Segment Polarity Gene, Hedgehog Alignment of the predicted amino acid sequences of Shh (SEQ ID No:12) and hh (SEQ ID No:34) revealed an identity of 47%, confirming that Shh is a homolog of the Drosophila gene. A striking conservation occurs within exon 2: an 80 amino acid long domain shows 72% identity between Shh and Drosophila hh. (FIG. 9A). This domain is also highly conserved in all hh-related genes cloned so far and is therefore likely to be essential to the function of hh proteins. A second domain of approximately 30 amino acids close to the carboxy-terminal end, though it shows only 61% amino-acid identity, possesses 83% similarity between Shh and hh when allowing for conservative substitutions and could also, therefore, be of functional importance (FIG. 9B). Although putative sites of post-translational modification can be noted, their position is not conserved between Shh and hh.

Lee, J. J. et al., (1992) *Cell* 71: 33–50, identified a hydrophobic stretch of 21 amino acids flanked downstream by a putative site of signal sequence cleavage (predicted by the algorithm of von Heijne, G. (1986) *Nuc. Acids Res.* 11) close to the amino-terminal end of hh. Both the hydrophobic stretch and the putative signal sequence cleavage sites of hh, which suggest it to be a signaling molecule, are conserved in Shh. In contrast to hh, Shh does not extend N-terminally to the hydrophobic stretch.

Using degenerate oligonucleotides corresponding to amino-acids flanking the domain of high homology between Drosophila hh and mouse Ihh exons 2 described above, fragments of the expected size were amplified from zebrafish genomic DNA by PCR. After subcloning and sequencing, it appeared that three different sequences were amplified, all of which show high homology to one another and to Drosophila hh (FIG. 10). One of these corresponds to Shh therein referred to as 2-hh(a) (SEQ ID No:16) and 2hh(b) (SEQ ID No:17), while the other two represent additional zebrafish hh homologs (SEQ ID No:5). cDNAs corresponding to one of these additional homologs have recently been isolated, confirming that it is transcribed. Therefore, Shh represents a member of a new vertebrate gene family.

(iv) Shh Expression in the Developing Zebrafish Embryo

Gastrula Stages

Shh expression is first detected at around the 60% epiboly stage of embryogenesis in the dorsal mesoderm. Transcript is present in a triangular shaped area, corresponding to the embryonic shield, the equivalent of the amphibian organizer, and is restricted to the inner cell layer, the hypoblast. During gastrulation, presumptive mesodermal cells involute to form the hypoblast, and converge towards the future axis of the embryo, reaching the animal pole at approximately 70% epiboly. At this stage, Shh -expressing cells extend over the posterior third of the axis, and the signal intensity is not entirely homogeneous, appearing stronger at the base than at the apex of the elongating triangle of cells.

This early spatial distribution of Shh transcript is reminiscent of that previously described for axial, a forkhead-related gene; however, at 80% epiboly, axial expression extends further towards the animal pole of the embryo and we do not see Shh expression in the head area at these early developmental stages.

By 100% epiboly, at 9.5 hours of development, the posterior tip of the Shh expression domain now constitutes a continuous band of cells that extends into the head. To determine the precise anterior boundary of Shh expression, embryos were simultaneously hybridized with probes of Shh and pax-2 (previously pax[b]), the early expression domain of which marks the posterior midbrain (Krauss, S. et al. (1991) Development 113: 1193–1206). By this stage, the anterior boundary of the Shh expression domain is positioned in the centre of the animal pole and coincides approximately with that of axial. At the same stage, prechordal plate cells expressing the homeobox gene goosecoid (gsc) overlap and underlay the presumptive forebrain (Statchel, S. E. et al., (1993) Development 117: 1261–1274). Whereas axial is also thought to be expressed in head mesodermal tissue at this stage, we cannot be certain whether Shh is expressed in the same cells. Sections of stained embryos suggest that in the head Shh may by this stage be expressed exclusively in neuroectodermal tissue.

(v) Somitogenesis

By the onset of somitogenesis (approximately 10.5 h of development), Shh expression in the head is clearly restricted to the ventral floor of the brain, extending from the tip of the diencephalon caudally through the hindbrain. At this stage, expression of axial has also disappeared from the head mesoderm and is similarly restricted to the floor of the brain; in contrast to Shh, however, it extends only as far as the anterior boundary of the midbrain. At this point, gsc expression has become very weak and is restricted to a ring of cells that appear to be migrating away from the dorsal midline.

As somitogenesis continues, Shh expression extends in a rostral-caudal progression throughout the ventral region of the central nervous system (CNS). Along the spinal cord, the expression domain is restricted to a single row of cells, the floor plate, but gradually broadens in the hindbrain and midbrain to become 5–7 cells in diameter, with a triangular shaped lateral extension in the ventral diencephalon and two strongly staining bulges at the tip of the forebrain, presumably in a region fated to become hypothalamus.

As induction of Shh in the floor plate occurs, expression in the underlying mesoderm begins to fade away, in a similar manner to axial (Strähle, U. et al., (1993) Genes& i Dev. 7: 1436–1446). This downregulation also proceeds in a rostral to caudal sequence, coinciding with the changes in cell shape that accompany notochord differentiation. By the 22 somite stage, mesodermal Shh expression is restricted to the caudal region of the notochord and in the expanding tail bud where a bulge of undifferentiated cells continue to express Shh at relatively high levels. Expression in the midbrain broadens to a rhombic shaped area; cellular rearrangements that lead to the 90° kink of forebrain structures, position hypothalamic tissue underneath the ventral midbrain. These posterior hypothalamic tissues do not express Shh. In addition to Shh expression in the ventral midbrain, a narrow stripe of expressing cells extends dorsally on either side of the third ventricle from the rostral end of the Shh domain in the ventral midbrain to the anterior end of, but not including, the epiphysis. The most rostral Shh expressing cells are confined to the hypothalamus. In the telencephalon, additional Shh expression is initiated in two 1–2 cell wide stripes.

By 36 hours of development, Shh expression in the ventral CNS has undergone further changes. While expression persists in the floor plate of the tailbud, more rostrally located floor plate cells in the spinal cord cease to express the gene. In contrast, in the hindbrain and forebrain Shh expression persists and is further modified.

At 26–28 h, Shh expression appears in the pectoral fin primordia, that are visible as placode like broadenings of cells underneath the epithelial cell layer that covers the yolk. By 33 hrs of development high levels of transcript are present in the posterior margin of the pectoral buds; at the same time, expression is initiated in a narrow stripe at the posterior of the first gill. Expression continues in the pectoral fin buds in lateral cells in the early larva. At this stage, Shh transcripts are also detectable in cells adjacent to the lumen of the foregut.

(vi) Expression of Shh in Cyclops and Notail Mutants

Two mutations affecting the differentiation of the Axial tissues that express Shh have been described in zebrafish embryos homozygous for the cyclops (cyc) mutation lack a differentiated floorplate (Hatta, K. et al., (1991) Nature 350: 339–341). By contrast, homozygous notail (ntl) embryos are characterized by a failure in notochord maturation and a disruption of normal development of tail structures (Halpern, M. E. et al., (1993) Cell 75: 99–111).

A change in Shh expression is apparent in cyc embryos as early as the end of gastrulation; at this stage, the anterior limit of expression coincides precisely with the two pax-2 stripes in the posterior midbrain. Thus, in contrast to wild-type embryos, no Shh expression is detected in midline structures of the midbrain and forebrain. By the 5 somite stage, Shh transcripts are present in the notochord which at this stage extends until rhombomere 4; however, no expression is detected in more anterior structures. Furthermore, no Shh expression is detected in the ventral neural keel, in particular in the ventral portions of the midbrain and forebrain.

At 24 hours of development, the morphologically visible cyc phenotype consists of a fusion of the eyes at the midline due to the complete absence of the ventral diencephalon. As at earlier developmental stages, Shh expression is absent from neural tissue. Shh expression in the extending tail bud of wild-type embryos is seen as a single row of floor plate cells throughout the spinal cord. In a cyc mutant, no such Shh induction occurs in cells of the ventral spinal cord with the exception of some scattered cells that show transient expression near the tail. Similarly, no Shh expression is seen rostrally in the ventral neural tube. However, a small group of Shh expressing cells is detected underneath the epiphysis which presumably correspond to the dorsal-most group of Shh expressing cells in the diencephalon of wild-type embryos.

In homozygous notail (nto) embryos, no Shh staining is seen in mesodermal tissue at 24 hours of development, consistent with the lack of a notochord in these embryos; by contrast, expression throughout the ventral CNS is unaffected. At the tail bud stage, however, just prior to the onset of somitogenesis, Shh expression is clearly detectable in notochord precursor cells.

(vii) Injection of Synthetic Shh Transcripts into Zebrafish Embryos Induces Expression of a Floor Plate Marker To investigate the activity of Shh in the developing embryo, an over-expression strategy, similar to that employed in the analysis of gene function in Xenopus, was adopted. Newly fertilized zebrafish eggs were injected with synthetic Shh RNA and were fixed 14 or 24 hours later. As an assay for possible changes in cell fate consequent upon the ectopic activity of Shh, we decided to analyze Axial expression, since this gene serves as a marker for cells in which Shh is normally expressed. A dramatic, though highly localized ectopic expression of Axial in a significant proportion (21/80) of the injected embryos fixed after 24 hours of development is observed. Affected embryos show a broadening of the Axial expression domain in the diencephalon and ectopic Axial expression in the midbrain; however, in no case has ectopic expression in the telencephalon or spinal cord been observed. Many of the injected embryos also showed disturbed forebrain structures, in particular smaller ventricles and poorly developed eyes. Arnongst embryos fixed after 14 h, a similar proportion (8/42) exhibit the same broadening and dorsal extension of the Axial stripe in the diencephalon as well as a dorsal extension of Axial staining in the midbrain; again, no changes in Axial expression were observed caudal to the hindbrain with the exception of an increased number of expressing cells at the tip of the tail.

(viii) Overexpression of Shh in Drosophila Embryos Activates the hh-Dependent Pathway In order to discover whether the high degree of structural homology between the Drosophila and zebrafish hh genes also extends to the functional level, an overexpression system was used to test the activity of Shh in flies. Expression of Drosophila hh driven by the HSP70 promoter results in the ectopic activation of both the normal targets of hh activity; the wg transcriptional domain expands to fill between one third to one half of each parasegment whereas ptc is ectopically activated in all cells except those expressing en (Ingham, P. W. (1993) Nature 366:560–562). To compare the activities of the fly and fish genes, flies transgenic for a HS Shh construct were generated described above and subjected to the same heat shock regime as H Shh transgenic flies. HS Shh embryos fixed immediately after the second of two 30 min heat shocks exhibit ubiquitous transcription of the Shh cDNA. Similarly treated embryos were fixed 30 or 90 min after the second heat shock and assayed for wg or ptc transcription. Both genes were found to be ectopically activated in a similar manner to that seen in heat shocked H Shh embryos; thus, the zebrafish Shh gene can activate the same pathway as the endogenous hh gene.

EXAMPLE 5

Cloning, Expression and Localization of Human Hedgehogs
(i) Experimental Procedures
Isolation of Human Hedgehog cDNA Clones Degenerate nucleotides used to clone chick Shh (Riddle et al., (1993) Cell 75:1401–1416) were used to amplify by nested PCR human genomic DNA. The nucleotide sequence of these oligos is as follows:

vHH5O:5'-GGAATTCCCAG(CA)GITG(CT)AA(AG)GA
(AG)(CA)(AG)I(GCT)TIAA-3'         (SEQ ID NO:18);

vHH3O:5'-TCATCGATGGACCCA(GA)TC(GA)AAI
CCIGC(TC)TC-3'                    (SEQ ID NO:19);

vHH3I:5'-GCTCTAGAGCTCIACIGCIA(GA)IC(GT)
IGGIA-3'                          (SEQ ID NO:20)

The expected 220 bp PCR product was subcloned into pGEM7zf (Promega) and sequenced using Sequenase v2.0 (U.S. Biochemicals). One clone showed high nucleotide similarity to mouse Ihh and mouse Shh sequence (Echelard et al., (1993) Cell 75:1417–1430) and it was used for screening a human fetal lung 5'-stretch plus cDNA library (Clontech) in λ gt10 phage. The library was screened following the protocol suggested by the company and two positive plaques were identified, purified, subcloned into pBluescript SK+ (Stratagene) and sequenced, identifying them as the human homologues of Shh (SEQ ID NO:6) and Ihh (SEQ ID NO:7).

One clone contained the full coding sequence of a human homolog of Shh as well as 150 bp of 5' and 36 bp of 3' untranslated sequence. The other clone, which is the human homolog of Ihh, extends from 330 bp 3' of the coding sequence to a point close to the predicted boundary between the first and second exon. The identity of these clones was determined by comparison to the murine and chick genes. The protein encoded by human Shh has 92.4% overall identity to the mouse Shh, including 99% identity in the amino-terminal half. The carboxyl-terminal half is also highly conserved, although it contains short stretches of 16 and 11 amino acids not present in the mouse Shh. The human Ihh protein is 96.8% identical to the mouse Ihh. The two predicted human proteins are also highly related, particularly in their amino-terminal halves where they are 91.4% identical. They diverge significantly in their carboxyl halves, where they show only 45.1% identity. The high level of similarity in the amino portion of all of these proteins implies that this region encodes domains essential to the activity of this class of signaling molecules.

Northern Blotting

Multiple Tissue Northern Blot (Clontech) prepared from poly A+RNA isolated from human adult tissues was hybridized with either full length $^{32}$P-labeled human Shh clone or $^{32}$P-labeled human Ihh clone following the protocol suggested by the company.

Digoxigenin in situ Hybridization

Sections: tissues from normal human second trimester gestation abortus specimens were washed in PBS and fixed overnight at 4° C. paraformaldehyde in PBS, equilibrated 24 hours at 4° C. in 50% sucrose in PBS and then placed in 50% sucrose in oct for one hour before embedding in oct. Cryostat sections (10–25 mm) were collected on superfrost plus slides (Fisher) and frozen at −80° C. until used. Following a postfixation in 4% paraformaldehyde the slides were processed as in Riddle et al., (1993) Cell 75:1401–1416 with the following alterations: proteinase K digestion was performed at room temperature from 1–15 minutes (depending on section thickness), prehybridization, hybridization and washes time was decreased to ¹⁄₁₀ of time.

Whole-mounts: tissues from normal second trimester human abortus specimens were washed in PBS, fixed overnight at 4° C. in 4% paraformaldehyde in PBS and then processed as in Riddle et al., (1993) Cell 75:1401–1416.

Isolation of an Shh P1 Clone

The human Shh gene was isolated on a P1 clone from a P1 library (Pierce and Stemberg, 1992) by PCR (polymerase chain reaction) screening. Two oligonucleotide primers were derived from the human Shh sequence. The two olignucleotide primers used for PCR were:

SHHF5'-ACCGAGGGCTGGGACGAAGATG
GC-3'                             (SEQ ID NO:43)

SHR5'-CGCTCGGTCGTACGGCATGAACG
AC-3'                             (SEQ ID NO:44)

The PCR reaction was carried using standard conditions as described previously (Thierfelder et al., 1994) except that the annealing temperature was 65° C. These primers amplified a 119 bp fragment from human and P1 clone DNA. The P1 clone was designated SHHP1. After the P1 clone was isolated these oligonucleotides were used as sequencing primers. A 2.5 KbEcoRI fragment that encoded a CA repeat was subcloned from this P1 clone using methods described previously (Thierfelder et al. 1994). Oligonucleotide primers that amplified this CA repeat sequence were fashioned from the flanking sequences:

SHHCAF5'-ATGGGGATGTGTGTGGTCAAGT
GTA-3' (SEQ ID NO:45)

SHHCAR5'-TTCACAGACTCTCAAAGTGTAT
TTT-3' (SEQ ID NO:46)

Mapping the Human Ihh and Shh Genes

The human Ihh gene was mapped to chromosome 2 using somatic cell hybrids from NIGMS mapping pannel 2 (GM10826B).

The Shh gene was mapped to chromosome 7 using somatic cell hybrids from NIGMS mapping panel 2 (GM10791 and GM10868).

Linkage between the limb deformity locus on chromosome 7 and the Shh gene was demonstrated using standard procedures. Family LD has been described previously (Tkukurov et al., (1994) *Nature Genet.* 6:282–286). A CA repeat bearing sequence near the Shh gene was amplified from the DNA of all members of Family LD by PCR using the SHHCAF and SHHCAR primers. Linkage between the CA repeat and the LD disease gene segregating in Family LD was estimated by the MLINK program (October, 1967). Penetrance was set at 100% and the allele frequencies were determined using unrelated spouses in the LD family.

Interspecific Backcross Mapping

Interspecific backcross progeny were generated by mating (C57BL/6J x *M spretus*) F1 females and C57BL/6J males as described (Copeland and Jenkins, (1991) *Trends Genet.* 7:113–118). A total of 205 N2 mice were used to map the Ihh and Dhh loci. DNA isolation, restriction enzyme digestions, agarose gel electrophoresis, Southern blot transfer and hybridization were performed essentially as described (Jenkins et al., (1982) *J. Virol* 43:26–36). All blots were prepared with Hybond-N+ nylon membrane (Amersham). The probe, an ~1.8 kb EcoRI fragment of mouse cDNA, detected a major fragment of 8.5 kb in C57BL/6j (B) DNA and a major fragment 6.0 kb in *M. spretus* (S) DNA following digestion with BglII. The Shh probe, an ~900 bp SmaI fragment of mouse cDNA, detected HincII fragments of 7.5 and 2.1 kb (B) as well as 4.6 and 2.1 (S). The Dhh probe, and ~800 bp BamHi/EcoRi fragment of mouse genomic DNA, detected major fragments of 4.7 and 1.3 kb (B) and 8.2 and 1.3 kb (S) following digestion with SphI. The presence or absence of *M spretus* specific fragments was followed in backcross mice.

A description of the probes and RFLPs for loci used to position the Ihh, Shh and Dhh loci in the interspecific backcross has been reported. These include: Fn1, Vil and Acrg, chromosome 1 (Wilkie et al., (1993) *Genomics* 18:175–184), Gnai1, En2, Il6, chromosomes 5 (Miao et al., (1994) *PNAS USA* 91:11050–11054) and Pdgfb, Gdc1 and Rarg, chromosome 15 (Brannan et al., (1992) *Genomics* 13:1075–1081). Recombination distances were calculated as described (Green, (1981) Linkage, recombination and mapping. In "*Genetics and Probability in Animal Breeding Experiments*", pp. 77–113, Oxford University Press, N.Y.) using the computer program SPRETUS MADNESS. Gene order was determined by minimizing the number of recombination events required to explain the allele distribution patterns.

(ii) Expression of Human Shh and Ihh

To investigate the tissue distribution of Shh and Ihh expression, poly(A)+RNA samples from various adult human tissues were probed with the two cDNA clones. Of the tissues tested, an Ihh-specific message of ~2.7 kb is only detected in liver and kidney. Shh transcripts was not detected in the RNA from any of the adult tissues tested. All the samples contained approximately equal amounts of intact RNA, as determined by hybridization with a control probe.

The hedgehog family of genes were identified as mediators of embryonic patterning in flies and vertebrates. No adult expression of these genes had previously been reported. These results indicate that Ihh additionally plays a role in adult liver and kidney. Since the hedgehog genes encode intercellular signals, Ihh may function in coordinating the properties of different cell types in these organs. Shh may also be used as a signaling molecule in the adult, either in tissues not looked at here, or at levels too low to be detected under these conditions.

In situ hybridization was used to investigate the expression of Shh in various mid-gestational human fetal organs. Shh expression is present predominantly in endoderm derived tissues: the respiratory epithelium, collecting ducts of the kidney, transitional epithelium of the ureter, hepatocytes, and small intestine epithelium. Shh was not detectable in fetal heart or placental tissues. The intensity of expression is increased in primitive differentiating tissues (renal blastema, base villi, branching lung buds) and decreased or absent in differentiated tissues (e.g. glomeruli). Shh expression is present in the mesenchyme immediately abutting the budding respiratory tubes. The non-uniform pattern of Shh expression in hepatocytes is consistent with expression of other genes in adult liver (Dingemanse et al., (1994) *Differentiation* 56:153–162). The base of villi, the renal blastema, and the lung buds are all regions expressing Shh and they are areas of active growth and differentiation, suggesting Shh is important in these processes.

(iii) The Chromosomal Map Location of Human Shh and Ihh

Since Shh is known to mediate patterning during the development of the mouse and chick and the expression of Shh and Ihh are suggestive of a similar role in humans, mutations in these genes would be expected to lead to embryonic lethality or congenital defects. One way of investigating this possibility is to see whether they are genetically linked to any known inherited disorders.

Shh- and Ihh-specific primers were designed from their respective sequences and were used in PCR reactions on a panel of rodent-human somatic cell hybrids. Control rodent DNA did not amplify specific bands using these primers. In contrast, DNA from several rodent-human hybrids resulted in PCR products of the appropriate size allowing us to assign Shh to chromosome 7q and Ihh to chromosome 2.

One of the central roles of chick Shh is in regulating the anterior-posterior axis of the limb. A human congenital polysyndactyly has recently been mapped to chromosome 7q36 (Tsukurov et al., (1994) *Nature Genet.* 6:282–286; Heutink et al., (1994) *Nature Genet.* 6:287–291). The phenotype of this disease is consistent with defects that might be expected from aberrant expression of Shh in the limb. Therefore, the chromosomal location of Shh was mapped more precisely, in particular in relation to the polysyndactyly locus.

A P1 phage library was screened using the Shh specific primers for PCR amplification and clone SHHP1 was isolated. Clone SHHP1 contained Shh sequence. A Southern blot of an EcoRi digest of this phage using [CA]/[GT] probe demonstrated that a 2.5 Kb EcoRi fragment contained a CA repeat. Nucleotide sequence analysis of this subcloned EcoRI fragment demonstrated that the CA repeat lay near the EcoRI sites. Primers flanking the CA repeat were designed and used to map the location of Shh relative to other markers on 7q in individuals of a large kindred with complex polysyndactyly (Tsukurov et al., (1994) *Nature Genet.* 6:282–286). Shh maps close to D75550 on 7q36, with no recombination events seen in this study. It is also extremely close to, but distinct from, the polysyndactyly locus with one recombination event observed between them (maximum lod score=4.82, Θ=0.05). One unaffected individual (pedigree ID V-10 in Tsukurov et al., (1994) *Nature Genet.* 6:282–286) has the Shh linked CA repeat allele found in all affected family members. No recombination was observed between the locus En2 and the Shh gene (maximum lod score=1.82, Θ=0.0).

(iv) Chromosomal Mapping of the Murine Ihh, Shh and Dhh Genes

The murine chromosomal location of Ihh, Shh and Dhh was determined using an interspecific backcross mapping panel derived from crosses of [(C57BL/6J x *M. spretus*)F1 X C57BL/J)] mice. cDNA fragments from each locus were used as probes in Southern blot hybridization analysis of C57BL/6J and *M. spretus* genomic DNA that was separately digested with several different restriction enzymes to identify informative restriction fragment length polymorphisms (RFLPs) useful for gene mapping. The strain distribution pattern of each RFLP in the interspecific backcross was then determined by following the presence or absence of RFLPs specific for *M. spretus* in backcross mice.

Ihh mapped to the central region of mouse chromosome 1, 2.7 cM distal of Fn1 and did not recombine with Vil in 190 animals typed in common, suggesting that the two loci are within 1.6 cM (upper 95% confidence level) (FIG. 16). Shh mapped to the proximal region of mouse chromosome 5, 0.6 cM distal of En2 and 1.9 cM proximal of Il6 in accordance to Chang et al., (1994) *Development* 120:3339–3353. Dhh mapped to the very distal region of mouse chromosome 15, 0.6 cM distal of Gdcl and did not recombine with Rarg in 160 animals typed in common, suggesting that the two loci are within 1.9 cM of each other (upper 95% confidence level) (FIG. 16).

Interspecific maps of chromosome 1, 5 and 15 were compared with composite mouse linkage maps that report the map location of many uncloned mouse mutations (compiled by M. T. Davisson, T. H. Roderick, A. L. Hillyard and D. P. Doolittle and provided from GBASE, a computerized database maintained at The Jackson Laboratory, Bar Harbor, Me.). The hemimelic extra-toe (Hx) mouse mutant maps 1.1 cM distal to En2 on chromosome 5 (Martin et al., (1990) *Genomics* 6:302–308), a location in close proximity to where Shh has been positioned. Hx is a dominant mutation which results in preaxial polydactyly and hemimelia affecting all four limbs (Dickie, (1968) *Mouse News Lett* 38:24; Knudsen and Kochhar, (1981) *J. Embryol. Exp. Morph.* 65: Suppl. 289–307). Shh has previously been shown to be expressed in the limb (Echelard et al., (1993) *Cell* 75:1417–1430). To determine whether Shh and Hx are tightly linked we followed their distribution in a backcross panel in which Hx was segregating. Two recombinants between Shh and Hx were identified, thus excluding the possibility that the two loci are allelic and these observations are again consistent with those of Chang et al., (1994) *Development* 120:3339–3353. While there are several other mutations in the vicinity of Ihh and Dhh, none is an obvious candidate for an alteration in the corresponding gene.

The central region of mouse chromosome 1 shares homology with human chromosome 2q (summarized in FIG. 16). Placement of Ihh in this interval suggests the human homolog of Ihh will reside on 2q, as well. Similarly, it is likely that human homolog of Dhh will reside on human chromosome 12q.

EXAMPLE 6

Proteolytic Processing Yields Two Secreted Forms of Sonic Hedgehog (i) Experimental Procedures In vitro Translation and Processing Mouse and chick sonic hedgehog coding sequences were inserted into the vector pSP64T (kindly provided by D. Melton) which contains an SP6 phage promoter and both 5' and 3' untranslated sequences derived from the Xenopus laevis β-Globin gene. After restriction endonuclease digestion with Sal I to generate linear templates, RNA was transcribed in vitro using SP6 RNA polymerase (Promega, Inc.) in the presence of 1 mM cap structure analog (m$^7$G (5')ppp(5')Gm; Boehringer-Mannheim, Inc.) Following digestion with RQ1 DNase I (Promega, Inc.) to remove the DNA template, transcripts were purified by phenol:choloroform extraction and ethanol precipitation.

Rabbit reticulocyte lysate (Promega, Inc.) was used according to the manufacturer's instructions. For each reaction, 12.5 μl of lysate was programmed with 0.5–2.0 μg of in vitro transcribed RNA. The reactions contained 20 μCi of Express labeling mix (NEN/DuPont, Inc.) were included. To address processing and secretion in vitro, 1.0–2.0 μl of canine pancreatic microsomal membranes (Promega, Inc.) were included in the reactions. The final reaction volume of 25 μl was incubated for one hour at 30° C. Aliquots of each reaction (between 0.25 and 3.0 μl) were boiled for 3 minutes in Laemmli sample buffer (LSB: 125 mM Tris-Hcl [pH 6.8]; 2% SDS; 1% 2-mercaptoethanol; 0.25 mg/ml bromophenol blue) before separating on a 15% polyacrylamide gel. Fixed gels were processed for fluorography using EnHance (NEN/DuPont, Inc.) as described by the manufacturer.

Glycosylation was addressed by incubation with Endoglycosidase H (Endo H; New England Biolabs, Inc.) according to the manufacturer's directions. Reactions were carried out for 1–2 hr at 37° C. before analyzing reaction products by polyacrylamide gel electrophoresis (PAGE).

Xenopus Oocyte Injection and Labeling

Oocytes were enzymatically defolliculated and rinsed with OR2 (50 mM HEPES [pH 7.2], 82 mM NaCl, 2.5 mM KCl, 1.5 mM Na2HPO4). Healthy stage six oocytes were injected with 30 ng of in vitro transcribed, capped mouse Shh RNA (prepared as described above). Following a 2 hr recovery period, healthy injected oocytes and uninjected controls were cultured at room temperature in groups of ten in 96-well dishes containing 0.2 ml of OR2 (supplemented with 0.1 mg/ml Gentamicin and 0.4 mg/ml BSA) per well. The incubation medium was supplemented with 50 μCi of Express labeling mix. Three days after injection, the culture media were collected and expression of Shh protein analyzed by immunoprecipitation. Oocytes were rinsed several times in OR2 before lysing in TENT (20 mM Tris-HCl [pH 8.0]; 150 mM NaCl, 2 mM EDTA; 1% Triton-X-100; 10 μl/oocyte) supplemented with 1 μg/ml aprotinin, 2 μg/ml leupeptin and 1 mM phenylmethylsufonylfluoride (PMSF). After centrifugation at 13000×g for 10 minutes at 4° C., soluble protein supernatants were recovered and analyzed by immunoprecipitation (see below).

Cos Cell Transfection and Labeling

Cos cells were cultured in Dulbecco's Modified Eagle Medium (DMEM; Sigma, Inc.) supplemented with 10% fetal bovine serum (Gibco/BRL), 2 mM L-Glutamine (Gibco/BRL) and 50 mU/ml penicillin and 50 μg/ml streptomycin (Gibco/BRL). Subconfluent cos cells in 35 mm or 60 mm dishes (Falcon, Inc.) were transiently transfected with 2 mg or 6 mg supercoiled plasmid DNA, respectively. Between 42 and 44 hr post-transfection, cells were labeled for 4–6 hr in 0.5 ml (35 mm dishes) or 1.5 ml (60 mm dishes) serum-free DMEM lacking Cysteine and Methionine (Gibco/BRL) and supplemented with 125 μCi/ml each of Express labeling mix and L-35S-Cysteine (NEN/DuPont). After labeling, media were collected and used for immunoprecipitation. Cells were rinsed with cold PBS and lysed in the tissue culture dishes by the addition of 0.5 ml (35 mm dishes) or 1.5 ml (60 mm dishes) TENT (with protease inhibitors as described above) and gentle rocking for 30 minutes at 4° C. Lysates were cleared by centrifugation (13000×g for 5 min. at 4° C.) and the supernatants were analyzed by immunoprecipitation (see below).

Baculovirus Production and Infection

A recombinant baculovirus expressing mouse sonic hedgehog with a myc epitope tag inserted at the carboxy terminus was generated using the Baculogold kit (Pharmingen, Inc.). The initial virus production used Sf 9 cells, followed by two rounds of amplification in High Five cells (Invitrogen, Inc.) in serum-free medium (ExCell 401; Invitrogen, Inc.). A baculovirus lacking Shh coding sequences was also constructed as a control. For protein induction, High Five cells were infected at a multiplicity of approximately 15. Three days later, medium and cells were collected by gentle pipetting. Cells were collected by centrifugation (1000×g) and the medium was recovered for Western blot analysis. Cell pellets were washed twice in cold PBS and lysed in TENT plus protease inhibitors (see above) by rotating for 30 minutes at 4° C. in a microcentrifuge tube. The lysate was cleared as described above prior to Western blotting.

Western Blotting

For Western blotting, 0.25 ml samples of media (1% of the total) were precipitated with TCA and redissolved in 15 μpl of LSB. Cell lysate samples (1% of total) were brought to a final volume of 15 μl with water and concentrated (5×) LSB. Samples were boiled S minutes prior to separation on a 15% acrylamide gel. Proteins were transferred to PVDF membrane (Immobilon-P; Millipore, Inc.) and blocked in BLOTTO (5% w/v non-fat dried milk in PBS) containing 0.2% Tween-20. Hybridoma supernatant recognizing the human c-myc epitope (9E10; Evan, G. I. et al., (1985) *Mol. Cell. Biol.* 5:3610–3616) was added at a dilution of 1:200 for one hour followed by a 1:5000 dilution of Goat anti-Mouse-Alkaline phosphatase conjugate (Promega, Inc.) for 30 minutes. Bands were visualized using the Lumi-Phos 530 reagent (Boehringer-Mannheim) according to the manufacturer's directions.

For Western blotting of COS cell material, cleared media (see above) were precipitated with TCA in the presence of 4 μg of BSA per ml as a carrier the protein pellets were dissolved in 20 μl of LSB. Dissolved medium protein and cell lysates (see above) were boiled for 5 min, and 10 μl (50%) of each medium sample and 10 μl (10%) of each cell lysate were separated on a 15% acrylamide gel. The gel was blotted to a polyvinylidene difluoride membrane as described above. The membrane was blocked as described above and incubated in a 1:200 dilution of affinity-purified Shh antiserum (see below) and then in a 1:5,000 dilution of horseradish peroxidase-conjugated donkey anti-rabbit immunoglobulin g (IgG; Jackson Immuno research, Inc.). Bands were visualized with the Enhanced Chemiluminescence kit (Amersham, Inc.) according to the manufacturer's instructions.

For Western blotting of mouse and chicken embryonic tissue lysates, 60 μg of each sample was separated on 15% acrylamide gels. Blotting and probing with affinity-purified Shh antiserum as well as chemiluminescence detection were carried out as described above for the COS cell material.

Immunoprecipitation

Cell lysates (Xenopus oocytes or cos cells) were brought to 0.5 ml with TENT (plus protease inhibitors as above). Media samples (OR2 or DMEM) were cleared by centrifugation at 13000×g for 5 min. (4° C.) and 10×TENT was added to a final concentration of 1× (final volume: 0.5–1.5 ml). The c-myc monoclonal antibody hybridoma supernatant was added to 1/20 of the final volume. Samples were rotated for 1 hr at 4° C., then 0.1 ml of 10% (v/v) protein A-Sepharose CL-4B (Pharmacia, Inc.) was added. Samples were rotated an additional 14–16 h. Immune complexes were washed 4 times with 1.0 ml TENT. Immunoprecipitated material was eluted and denatured by boiling for 10 minutes in 25 μl×LSB. Following centrifugation, samples were separated on 15% acrylamide gels and processed for fluorography as described previously. Samples for Endo H digestion were eluted and denatured by boiling for 10 minutes in the provided denaturation buffer followed by digestion with Endo H for 1–2 hr at 37° C. Concentrated (5×) LSB was added and the samples were processed for electrophoresis as described.

For immunoprecipitation with the anti-mouse Shh serum, samples (Cos cell lysates and DMEM) were precleared by incubating 1 hr on ice with 3 μl pre-immune serum, followed by the addition of 0.1 ml 10% (v/v) Protein A-Sepharose. After rotating for 1 hr at 4 C., supernatants were recovered and incubated for 1 hr on ice with 3 μl depleted anti-mouse Shh serum (see below). Incubation with Protein A-Sepharose, washing, elution and electrophoresis were then performed as described above.

Immunofluorescent Staining of Cos Cells

Twenty-four hours after transfection, cells were transferred to 8-chamber slides (Lab-Tek, Inc.) and allowed to attach an additional twenty-four hours. Cells were fixed in 2% paraformaldehyde/0.1% glutaraldehyde, washed in PBS and permeabilized in 1% Triton-X-100 (Munro, S. and Pelham, H. R. B., (1987) *Cell* 48:899–907). After washing in PBS, cells were treated for 10 minutes in 1 mg/ml sodium borohydride. Cells were incubated with the c-myc monoclonal antibody hybridoma supernatant (diluted 1:10) and the affinity purified mouse Sonic hedgehog antiserum (diluted 1:4) for 45 minutes followed by incubation in 1:100 Goat-anti Mouse IgG-RITC plus 1:100 Goat anti Rabbit IgG FITC (Southern Biotechnology Associates, Inc.) for 45 minutes. DAPI (Sigma, Inc.) was included at 0.3 μg/ml The slides were mounted in Slo-Fade (Molecular Probes, Inc.) and photographed on a Leitz DMR compound microscope.

Embryonic Tissue Dissection and Lysis

Mouse forebrain, midbrain, hindbrain, lung, limb, stomach, and liver tissues form 15.5-day-postcoitum Swiss Webster embryos were dissected into cold PBS, washed several times in PBS, and then lysed by trituraton and gentle sonication in LSB lacking bromophenol blue. Lysates were cleared by brief centrifugation, and protein concentrations were determined by the Bradford dye-binding assay.

To obtain chicken CNS and limb bud tissue, fertilized eggs (Spafas, Inc.) were incubated at 37° C. until the embryos reached stages 20 and 25, respectively (Hamburg and Hamilton (1951) *J. Exp. Morphol.* 88:49–92). By using sharp tungsten needles, dorsal and ventral pieces of the anterior CNS were obtained from the stage 15 embryos, and limb buds from the stage 25 embryos were cut into anterior and posterior halves. Tissues were lysed, and protein concentrations were determined as described above. Prior to electrophoresis of the mouse and chicken proteins (see above), samples were brought to 20 μl with LSB containing bromophenol blue and boiled for 5 minutes.

Antibody Production and Purification

A PCR fragment encoding amino acids 44–143 of mouse Sonic hedgehog was cloned in frame into the Eco Rl site of pGEX-2T (Pharmacia, Inc.). Transformed bacteria were induced with IPTG and the fusion protein purified on a Glutathione-Agarose affinity column (Pharmacia, Inc.) according to the manufacturer's instructions. Inoculation of New Zealand White rabbits, as well as test and production bleeding were carried out at Hazelton Research Products, Inc.

To deplete the serum of antibodies against Glutathione-S-transferase (GST) and bacterial proteins, a lysate of E. coli transformed with pGEX-2T and induced with IPTG was coupled to Affi-Gel 10 (Bio-Rad, Inc.) The serum was incubated in batch for two hours with the depletion matrix before centrifugation (1000×g for 5 min.) and collection of the supernatant. To make an affinity matrix, purified bacterially expressed protein corresponding to the amino terminal two-thirds of mouse Sonic hedgehog was coupled to Affi-Gel 10 (Bio-Rad, Inc.). The depleted antiserum was first adsorbed to this matrix in batch, then transferred to a column. The matrix was washed with TBST (25 mM Tris-HCl [pH 7.5], 140 mM NaCl, 5 mM KCl, 0.1% Triton-X-100), and the purified antibodies were eluted with ten bed volumes of 0.15 M Glycine [pH 2.5]. The solution was neutralized with one volume of 1 M Tris-HCl [pH 8.0], and dialyzed against 160 volumes of PBS.

Other antibodies have been generated against hedgehog proteins and three polyclonal rabbit antisera obtained to hh proteins can be characterized as follows:Ab77-reacts only with the carboxyl processed chick Shh peptide (27 kd); Ab79-reacts with amino processed chick, mouse and human Shh peptide (19 kd). Weakly reacts with 27 kd peptide from chick and mouse. Also reacts with mouse Ihh; and Ab80-reacts with only amino peptide (19 kd) of chick, mouse and human.

Figure 11:
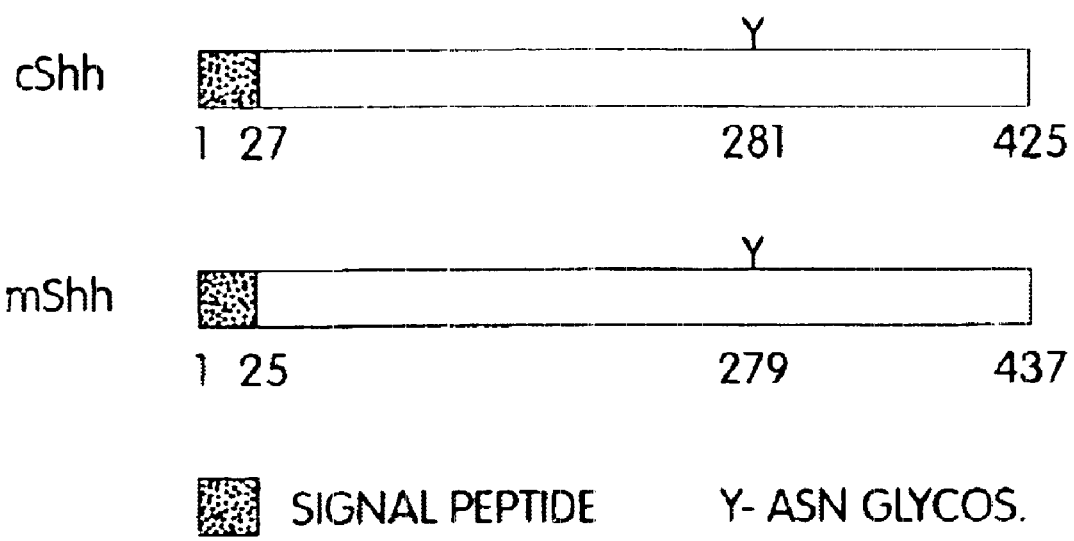
FIG. 11 is a schematic representations of chick and mouse Shh proteins. The putative signal peptides and Asn-linked glycosylation sites are shown. The numbers refer to amino acid positions.

(ii) In Vitro Translated Sonic Hedgehog is Proteolytically Processed and Glycosylated The open reading frames of chick and mouse Shh encode primary translation products of 425 and 437 amino acids, respectively, with predicted molecular masses of 46.4 kilodaltons (kDa) and 47.8 kDa (Echelard, Y. et al., (1993) Cell 75:1417–1430; Riddle, R. D. et al., (1993) Cell 75:1401–1416). Further examination of the protein sequences revealed a short stretch of amino terminal residues (26 for chick, 24 for mouse) that are highly hydrophobic and are predicted to encode signal peptides. Removal of these sequences would generate proteins of 43.7 kDa (chick Shh) and 45.3 kDa (mouse Shh). Also, each protein contains a single consensus site for N-linked glycosylation (Tarentino, A. L. et al., (1989) Methods Cell Biol. 32:111–139) at residue 282 (chick) and 279 (mouse). These features of the Shh proteins are summarized in FIG. 11.

A rabbit reticulocyte lysate programmed with in vitro translated messenger RNA encoding either chick or mouse Shh synthesizes proteins with molecular masses of 46 kDa and 47 kDa, respectively. These values are in good agreement with those predicted by examination of the amino acid sequences. To examine posttranslational modifications of Shh proteins, a preparation of canine pancreatic microsomal membranes was included in the translation reactions. This preparation allows such processes as signal peptide cleavage and core glycosylation. When the Shh proteins are synthesized in the presence of these membranes, two products with apparent molecular masses of approximately 19 and 28 kDa (chick), or 19 and 30 kDa (mouse) are seen in addition to the 46 kDa and 47 kDa forms. When the material synthesized in the presence of the membranes is digested with Endoglycosidase H (Endo H), the mobilities of the two larger proteins are increased. The apparent molecular masses of the Endo H digested forms are 44 kDa and 26 kDa for chick Shh, and 45kDa and 27 kDa for mouse Shh. The decrease in the molecular masses of the largest proteins synthesized in the presence of the microsomal membranes after Endo H digestion is consistent with removal of the predicted signal peptides. The mobility shift following Endo H treatment indicates that N-linked glycosylation occurs, and that the 26 kDa (chick) and 27 kDa (mouse) proteins contain the glycosylation sites.

The appearance of the two lower molecular weight bands (hereafter referred to as the "processed forms") upon translation in the presence of microsomal membranes suggests that a proteolytic event in addition to signal peptide cleavage takes place. The combined molecular masses of the processed forms (19 kDa and 26 kDa for chick; 19 kDa and 27 kDa for mouse) add up to approximately the predicted masses of the signal peptide cleaved proteins (44 kDa for chick and 45 kDa for mouse) suggesting that only a single additional cleavage occurs.

The mouse Shh protein sequence is 12 amino acid residues longer than the chick sequence (437 versus 425 residues). Alignment of the chick and mouse Shh protein sequences reveals that these additional amino acids are near the carboxy terminus of the protein (Echelard, Y. et al., (1993) Cell 75:1417–1430). Since the larger of the processed forms differ in molecular mass by approximately 1 kDa between the two species, it appears that these peptides contain the carboxy terminal portions of the Shh proteins. The smaller processed forms, whose molecular masses are identical, presumably consist of the amino terminal portions.

(iii) Secretion of Shh Peptides

To investigate the synthesis of Shh proteins in vivo, the mouse protein was expressed in several different eukaryotic cell types. In order to detect synthesized protein, and to facilitate future purification, the carboxy terminus was engineered to contain a twenty-five amino acid sequence containing a recognition site for the thrombin restriction protease followed by a ten amino acid sequence derived from the human c-myc protein and six consecutive histidine residues. The c-myc sequence serves as an epitope tag allowing detection by a monoclonal antibody (9E10; Evan, G. I. et al., (1985) Mol. Cell Biol. 5:3610–3616). The combined molecular mass of the carboxy terminal additions is approximately 3 kDa Xenopus laevis Oocytes Immunoprecipitation with the c-myc antibody detects several proteins in lysates of metabolically labeled Xenopus laevis oocytes injected with Shh MRNA. Cell lysates and medium from $^{35}$S labeled oocytes injected with RNA encoding mouse Shh with the c-myc epitope tag at the at the carboxy terminus, or from control oocytes were analyzed by immunoprecipitation with c-myc monoclonal antibody. A band of approximately 47 kDa is seen, as is a doublet migrating near 30 kDa. Treatment with Endo H increases the mobility of the largest protein, and resolves the doublet into a single species of approximately 30 kDa. These observations parallel the behaviors seen in vitro. Allowing for the added mass of the carboxy terminal additions, the largest protein would correspond to the signal peptide cleaved form, while the doublet would represent the glycosylated and unglycosylated larger processed form. Since the epitope tag was placed at the carboxy terminus of the protein, the identity of the 30 kDa peptide as the carboxy terminal portion of Shh is confirmed. Failure to detect the 19 kDa species supports its identity as an amino terminal region of the protein.

To test whether Shh is secreted by Xenopus oocytes, the medium in which the injected oocytes were incubated was probed by immunoprecipitation with the c-myc antibody. A single band migrating slightly more slowly than the glycosylated larger processed form was observed. This protein is insensitive to Endo H. This result is expected since most secreted glycoproteins lose sensitivity to Endo H as they travel through the Golgi apparatus and are modified by a series of glycosidases (Kornfeld, R. and Kornfeld, S., (1985) *Annu. Rev. Biochem.* 54:631–664). The enzymatic maturation of the Asn-linked carbohydrate moiety could also explain the slight decrease in mobility of the secreted larger protein versus the intracellular material. Following Endo H digestion, a band with a slightly lower mobility than the signal peptide cleaved protein is also apparent, suggesting that some Shh protein is secreted without undergoing proteolytic processing. Failure to detect this protein in the medium without Endo H digestion suggests heterogeneity in the extent of carbohydrate modification in the Golgi preventing the material from migrating as a distinct band. Resolution of this material into a single band following Endo H digestion suggests that the carbohydrate structure does not mature completely in the Golgi apparatus. Structural differences between the unprocessed protein and the larger processed form could account for this observation (Kornfeld, R. and Kornfeld, S., (1985) *Annu. Rev. Biochem.* 54:631–664).

Cos Cells

The behavior of mouse Shh in a mammalian cell type was investigated using transfected cos cells. Synthesis and secretion of the protein was monitored by immunoprecipitation using the c-myc antibody. Transfected cos cells express the same Sonic hedgehog species that were detected in the injected Xenopus oocytes, and their behavior following Endo H digestion is also identical. Furthermore, secretion of the 30 kDa glycosylated form is observed in cos cells, as well as the characteristic insensitivity to Endo H after secretion. Most of the secreted protein co-migrates with the intracellular, glycosylated larger processed form, but a small amount of protein with a slightly lower mobility is also detected in the medium. As in the Xenopus oocyte cultures, some Shh which has not undergone proteolytic processing is evident in the medium, but only after Endo H digestion.

Baculovirus Infected Cells

To examine the behavior of the mouse Shh protein in an invertebrate cell type, and to potentially purify Shh peptides, a recombinant baculovirus was constructed which placed the Shh coding sequence, with the carboxy terminal tag, under the control of the baculoviral Polyhedrin gene promoter. When insect cells were infected with the recombinant baculovirus, Shh peptides could be detected in cell lysates and medium by Western blotting with the c-myc antibody.

The Shh products detected in this system were similar to those described above. However, virtually no unprocessed protein was seen in cell lysates, nor was any detected in the medium after Endo H digestion. This suggests that the proteolytic processing event occurs more efficiently in these cells than in either of the other two cell types or the in vitro translation system. A doublet corresponding to the glycosylated and unglycosylated 30 kDa forms is detected, as well as the secreted, Endo I resistant peptide as seen in the other expression systems. Unlike the other systems, however, all of the secreted larger processed form appears to comigrate with the glycosylated intracellular material.

(iv) Secretion of a Highly Conserved Amino Terminal Peptide

Figure 12:
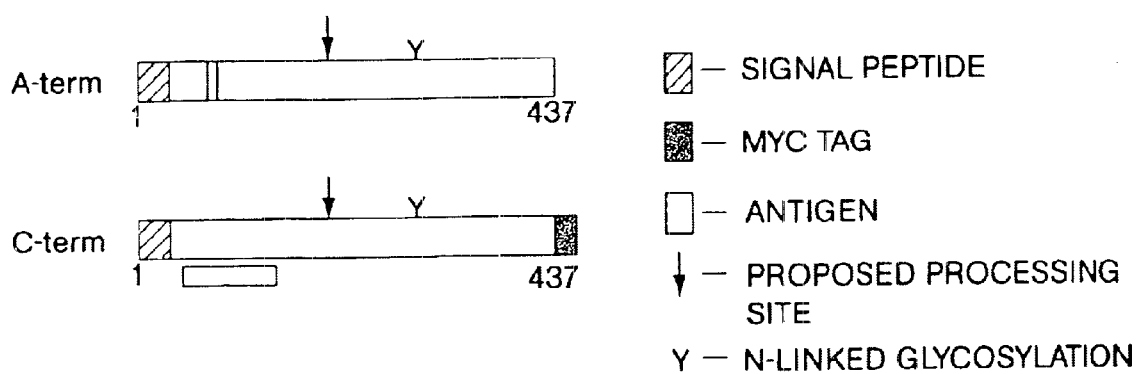
FIG. 12 is a schematic representation of myc-tagged Shh constructs. The positions of the c-myc epitope tags are shown, as is the predicted position of the proteolytic cleavage site. The shaded area following the signal peptide of the carboxy terminal tagged construct represents the region included in the Glutathione-S-transferase fusion protein used to generate antisera in rabbits.

To determine the behavior of the amino terminal portion of the processed Sonic hedgehog protein, the c-myc epitope tag was positioned 32 amino acids after the putative signal peptide cleavage site (FIG. 12). Cos cells were transfected with Shh expression constructs containing the c-myc tag at the carboxy terminus or near the amino terminus. When this construct was expressed in cos cells, both the full length protein and the smaller processed form (approximately 20 kDa due to addition of the c-myc tag) were detected by immunoprecipitation of extracts from labeled cells. However, the 20 kDa product is barely detected in the medium. In cells transfected in parallel with the carboxy terminal c-myc tagged construct, the full length and 30 kDa products were both precipitated from cell lysates and medium as described earlier.

As the amino terminal c-myc tag may affect the secretion efficiency of the smaller processed form, the expression of this protein was examined in cos cells using an antiserum directed against amino acids 44 through 143 of mouse Shh (FIG. 12). After transfection with the carboxy-terminal c-myc tagged construct, immunoprecipitation with the anti-Shh serum detected a very low level of the smaller processed form in the medium despite a strong signal in the cell lysate. This recapitulates the results with the myc antibody.

To examine the subcellular localization of Shh proteins, cos cells were transfected with the carboxy terminal tagged Shh construct and plated on multi-chamber slides, fixed and permeabilized. The cells were incubated simultaneously with the anti-Shh serum and the c-myc antibody followed by FITC conjugated Goat anti-Rabbit-IgG and RITC conjugated Goat anti-Mouse-IgG. DAPI was included to stain nuclei. Strong perinuclear staining characteristic of the Golgi apparatus was observed with the anti-Shh serum. The same subcellular region was also stained using the c-myc antibody. The coincidence of staining patterns seen with the two antibody preparations suggest that the low level of the smaller processed form detected in the medium is not due to its retention in the endoplasmic reticulum, since both processed forms traffic efficiently to the Golgi apparatus.

One explanation for the failure to detect large amounts of the smaller processed form in the culture medium could that this protein associates tightly with the cell surface or ECM. To examine this, cells were treated with the polyanionic compounds herparin and suramin. These compounds have been shown to increase the levels of some secreted proteins in culture medium, possibly by displacing them from cell surface or ECM components or by directly binding the proteins and perhaps protecting them from proteolytic degradation (Bradley and Brown (1990) *EMBO J.* 9:1569–1575; Middaugh et al. (1992) *Biochem.* 31:9016–9024; Smolich et al. (1993) *Mol. Biol. Cell* 4:1267–1275). The 19-kDa amino-terminal form of Shh is barely detectable in the medium of transfected COS cells, despite its obvious presence in the cell lysate. However, in the presence of 10 mg of heparin per ml, this peptide is readily detected in the medium. The addition of 10 mM suramin to the medium has an even greater effect. Since the concentrations used where those previously determined to elicit maximal responses, it is clear that suramin is more active than heparin in this assay.

The ability of heparin and suramin to increase the amount of the smaller processed form in the medium of transfected cells implies that this peptide may be tightly associated with the cell surface of ECM. As a first step toward determining which region(s) of the Shh protein may be responsible for this retention, a truncated form of mouse Shh deleted of all sequence downstream of amino acid 193 was expressed in COS cells. This protein contains all of the sequences encode by exons one and two, as well as five amino acids derived for exon three. Since its predicted molecular mass (19.2 kDa) is very close to the observed molecular mass of the smaller processed form, the behavior of this protein would be expected to mimic that of the smaller processed form. This protein is detected at a very high level in the medium, even in the absence of heparin or suramin, and migrates at a position indistinguishable form that of the amino-terminal cleavage product generated from the full-length protein. In fact, virtually no protein is seen in the cell lysates, suggesting nearly quantitative release of the protein into the medium. This raises the possibility that the actual amino terminally processed form may extend a short distance beyond amino acid 193 and that these additional amino acids contain a cell surface-ECM retention signal.

The influence of sequences located at the extreme amino and carboxy termini of mouse Shh on the behavior of the protein in transfected cells was examined using the amino terminus-specific antiserum. Expression of a mouse Shh construct lacking a signal peptide results in the accumulation of approximately 28-kDa protein, as well as a small amount of protein which comigrates with the smaller processed form. This implies that correct cleavage of Shh requires targeting of the protein to the endoplasmic reticulum, since the bulk of the processed form of Shh expressed in the cytoplasm is cleaved at a new position that is approximately 9kDa carboxy terminal to the normal cleavage site. Expression of a mouse Shh protein engineered to terminate after amino acid 428 (lacking nine carboxy-terminal amino acids [ΔCt]) results in the expected amino-terminal cleavage product; however, the efficiency of cleavage is significantly decreased compared with that seen with the wild-type protein. Therefore, sequences located at a distance from the proteolytic processing site are able to affect the efficiency of processing.

(v) Sonic Hedgehog Processing in Embryonic Tissues

In order to determine whether the proteolytic processing of Shh observed in the different expression systems reflects the behavior of the protein in embryos, the amino terminus-specific mouse Shh antiserum was used to probe Western blots of various chicken and mouse embryonic tissues. A protein with an electrophoretic mobility identical to that of COS cell-synthesized amino terminally processed form is detected at a substantial level in the stomach and lung tissue and at a markedly lower level in the forebrain, midbrain, and hindbrain tissues of 1 5.5-day-postcoitum mouse embryos. These tissues have all been shown to express Shh RNA. The 19 kDa peptide is not detected in liver or late limb tissues, which do not express Shh RNA. Thus, the proteolytic processing of Shh observed in cell culture also occurs in embryonic mouse tissue.

The cross-reactivity of the amino terminus-specific mouse Shh antiserum with chicken Shh protein allowed for examination of expression of Shh in chicken embryonic tissue. The antiserum detects the 19-kDa amino terminally processed form of chicken Shh in transfected COS cells, as well as in two tissues which have been shown by whole-mount in situ hybridization and antiserum staining to express high levels of Shh RNA and protein, i.e., the posterior region of the limb bud and the ventral region of the anterior CNA (Riddle et al. (1993) *Cell* 75:1401–1416). Therefore, the expected proteolytic processing of Shh occurs in chicken embryonic tissues, and diffusion of the 19-kDa protein does not extend into the anterior limb buds and dorsal CNS.

(v) Hedgehog Processing

Figure 13:
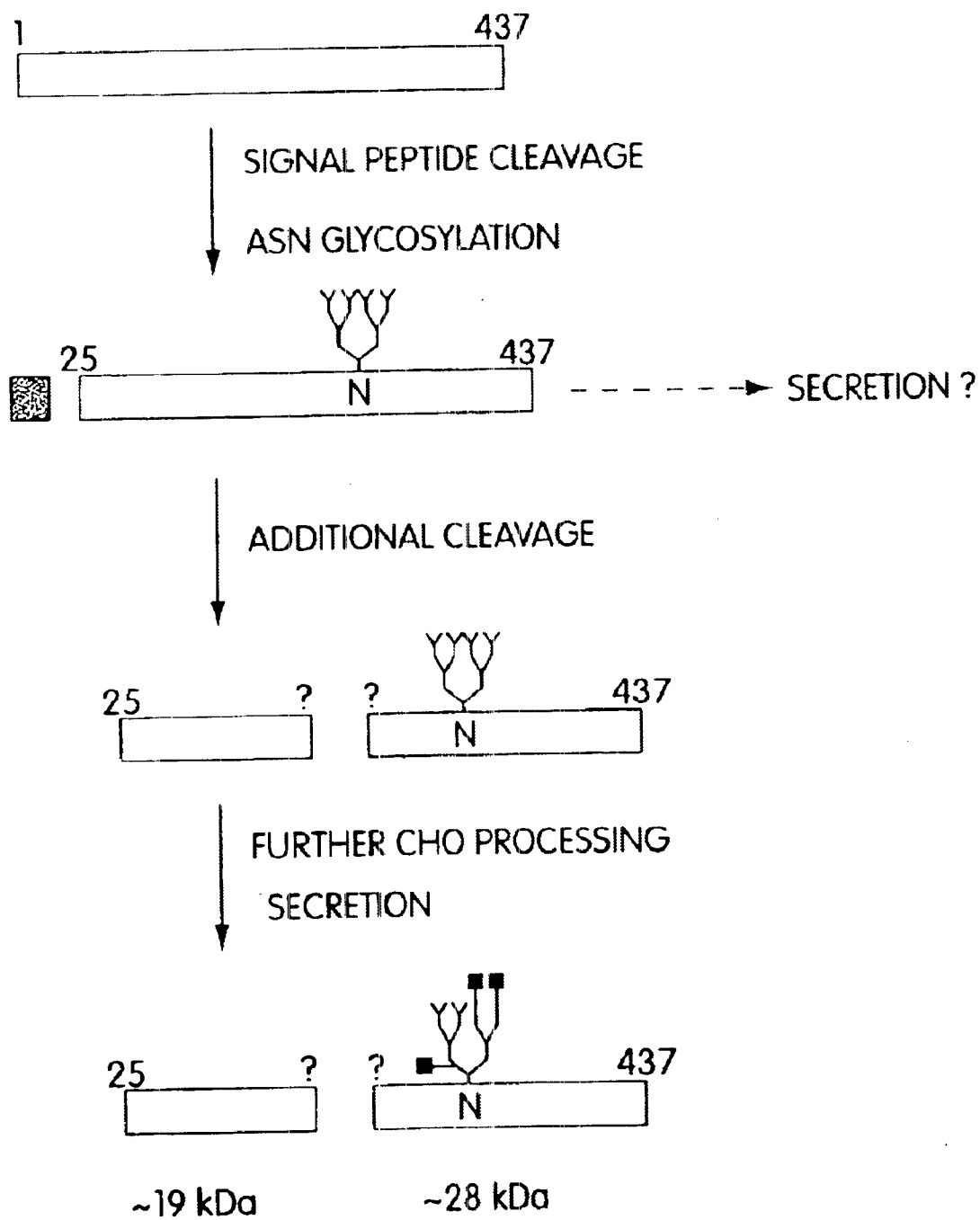
FIG. 13 is a schematic diagram of Shh processing. Illustrated are cleavage of the signal peptide (black box), glycosylation at the predicted Asn residue (N), and the secondary proteolytic cleavage. The question marks indicate that the precise site of proteolytic cleavage has not been determined. The different symbols representing the carbohydrate moiety indicated maturation of this structure in the Golgi apparatus. The dashed arrow leading from the signal peptide cleaved protein indicates that secretion of this species may be an artifact of the incomplete proteolytic processing of Shh seen in Xenopus oocytes and cos cells.

In summary, the results discussed above demonstrate that the mouse and chick Shh genes encode secreted glycoproteins which undergo additional proteolytic processing. Data indicate that this processing occurs in an apparently similar fashion in a variety of cell types suggesting that it is a general feature of the Shh protein, and not unique to any particular expression system. For mouse Shh, data indicate that both products of this proteolytic processing are secreted. These observations are summarized in FIG. 13.

It was observed that the 19 kDa amino peptide accumulates to a lower level in the medium than the 27 kDa carboxyl peptide. This may reflect inefficient secretion or rapid turnover of this species once secreted. Alternatively, the smaller form may associate with the cell surface or extracellular matrix components making it difficult to detect in the medium. The insensitivity of the secreted, larger form to Endo H is a common feature of secreted glycoproteins. During transit through the Golgi apparatus, the Asn-linked carbohydrate moiety is modified by a series of specific glycosidases (reviewed in Kornfeld, R. and Kornfeld, S., (1985) *Annu. Rev. Biochem* 54:631–664; Tarentino, A. L. et al., (1989) *Methods Cell Biol.* 32:111–139). These modifications convert the structure from the immature "high mannose" to the mature "complex" type. At one step in this process, a Golgi enzyme, (α-mannosidase II, removes two mannose residues from the complex rendering it insensitive to Endo H (Kornfeld, R. and Kornfeld, S., (1985) *Annu. Rev. Biochem* 54:631–664).

The biochemical behavior of mouse Shh appears to be quite similar to that described for the Drosophila Hedgehog (Dros-HH) protein (Lee, J. L. et al., (1992) *Cell* 71:33–50; Tabata, T. et al., (1992) *Genes & Dev.* 6:2635–2645). In vitro translation of Drosophila hh mRNA, in the presence of microsomes, revealed products with molecular masses corresponding to full length protein, as well as to the product expected after cleavage of the predicted internal (Type II) signal peptide (Lee, J. L. et al., (1992) *Cell* 71:33–50). Interestingly, no additional, processed forms were observed. However, such forms could have been obscured by breakdown products migrating between 20 and 30 kDa. When an RNA encoding a form of the protein lacking the carboxyterminal 61 amino acids was translated, no breakdown products were seen, but there is still no evidence of the proteolytic processing observed with mouse Shh. A similar phenomenon has been observed in these experiments. A reduction in the extent of proteolytic processing is seen when a mouse Shh protein lacking 10 carboxy-terminal amino acids is translated in vitro or expressed in cos cells (data not shown). This suggests that sequences at the carboxy termini of Hh proteins act at a distance to influence the efficiency of processing.

Recently, Lee et al. (*Science* 266:1528–1537, 1994) described the biochemical behavior of the Drosophila HH protein. Using region-specific antisera, they detected similar processed forms of HH in embryonic tissues, thus confirming studies in which processing of HH was observed in embryos forced to express high levels of HH from a heat shock promoter (Tabata and Kornberg (1994) *Cell* 76:89–102). Thus, Drosophila HH is processed to yield a 19 kDa amino-terminal peptide and a 25 kDa carboxy-terminal peptide. Furthermore, Lee et al. concluded that the production of the processed forms occurs via an autocatalytic mechanism and identified a conserved histidine residue (at position 329, according to Lee et al. (*Science* 266:1528–1537, 1994)) which is required for self-cleavage of HH protein in vitro and in vivo. The significance of the proteolytic processing is demonstrated by the inability of self-processing-either because of mutation of this histidine residue or because of truncation of sequences at the extreme carboxy terminus-to carry out HH functions in Drosophila embryos.

Their studies of the biochemical behavior of mouse and chicken Shh and mouse Ihh proteins correlate well with the Drosophila studies of Lee et al. (*Science* 266:1528–1537, 1994) in that the similar proteolytic processing of endogenous vertebrate proteins in embryonic tissues was demonstrated. Furthermore, it was demonstrated that the efficiency of processing depends on sequences located at the extreme carboxy terminus of mouse Shh. Interestingly, it has also been shown that he specificity of mouse Shh cleavage may depend on targeting of the protein to the secretory pathway, since a form lacing a signal peptide is processed into an approximately 28-kDa amino-terminal form. A similar protein is observed as the predominant species when it was attempted to express full-length mouse Shh in bacteria (data no shown). Lee et al. (*Science* 266:1528–1537, 1994) have demonstrated that two zebra fish hedgehog proteins undergo proteolytic processing when translated in vitro, even in the absence of microsomal membranes. The electrophoretic mobilities of the processed peptides are consistent with cleavage occurring at a position similar to that of the Drosophila HH cleavage site. Furthermore, they showed that the cleavage fails to occur if the conserved histidine residue is mutated, arguing for an autoproteolytic mechanism similar to that of the Drosophila protein. However, the processing of mouse or chicken Shh protein translated in vitro was not detected unless microsomal membrane are included. Therefore, it is possible that correct proteolytic processing of vertebrate hedgehog proteins is dependent on specific incubation conditions or may require cellular factors in addition to Shh itself.

An additional correlation between the work presented here and that of Lee et al. (*Science* 266:1528–1537, 1994) concerns the different behaviors of the amino (smaller) and carboxy (larger) terminally processed forms of the hedgehog proteins. The evidence is presented that the 27 kDa carboxy-terminal form diffuses more readily from expressing cells than the 19 kDa amino-terminal form, which seems to be retained near the cell surface. The polyanions heparin and suramin appear capable of releasing the amino peptide into the medium. Similarly, the amino-terminal form of Drosophila HH is more closely associated with the RNA expression domain in embryonic segments than is the carboxy-terminal form, and the amino-terminal form binds to heparin agarose beads. Therefore, the distinct behaviors of the different hedgehog peptides have been conserved across phyla.

The observed molecular masses of the amino terminally processed forms of mouse and chicken Shh, mouse Ihh proteins, and Drosophila HH are between 19 and 20 kDa. Therefore, the predicted secondary proteolytic cleavage site would be located near the border of the sequences encoded by the second and third exons. Interestingly, the region marks the end of the most highly related part of the hedgehog proteins. The amino terminal (smaller) form would contain the most highly conserved portion of the protein. In fact, the amino acids encoded by exons one and two (exclusive of sequences upstream of the putative signal peptide cleavage sites) share 69% identity between Drosophila Hh and mouse Shh, and 99% identity between chick and mouse Shh. Amino acid identity in the region encoded by the third exon is much lower 30% mouse to Drosophila and 71% mouse to chick (Echelard, Y. et al., (1993) *Cell* 75:1417–1430).

However, the boundary between sequences encoded by exons 2 and 3 is unlikely to be the actual proteolytic processing site, because a Drosophila HH protein containing a large deletion which extends three amino acids beyond this boundary is still cleaved at the expected position in vitro (Lee et al. (1994) *Science* 266:1528–1537). Moreover, the analysis of an amino-terminal mouse Shh peptide truncated at amino acid 193 (the fourth amino acid encoded by exon 3, described below) suggests that normal cleavage must occur downstream of this position. Close examination of hedgehog protein sequences reveals that strong sequence conservation between the Drosophila and vertebrate proteins continues for only a short distance into the third exon. If it is assumed that cleavage will generate an amino terminal product of no greater than 20 kDa, given the resolution of analysis, all of the data would indicate that cleavage occurs at 1 of the 10 amino acids within the mouse Shh positions 194–203, according to Echelard et al. (*Cell* 75:1417–1430, 1993).

(vi) Hedgehog Signalling

In order to satisfy the criteria for intercellular signaling, hedgehog proteins must be detected outside of their domains of expression. This has been clearly demonstrated for Drosophila HH. Using an antiserum raised against nearly full length Dros-HH protein, Tabata and Kornberg (Tabata, T. and Kornberg, T. B., (1992) *Cell* 76:89–102) detect the protein in stripes that are slightly wider than the RNA expression domains in embryonic segments, and just anterior to the border of the RNA expression domain in wing imaginal discs. Similarly, Taylor, et. al., (1993) *Mech. Dev.* 42:89–96, detected HH protein in discrete patches within cells adjacent to those expressing hh RNA in embryonic segments using an antiserum directed against an amino-terminal portion of Hh which, based on the proteolytic processing data (Tabata, T. et al., (1992) *Genes & Dev.* 6:2635–2645), is not likely to recognize the carboxyl cleavage product.

The detection of Hh beyond cells expressing the hh gene is consistent with the phenotype of hh mutants. In these animals, cellular patterning in each embryonic parasegment in disrupted resulting in an abnormal cuticular pattern reminiscent of that seen in wg mutants. Further analysis has revealed that the loss of hh gene function leads to loss of wg expression in a thin stripe of cells just anterior to the hh expression domain (Ingham, P. W. and Hidalgo, A., (1993) *Development* 117:283–291). This suggests that Hh acts to maintain wg expression in neighboring cells. The observation that ubiquitously expressed Hh leads to ectopic activation of wg supports this model (Tabata, T. and Kornberg, T. B., (1992) *Cell* 76:89–102). In addition to these genetic studies, there is also indirect evidence that Hh acts at a distance from its site of expression to influence patterning of the epidermis (Heemskerk, J. and DiNardo, S., (1994) *Cell* 76:449460).

The apparent effect of Drosophila Hh on neighboring cells, as well as on those located at a distance from the site of hh expression is reminiscent of the influence of the notochord and floor plate on the developing vertebrate CNS, and of the ZPA in the limb. The notochord (a site of high level Shh expression) induces the formation of the floor plate in a contact dependent manner, while the notochord and floor plate (another area of strong Shh expression) are both capable of inducing motorneurons at a distance (Placzek, M. et al., (1993) *Development* 117:205–218; Yamada, T. et al., (1993) *Cell* 73:673–686).

Moreover ZPA activity is required not only for patterning cells in the extreme posterior of the limb bud where Shh is transcribed, but also a few hundred microns anterior of this zone. Several lines of evidence indicate that Shh is able to induce floor plate (Echelard, Y. et al., (1993) *Cell* 75:1417–1430; Roelink, H. et al., (1994) *Cell* 76:761–775)

and mediate the signaling activity of the ZPA (Riddle, R. D. et al., (1993) *Cell* 75:1401–1416). Since it has been shown that Shh is cleaved, it can be speculated that the processed peptides may have distinct activities. The smaller amino terminal form, which appears to be more poorly secreted, less stable or retained at the cell surface or in the extracellular matrix, may act locally. In contrast, the larger carboxy terminal peptide could possibly function at a distance. In this way, Shh peptides may mediate distinct signaling functions in the vertebrate embryo. Alternatively, the carboxy-terminal peptide may be necessary only for proteolytic processing, with all signaling activity residing in the amino-terminal peptide.

EXAMPLE 7

Sonic Hedgehog and Fgf-4 Act through a Signaling Cascade and Feedback Loop to Integrate Growth and Patterning of the Developing Limb Bud (i) Experimental Procedures Cloning of Chicken Fgf-4 and Bmp-2

A 246 bp fragment of the chicken Fgr-4 gene was cloned by PCR from a stage 22 chicken limb bud library. Degenerate primers were designed against previously cloned Fgf-4 and Fgf-6 genes: fgf5' (sense) AAA AGC TTT AYT GYT AYG TIG GIA THG G (SEQ ID No:38) and fgf3' (antisense) AAG AAT TCT AIG CRT TRT ART TRT TIG G (SEQ ID No:39). Denaturation was at 94° C. for 2 min, followed by 30 cycles of 94° C. for 30 sec, 50° C. for 60 sec, and 72° C. for 30 sec, with a final extension at 72° C. for 5 min. The PCR product was subcloned into the Bluescript SK+ vector. A clone was sequenced and confirmed as Fgf-4 by comparison with previously published Fgf-4 genes and a chicken Fgf-4 gene sequence kindly provided by Lee Niswander.

BMP-related sequences were amplified from a stage 22 posterior limb bud cDNA library prepared in Bluescript using primers and conditions as described by Basler, et al. (1993). Amplified DNAs were cloned and used to screen a stage 22 limb bud library prepared in λ-Zap (Stratagene). Among the cDNAs isolated was chicken Bmp-2. Its identity was confirmed by sequence comparison to the published clones (Francis, et al., (1994) Development 120:209–218) and by its expression patterns in chick embryos.

Chick Surgeries and Recombinant Retroviruses

All experimental manipulations were performed on White Leghorn chick embryos (S-SPF) provided by SPAFAS (Norwich, Conn.). Eggs were staged according to Hamburger and Hamilton (1951) *J. Exp. Morph.* 88:49–92.

Viral supernatants of Sonic/RCAS-A2 or a variant containing an influenza hemaglutinin epitope tag at the carboxyl terminus of the hedgehog protein (Sonic7. 1/RCAS-A2, functionally indistinguishable from Sonic/RCAS-A2), were prepared as described (Hughes, et al., (1987) *J. Virol.* 61:3004–13; Fekete and Cepko, (1993) *Mol. & Cell. Biol.* 13:2604–13; Riddle, et al., (1993) *Cell* 75:1401–16). For focal injections the right wings of stage 18–21 embryos were transiently stained with nile blue sulfate (0.01 mg/ml in Ringer's solution) to reveal the AER. A trace amount of concentrated viral supernatant was injected beneath the AER.

The AER was removed using electrolytically sharpened tungsten wire needles. Some embryos had a heparin-acrylic bead soaked in FGF-4 solution (0.8 mg/ml; a gift from Genetics Institute) or PBS stapled to the limb bud with a piece of 0.025 mm platinum wire (Goodfellow, Cambridge UK) essentially as described by Niswander et al, (1993) *Cell* 75:579–87.

Limbs which were infected with Sonic/RCAS virus after AER removal were infected over a large portion of the denuded mesoderm to ensure substantial infection. Those embryos which received both an Fgf-4 soaked bead and virus were infected only underneath the bead.

In Situ Hybridizations and Photography

Single color whole mount in situ hybridizations were performed as described (Riddle, et al., (1993) *Cell* 75:1401–16). Two color whole mount in situ hybridizations were performed essentially as described by Jowett and Lettice (1994) *Trends Genet.* 10:73–74. The second color detection was developed using 0.125 mg/ml magenta-phos (Biosynth) as the substrate. Radioactive in situ hybridizations on 5 μm sections was performed essentially as described by Tessarollo, et al. (1992) *Development* 115:11–20.

The following probes were used for whole mount and section in situ hybridizations: Sonic: 1.7 kb fragment of pHH2 (Riddle, et al., (1993) *Cell* 75:1401–16). Bmp-2: 1.5 kb fragment encoding the entire open reading frame. Fgf-4: 250 bp fragment described above. Hox d-11: a 600 bp fragment, Hoxd-13: 400 bp fragment both including 5' untranslated sequences and coding sequences upstream of the homeobox. RCAS: 900 bp SalI-ClaI fragment of RCAS (Hughes et al., (1987) *J Virol.* 61:3004–12).

(ii) Relationship of Sonic to Endogenous Bmp-2 and Hoxd Gene Expression

The best candidates for genes regulated by Sonic in vivo are the distal members of the Hoxd gene cluster, Hoxd-9 through -13, and Bmp-2. Therefore, the relationships of the expression domains of these genes in a staged series of normal chick embryos were analyzed. Hoxd-9 and Hoxd-10 are expressed throughout the presumptive wing field at stage 16 (Hamburger and Hamilton, (1951) *J. Exp. Morph.* 88:49–92), prior to the first detectable expression of Sonic at early stage 18. Hoxd-11 expression is first detectable at early stage 18, the same time as Sonic, in a domain coextensive with Sonic. Expression of Hoxd-12 and Hoxd-13 commence shortly thereafter. These results suggest that Sonic might normally induce, directly or indirectly, the expression of only the latter three members of the cluster, even though all five are nested within the early limb bud.

As limb outgrowth proceeds Sonic expression remains at the posterior margin of the bud. In contrast the Hoxd gene expression domains, which are initially nested posteriorly around the Sonic domain, are very dynamic and lose their concentric character. By stage 23 the Hoxd-11 domain extends anteriorly and distally far beyond that of Sonic, while Hoxd-13 expression becomes biased distally and displaced from Sonic.

While it is not clear whether Bmp-2 is expressed before Sonic (see Francis et. al., (1994) *Development* 120:209–218) Bmp-2 is expressed in a mesodermal domain which apparently overlaps and surrounds that of Sonic at the earliest stages of Sonic expression. As the limb bud develops, the mesodermal expression of Bmp-2 remains near the posterior limb margin, centered around that of Sonic, but in a larger domain than Sonic. This correspondence between Sonic and Bmp-2 expression lasts until around stage 25, much longer than the correspondence between Sonic and Hoxd gene expression. After stage 25 Bmp-2 expression shifts distally and is no longer centered on Sonic.

(iii) Relationship of Sonic to Induced Bmp-2 and Hoxd Gene Expression

The fact that the expression domains of the Hoxd genes diverge over time from that of Sonic hedgehog implies that Sonic does not directly regulate their later patterns of expression. This does not preclude the possibility that the later expression domains are genetically downstream of Sonic. If this were the case, exogenously expressed Sonic would be expected to initiate a program of Hoxd gene expression which recapitulates that seen endogenously. Therefore, the spatial distribution of Hoxd gene expression at various times following Sonic misexpression was compared. The anterior marginal mesoderm of early bud (Stage 18–20) wings was injected at a single point under the AER with a replication competent virus that expresses a chicken Sonic cDNA. Ectopic Sonic expressed by this protocol leads to both anterior mesodermal outgrowth and anterior extension of the AFR.

The Sonic and Hoxd gene expression domains in the infected limbs were analyzed in sectioned and intact embryos. Viral Sonic message is first detected approximately 18 hours after infection at the anterior margin, at the same time as, and approximately coextensively with, induced Hoxd-11. This suggests that Sonic can rapidly induce Hoxd-11 expression and that the lag after injection represents the time required to achieve Sonic expression. By 35 hours post infection distal outgrowth of infected cells combined with lateral viral spread within the proliferating cells leads to viral expression in a wedge which is broadest at the distal margin and tapers proximally. By this time, Hoxd-11 expression has expanded both antero-proximally and distally with respect to the wedge of Sonic-expressing cells, into a domain which appears to mirror the more distal aspects of the endogenous Hoxd-11 domain. Weak Hoxd-13 expression is also detected at 35 hours in a subset of the Sonic expressing domain at its distal margin. 51 hours after infection the relationship of Sonic and Hoxd-11 expression is similar to that seen at 35 hours, while the induced Hoxd-13 expression has reached wild type levels restricted to the distal portions of the ectopic growth. Thus the ectopic Hoxd expression domains better reflect the endogenous patterns of expression than they do the region expressing Sonic. This suggests that there are multiple factors regulating Hoxd expression but their actions lie downstream of Sonic.

Since the endogenous Bmp-2 expression domain correlates well with that of Sonic, and Bmp-2 is induced by ZPA grafts, it was looked to see if Bmp-2 is also induced by Sonic. Bmp-2 is normally expressed in two places in the early limb bud, in the posterior mesoderm and throughout the AER (Francis, et al., (1994) *Development* 120:209–218). In injected limb buds additional Bmp-2 expression is seen in both the anterior mesoderm and in the anteriorly extended AER. The domain of Bmp-2 expression is slightly more restricted than that of viral expression, suggesting a delay in Bmp-2 induction. Bmp-2 expression in both the mesoderm and ectoderm is thus a downstream target of Sonic activity in the mesoderm. In contrast to the expression domains of the Hoxd genes, the endogenous and ectopic Bmp-2 expression domains correlate well with that of Sonic. This suggests that Bmp-2 expression is regulated more directly by Sonic than is expression of the Hoxd genes.

(iv) The AER and Competence to Respond to Sonic

Ectopic activation of Hoxd gene expression is biased distally in virally infected regions, suggesting that ectodermal factors, possibly from the AER, are required for Hoxd gene induction by Sonic. To test this, Sonic virus was injected into the proximal, medial mesoderm of stage 21 limb buds, presumably beyond the influence of the AER. Although the level of Sonic expression was comparable to that observed in distal injections, proximal misexpression of Sonic did not result in ectopic induction of the Hoxd genes or Bmp-2, nor did it result in any obvious morphological effect (data not shown). The lack of gene induction following proximal misexpression of Sonic suggests that exposure to Sonic alone is insufficient to induce expression of these genes.

This was tested more rigorously by injection of Sonic virus into the anterior marginal mesoderm of stage 20/21 limb buds after the anterior half of the AER had been surgically removed. Embryos were allowed to develop for a further 36 to 48 hours before harvesting. During this time the AER remaining on the posterior half of the limb bud promotes almost wild type outgrowth and patterning of the bud. Gene expression was monitored both in sectioned and intact embryos. In the presence of the AFR, Sonic induces both anterior mesodermal proliferation and expression of Hoxd-11, Hoxd-13 and Bmp-2. In the absence of the overlying AER, Sonic does not induce either mesodermal proliferation or expression of these genes above background. Signals from the AER are thus required to allow both the proliferative and patterning effects of Sonic on the mesoderm.

Since application of FGF protein can rescue other functions of the AER such as promoting PD outgrowth and patterning, it was sought to determine whether FGFs might also promote mesodermal competence to respond to Sonic. FGF4-soaked beads were stapled to AER-denuded anterior mesoderm which was infected with Sonic virus. Gene expression and mesodermal outgrowth were monitored as described previously. In the presence of both Sonic virus and FGF-4 protein, Hoxd-11, Hoxd-13 and Bmp-2 expression are all induced. The expression levels of the induced genes are similar to or greater than the endogenous expression levels, and are equivalent in magnitude to their induction in the presence of the AER. Thus Fgf-4 can induce the competence of the mesoderm to respond to Sonic.

Sonic alone is insufficient to induce either gene expression or mesodermal proliferation in the absence of the AER, while the combination of Sonic and FGF-4 induces both proliferation and gene expression. It was than asked whether FGF4 alone has any effect on gene induction or mesodermal proliferation. Application of FGF4 in the absence of Sonic virus does not induce Hoxd or Bmp-2 gene expression above control levels, however FGF4 alone induces mesodermal outgrowth. These results suggest that mesodermal gene activation requires direct action of Sonic on the mesoderm and that proliferative response to Sonic is indirect, due to the induction of FGFs.

(v) Sonic Induces Polarized Fgf-4 Expression in the AER

Fgf-4 is expressed in a graded fashion in the AER of the mouse limb bud, with maximal expression at the posterior region of the AER tapering to undetectable levels in the anterior ridge (Niswander and Martin, (1992) *Development* 114:755–68). Therefore, it was appropriate to investigate whether Fgf-4 is asymmetrically expressed in the chick AER, and whether its expression is induced by Sonic. A fragment of the chicken Fgf-4 gene was cloned from a stage 22 chicken limb library by PCR using degenerate primers designed from mouse Fgf-4 and Xenopus e-Fgf sequence; based on information provided by L. Niswander and G. Martin. Assignment of gene identity was based on primary sequence as well as comparison of expression patterns with that of murine Fgf-4 (Niswander and Martin, (1992) *Development* 114:755–68). Whole mount in situ hybridization analysis showed strong limb expression of chick Fgf-4 in the AER. Fgf-4, like Bmp-2, is expressed all the way to the posterior border of the AER, but its anterior domain ends before the morphological end of the AER creating a posterior bias that has also been observed by Niswander et al., (1994) *Nature* (in press). Expression is first detected in the distal AER at about stage 18. As outgrowth proceeds the posterior bias develops. Expression peaks around stage 24/25 and then fades by stage 28/29.

The expression domain of Fgf-4 becomes posteriorly biased as Sonic is expressed in the posterior mesoderm. This observation is consistent with Sonic influencing the expression of Fgf-4 in the posterior AER. To test the effect of Sonic on Fgf-4 expression in the AER, stage 18–20 embryos were infected with Sonic virus in a single point at their anterior margin beyond the anterior limit of the AER. The embryos were harvested one to two days later, when an extension of the anterior AER became apparent. The expression of Fgf-4 was analyzed by in situ hybridization. Fgf-4 expression is induced in the anteriormost segment of the AER, in a region which is discontinuous with the endogenous expression domain, and overlies the domain of viral Sonic infection. This result contrasts with the Bmp-2 expression induced in the extended AER, which is always continuous with the endogenous expression domain. The asymmetry of the induced Fgf-4 expression indicates that Sonic polarizes the extended AER, much as a ZPA graft does (Maccabe and Parker, (1979) *J. Embryol. Exp. Morph.* 53:67–73). Since FGFs by themselves are mitogenic for limb mesoderm, these results are most consistent with Sonic inducing distal proliferation indirectly, through the induction of mitogens in the overlying AER.

(vi) Reciprocal Regulation of Sonic by Fgf-4

Sonic thus appears to be upstream of Fgf-4 expression in the AER. However, since the AER is required to maintain polarizing activity in the posterior mesoderm (Vogel and Tickle, (1993) *Development* 19:199–206; Niswander et al., (1993) *Cell* 75:579–87), Sonic may also be downstream of the AER. If Sonic is regulated by the AER and the AER by Sonic, this would imply that they are reinforcing one another through a positive feedback loop.

To test whether the AER dependence of ZPA activity is controlled at the level of transcription of the Sonic gene, Sonic expression following removal of the AER from the posterior half of the limb bud was assayed. Sonic expression is reduced in an operated limb compared to the contralateral control limb within ten hours of AER removal, indicating that Sonic expression is indeed AER dependent. The dependence of Sonic expression on signals from the AER suggests that one of the functions of the AER is to constrain Sonic expression to the more distal regions of the posterior mesoderm.

In addition to their mitogenic and competence-inducing properties, FGFs can also substitute for the AER to maintain the ZPA. In order to test whether FGFs can support the expression of Sonic, beads soaked in FGF-4 protein were stapled to the posterior-distal tips of limb buds after posterior AER removal. Embryos were assayed for Sonic expression approximately 24 hours later, when Sonic expression is greatly reduced in operated limb buds which had not received an FGF4 bead. Strong Sonic expression is detectable in the posterior mesoderm, slightly proximal to the bead implant, and reflecting the normal domain of Sonic expression seen in the contralateral limb. With the finding that FGF-4 can maintain Sonic expression, the elements required for a positive feedback loop between Sonic expression in the posterior mesoderm and Fgf-4 expression in the posterior AER are established (see also Niswander et al. (1994) *Nature* (in press)).

The induction of Bmp-2 expression by Sonic requires signals from the AER, and its domain correlates over time with that of Sonic. Therefore, it was interesting to learn if the continued expression of Bmp-2 also requires signals from the AER, and if so, whether they could be replaced by FGF-4. To test this, Bmp-2 expression following posterior AER removal, and following its substitution with an FGF4 bead was assayed. Bmp-2 expression fades within hours of AER removal, and can be rescued by FGF-4. These data indicate that the maintenance of Bmp-2 expression in the posterior mesoderm, like that of Sonic, is dependent on signals from the AER, which are likely to be FGFs.

(vii) The Mesodermal Response to Sonic

It has been found that only mesoderm underlying the AER is responsive to Sonic, apparently because the AER is required to provide competence signals to the limb mesoderm. Fgf-4, which is expressed in the AER, can substitute for the AER in this regard, and thus might act in combination with Sonic to promote Hoxd and Bmp-2 gene expression in the mesoderm. FGFs may be permissive factors in a number of instructive pathways, as they are also required for activins to pattern Xenopus axial mesoderm (Cornell and Kimelman, (1994) *Development* 120:2187–2198; LaBonne and Whitman, (1994) *Development* 120:463–472).

The induction of Hoxd and Bmp-2 expression in response to Sonic and FGF-4 in the absence of an AER suggests that the mesoderm is a direct target tissue of Sonic protein. Since Sonic can induce Fgf-4 expression in the AER, it follows that Sonic also acts indirectly on the mesoderm through the induction of competence factors in the AER.

(viii) Downstream Targets and a Cascade of Signals Induced by Sonic

The five AbdB-like Hoxd genes, Hoxd-9 through -13, are initially expressed in a nested pattern centered on the posterior of the limb bud, a pattern which suggests they might be controlled by a common mechanism (Dolle, et al., (1989) *Cell* 75:431–441; Izpisua-Belmonte, et al., (1991) *Nature* 350:585–9). The analysis of the endogenous and induced domains of Hoxd gene expression suggests that Sonic normally induces expression of Hoxd-11, -12 and -13. In contrast it was found that Hoxd-9 and -10 expression initiate before Sonic mRNA is detectable. This implies that at least two distinct mechanisms control the initiation of Hoxd gene expression in the wing bud, only one of which is dependent on Sonic.

Several observations suggest that the elaboration of the Hoxd expression domains is not controlled directly by Sonic, but rather by signals which are downstream of Sonic. The Hoxd expression domains rapidly diverge from Sonic, and evolve into several distinct subdomains. Moreover these subdomains appear to be separately regulated, as analysis of the murine Hoxd-11 gene promoter suggests that it contains independent posterior and distal elements (Gerard, et al., (1993) *Embo. J.* 12:3539–50). In addition, although initiation of Hoxd-11 through -13 gene expression is dependent on the AER, their expression is maintained following AER removal (Izpisua-Belmonte, et al., (1992) *Embo. J.* 11:1451–7). As Sonic expression fades rapidly under similar conditions, this implies that maintenance of Hoxd gene expression is independent of Sonic. Since ectopic Sonic can induce a recapitulation of the Hoxd expression domains in the limb, it can be concluded that although indirect effectors appear to regulate the proper patterning of the Hoxd expression domains, they are downstream of Sonic. Potential mediators of these indirect effects include Bmp-2 in the mesoderm and Fgf-4 from the AER.

In contrast to the Hoxd genes, Bmp-2 gene expression in the posterior limb mesoderm appears to be continually regulated by Sonic. It was found that both endogenous and ectopic Bmp-2 expression correspond to that of Sonic. Furthermore, continued Bmp-2 expression is dependent on the AER and can be rescued by FGF-4. It is likely that this is an indirect consequence of the fact that Sonic expression is also maintained by the AER and can be rescued by FGF-4. In fact, Bmp-2 expression might be a direct response of cells to secreted Sonic protein. The differences between Bmp-2 and Hoxd gene expression suggest that multiple pathways downstream of Sonic regulate gene expression in the mesoderm.

Bmp-2 itself is a candidate for a secondary signaling molecule in the cascade of patterning events induced by Sonic. Bmp-2 is a secreted molecule of the TGF-β family and its expression can be induced by Sonic. This appears to be an evolutionarily conserved pathway, as HH, the Drosophila homolog of Sonic, activates the expression of dpp, the homolog of Bmp-2, in the eye and wing imaginal discs (Heberlein, et al., (1993) *Cell* 75:913–26; Ma, et al., (1993) *Cell* 75:927–38; Tabata and Kornberg, (1994) *Cell* 76:89–102). Expression of HH is normally confined to the posterior of the wing disc. Ectopic expression of HH in the anterior of the disc results in ectopic expression of dpp and ultimately in the duplication of wing structure with mirror image symmetry (Bassler and Struhl, (1994) *Nature* 368:208–214). This effect is strikingly parallel to the phenotypic results of ectopic expression of Sonic in the chick limb.

(ix) Regulation of Sonic Expression

Sonic expression is activated in the posterior of the limb bud very early during mesodermal outgrowth (Riddle et al., (1993) *Cell* 75:1401–16). The factors which initiate this localized expression are not yet identified but ectopic expression of Hoxb-8 at the anterior margin of the mouse limb bud results in the activation of a second domain of Sonic expression under the anterior AER (Charité el al., (1994) *Cell* 78:589–601). Since retinoic acid is known to be able to induce the expression of Hoxb-8 and other Hox genes in vitro (Mavilio et al., (1988) *Differentiation* 37:73–79) it is possible that endogenous retinoic acid acts to make cells competent to express Sonic by inducing expression of upstream Hox genes, either in the very early limb bud or in the flank prior to the limb bud formation.

Several lines of evidence suggest that once induced Sonic expression is dependent on signals from the posterior AER. Following its initiation in the posterior limb mesoderm, the Sonic expression domain moves distally as the limb bud grows out, always remaining subjacent to the AER. Similarly, Sonic expression can also be induced on the anterior margin of the limb bud by implantation of a retinoic acid bead, but the induced ectopic expression is limited to the mesoderm directly underlying the AER (Riddle, et al., (1993) *Cell* 75:1401–16). In addition, ZPA activity fades rapidly following removal of the AER (Niswander, et al., (1993) *Cell* 75:579–87; Vogel and Tickle, (1993) *Development* 119:199–206), and ZPA grafts only function when placed in close proximity to the AER (Tabin, (1991) *Cell* 66:199–217; Tickle, (1991) *Development Supp.* 1:113–21). The observation that continued Sonic expression depends on signals from the posterior AER reveals the mechanism underlying these observations.

The reliance of Sonic expression on AER-derived signals suggests an explanation for the distal shift in Sonic expression during limb development (Riddle et al., (1993) *Cell* 75:1401–16). Signals from the AER also promote distal outgrowth of the mesodermal cells of the progress zone, which in turn results in the distal displacement of the AER. Hence, as maintenance of Sonic expression requires signals from the AER, its expression domain will be similarly displaced.

It was found that replacement of the AER with FGF-4 soaked beads results in the maintenance of Sonic expression. This result is consistent with the previous findings that ZPA activity can be maintained in vivo and in vitro by members of the FGF family (Anderson, et al., (1993) *Development* 117:1421–33; Niswander et al., (1993) *Cell* 75:1401–16; Vogel and Tickle, (1993) *Development* 119:199–206). Since Fgf-4 is normally expressed in the posterior AER, these results suggest that Fgf-4 is the signal from the ectoderm involved in maintaining Sonic expression.

(x) Sonic and Regulation and Maintenance of the AER

Sonic can induce anterior extensions of the AER which have an inverted polarity relative to the endogenous AER. This polarity is demonstrated by examining the expression of two markers in the AER. In normal limbs Bmp-2 is expressed throughout the AER, while Fgf-4 is expressed in the posterior two thirds of the AER. In the extended AER resulting from ectopic Sonic expression, Bmp-2 is again found throughout the AER, while Fgf-4 expression is biphasic, found at either end of the AER, overlying the anterior and posterior mesodermal domains expressing Sonic. These results are consistent with previous observations that antero-posterior polarity of the AER appears to be regulated by the underlying mesoderm, and that ZPA grafts lead to the induction of ectopic, polarized AER tissue (Maccabe and Parker, (1979) *J. Embryol. Exp. Morph.* 53:67–73). Our results also suggest that the normal AP polarity of the AER is a reflection of endogenous Sonic expression. The induced AER is sufficient to promote complete PD outgrowth of the induced structures (Riddle et al., (1993) *Cell* 75:1401–16). Hence whatever factors are necessary to maintain the AER are also downstream of Sonic.

(xi) A Positive Feedback Loop Between Sonic and Fgf-4

The induction of Fgf-4 expression by Sonic in the ectopic AER, and the maintenance of Sonic expression by FGF-4 suggest that Sonic and Fgf-4 expression are normally sustained by a positive feedback loop. Such a feedback loop would allow the coordination of mesodermal outgrowth and patterning. This coordination is possible because Sonic patterns mesodermal tissue and regulates Fgf-4 expression, while FGF-4 protein induces mesodermal proliferation and maintains Sonic expression. Moreover mesodermal tissue can only be patterned by Sonic in the context of a competence activity provided by F8f-4. Thus patterning is always coincident with proliferation.

It remains possible that exogenously applied Fgf-4 might be mimicking the activity of a different member of the FGF family. For example, Fgf-2 is expressed in the limb mesoderm and the AER (Savage et al., (1993) *Development Dynamics* 198:159–70) and has similar effects on limb tissue as Fgf-4 (Niswander and Martin, (1993) *Nature* 361:68–71; Niswander, et al., (1993) *Cell* 75:579–87; Riley, et al., (1993) *Development* 118:95–104; Fallon, et al., (1994) *Science* 264:104–7).

(xii) Coordinated Regulation of Limb Outgrowth and Patterning

Patterning and outgrowth of the developing limb are known to be regulated by two major signaling centers, the ZPA and AER. The identification of Sonic and FGFs as molecular mediators of the activities of the ZPA and AER has allowed for dissociation of the activities of these signaling centers from their regulation, and investigation of the signaling pathways through which they function.

The results presented above suggest that the ability of cells to respond to Sonic protein is dependent on FGFs produced by the AER. It was also found that Sonic induces a cascade of secondary signals involved in regulating mesodermal gene expression patterns. In addition evidence was found for a positive feedback loop initiated by Sonic, which maintains expression of Sonic in the posterior mesoderm and Fgf-4 in the AER. The feedback loop described suggests a mechanism whereby outgrowth and patterning along the AP and PD axes of the limb can be coordinately regulated.

Figure 14:
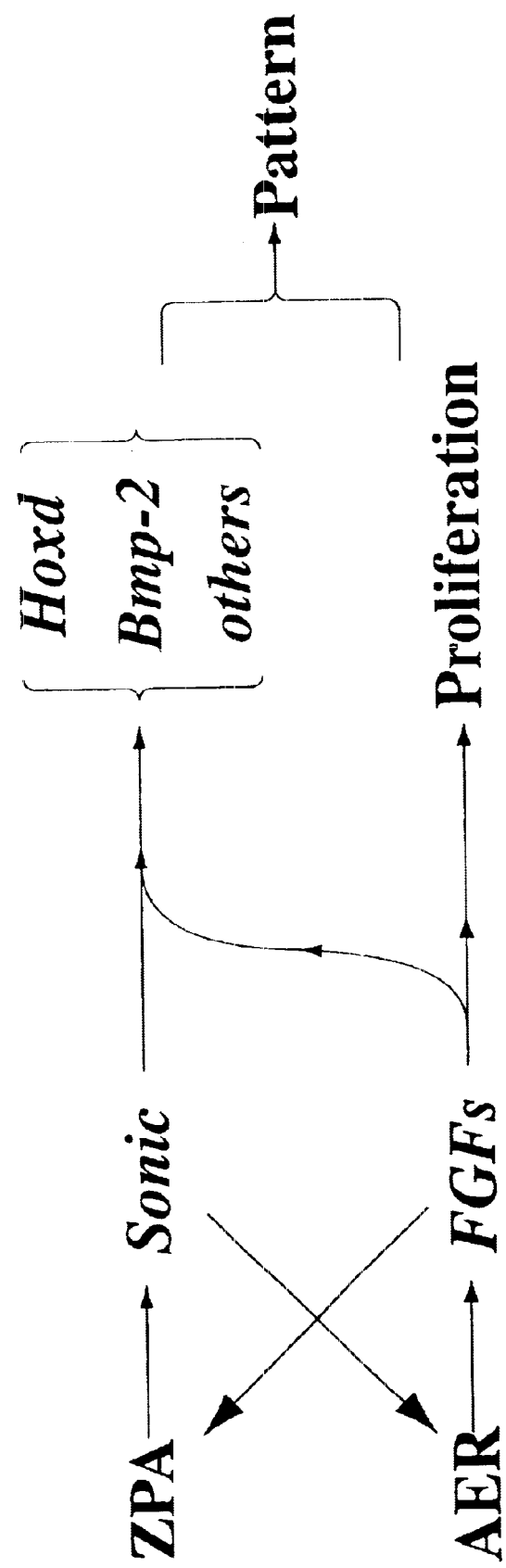
FIG. 14 is a schematic diagram of a model for the coordinated growth and patterning of the limb. Sonic is proposed to signal directly to the mesoderm to induce expression of the Hoxd and Bmp-2 genes. The induction of these mesodermal genes requires competence signals from the overlying AER. One such signal is apparently Fgf-4.

The results described above further suggest that Sonic acts as a short range signal which triggers a cascade of secondary signals whose interplay determines the resultant pattern of structures. The data suggest a number of inductive pathways that can be combined to generate a model (FIG. 14) which describes how Sonic, in coordination with the AER, acts to pattern mesodermal tissues along the anterior-posterior limb axis, while simultaneously regulating proximal-distal outgrowth.

Following its induction, Sonic signals to both the limb ectoderm and mesoderm. Sonic imposes a distinct polarity on the forming AER, including the posteriorly biased expression of Fgf-4, and the AER becomes dependent on continued Sonic expression. The mesoderm, as long as it is receiving permissive signals from the overlying ectoderm, responds to the Sonic signal by expressing secondary signaling molecules such as Bmp-2 and by activating Hoxd genes. Bmp-2 expression is directly dependent on continued Sonic expression, while the continued expression of the Hoxd genes, rapidly becomes Sonic. independent. In a reciprocal fashion, maintenance of Sonic hedgehog expression in the posterior mesoderm becomes dependent on signals from the AER. Since the factors expressed by the AER are not only required for the maintenance of Sonic expression and activity, but are also mitogenic, growth and patterning become inextricably linked. Coordination of limb development through interdependent signaling centers forces the AP and PD structures to be induced and patterned in tandem. The pathways elucidated herein thus provide a molecular framework for the controls governing limb patterning

EXAMPLE 8

Sonic, BMP-4, and Hox Gene Expression Suggest a Conserved Pathway in Patterning the Vertebrate and Drosophila Gut (i) Experimental Procedure
In Situ Hybridization and Photography BMP probes were isolated using primers designed to amplify members of the TGF- and BMP families (Basler, K. et al., (1993) Cell 73:687–702, eight independent 120 bp BMP fragments were amplified from a stage 22 chicken posterior limb bud plasmid cDNA library. These fragments were pooled and used to screen an unamplified stage 22 limb bud lambda zap cDNA library constructed as in Riddle et al., (1993) Cell 75:1401–16. Among the BMP related clones isolated were an approximately 1.9 kb cDNA clone corresponding to chicken BMP-2 and an approximately 1.5 kb cDNA clone corresponding to chicken BMP-4. Both clones contain the entire coding regions. The Sonic clone was obtained as described in Riddle et al, (1993) Cell 75:1401–16. Digoxigenin-UTP labeled RNA probes were transcribed as per Riddle et al., (1993) Cell 75:1401–16. Briefly, harvested chick embryos were fixed overnight in 4% paraformaldehyde, washed in PBS then processed for whole mount in situ hybridization methods are per Riddle et al., (1993)Cell 75:1401–16. Embryos were photographed from either ventral or dorsal surfaces under transmitted light using a Nikon zoom stereo microscope with Kodak Ektar 100 ASA film. Whole mount in situ hybridization embryos and viscera were processed for sectioning as described in Riddle et al., (1993)Cell 75:1401–16. 15–25 μm transverse sections were air dried and photographed with brightfield or numarski optics using a Zeiss Axiophot microscope and Kodak Ektar 25 ASA film.

Chick Embryos and Recombinant Retroviruses

A retroviral vector engineered to express a full length cDNA of chicken Sonic, as in Riddle et al. (1993) Cell 75:1401–16, was injected unilaterally into stage 8–13 chicken embryos targeting the definitive endoderm at the mid-embryo level. At this stage the CIP has not formed and neither Sonic nor BMP-4 are expressed in the region injected. Injections were performed on the ventral surface on embryos cultured with their ventral surface facing up (New, D.A.T. (1955) Embryol. Exp. Morph. 3:320–31. Embryos were harvested 18–28 hours after injection and prepared for whole mount in situ hybridization (see above description of in situ experiment), hybridized with Sonic or BMP-4 digoxigenin labeled probes.

In Situ Hybridization with Hox Genes

Cloned cDNA of the chicken homologues of Hoxa-9,-10,-11,-13; b-9, c-9,-10,-11; d-9,-10,-11,-12,and -13 were used to transcribe digoxigenen-UTP labeled riboprobes for whole mount in situ hybridization. Domestic chick embryos were harvested into PBS and eviscerated. The visceral organ block was fixed in 4% paraformaldehyde overnight and processed for whole mount in situ hybridization. Methods and photographic technique as described above.

(ii) Expression of Sonic and BMP-4 in Stage 13 Chick Embryos Determined by Whole Mount In Situ Hybridization Chick gut morphogenesis begins at stage 8 (Hamberger and Hamilton, (1987) *Nutr.* 6:14–23 with a ventral in-folding of the anterior definitive endoderm to form the anterior intestinal portal (AIP) (Romanoff, A. L., (1960) *The Avian Embryo,* The Macmillan Co., N.Y. This lengthens posteriorly forming the foregut. A second wave of endodermal invagination is initiated posteriorly at stage 13, creating the caudal intestinal portal (CIP). The CIP extends anteriorly forming the hindgut. Sonic expression, previously noted in the endoderm of the vertebrate gut (Riddle et al., (1993) Cell 75:1401–16; Echelard et al., (1993) Cell 75:1417–1430), is expressed early in a restricted pattern in the endodermal lips of the AIP and CIP. Sonic expression is detected in the endoderm of the AIP and CIP in pre gut closure stages. At later stages, stage 28 embryos, Sonic is expressed in the gut in all levels (fore-, mid-, and hind-gut) restricted to the endoderm. Sonic is known to be an important inductive signal in other regions of the embryo including the limb bud (Riddle et al., (1993) Cell 75:1401–16) and neural tube (Echelard et al., (1993) Cell 75:1417–1430; Kraus et al., (1994) Cell 75:1437–1444; Roelink et al., (1994) Cell 76:761–775). Since primitive gut endoderm is known to cause gut-specific mesodermal differentiation when combined with non-gut mesenchyme (Haffen et al., (1987) *Nutr.* 6:14–23), we speculated that Sonic might function as an inductive signal to the visceral mesoderm. A potential target gene for the action of Sonic was suggested by analogy to the Drosophila imaginal discs where HH, the homologue of vertebrate Sonic, activates the expression of the TGF-β related gene dpp in adjacent cells (Tabata abd Komberg, (1994) Cell 76:89–102; Heberlein et al., (1993) Cell 75:913–926; Ma et al., (1993) Cell 75:913–926; Basler et al., (1993) Cell 73:687–702). There are two vertebrate homologues of dpp, BMP-2 and BMP-4. The earliest detectable expression of BMP-4 occurs simultaneously with the first observable expression of Sonic in the developing gut. BMP-4 is expressed in a domain abutting Sonic at the AIP and the CIP, but is restricted to the adjacent ventral mesoderm. BMP-4 gut expression persists into later stage embryos, stage 33 embryos, in the visceral mesoderm only. The tissue restricted expression of both genes is maintained in all stages studied. BMP-2 is not expressed in the gut at the AIP or CIP, but is expressed in clusters of cells in the gut mesoderm in later stages, a pattern distinct from that of BMP-4.

(iii) Ectopic Expression of Sonic Induces Ectopic Expression of BMP-4 in Mesodermal Tissues of the Developing Chick To test whether Sonic is capable of inducing BMP-4 in the mesoderm we an ectopic expression system previously used to study the role of Sonic in limb development was utilized (Riddle et al., (1993) Cell 75:1401–16). A replication competent retrovirus engineered to express Sonic was injected unilaterally into the presumptive endoderm and visceral mesoderm at mid-embryo positions in stage 8-13 chick embryos in vitro (New, D.A.T. (1955) Embryol. Exp. Morph. 3:320–321). When embryos were examined by in situ hybridization 18–26 hours later, the normal wild type expression of Sonic is detected at the AIP, CIP, and in the midline (neural tube and notochord). Ectopic Sonic expression is present unilaterally on the left ventral surface. Also, wild type Sonic expression is seen in the floor plate of the neural tube and notochord. Ectopic expression is seen unilaterally in the visceral endoderm, its underlying splanchnic mesoderm, and somatic mesoderm. BMP-4 expression can be seen induced in the mesoderm at the site of injection, in addition to its normal expression in the mesoderm of the CIP. Wild type BMP-4 expression is seen in the most dorsal aspects of the neural tube and symmetrical lateral regions adjacent to the neural tube. Induced BMP-4 expression is present unilaterally in the splanchnic mesoderm at the site of Sonic viral injection, and not in the visceral endoderm.

Since BMP-4 is, itself, a secreted protein, it could function as a secondary signal in an inductive cascade, similar to the signal cascades from HH to dpp in Drosophila imaginal discs (Tabata abd Kornberg, (1994) Cell 76:89–102; Heberlein et al., (1993) Cell 75:913–926; Ma et al., (1993) Cell 75:913–926; Basler et al., (1993) Cell 73:687–702) and from Sonic to BMP-2 in the limb bud. In the gut, BMP-4 could act as a secondary signal either as part of a feedback loop to the endoderm or within the visceral mesoderm. This latter possibility is consistent with the finding that in mice homozygous for a deletion in the BMP-4 gene, the ventral mesoderm fails to close.

(iv) Expression of Hox Genes in the Developing Chick Gut

There is a striking parallel between the apparent role of Sonic as an endoderm-to-mesoderm signal in early vertebrate gut morphogenesis and that of its Drosophila homologue, HH. HH (like Sonic) is expressed in the Drosophila gut endoderm from the earliest stages of morphogenesis (Taylor et al., (1993) Mech. Dev. 42:89–96). Its putative receptor, patched, is found in the visceral mesoderm implicating HH (like Sonic) in endodermal-mesodermal inductive interactions. This led to consideration whether other genes known to be involved in regulating Drosophila gut development might also play a role in regulating chick gut morphogenesis. Regionally specific pattern in Drosophila gut endoderm is regulated by a pathway involving restricted expression of homeotic genes in the mesoderm (McGinnis and Krumlauf, (1992) Cell 68:283–302). Although the basis for patterning the vertebrate gut is poorly understood, in several other regions of the embryo Hox genes have been implicated as key regulators of patterns. Vertebrate Hox genes are expressed in overlapping anteroposterior domains which correlate with structural boundaries in the developing hindbrain, vertebrae, and limbs (McGinnis and Krumlauf, (1992) Cell 68:283–302). Whole mount in situ hybridization was used to test whether these genes are also expressed in the developing vertebrate hindgut and whether their domains of expression correlate with morphologic borders of the chick gut.

Lumenal gut differentiation creates three morphologically and physiologically distinct regions: fore-, mid-, and hind-gut. The fore-gut and hind-gut are the derivatives of the primitive gut tubes initiated at the AIP and CIP respectively. Ultimately these tubes meet and fuse at the yolk stalk around stage 24–28. The midgut is formed from both foregut and hindgut primordia, just anterior and posterior to the yolk stalk.

The most posterior derivative of the hindgut is the cloaca, the common gut-urogenital opening. The rest of the hindgut develops into the large intestine. The midgut/hindgut border is demarcated by a paired tubal structure, the ceca (analogous to the mammalian appendix), which forms as budding expansions at the midgut/hindgut border at stage 19–20. Anterior to the ceca, the midgut forms the small intestine.

The expression pattern of the 5' members of the Hox gene clusters in the chick hindgut by whole mount in situ hybridization was studied. Hox gene expression patterns in the gut are dynamic. They are initially expressed (by stage 10) in broad mesodermal domains extending anteriorly and laterally. Later they become restricted. By stage 25, the Abd-B like genes of the Hoxa and Hoxd cluster are regionally restricted in their expression in hindgut mesoderm. The most anteriorly expressed gene, Hoxa-9, has an anterior border of expression within the mesoderm of the distal midgut (to a point approximating the distal third of the midgut length). Each successive gene within the A and D Hox clusters has a more posterior domain of expression. Hoxa-10, Hoxd-9 and Hoxd-10 are restricted in their expression to the ceca Hoxa-11 and Hoxd-11 have an anterior limit of expression in the mid-ceca at the approximate midgut/hindgut boundary (Romanoff, A. L. (1960) The Avian Embryo, The Macmillan Co. NY.). Hoxd-12 has an anterior limit at the posterior border of the ceca and extends posteriorly throughout the hindgut to the cloaca. Hoxa-13 and Hoxd-13 are expressed in the most posteriorly restricted domain, in the ventral mesoderm surrounding the cloaca Hoxa-13 and Hoxd-13 are the only Abd-B like genes which are also expressed within the gut endoderm, from the ceca to the cloaca.

The only member of the B or C Hox clusters which we found to be expressed in the hindgut is Hoxc-9. The expression of Hoxc-9 overlaps with its paralogues Hoxa-9 and Hoxd-9 in the midgut mesoderm, but has a sharp posterior boundary, complementary to Hoxa-11 and Hoxd-11 in the mid-ceca.

The restricted expression of the Abd-B like Hox genes appear to demarcate the successive regions of the gut which will form the cloaca, the large intestine, the ceca, the mid-ceca at the midgut/hindgut border, and the lower portion of the midgut (perhaps identifying that portion of the midgut derived from the posterior gut tube3). Moreover, these molecular events presage regional distinctions. Expression of all Hox genes could be detected by stage 14, well before the hindgut lumen is closed (by stage 28) and is maintained in subsequent stages studied. Cytodifferentiation of the hindgut mesoderm and epithelium begins later, at stages 29–31 (Romanoff, A. L. (1960) The Avian Embryo, The Macmillan Co. NY.).

These results suggest that specific Hox genes might be responsible for regulating morphogenesis of the gut. Consistent with this, there is an apparent homeotic alteration in the gut of a transgenic mouse in which the anterior limit of expression of Hoxc-8 is shifted rostrally: a portion of foregut epithelium mis-differentiates as midgut (Pollock and Bieberich, (1992) *Cell* 71:911–923).

(v) Conservation in the Expression of Regulatory Genes Involved in the Formation of Vertebrate and Drosophila Gut There is an intriguing parallel between the expression patterns of Sonic, BMP-4, and the Hox genes in the vertebrate gut and those of their homologues during Drosophila gut morphogenesis (FIG. 15). This conservation is of particular interest because in Drosophila the role played by these genes has been clarified genetically. HH (like its vertebrate homologue, Sonic) is expressed at the earliest stages in the gut endoderm and may be a signal to visceral mesoderm (Taylor et al., (1993) *Mech. Dev.* 42:89–96). Nothing is known directly of the relationship between HH expression and activation of expression of other genes in the Drosophila gut. However, in Drosophila imaginal discs, HH is known to activate the expression of dpp in a signaling cascade (Kraus et al., (1994) *Cell* 75:1437–1444; Heberlein et al., (1993) *Cell* 75:913–926; Ma et al., (1993) *Cell* 75:913–926; Basler et al., (1993) *Cell* 73:687–702). Later in gut development, the production of dpp in the mesoderm contributes to the regulation of the expression of homeotic genes in both the mesoderm and the endoderm (Bienz, M. (1994) *TIG* 10:22–26). Drosophila homeotic genes are expressed in the gut visceral mesoderm and their expression is known to determine the morphologic borders of the midgut. This involves proper induction of gene expression in the adjacent endoderm, one of the mediators of the interaction is dpp (Bienz, M. (1994) *TIG* 10:22–26). If HH is required for the ultimate activation of the homeotic genes in the Drosophila midgut, this would parallel the situation in the vertebrate limb bud where Sonic functions as an upstream activator of the Hox genes (Riddle et al., (1993) *Cell* 75:1401–1416), perhaps in a signaling cascade involving BMP-2.

The extraordinary conservation in the expression of regulatory genes in the vertebrate and Drosophila gut strongly suggests a conservation of patterning mechanisms. Pathways established by genetic studies in Drosophila provide direct insights into the molecular basis for the regionalization and morphogenesis of the vertebrate gut.

EXAMPLE 9

Bacterially Expressed Hedgehog Proteins Retain Motorneuron-inducing Activity

Various fragments of the mouse Shh gene were cloned into the pET11D vector as fusion proteins with a poly(His) leader sequence to facilitate purification. Briefly, fusion genes encoding the mature M-Shh protein (corresponding to Cys-25 through Ser-437 of SEQ ID No. 11) or N-terminal containing fragments, and an N-terminal exogenous leader having the sequence M-G-S-S-H-H-H-H-H-H-L-V-P-R-G-S-H-M (SEQ ID No. 47) were cloned in pET11D and introduced into *E. coli*. The poly(His)-Shh fusion proteins were purified using nickel chelate chromatography according to the vendor's instructions (Qiagen catalog 30210), and the poly(His) leader cleaved from the purified proteins by treatment with thrombin.

Preparations of the purified Shh proteins were added to tissue explants (neural tube) obtained from chicken embryos and cultured in a defined media (e.g., no serum). M-Shh protein was added to final concentrations of between 0.5 pM to 5 nM, and differentiation of the embryonic explant tissue to motomeuron phenotype was detected by expression of Islet-1 antigen. The bacterially produced protein was demonstrated to be active in the explant cultures at concentrations as low as 5 to 50 pM. An Shh polypeptide containing all 19 kd of the amino terminal fragment and approximately 9 kd of the carboxyl terminal fragment (see Example 6) displayed both motor neuron inducing activity and weak floor plate inducing activity, indicating that these activities likely reside with the N-terminal fragment.

EXAMPLE 10

Induction of Dopaminergic Neuron Phenotype with Sonic Hedgehog

Hamburger-Hamilton stage 8–10 chick embryos were dissected free of the vitelline membranes and the areas opaca and pellucida. The embryos were then incubated in Dulbecco's Modified Eagle's Medium containing 0.5% dispase (Boehringer), 10 µg/ml hyaluronidase (Sigma), and 0.04% DNAse I (Sigma). The neural plate was then separated from its underlying mesoderm and notochord. The presumptive midbrain was identified and located according to its fate map (Couly and Le Douarin, 1987, *Developmental Biol.* 120:198–214) and isolated. The ventral one-third of the mesencephalic neural plate, comprising the presumptive floor plate and adjacent prospective dopaminergic neurons was then removed and discarded. The dorsal one-third was likewise dissected and removed. The remaining intermediate region was then incubated in vitro on a 2% agarose (Sigma) containing substrate made with alpha medium (Gibco). Recombinant Shh hedgehog, both human and mouse (full length cDNA), was then introduced to the tissue in one of two ways: (1) Bound to nickel-agarose beads (Qiagen) via the 6-histidine tag engineered onto the amino terminus of the protein, or (2) was incorporated in a soluble form directly into the agarose substrate. Dihydrofolate reductase was used as the control protein for these experiments. The tissue was then incubated at 37° C. for periods ranging from 36–48 hours. For analysis, tissue was fixed at 4° C. in 4% paraformaldehyde and stored in 50% MeOH until staining. Staining was done for both tyrosine hydroxylase (TH) (Boehringer), L-DOPA (Chemicon), and dopamine (DA) (Chemicon).

The data indicate that both mouse and human recombinant Shh hedgehog were active in the above described experiments. Furthermore, results indicate that addition of Shh induces both islet-1 (a motor neuron marker) and TH (a catecholaminergic neuron) as well as the accumulation of L-DOPA in the mesencephalon, which is indicative of a dopaminergic phenotype.

EXAMPLE 11

Sonic Hedgehog Induces Bone Formation

The ectopic bone formation assay was essentially done as described in Sampath and Reddi, 1983, *PNAS USA* 80:6591–6595. The mouse Shh protein was frozen and lyophilized, and the powder was enclosed in no. 5 gelatin capsule. Alternatively, 0.9–2.0 mg of collagen sponge (Collastat) was used as matrix. The Shh protein (12.5 µg) was added directly to the washed sponge, the sponge lyophilized, and the sponge implanted. The capsules or collagen sponges were implanted subcutaneously in the abdominal thoracic area of 21- to 49-day female Long-Evans rats and routinely removed at 11 days. Samples were processed for histological analysis, with 1-µm glycolmethacrylate sections stained with Von Kossa and acid fuschin or toluidine blue. Von Kossa staining shows mineral (hydroxyapatite) formation. The collagen sponge by itself was used as a control in these experiments. The results indicate that the addition of mouse Shh protein induced bone formation in these rats.

All of the above-cited references and publications are hereby incorporated by reference.

Equivalents

Those skilled in the art will recognize, or be able to ascertain using no more than routine experimentation, numerous equivalents to the specific polypeptides, nucleic acids, methods, assays and reagents described herein. Such equivalents are considered to be within the scope of this invention and are covered by the following claims.

What is claimed is:

1. A composition comprising a hedgehog polypeptide that includes a hedgehog amino acid sequence formulated in a pharmaceutically acceptable carrier, wherein said hedgehog amino acid sequence is encoded by a nucleic acid which hybridizes under stringent conditions, including a wash step of 0.2×SSC at 65° C., to a nucleic acid sequence selected from SEQ ID NO. 1, SEQ ID NO. 2, SEQ ID NO. 3, SEQ ID NO. 4, SEQ ID NO. 5, SEQ ID NO. 6, and SEQ ID NO. 7, which hedgehog amino acid sequence binds to a naturally occurring patched receptor.

2. The composition of claim 1, wherein said polypeptide comprises a hedgehog amino acid sequence selected from SEQ ID NO: 8, SEQ ID NO: 9, SEQ ID NO: 10, SEQ ID NO: 11, SEQ ID NO: 12, SEQ ID NO: 13 and SEQ ID NO: 14, or a fragment thereof.

3. The composition of claim 1, wherein said polypeptide comprises a hedgehog amino acid sequence encoded by a naturally occurring vertebrate hedgehog gene.

4. The composition of claim 3, wherein the hedgehog gene is a mammalian hedgehog gene.

5. The composition of claim 4, wherein the hedgehog gene is a human hedgehog gene.

6. The composition of claim 1, A wherein the hedgehog amino acid sequence is represented by the general formula SEQ ID NO: 41.

7. The composition of claim 1, wherein the hedgehog amino acid sequence has a molecular weight of about 19 kD.

8. The composition of claim 1, wherein said hedgehog amino acid sequence includes at least 150 contiguous amino acid residues of the N-terminal half of a hedgehog protein.

9. The composition of claim 1, wherein said patched receptor is a patched receptor of a vertebrate organism.

10. The composition of claim 1, wherein said polypeptide promotes the differentiation of neuronal cells or survival of a differentiated neuronal cells.

11. The composition of claim 10, wherein said neuronal cell is a dopaminergic neuron.

12. The composition of claim 10, wherein said neuronal cell is a motor neuron.

13. The composition of claim 1, wherein said polypeptide promotes proliferation of chondrocytes.

14. The composition of claim 1, wherein said polypeptide induces expression of BMP-2, BMP-4, or Hoxd genes.

15. The composition of claim 1, wherein said polypeptide is provided in a sterile preparation.

16. The composition of claim 1, wherein said pharmaceutically acceptable carrier is selected from the group consisting of water, buffered saline and polyol, or suitable mixtures thereof.

17. The composition of claim 1, wherein said pharmaceutically acceptable carrier iso-osmotic with physiological fluids of an animal.

18. The composition of claim 1, wherein said polypeptide is provided as a freeze-dried powder.

19. The composition of claim 1, wherein said polypeptide is provided in a solution.

20. The composition of claim 1, further comprising at least one trophic factor.

21. The composition of claim 20, wherein said trophic factor is selected from nerve growth factor, cilliary neurotrophic growth factor, schwanoma-derived growth factor, glial growth factor, striatal-derived neuronotrophic factor, platelet-derived growth factor, and scatter factor (HGF-SF).

22. The composition of claim 1, further comprising an antimitogenic agent.

23. The composition of claim 22, wherein said antimitotic agent inhibits the proliferation of glial cells and/or astrocytes.

24. The composition of claim 22, wherein said antimitotic agent is selected from cytosine, arabinoside, 5-fluorouracil, hydroxyurea, and methotrexate.

25. The composition of claim 1, wherein the hedgehog amino acid sequence is represented by the general formula SEQ ID NO: 40.

26. The composition of claim 1, wherein the hedgehog amino acid sequence includes at least 150 contiguous amino acids of the extracellular domain of said polypeptide.

27. The composition of claim 1, wherein the hedgehog amino acid sequence includes at least 100 contiguous amino acids of the extracellular domain of said polypeptide.

28. The composition of claim 1, wherein the hedgehog amino acid sequence includes at least 50 contiguous amino acids of the extracellular domain of said polypeptide.

29. The composition of claim 1, wherein said polypeptide is post-translationally modified with one or more glycosyl groups.

30. The composition of claim 1, which polypeptide is post-translationally modified with one or more lipids.

31. The composition of claim 1, which polypeptide is post-translationally modified with one or more phosphate groups.

32. The composition of claim 1, which polypeptide is post-translationally modified with one or more and acetyl groups.

33. The composition of claim 1, which hedgehog amino acid sequence comprises an N-terminal portion of a vertebrate hedgehog protein comprising Cys-24 through Glu-188 of SEQ ID-NO: 13.

34. The composition of claim 1, which hedgehog amino acid sequence comprises an N-terminal portion of a vertebrate hedgehog protein comprising Cys-23 through Asp 189 of SEQ ID NO: 9.

35. The composition of claim 1, which hedgehog amino acid sequence comprises a C-terminal portion of a vertebrate hedgehog protein comprising Asn-189 through Ala-475 of SEQ ID NO: 13.

36. The composition of claim 1, wherein the polypeptide is recombinantly produced.

37. The composition of claim 1, wherein the hedgehog amino acid sequence is encoded by a nucleic acid which hybridizes under stringent conditions, including a wash step of 0.2×SSC at 65° C., to a nucleic acid sequence selected from SEQ ID NO: 1, SEQ ID NO: 4, SEQ ID NO: 5 and SEQ ID NO: 6.

38. The composition of claim 37, wherein the hedgehog amino acid sequence is encoded by a nucleic acid which hybridizes under stringent conditions, including a wash step of 0.2×SSC at 65° C., to the nucleic acid of SEQ ID NO: 6.

39. The composition of claim 37, wherein the hedgehog amino acid sequence is encoded by a nucleic acid which hybridizes under stringent conditions, including a wash step of 0.2×SSC at 65° C., to the nucleic acid of SEQ ID NO: 7.

40. The composition of claim 1, wherein the hedgehog amino acid sequence is encoded by a nucleic acid which hybridizes under stringent conditions, including a wash step of 0.2×SSC at 65° C., to the nucleic acid sequence of SEQ ID NO: 2.

41. The composition of claim 1, wherein the hedgehog amino acid sequence is encoded by a nucleic acid which hybridizes under stringent conditions, including a wash step of 0.2×SSC at 65° C., to a nucleic acid sequence selected from SEQ ID NO: 3 and SEQ ID NO: 7.

42. The composition of claim 1, wherein the protein is purified to have less than 20% by dry weight of contaminating proteins.

43. The composition of claim 1, wherein the protein is purified to have less than 5% by dry weight of contaminating proteins.

44. The composition of claim 1 or 15, wherein said polypeptide is formulated for topical administration to an animal.

45. The composition of claim 1 or 15, wherein said polypeptide is formulated for systemic administration to an animal.

46. The composition of claim 1 or 15, wherein said polypeptide is formulated for intradermal, intramuscular, intraperitoneal, intravenous, subcutaneous, oral, intraventricular, intrathecal or intranasal delivery to an animal.

47. The composition of claim 1 or 15, wherein said polypeptide is provided in a rechargeable or biodegradable implantable device.

48. The composition of claim 47, wherein said polypeptide is encapsulated in an implantable polymer.

49. A composition comprising a polypeptide that includes a hedgehog amino acid sequence, formulated in a pharmaceutically acceptable carrier, wherein said hedgehog amino acid sequence is at least 80% identical to a polypeptide selected from SEQ ID NO: 8, SEQ ID NO: 9, SEQ ID NO: 10, SEQ ID NO: 11, SEQ ID NO: 12, SEQ ID NO: 13 and SEQ ID NO: 14, or a fragment thereof of at least 50 contiguous amino acid residues, wherein said hedgehog amino acid sequence binds to a naturally occurring patched receptor.

50. A composition of claim 49, comprising a polypeptide that includes a hedgehog amino acid sequence at least 90% identical to a polypeptide selected from SEQ ID NO: 8, SEQ ID NO: 9, SEQ ID NO: 10, SEQ ID NO: 11, SEQ ID NO: 12, SEQ ID NO: 13 and SEQ ID NO: 14, or a fragment thereof of at least 50 contiguous amino acid residues, wherein said hedgehog amino acid sequence binds to a naturally occurring patched receptor.

51. A composition of claim 49, comprising a polypeptide that includes a hedgehog amino acid sequence at least 95% identical to a polypeptide selected from SEQ ID NO: 8, SEQ ID NO: 9, SEQ ID NO: 10, SEQ ID NO: 11, SEQ ID NO: 12, SEQ ID NO: 13 and SEQ ID NO: 14, or a fragment thereof of at least 50 contiguous amino acid residues, wherein said hedgehog amino acid sequence binds to a naturally occurring patched receptor.

52. A composition of claim 49, comprising a polypeptide that includes a hedgehog amino acid sequence at least 98% identical to a polypeptide selected from SEQ ID NO: 8, SEQ ID NO: 9, SEQ ID NO: 10, SEQ ID NO: 11, SEQ ID NO: 12, SEQ ID NO: 13 and SEQ ID NO: 14, or a fragment thereof of at least 50 contiguous amino acid residues, wherein said hedgehog amino acid sequence binds to a naturally occurring patched receptor.

* * * * *

UNITED STATES PATENT AND TRADEMARK OFFICE
CERTIFICATE OF CORRECTION

PATENT NO. : 6,630,148 B1
DATED : October 7, 2003
INVENTOR(S) : Ingham et al.

It is certified that error appears in the above-identified patent and that said Letters Patent is hereby corrected as shown below:

Column 189,
Line 44, between the word "carrier" and "iso-osmotic," please add the word -- is --.

Signed and Sealed this

Thirteenth Day of January, 2004

JON W. DUDAS
*Acting Director of the United States Patent and Trademark Office*